United States Patent
Margulies et al.

(10) Patent No.: US 9,696,310 B2
(45) Date of Patent: Jul. 4, 2017

(54) MOLECULAR SENSOR AND METHODS OF USE THEREOF

(71) Applicant: YEDA RESEARCH AND DEVELOPMENT CO. LTD., Rehovot (IL)

(72) Inventors: David Margulies, Rehovot (IL); Leila Motiei, Rehovot (IL); Linor Unger, Rehovot (IL)

(73) Assignee: YEDA RESEARCH AND DEVELOPMENT CO. LTD., Rehovot (IL)

(*) Notice: Subject to any disclaimer, the term of this patent is extended or adjusted under 35 U.S.C. 154(b) by 0 days.

(21) Appl. No.: 14/738,894

(22) Filed: Jun. 14, 2015

(65) Prior Publication Data
US 2015/0276753 A1    Oct. 1, 2015

Related U.S. Application Data

(63) Continuation-in-part of application No. PCT/IL2013/051099, filed on Dec. 31, 2013.

(60) Provisional application No. 61/747,426, filed on Dec. 31, 2012.

(51) Int. Cl.
| | |
|---|---|
| C07D 417/14 | (2006.01) |
| G01N 33/573 | (2006.01) |
| C07D 417/06 | (2006.01) |
| C09K 11/06 | (2006.01) |
| G01N 33/58 | (2006.01) |
| C07F 9/6541 | (2006.01) |
| C07K 7/06 | (2006.01) |
| G01N 33/574 | (2006.01) |

(52) U.S. Cl.
CPC ......... *G01N 33/573* (2013.01); *C07D 417/06* (2013.01); *C07D 417/14* (2013.01); *C07F 9/6541* (2013.01); *C07K 7/06* (2013.01); *C09K 11/06* (2013.01); *G01N 33/582* (2013.01); *C09K 2211/1029* (2013.01); *C09K 2211/1037* (2013.01); *G01N 33/574* (2013.01); *G01N 2333/918* (2013.01); *G01N 2333/91177* (2013.01); *G01N 2333/96494* (2013.01)

(58) Field of Classification Search
CPC .. C07D 215/00; C07D 417/06; C07D 417/14; C07F 9/6541; C07K 7/06; C09K 11/06; C09K 2211/1029; C09K 2211/1037; G01N 33/573; G01N 33/582; G01N 33/574; G01N 2333/96494; G01N 2333/91177; G01N 2333/918
IPC .................................................. C07D 215/00
See application file for complete search history.

(56) References Cited

U.S. PATENT DOCUMENTS 8,742,114 B2 * 6/2014 Ying .................... C07D 215/00
                                                    546/165
2011/0210017 A1    9/2011 Lai et al.

FOREIGN PATENT DOCUMENTS

| EP | 2320230 A1 | 5/2011 |
| WO | WO 02/22882 A2 | 3/2002 |
| WO | WO 03/014375 A2 | 2/2003 |
| WO | WO 2007/100392 A2 | 9/2007 |

OTHER PUBLICATIONS

Hanafi-Bagby, Analytica Chimica Acta, 411 (2000) 19-30.*
Wang, Analytica Chimica Acta, 470 (2002) 57-70.*
Mahon, Chem & Biology, 14, 923-930, 2007.*
Pei, Nucleic Acids Research, 2009, vol. 37(8), e59, 1-6.*
Alhamdani et al. "Oncoproteomic profiling with antibody microarrays", Genome Med. Jul. 6, 2009;1(7):68.
Anslyn "Supramolecular analytical chemistry", J Org Chem. Feb. 2, 2007;72(3):687-99.
Arai et al. "Fluorescent "Turn-on" system utilizing a quencher-conjugated peptide for specific protein labeling of living cells", Biochem Biophys Res Commun. Jan. 7, 2011; 404(1):211-6.
Baldini et al. "Pattern-based detection of different proteins using an array of fluorescent protein surface receptors", J Am Chem Soc. May 12, 2004;126(18):5656-7.
Behera et al. "Cyanine Dyes: Self Aggregation and Behaviour in Surfactants. A Review", J. Surface Sci. Technol., 2007, vol. 23, No. 1-2, pp. 1-31, 2007.
Berman et al. "The Protein Data Bank", Nucleic Acids Res. Jan. 1, 2000;28(1):235-42.
Biver et al. "Cyanine dyes as intercalating agents: kinetic and thermodynamic studies on the DNA/Cyan40 and DNA/CCyan2 systems", Biophys J. Jul. 2005;89(1):374-83.
Cameron et al. "Structural analysis of human alpha-class glutathione transferase A1-1 in the apo-form and in complexes with ethacrynic acid and its glutathione conjugate", Structure. Jul. 15, 1995;3(7):717-27.
Collins et al. "Pattern-based peptide recognition", Chemistry. 2007;13(17):4700-8.
Dajani et al. "Development of a rapid and sensitive immunofluorometric assay for glutathione S-transferase A", Clin Chem. May 2001;47(5):867-73.
De et al. "Sensing of proteins in human serum using conjugates of nanoparticles and green fluorescent protein", Nat Chem. Sep. 2009;1(6):461-5.

(Continued)

*Primary Examiner* — D M Seaman
(74) *Attorney, Agent, or Firm* — Mark S. Cohen; Pearl Cohen; Zedek Latzer Baratz LLP

(57) ABSTRACT

The present invention is directed to fluorescent molecular sensor based on Thiazole Orange for protein detection. Interaction of the protein target with the molecular sensors of this invention results in a significant increase in the fluorescence emission. The generation of light output signal enables one to detect protein biomarkers associated with different diseases or detecting the protein of interest also in living cells.

50 Claims, 44 Drawing Sheets
(1 of 44 Drawing Sheet(s) Filed in Color)

(56) References Cited

OTHER PUBLICATIONS

Deligeorgiev et al. "Synthesis of novel cyanine dyes containing carbamoylethyl component—Noncovalent labels for nucleic acids detection", Dyes and Pigments vol. 74, Issue 2, 2007, pp. 320-328.
Dsouza et al. "Supramolecular tandem enzyme assays", Chemistry. Mar. 19, 2012;18(12):3444-59.
Ellman et al. "A new and rapid colorimetric determination of acetylcholinesterase activity", Biochem Pharmacol. Jul. 1961;7:88-95.
Fairhead et al. "Plug-and-play pairing via defined divalent streptavidins", J Mol Biol. Jan. 9, 2014;426(1):199-214.
Fasting et al. "Multivalency as a chemical organization and action principle", Angew Chem Int Ed Engl. Oct. 15, 2012;51(42):10472-98.
Fei et al. "Thiazole Orange derivatives: synthesis, fluorescence properties, and labeling cancer cells", Bioorg Med Chem. Jan. 15, 2009;17(2):585-91.
Fei et al. "Synthesis and Crystal Structure of Thiazole Orange Derivative", Journal of Chemical Crystallography Aug. 2011, vol. 41, Issue 8, pp. 1232-1236.
Feng et al. "A graphene oxide-peptide fluorescence sensor tailor-made for simple and sensitive detection of matrix metalloproteinase 2", Chem Commun (Camb). Oct. 14, 2011;47(38):10680-2.
Fletcher et al. "Targeting protein-protein interactions by rational design: mimicry of protein surfaces", J R Soc Interface. Apr. 22, 2006;3(7):215-33.
Fujikawa et al. "Design and synthesis of highly sensitive fluorogenic substrates for glutathione S-transferase and application for activity imaging in living cells", J Am Chem Soc. Nov. 5, 2008;130(44):14533-43.
Grate et al. "Laser-mediated, site-specific inactivation of RNA transcripts", Proc Natl Acad Sci U S A. May 25, 1999;96(11):6131-6.
Griffin et al. "Specific covalent labeling of recombinant protein molecules inside live cells", Science. Jul. 10, 1998;281(5374):269-72.
Habig et al. "Glutathione S-transferases. The first enzymatic step in mercapturic acid formation", J Biol Chem. Nov. 25, 1974;249(22):7130-9.
Halo et al. "Selective recognition of protein tetraserine motifs with a cell-permeable, pro-fluorescent bis-boronic acid", J Am Chem Soc. Jan. 21, 2009;131(2):438-9.
Hanash "Harnessing immunity for cancer marker discovery", Nature Biotechnology 21, 37-38 (2003).
Honda et al. "Pyrene excimer-based dual-emission detection of a oligoaspartate tag-fused protein by using a Zn(II)-DpaTyr probe", Chembiochem. Aug. 13, 2007;8(12):1370-2.
Hoque et al. "Induction of glutathione S-transferase in biofilms and germinating spores of Mucor hiemalis strain EH5 from cold sulfidic spring waters", Appl Environ Microbiol. Apr. 2007;73(8):2697-707.
Hövelmann et al. "Single labeled DNA FIT probes for avoiding false-positive signaling in the detection of DNA/RNA in qPCR or cell media", Chembiochem. Sep. 24, 2012;13(14):2072-81.
Hövelmann et al. "Brightness enhanced DNA FIT-probes for wash-free RNA imaging in tissue", J Am Chem Soc. Dec. 18, 2013;135(50):19025-32.
International Search for PCT Application No. PCT/IL2013/051102 mailed Mar. 20, 2014.
International Search for PCT Application No. PCTIL2013051099 mailed Apr. 1, 2014.
Jochum et al. "Glutathione-S-transferase subtypes α and π as a tool to predict and monitor graft failure or regeneration in a pilot study of living donor liver transplantation", Eur J Med Res. Jan. 27, 2011;16(1):34-40.
Kam et al. "Detection of endogenous K-ras mRNA in living cells at a single base resolution by a PNA molecular beacon", Mol Pharm. Mar. 5, 2012;9(3):685-93.
Kamoto et al. "Novel probes showing specific fluorescence enhancement on binding to a hexahistidine tag", Chemistry. 2008;14(26):8004-12.
Kapanidis et al. "Site-specific incorporation of fluorescent probes into protein: hexahistidine-tag-mediated fluorescent labeling with (Ni(2+):nitrilotriacetic Acid (n)-fluorochrome conjugates", J Am Chem Soc. Dec. 5, 2001;123(48):12123-5.
Karunakaran e al. "Large dynamic Stokes shift of DNA intercalation dye Thiazole Orange has contribution from a high-frequency mode", J Am Chem Soc. Mar. 8, 2006;128(9):2954-62.
Khoudoli et al. "Optimisation of the two-dimensional gel electrophoresis protocol using the Taguchi approach", Proteome Sci. Sep. 9, 2004;2(1):6.
Kobayashi et al. "New strategies for fluorescent probe design in medical diagnostic imaging", Chem Rev. May 12, 2010;110(5):2620-40.
Kolusheva et al. "Color fingerprinting of proteins by calixarenes embedded in lipid/polydiacetylene vesicles", J Am Chem Soc. Oct. 18, 2006;128(41):13592-8.
Krueger et al. "Fluorescent amino acids: modular building blocks for the assembly of new tools for chemical biology", Chembiochem. May 10, 2013;14(7):788-99.
Lavis et al. "Bright Ideas for Chemical Biology", ACS Chem. Biol., 2008, 3 (3), pp. 142-155.
Levy et al. "3D complex: a structural classification of protein complexes", PLoS Comput Biol. Nov. 17, 2006;2(11):e155.
Lombard et al. "Assays of matrix metalloproteinases (MMPs) activities: a review", Biochimie. Mar.-Apr. 2005;87(3-4):265-72.
Mahajan et al. "Optimization of bivalent glutathione S-transferase inhibitors by combinatorial linker design", J Am Chem Soc. Jul. 5, 2006;128(26):8615-25.
Margulies et al. "Combinatorial protein recognition as an alternative approach to antibody-mimetics", Curr Opin Chem Biol. Dec. 2010;14(6):705-12.
Margulies et al. "Protein recognition by an ensemble of fluorescent DNA G-quadruplexes", Angew Chem Int Ed Engl. 2009;48(10):1771-4.
McIlwain et al. "Glutathione S-transferase polymorphisms: cancer incidence and therapy", Oncogene. Mar. 13, 2006;25(11):1639-48.
Miranda et al. "Array-based sensing with nanoparticles: 'chemical noses' for sensing biomolecules and cell surfaces", Curr Opin Chem Biol. Dec. 2010;14(6):728-36.
Miranda et al. "Array-based sensing of proteins using conjugated polymers", J Am Chem Soc. Aug. 15, 2007;129(32):9856-7.
Mizusawa et al. "Disassembly-driven turn-on fluorescent nanoprobes for selective protein detection", J Am Chem Soc. Jun. 2, 2010;132(21):7291-3.
Mizusawa et al. "Specific cell surface protein imaging by extended self-assembling fluorescent turn-on nanoprobes", J Am Chem Soc. Aug. 15, 2012;134(32):13386-95.
Moerke "Fluorescence Polarization (FP) Assays for Monitoring Peptide-Protein or Nucleic Acid-Protein Binding", Curr Protoc Chem Biol. Dec. 1, 2009;1(1):1-15.
Motiei et al. "Targeted protein surface sensors as a tool for analyzing small populations of proteins in biological mixtures", Angew Chem Int Ed Engl. Aug. 25, 2014;53(35):9289-93.
Ogoshi et al. "Chemical Sensors Based on Cyclodextrin Derivatives", Sensors 2008, 8, 4961-4982.
Oh et al. "Excimer-based peptide beacons: a convenient experimental approach for monitoring polypeptide-protein and polypeptide-oligonucleotide interactions", J Am Chem Soc. Nov. 1, 2006;128(43):14018-9.
Owicki "Fluorescence polarization and anisotropy in high throughput screening: perspectives and primer", J Biomol Screen. Oct. 2000;5(5):297-306.
Olympus Microscopy Resource Center Solvent Effects on Fluorescence Emission, 2012; downloaded from: http://www.olympusmicro.com/primer/java/jablonski/solventeffects/index.html.
Pei et al. "Light-up properties of complexes between thiazole orange—small molecule conjugates and aptamers", Nucleic Acids Res. May 2009;37(8):e59.

(56) References Cited

OTHER PUBLICATIONS

Pietras et al. "PDGF receptors as cancer drug targets", Cancer Cell. May 2003; 3(5):439-43.
Qi et al. "Fluorescence Polarization Binding Assay for Aspergillus fumigatus Virulence Factor UDP-Galactopyranose Mutase", Enzyme Res. 2011;2011:513905.
Reddy et al. "Protein "fingerprinting" in complex mixtures with peptoid microarrays", Proc Natl Acad Sci U S A. Sep. 6, 2005;102(36):12672-7.
Rout et al. "Medication detection by a combinatorial fluorescent molecular sensor", Angew Chem Int Ed Engl. Dec. 7, 2012;51(50):12477-81.
Rout et al. "Authorizing multiple chemical passwords by a combinatorial molecular keypad lock", J Am Chem Soc. Oct. 16, 2013;135(41):15330-3.
Rydberg et al. "Complexes of Alkylene-Linked Tacrine Dimers with Torpedo californicaAcetylcholinesterase: Binding of Bis(5)-tacrine Produces a Dramatic Rearrangement in the Active-Site Gorge", J. Med. Chem., 2006, 49 (18), pp. 5491-5500.
Sainlos et al. "A general screening strategy for peptide-based fluorogenic ligands: probes for dynamic studies of PDZ domain-mediated interactions", J Am Chem Soc. May 20, 2009;131(19):6680-2.
Silva et al. "Experimental and computational investigation of unsymmetrical cyanine dyes: understanding torsionally responsive fluorogenic dyes", J Am Chem Soc. May 2, 2007;129(17):5710-8.
Sinkeldam et al. "Fluorescent analogs of biomolecular building blocks: design, properties, and applications", Chem Rev. May 12, 2010;110(5):2579-619.
Socher et al. "Low-noise stemless PNA beacons for sensitive DNA and RNA detection", Angew Chem Int Ed Engl. 2008;47(49):9555-9.
Soh "Selective Chemical Labeling of Proteins with Small Fluorescent Molecules Based on Metal-Chelation Methodology", Sensors 2008, 8(2), 1004-1024.
Stewart et al. "Identifying protein variants with cross-reactive aptamer arrays", Chembiochem. Sep. 5, 2011;12(13):2021-4.
Stoehlmacher et al. "Association between glutathione S-transferase P1, T1, and M1 genetic polymorphism and survival of patients with metastatic colorectal cancer", J Natl Cancer Inst. Jun. 19, 2002;94(12):936-42.
Szent-Gyorgyi et al. "Fluorogen-activating single-chain antibodies for imaging cell surface proteins", Nat Biotechnol. Feb. 2008;26(2):235-40.
Takahashi et al. "Molecular subclassification of kidney tumors and the discovery of new diagnostic markers", Oncogene. Oct. 2, 2003;22(43):6810-8.
Takaoka et al. "Protein organic chemistry and applications for labeling and engineering in live-cell systems", Angew Chem Int Ed Engl. Apr. 8, 2013;52(15):4088-106.
Thurley et al. "Hairpin peptide beacon: dual-labeled PNA-peptide-hybrids for protein detection", J Am Chem Soc. Oct. 24, 2007;129(42):12693-5.
Tsuchida et al. "Elevation of the placental glutathione S-transferase form (GST-pi) in tumor tissues and the levels in sera of patients with cancer", Cancer Res. Sep. 15, 1989;49(18):5225-9.
Tsuchida et al. "Glutathione transferases and cancer", Crit Rev Biochem Mol Biol. 1992; 27(4-5):337-84.
Ueda et al. "Current and prospective applications of metal ion-protein binding", J Chromatogr A. Feb. 21, 2003;988(1):1-23.
Venkatraman et al. "Fluorogenic probes for monitoring peptide binding to class II MHC proteins in living cells", Nat Chem Biol. Apr. 2007;3(4):222-8.
Wright et al. "Differential receptors create patterns that distinguish various proteins", Angew Chem Int Ed Engl. Oct. 7, 2005;44(39):6375-8.
Yang et al. "Detection of MMP activity in living cells by a genetically encloded surface-displayed FRET sensor", Biochimica et Biophysica Acta 1773 (2007) 400-407.
You et al. "Detection and identification of proteins using nanoparticle-fluorescent polymer 'chemical nose' sensors", Nat Nanotechnol. May 2007;2(5):318-23.
Zhi-Qiang et al. "Specific survivin dual fluorescence resonance energy transfer molecular beacons for detection of human bladder cancer cells", Acta Pharmacol Sin. Dec. 2011;32(12):1522-8. doi: 10.1038/aps.2011.122. Epub Oct. 24, 2011.
Zhou et al. "Pattern recognition of proteins based on an array of functionalized porphyrins", J Am Chem Soc. Feb. 22, 2006;128(7):2421-5.
Zhuang et al. "Environment-sensitive fluorescent turn-on probes targeting hydrophobic ligand-binding domains for selective protein detection", Angew Chem Int Ed Engl. Jul. 29, 2013;52(31):8124-8.

* cited by examiner

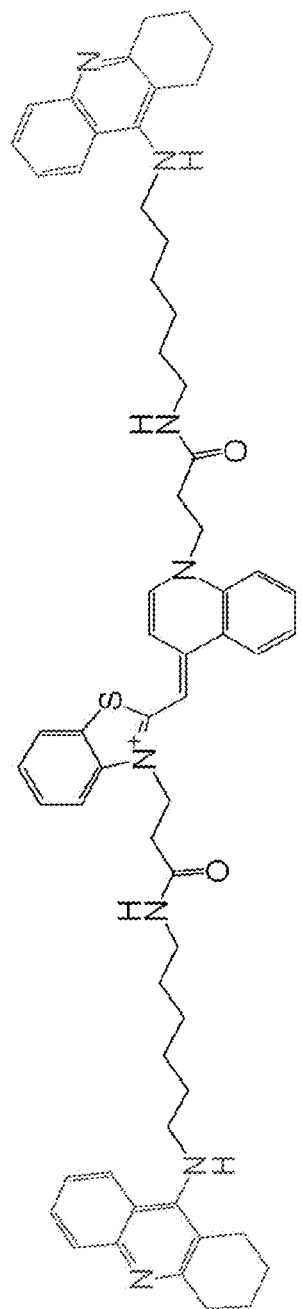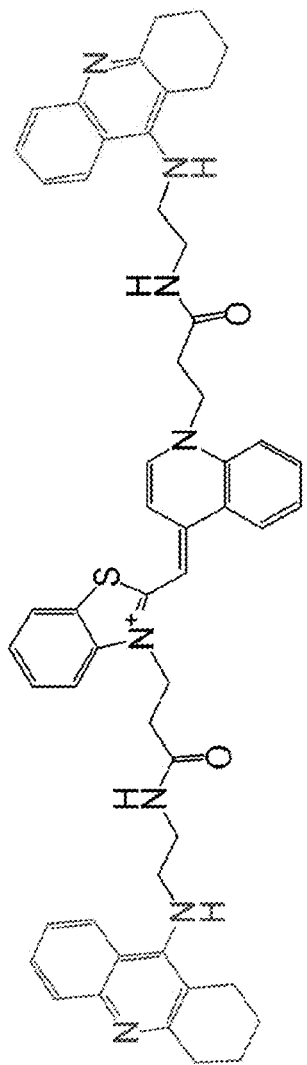
FIGURE 2G
FIGURE 2H

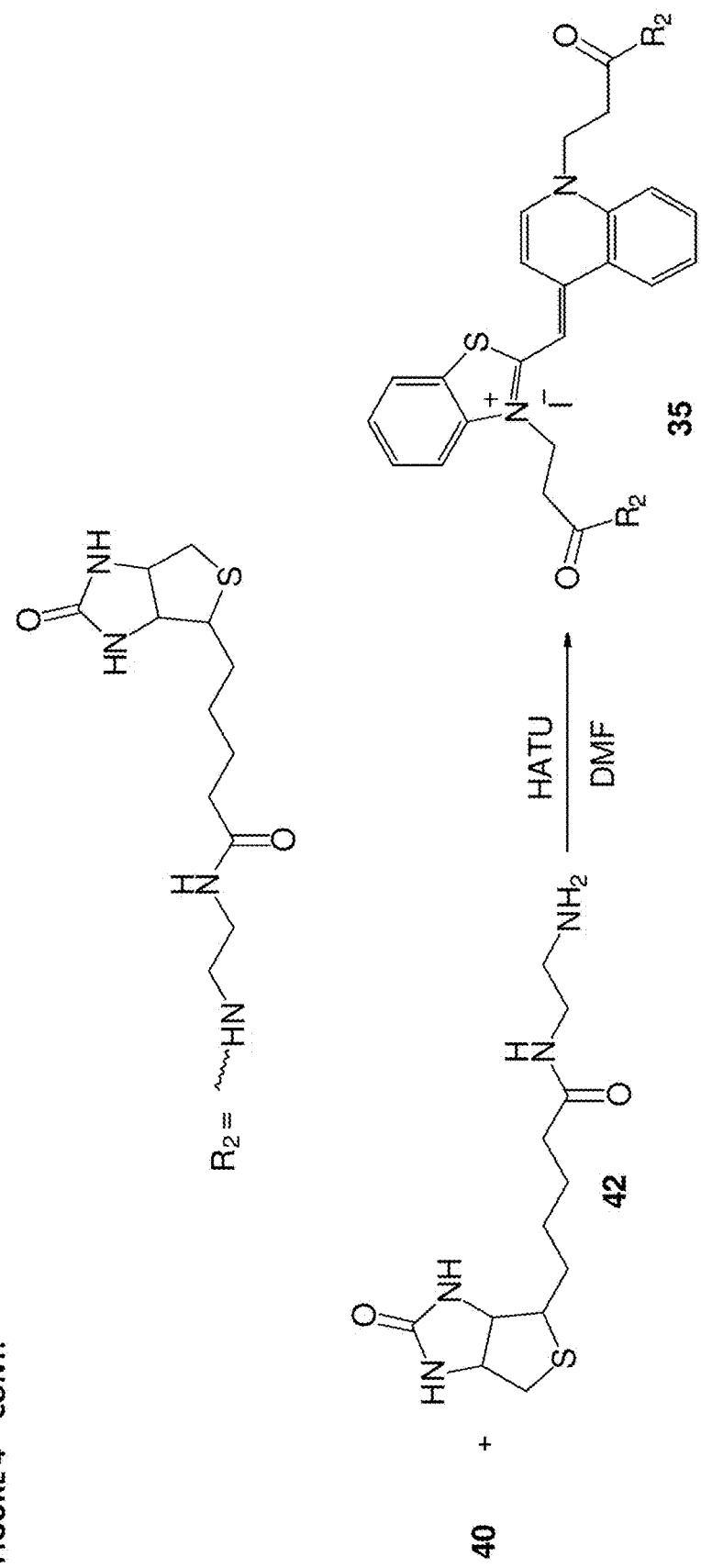
FIGURE 4 – CONT.

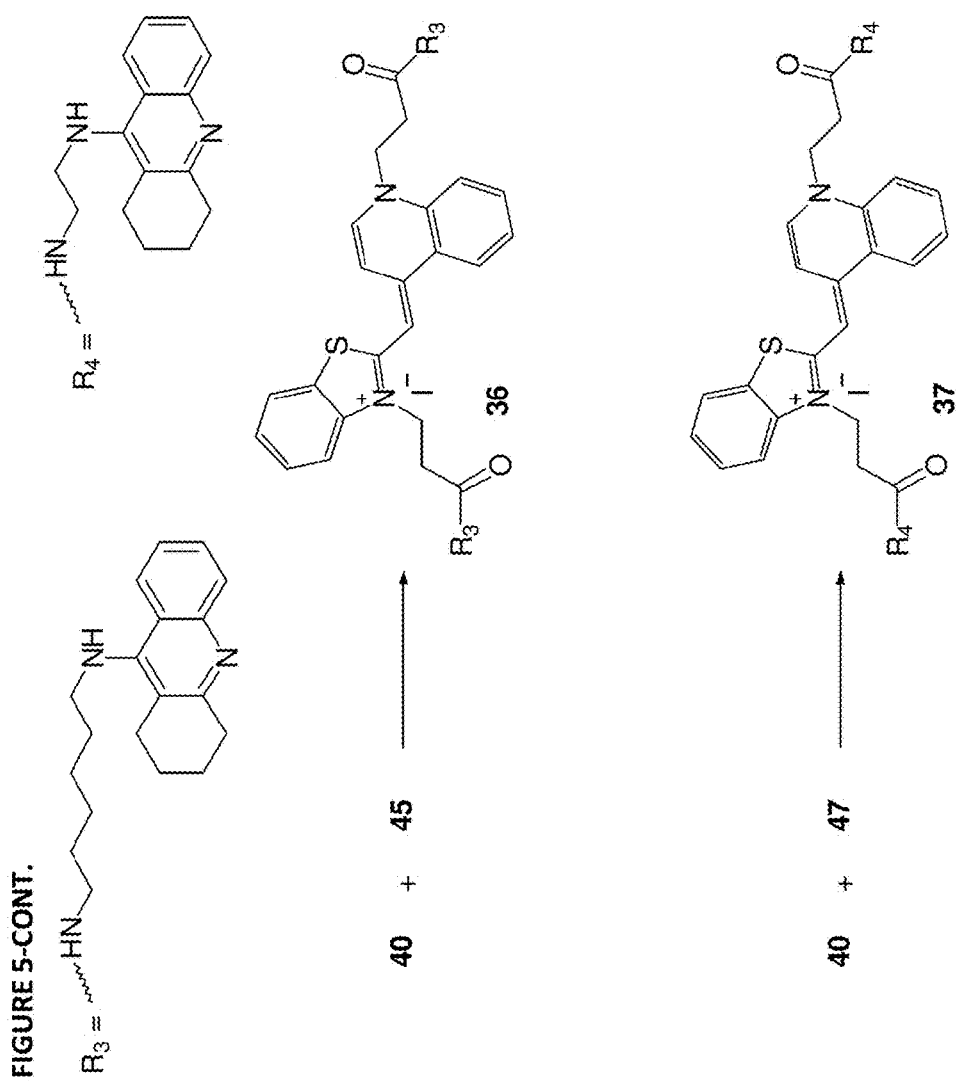
FIGURE 5-CONT.

FIGURE 30

| | | |
|---|---|---|
| SEQ ID NO. 9 | A1-1: 63-78 | MKLVQTRAILNYIASK |
| SEQ ID NO. 10 | A2-2: 63-78 | MKLVQTRAILNYIASK |
| SEQ ID NO. 11 | P1-1: 60-75 | LTLYQSNTILRHLGRT |
| SEQ ID NO. 12 | M1-1: 67-82 | HKITQSNAILCYIARK |
| SEQ ID NO. 13 | A1-1: 86-108 | IKERALIDMYIEGIADLGEMILL |
| SEQ ID NO. 14 | A2-2: 86-108 | IKEKALIDMYIEGIADLGEMILL |
| SEQ ID NO. 15 | P1-1: 83-105 | QQEAALVDMVNDGVEDLRCKYIS |
| SEQ ID NO. 16 | M1-1: 90-112 | EEEKIRVDILENQTMDNHMQLGM |

SEQUENCE LISTING

<160> NUMBER OF SEQ ID NOS: 16

<210> SEQ ID NO 1
<211> LENGTH: 10
<212> TYPE: PRT
<213> ORGANISM: Artificial Sequence
<220> FEATURE:
<223> OTHER INFORMATION: Polyhistidine Peptide

<400> SEQUENCE: 1

His His His His His His His His His His
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Polyhistidine Peptide

<400> SEQUENCE: 2

His His His His Trp Trp His His His His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Polyhistidine Peptide

<400> SEQUENCE: 3

His His His His Trp Trp His His His His
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Polyhistidine Peptide

<400> SEQUENCE: 4

His His His His Phe Phe His His His His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Polyhistidine Peptide

<400> SEQUENCE: 5

His His Phe Phe His His Trp Trp His His
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Polyhistidine Peptide

<400> SEQUENCE: 6

His His Trp Trp His His Trp Trp His His
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Polyhistidine Peptide

<400> SEQUENCE: 7

```
His His Trp Trp His His Leu Leu His His
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: Polyhistidine Peptide

<400> SEQUENCE: 8

```
His His His His Phe Phe His His Leu Leu
1               5                   10
```

<210> SEQ ID NO 9
<211> LENGTH: 16
<212> TYPE: PRT
<213> ORGANISM: Homo sapiens

<400> SEQUENCE: 9

```
Met Lys Leu Val Gln Thr Arg Ala Ile Leu Asn Tyr Ile Ala Ser Lys
1               5                   10                  15
```

<210> SEQ ID NO 10
<211> LENGTH: 16
<212> TYPE: PRT
<213> ORGANISM: Homo sapiens

<400> SEQUENCE: 10

```
Met Lys Leu Val Gln Thr Arg Ala Ile Leu Asn Tyr Ile Ala Ser Lys
1               5                   10                  15
```

<210> SEQ ID NO 11
<211> LENGTH: 16
<212> TYPE: PRT
<213> ORGANISM: Homo sapiens

<400> SEQUENCE: 11

```
Leu Thr Leu Tyr Gln Ser Asn Thr Ile Leu Arg His Leu Gly Arg Thr
1               5                   10                  15
```

<210> SEQ ID NO 12
<211> LENGTH: 16
<212> TYPE: PRT
<213> ORGANISM: Homo sapiens

<400> SEQUENCE: 12

```
His Lys Ile Thr Gln Ser Asn Ala Ile Leu Cys Tyr Ile Ala Arg Lys
1               5                   10                  15
```

<210> SEQ ID NO 13
<211> LENGTH: 22
<212> TYPE: PRT
<213> ORGANISM: Homo sapiens

<400> SEQUENCE: 13

```
Lys Glu Arg Ala Leu Ile Asp Met Tyr Ile Glu Gly Ile Ala Asp Leu
1               5                   10                  15

Gly Glu Met Ile Leu Leu
            20

<210> SEQ ID NO 14
<211> LENGTH: 23
<212> TYPE: PRT
<213> ORGANISM: Homo sapiens

<400> SEQUENCE: 14

Ile Lys Glu Lys Ala Leu Ile Asp Met Tyr Ile Glu Gly Ile Ala Asp
1               5                   10                  15

Leu Gly Glu Met Ile Leu Leu
            20

<210> SEQ ID NO 15
<211> LENGTH: 23
<212> TYPE: PRT
<213> ORGANISM: Homo sapiens

<400> SEQUENCE: 15

Gln Gln Glu Ala Ala Leu Val Asp Met Val Asn Asp Gly Val Glu Asp
1               5                   10                  15

Leu Arg Cys Lys Tyr Ile Ser
            20

<210> SEQ ID NO 16
<211> LENGTH: 23
<212> TYPE: PRT
<213> ORGANISM: Homo sapiens

<400> SEQUENCE: 16

Glu Glu Glu Lys Ile Arg Val Asp Ile Leu Glu Asn Gln Thr Met Asp
1               5                   10                  15

Asn His Met Gln Leu Gly Met
            20
```

MOLECULAR SENSOR AND METHODS OF USE THEREOF

CROSS-REFERENCE TO RELATED APPLICATIONS

This application is a Continuation-In-Part of PCT Application Number PCT/IL2013/051099, filed Dec. 31, 2013; which claims priority of U.S. Provisional Application Ser. No. 61/747,426, filed Dec. 31, 2012; both of which are herein incorporated by reference in their entirely.

FIELD OF THE INVENTION

The present invention is directed to fluorescent molecular sensor based on Thiazole Orange for protein detection. Interaction of the protein target with the molecular sensors of this invention results in a significant enhancement in the fluorescence emission. The generation of light output signal enables one to detect protein biomarkers associated with different diseases or detecting the protein of interest also in living cells. In particular, this invention describes an approach for obtaining sensitive, selective and widely applicable method for detecting and labelling a wide range of proteins in their native environment. The modification of Thiazole Orange with one or several protein binders leads to the creation of novel class of fluorescent molecular sensors that can detect various proteins in biofluids and in living cells with excellent signal-to-noise ratios.

BACKGROUND OF THE INVENTION

Fluorescent molecular probes that can label, detect, or image specific proteins serve as a powerful tool for developing in-vitro proteomic assays, for identifying disease biomarkers, as well as for tracking proteins in their native environments. Ideally, such probes should act as 'turn-on' fluorescent molecular sensors, which do not generate any background signal in the absence of the bioanalyte, but emit very strongly in the presence of the protein target. In practice, however, developing fluorescent molecular switches that can recognize their target proteins with high affinity, selectivity, and sensitivity is challenging. Obtaining highly selective sensors is complicated by the fact that many protein groups, which can be targeted by small-molecule-based sensors, possess well-defined recognition sites that are conserved among structurally similar isoforms of the same family. High sensitivity is also difficult to achieve because common fluorescence signaling mechanisms, such as photo-induced electron transfer (PET), charge transfer (CT), or fluorescence resonance energy transfer (FRET) often lead to a background emission signal by the unbound sensors. Consequently, an excess of protein is generally required to obtain a sufficient fluorescence response. Finally, a limitation of many molecular sensors, when compared with the corresponding antibodies or aptamers, is that they bind their target with lower affinities, which prevents them from detecting proteins at low concentrations.

Asymmetrical cyanine dyes constitute a unique class of fluorescent molecular sensors whose activation does not involve FRET, ICT, or PET processes. Instead, their fluorescence emission is turned on upon restriction of their torsional motion. For example, the emission of Thiazole Orange (TO) is quenched due to excited state twisting of benzothiazole and quinoline rings around the methine bridge, which leads to a non-radiative decay. Binding to DNA or peptide aptamers, or interchelation into DNA duplexes restricts this torsional motion and leads to an enhanced fluorescence signal.

Human soluble GSTs can be mainly subdivided into 7 classes, namely, α (A), μ (M), π(P), 0 (T), σ (S), κ (K), and ω (O), which differ in their electrophilic substrate preferences as well as in their tissue distribution. Comparative analysis of GST expression in normal and diseased tissues or serum has shown a clear correlation between their expression profiles and disease states. For example, abnormal tissue expression of GST α(A) has been associated with an increased risk for colorectal cancer, ovarian cancer, and clear cell renal cell carcinoma. μ (M) class expression alteration was detected in cases of lung, colon, and bladder cancer, whereas the π (P) class isozymes are overexpressed in the majority of human tumors. Moreover, several metabolic conditions led to excretion of GST proteins into urine or the blood circulation. For instance, the presence of GST-A1 in urine or in blood plasma is an early biomarker for hepatocellular damage, whereas elevated serum levels of GST-P1 is an indicator of various cancers (breast, lung and gastric cancers). GST-A1 is an indicator for colorectal, prostate, breast and lung cancers. GST-A2 is an indicator for prostate and lung cancers. GST-M1 is an indicator for prostate and breast cancers. An issue of high importance is distinguishing between combinations of several GST subtypes in urine. For example, measurements of GST-A and GST-P in urine provide information about the site of renal tubular injury. In addition, a combination of plasma α and π levels was proposed as a tool to predict and monitor graft failure or regeneration following living donor liver transplantation.

GSTs are also commonly used as fusion proteins, which facilitate the purification of GST-labeled protein with a GSH column Fluorescent molecular sensors for GSTs could therefore be used for detecting GST-labeled proteins in living cells.

Acetylcholinesterase, an important biomarker for the Alzheimer's disease, is a hydrolase that hydrolyzes the neurotransmitter acetylcholine and regulates the concentration of this transmitter at the synapse. AChE is found at mainly neuromuscular junctions and cholinergic brain synapses, where its activity serves to terminate synaptic transmission. It is the primary target of inhibition by organophosphorus compounds such as nerve agents and pesticides.

Avidin/streptavidin-biotin system is a powerful tool in biological sciences. The strength and specificity of the avidin/streptavidin-biotin complex, is exploited by researches for their use as probes and affinity matrices in numerous research projects and biologica assays including western blot, ELISA, ELISPOT and pull-down assays. Avidin and Streptavidin are used in applications ranging from research and diagnostics to medical devices and pharmaceuticals.

Fibroblast Growth Factors (FGFs) are a family comprising 22 heparin-binding proteins whose over-expression is associated with different types of cancers. Fluorescent molecular sensors, specific particular FGFs, could therefore facilitate identifying medicinally relevant samples involving different combinations or concentrations of FGFs.

Estrogen Receptors (ERα) have been mainly implicated in the development and progression of breast cancer, where much research has focused on identifying alterations within the coding sequence of these receptors in clinical samples. Mutations within ERα have been identified in several different diseases, indicating that the most common technique for determining tumor ER status, namely, immunohistochemical assays or ligand binding assays, might not be efficient for identifying ERs with abnormal ligand binding capacity or reduced functionality. Therefore, fluorescent molecular sensors, specific for ERs, might serve as an additional tool for characterizing ER biomarkers.

Matrix Metalloproteases (MMPs) family of enzymes comprising more than 20 zinc-dependent endopeptidases that share a similar, zinc-dependent binding site, and are capable of degrading virtually every component of the extracellular matrix (ECM). These isozymes can be divided into several subgroups, based on their structures or preferential substrates, which include, among others, collagen, gelatin, and various extracellular matrix proteins.

Owing to their role in tumor growth, metastasis, and angiogenesis, MMPs are considered as important therapeutic targets for treating human cancers. In addition, high levels of members of the MMP family in serum, urine, or tissue have been identified in a variety of human cancers, including breast, pancreatic, bladder, colorectal, ovarian, and prostate cancer (for example, MMP-1 is identified in breast cancer, lung cancer and colorectal cancer; MMP-2 is identified in pancreas cancer, bladder cancer, colorectal cancer, ovarian cancer, prostate cancer and brain cancer; MMP-7 is identified in pancreas cancer, lung cancer and colorectal cancer; MMP-9 is identified in breast cancer, pancreas cancer, bladder cancer, lung cancer, colorectal cancer, ovarian cancer, prostate cancer and brain cancer). Thus, MMPs are considered to be promising biomarkers for different cancers, both for diagnostic and prognostic purposes. Glutathione S-Transferases (GSTs) are a family of widely distributed enzymes that play a role in cell detoxification by catalyzing the conjugation of γ-L-glutamyl-L-cysteinylglycine (gluthation) to a broad range of electrophilic endotoxins and xenobiotics that are subsequently excreted from the cell. This activity is a crucial part of a self-defense mechanism that protects the organism from toxic and sometimes carcinogenic species.

Genetically encoded fluorescent proteins (FPs) have revolutionized the study of biology by allowing one to track protein expression and localizations in living cells at spatial and temporal resolution. This method, however, involves the use of very large protein tags that can interfere with the normal function of the labeled protein. Over the last few years, it has been demonstrated that this problem can be circumvented by expressing the proteins with a very short peptide sequence to which a small fluorescent molecular sensor, termed "genetically-targeted sensors" can attach. Sensors that can bind to an oligohistidine sequence (i.e. His-tag) with high affinity and can be applied for labeling and detecting a wide range of His-tagged proteins in living cells.

The above examples not only stress the importance of developing methods for high-throughput protein analysis in biological fluids but also highlight GSTs, AChE, FGFs, ER and MMPs as potential biomarkers for detecting early stages of various diseases, including cancer and Alzheimer.

Surprisingly, despite the remarkable analytical power of fluorescent molecular sensors and their success in detecting various biomolecules and ions in aqueous solutions, the development of 'turn-on' fluorescent molecular switches for proteins, which do not rely on enzymatic reactions, has been relatively scarce.

This invention shows that the conversion of a known intercalating dye (e.g., Thiazole Orange) into a bivalent protein binder could lead to the realization of a novel class of fluorescent molecular sensors that detect proteins, including individual protein isoforms, with high affinity, selectivity, and excellent signal-to-noise (S/N) ratio. The feasibility of the approach is demonstrated with monomolecular sensors that light-up in the presence of various proteins (e.g. glutathione-s-transferase (GST), avidin (Av), acetylcholinesterase (AChE) etc.) at low concentrations and with minimal background signal. Such sensors are also able to respond differently to the surfaces of distinct protein isoforms, which circumvents the challenge of developing a highly selective binder for each family member. This property, thus, opens up new possibilities for using sensors appended with broad-spectrum protein binders in order to obtain isoform-specific detection.

Therefore, and given that about 30% of human proteins are homodimers, the protein sensors presented herein are expected to contribute to the development of 'turn-on' fluorescent molecular switches for proteins, which do not rely on enzymatic reactions, by affording a novel methodology for selective and sensitive detection of a wide range of different proteins and protein isoforms.

SUMMARY OF THE INVENTION

In one embodiment, this invention is directed to a fluorescent monomolecular sensor, wherein said sensor comprises a Thiazole Orange (TO) derivative and at least one selective protein binder. In another embodiment, the sensor is a Thiazole Orange-based protein identifier (TOPI). In another embodiment, the TOPI comprises a Thiazole Orange (TO) derivative and two selective protein binders. In another embodiment, the protein is a homodimer. In another embodiment, the selective protein binder is covalently attached to said TO derivative. In another embodiment, the selective protein binder is covalently attached to the TO derivative through a linker.

In another embodiment, the sensor is represented by the structure of formula IX:

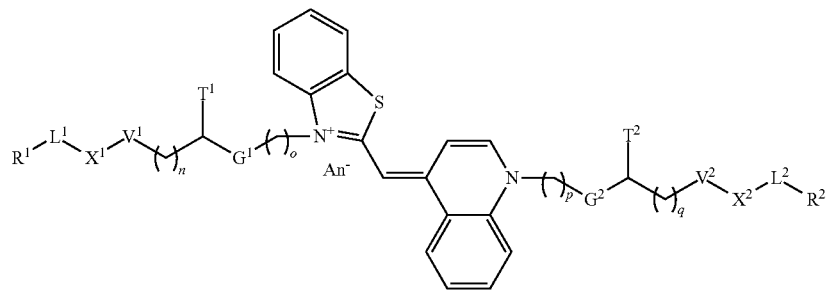

wherein
n, o, p and q are independently integers between 0 to 15;
An⁻ is tosylate (p-toluenesulfonate; $CH_3C_6H_4SO_3^-$), $PF_6^-$, $CF_3COO^-$ I⁻, Cl⁻, Br⁻, or F⁻;

wherein at least one of $R^1$, $R^{1'}$, $R^2$ and $R^{2'}$ is a protein selective binder.

In another embodiment, the sensor is represented by the structure of formula XIII:

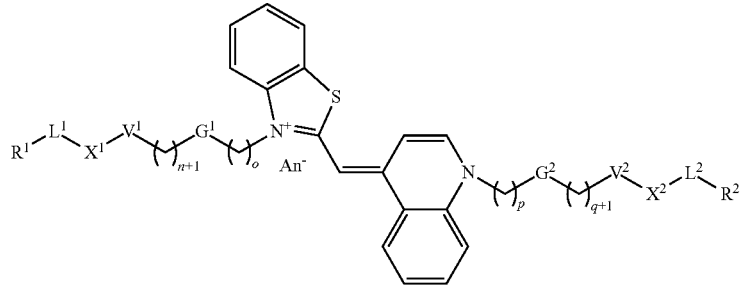

XIII $G^1$ and $G^2$ are independently a bond, carbamate, amide, amine, $C_1$-$C_{12}$ alkyl amine, ester, ketone, O, N, S, carbonate, —O-alkyl-NH—, carbamoyl phosphate or phosphate;

$T^1$ is hydrogen or

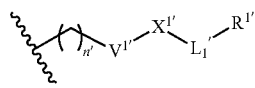

wherein, n' is between 0 and 15.

$T^2$ is hydrogen or

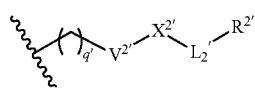

wherein q' is between 0 and 15.

$V^1$, $V^{1'}$, $V^2$ and $V^{2'}$ are independently a bond, a triazole, an amide [—C(O)NH or NHC(O)], —C(O)O—, —OC(O)—, O, NH, N-alkyl, S, —$PO_4H$—, $C_1$-$C_{12}$ alkyl ether, —NH— alkyl-NH—, —O-alkyl-NH—, —NH-alkyl-O— wherein said alkyl is optionally substituted and wherein said alkyl is optionally interrupted by an heteroatom consisting of O, N, P, S or combination thereof $X^1$, $X^{1'}$, $X^2$ and $X^{2'}$ are independently a bond or $C_1$-$C_{12}$alkyl, —C(O)NH—, —NHC(O), —C(O)O—, —OC(O)—, O, NH, N-alkyl, S, —$PO_4H$—, $C_1$-$C_{12}$ alkyl ether, $C_1$-$C_{12}$ alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$L^1$, $L^{1'}$, $L^2$ and $L^{2'}$ are independently a bond or $C_1$-$C_{12}$ alkyl, C(O), —C(O)NH—, —NHC(O)—, —C(O)O—, —OC(O)—, O, NH, $C_1$-$C_{12}$N-alkyl, S, —$PO_4H$, —$PO_4H$—{[($CH_2$)$_y$O]$_x$}$_z$—$PO_3H$—, wherein y is between 1-5, x is between 1-10 and z is between 1-10, —$PO_4H$-PEG, $C_1$-$C_{12}$ alkyl ether, $C_1$-$C_{12}$ alkylamine, $C_1$-$C_{12}$ alkyl-NH, —C(O)NH-alkyl, —NHC(O)— alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof; and $R^1$, $R^{1'}$, $R^2$ and $R^{2'}$ are independently hydrogen, halide, $SO_3^-$, CN, $NO_2$, phosphate, $SO_3^-$ or a selective protein binder;

wherein n, o, p, q, An⁻, $V^1$, $V^2$, $G^1$, $G^2$, $X^1$, $X^2$, $L^1$, $L^2$, $R^1$ and $R^2$ are as defined herein above.

In another embodiment, this invention is directed to a sensor represented by the structure of formula X:

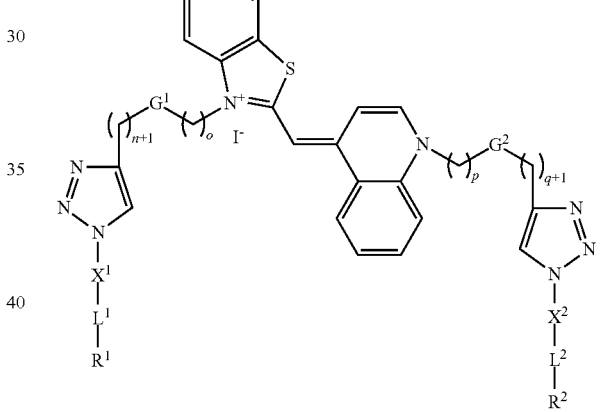

X wherein n, o, p, q, $G^1$, $G^2$, $X^1$, $X^2$, $L^1$, $L^2$, $R^1$ and $R^2$ are as defined herein above.

In another embodiment, the selective protein binder is ethacrynic acid, bisethacrynic acid, marimastat, biotin, tacrine, a metal complex of nitrilotriacetic acid (NTA), a metal complex of bis-NTA, a metal complex of tris-NTA, Ni-nitrilotriacetic acid (Ni-NTA), bis-Ni-NTA, tris-Ni-NTA, PDGF-BB, heparin, FGF aptamer, estrogen, DNA aptamer, RNA aptamer, peptide aldehyde, suberoylanilidehydroxamic acid (SAHA), estrogen, or a peptide binder.

In another embodiment, $T^1$ and $T^2$ are hydrogens. In another embodiment, $G^1$ and $G^2$ are each independently a carbamate or an amide. In another embodiment, $V^1$ and $V^2$ are each independently a triazole, an O, an NH or a bond. In another embodiment, $X^1$ and $X^2$ are each independently a $C_1$-$C_{12}$ alkyl, a $C_1$-$C_{12}$ alkyl-NH, a $C_1$-$C_{12}$ alkylether, -alkyl-C(O)NH-alkyl or a bond. In another embodiment, $L^1$ and $L^2$ are each independently a bond, —$PO_4H$—{[($CH_2$)$_y$O]$_x$}$_z$, —$PO_3H$—; wherein y is 2, x is 3 and z is 6, —$PO_4H$-PEG, $C_1$-$C_{12}$ alkyl-NH or a $C_1$-$C_{12}$ alkyl. In another embodiment, o and p are each independently 2 or 3. In another embodiment, n and q are each independently 0, 1, 2 or 5. In another embodiment, $R^1$ and $R^2$ are both selective binders. In another embodiment, $V^1$ and $V^2$ are identical; $X^1$ and $X^2$ are identical; $L^1$ and $L^2$ are identical; W and $R^2$ are identical; o and p are identical; and n and q are identical.
In another embodiment, the selective sensor of this invention is represented by compound 14, 140, 20, 26, 33, 34, 35, 36 or 37:
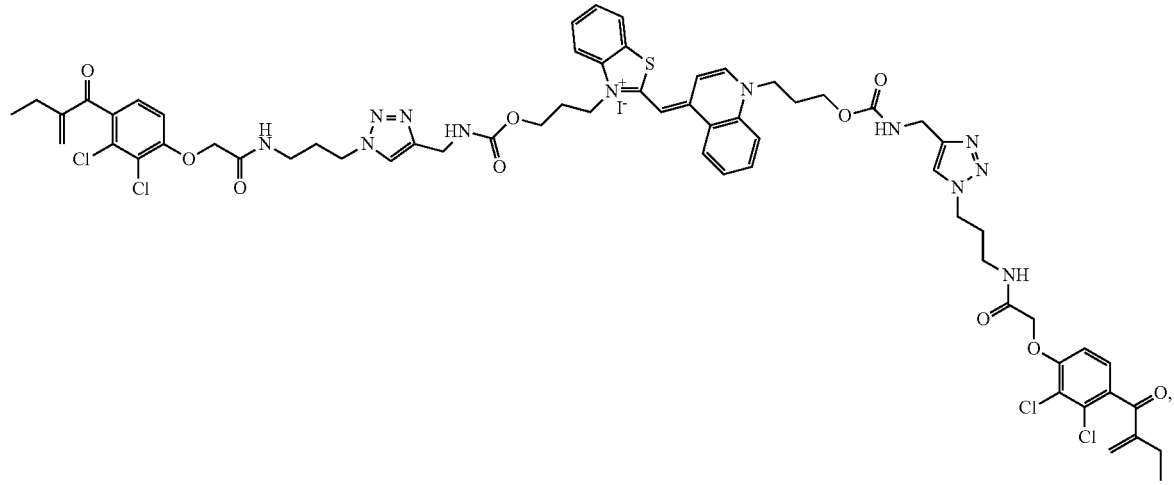
14
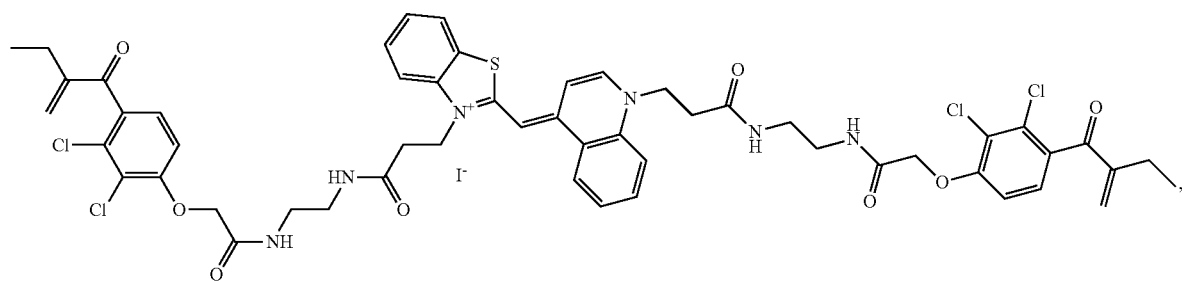
140
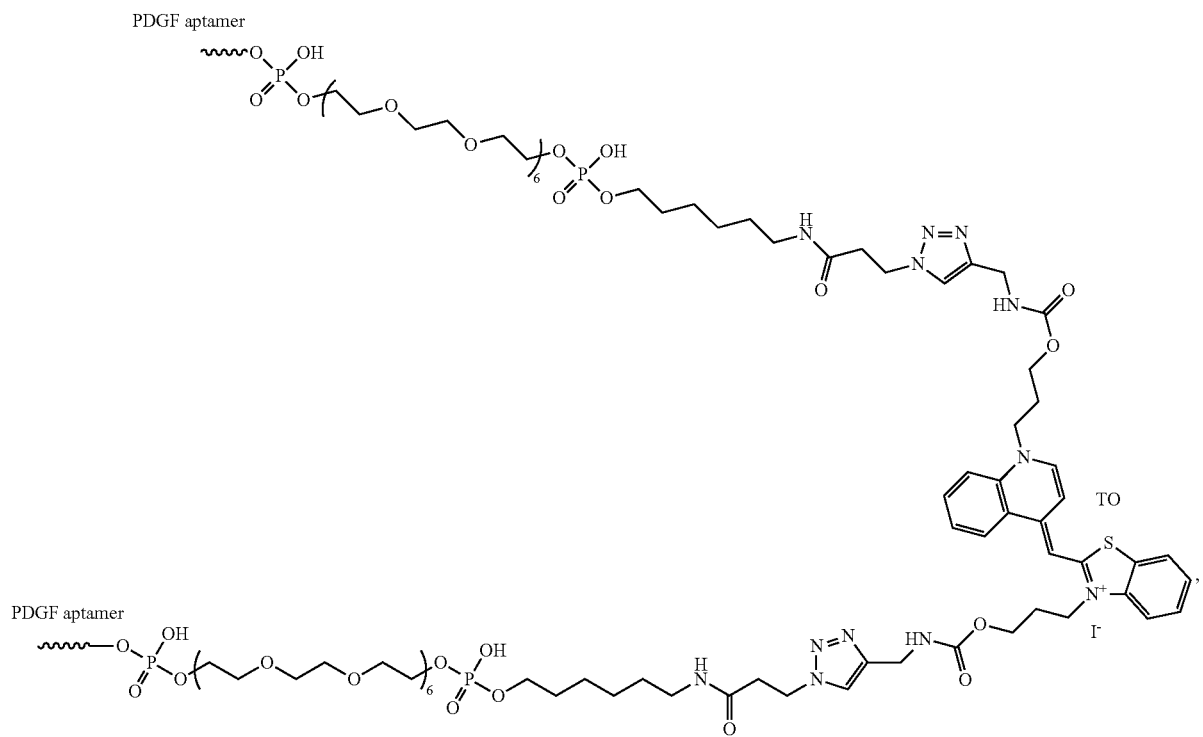
20

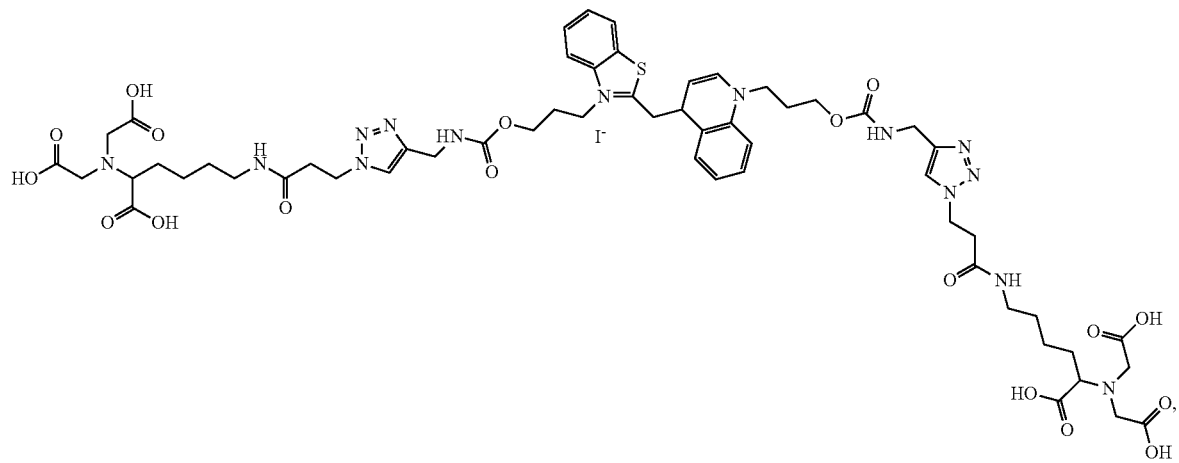
26
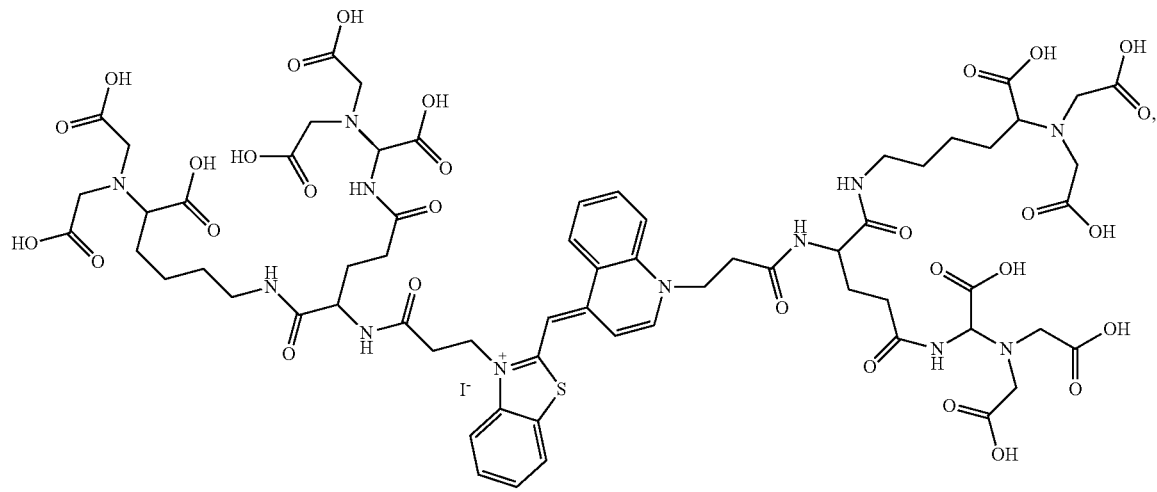
33
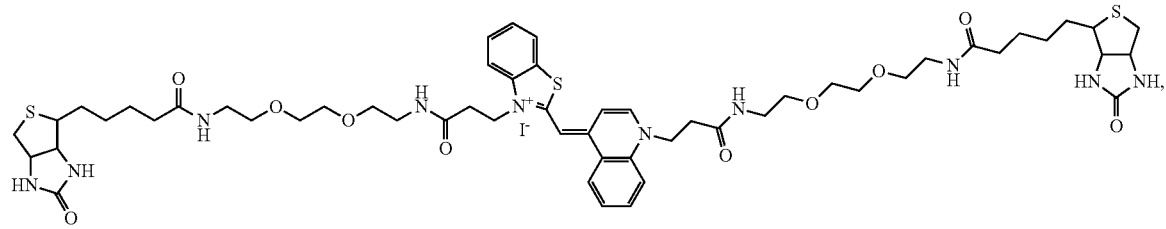
34
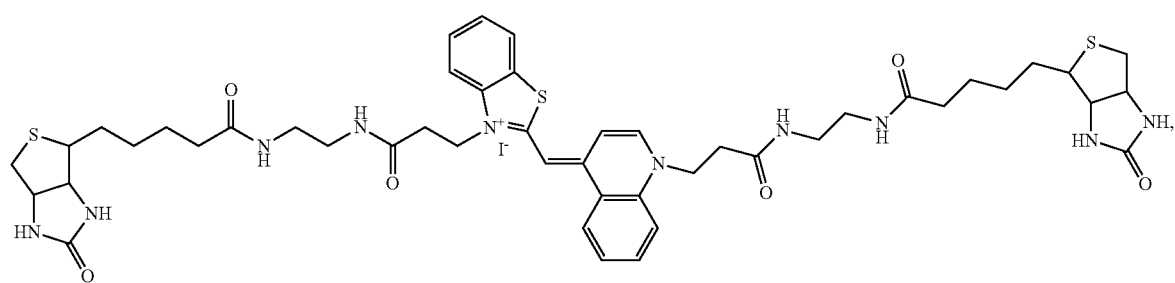
35

-continued

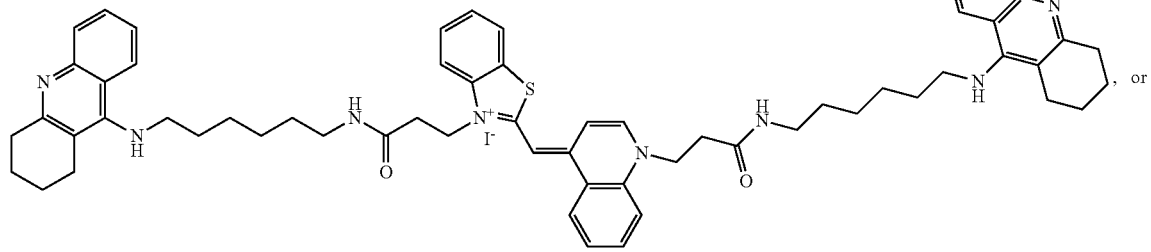

36

, or

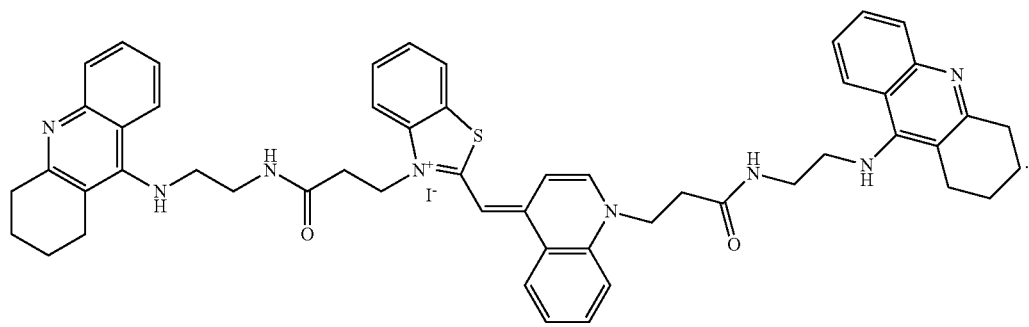

37

In another embodiment, this invention is directed to a method of detecting a protein in a biological medium comprising contacting a sensor of this invention and a protein or interest (POI), wherein contacting said POI with said sensor leads to an enhancement in the optical signal of said sensor, thereby detecting said POI. In another embodiment, the optical signal is fluorescence emission. In another embodiment the protein is matrix metalloproteases (MMPs) protein and its isoforms, glutathione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, avidin, streptavidin, Acetylcholinesterase or histone deacetylases (HDACs). In another embodiment the sensor is compound 14, 140, 20, 26, 33, 34, 35, 36, or 37.

In one embodiment, this invention is directed to a method of for identifying a disease biomarker in a subject, said method comprises:
(a) collecting a biological sample from a subject;
(b) incubating said biological sample with a sensor of to this invention;
(c) measuring the fluorescence resulting from binding of said sensor to a protein of interest (POI), which is a biomarker for a disease, in said sample;
wherein an enhancement in the emission intensity from said sample is an indicator of the presence of said POI in said sample. In another embodiment, the disease is cancer or Alzheimer.

In one embodiment, this invention is directed to a method of identifying a compound that binds a protein of interest (POI), said method comprises:
a. incubating a sensor of this invention with said POI in solution;
b. measuring the fluorescence intensity of said solution;
c. adding a test compound to said solution;
d. re-measuring the fluorescence intensity of said solution; and e. determining binding of said test compound to said POI based on a change in fluorescence intensity, wherein decreased fluorescent intensity indicates binding of said test compound to said POI;
thereby identifying a compound that binds said POI.

In one embodiment, this invention is directed to a method for localizing a protein of interest (POI) within a cell, said method comprises:
a. incubating cells comprising said POI with a sensor of this invention;
b. visualizing the fluorescence emission of said cells;
wherein an enhancement in the fluorescence emission is indicative of binding of said sensor to a protein of interest (POI) in said cells.

BRIEF DESCRIPTION OF THE DRAWINGS

The patent or application file contains at least one drawing executed in color, Copies of this patent or patent application publication with color drawing(s) will be provided by the Office upon request and payment of the necessary fee, The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 2A-2G depict the molecular structures of fluorescence sensors of this invention. FIG. 2A—GST sensors based on a TO-bisethacrynic acid conjugate (sensors 14, 140). FIG. 2B—A PDGF-BB sensor based on a TO-bis PDGF-BB aptamer conjugate (sensor 20). FIG. 2C—A sensor for His-tag-labelled proteins based on a TO-bis-Ni-NTA conjugate (sensor 26). FIG. 2D—A sensor for His-tagged proteins based on a TO-tetrakis-Ni-NTA derivative (sensor 33). FIGS. 2E and 2F—depict sensors for avidin/streptavidin based on a TO-bis-biotin conjugates (sensors 34, 35). FIGS. 2G and 2H—depict sensors for acetylcholinesterase based on a TO-bis-tacrine conjugates (sensors 36, 37).

FIG. 11 depicts fluorescence/emission spectra of TO compounds, under different experimental conditions. A) an emission spectrum of 3 μM of an unmodified TO at RT. B) emission of 30 μM unmodified TO at (dashed line) 5° C. and (solid line) 25°. C) fluorescence emission spectrum of 3 μM of sensor 14. All experiments were performed in PBS buffer, pH=6.5. $\lambda_{ex}$=480 nm. An emission at 540 nm refers to a monomeric TO. An emission at 625 nm refers to a dimmer of TO.

FIG. 30 depicts an alignment of sequence segments that form the inter monomer crevice. Residues shown in bold point into the central region of the crevice and can interact with a putative ligand.

Figure 1A:
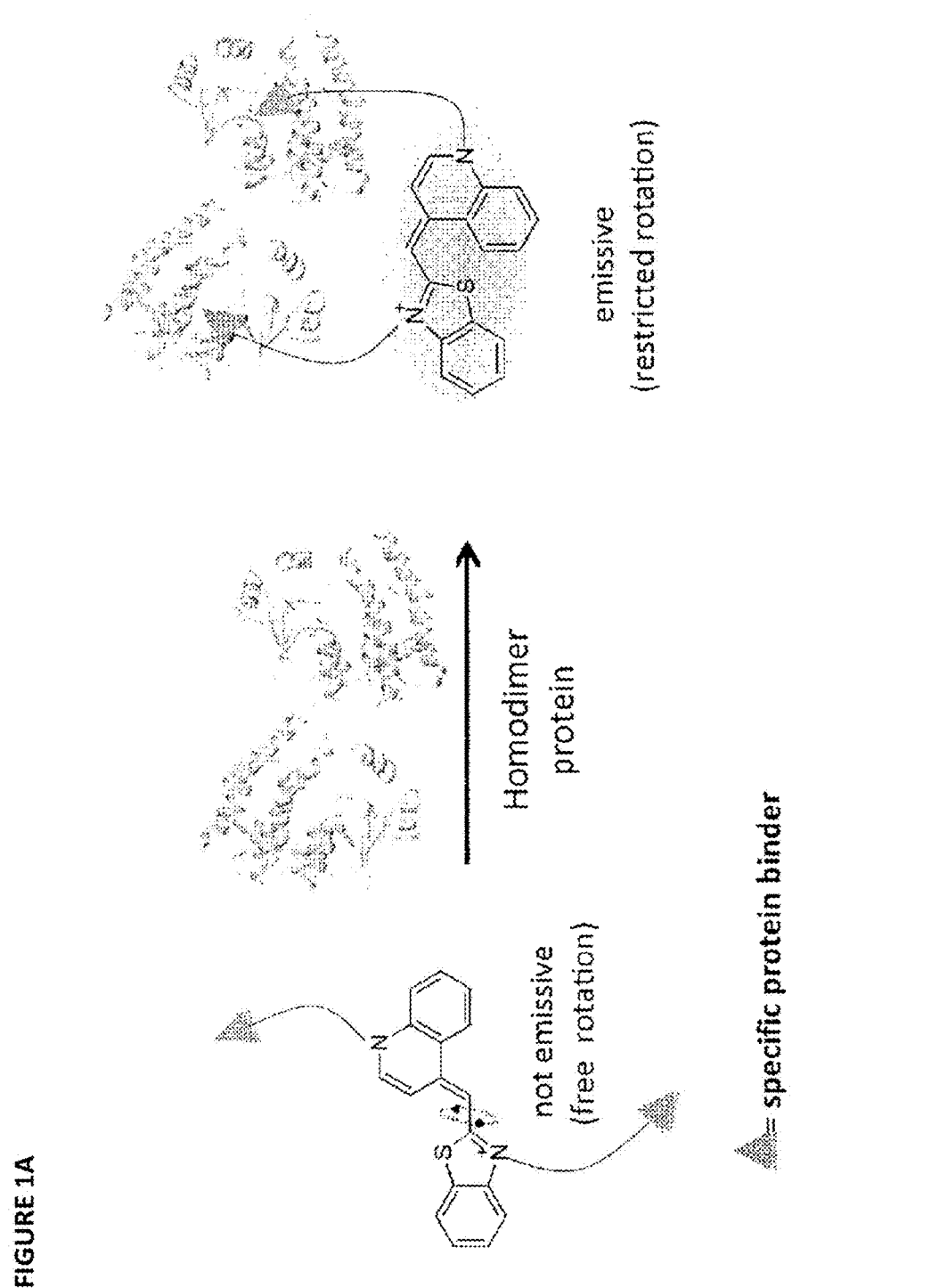
FIG. 1A is a schematic presentation of a Thiazole Orange (TO)-based protein sensor including two selective protein binders.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention is directed to a new class of Thiazole Orange based fluorescent molecular sensors for the sensitive and selective detection of different proteins.

Figure 1B:
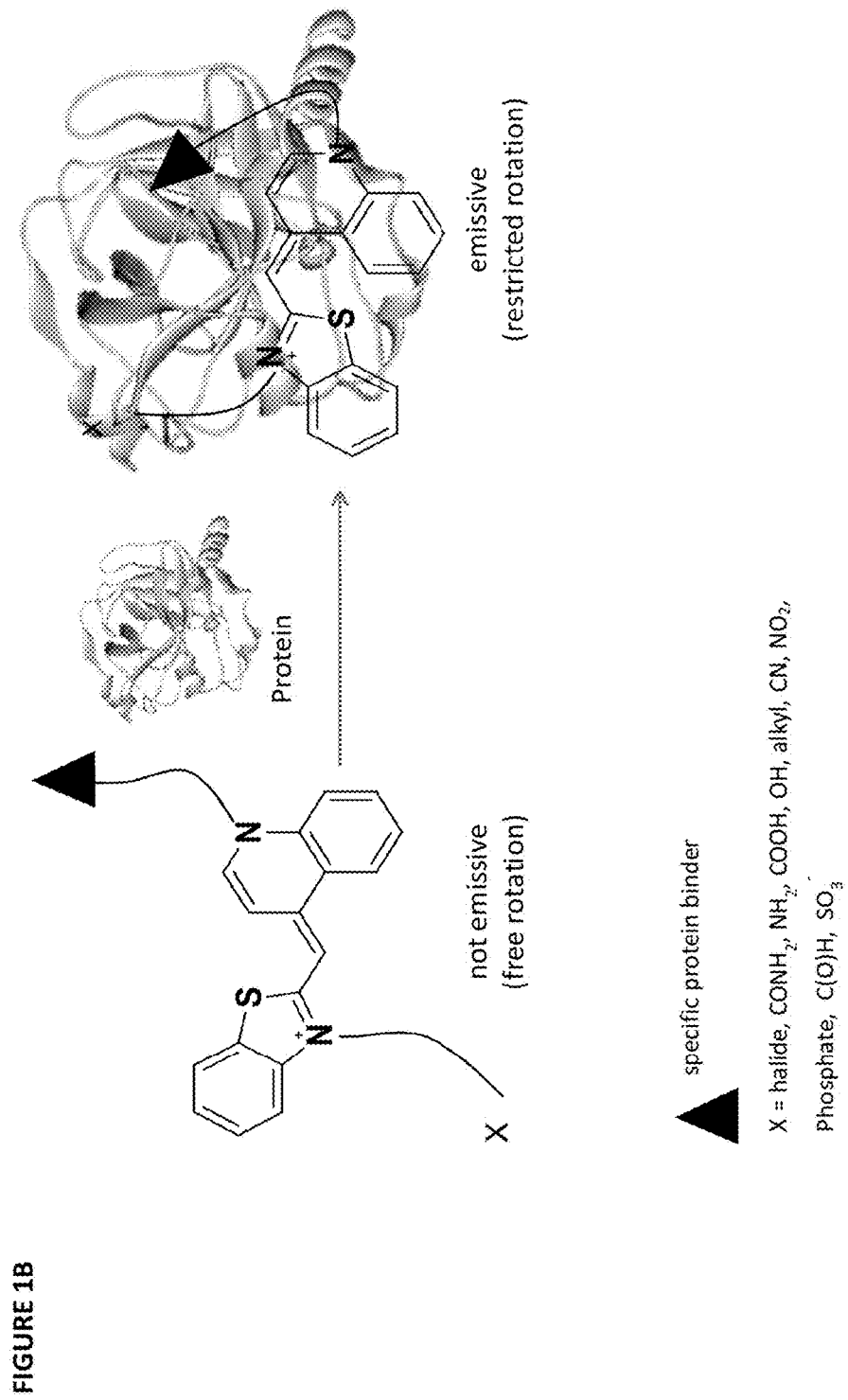
FIG. 1B is a schematic presentation of a Thiazole Orange (TO)-based protein sensor including one selective protein binder. Upon binding to a protein the free rotation of TO is restricted and consequently a fluorescent signal is generated.
Figure 1C:
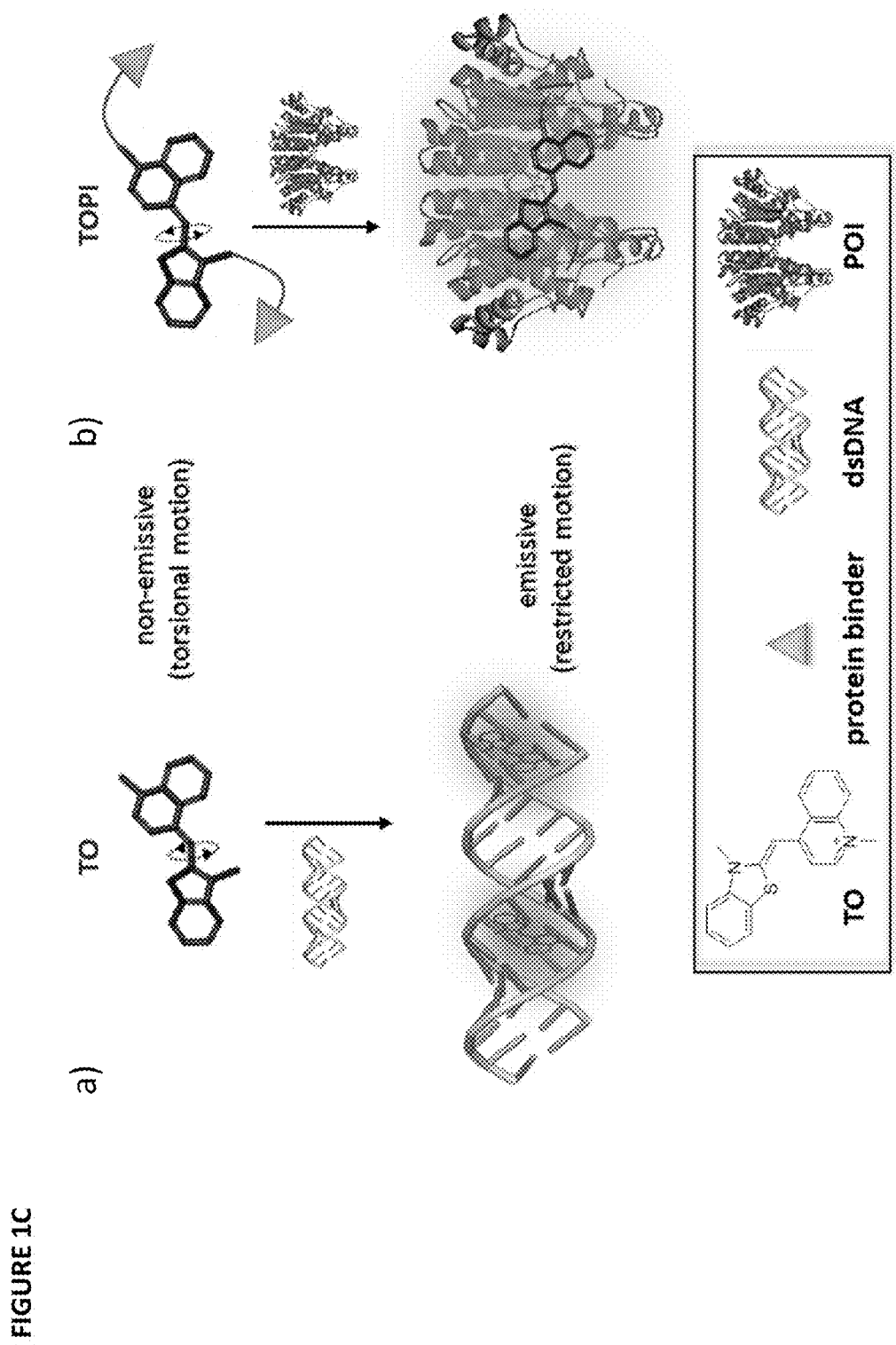
FIG. 1C is a schematic representation of the mechanism responsible for the 'turn-on' fluorescence signal generated upon a) the binding of Thiazole Orange (TO) to double-stranded DNA (dsDNA), and b) the binding of a TO-based protein identifier (TOPI) to the protein of interest (POI).
Figure 2A:
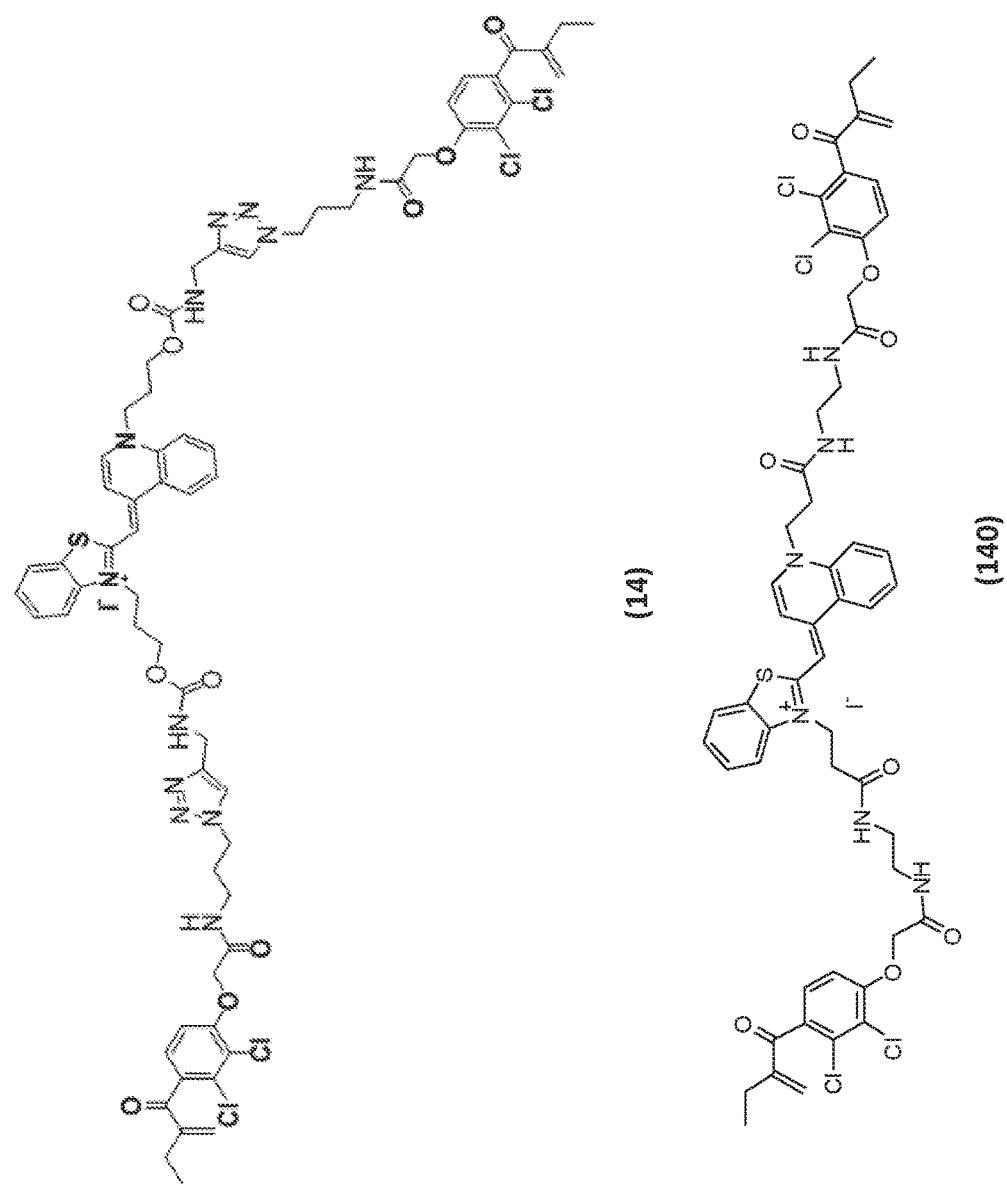
Figure 2B:
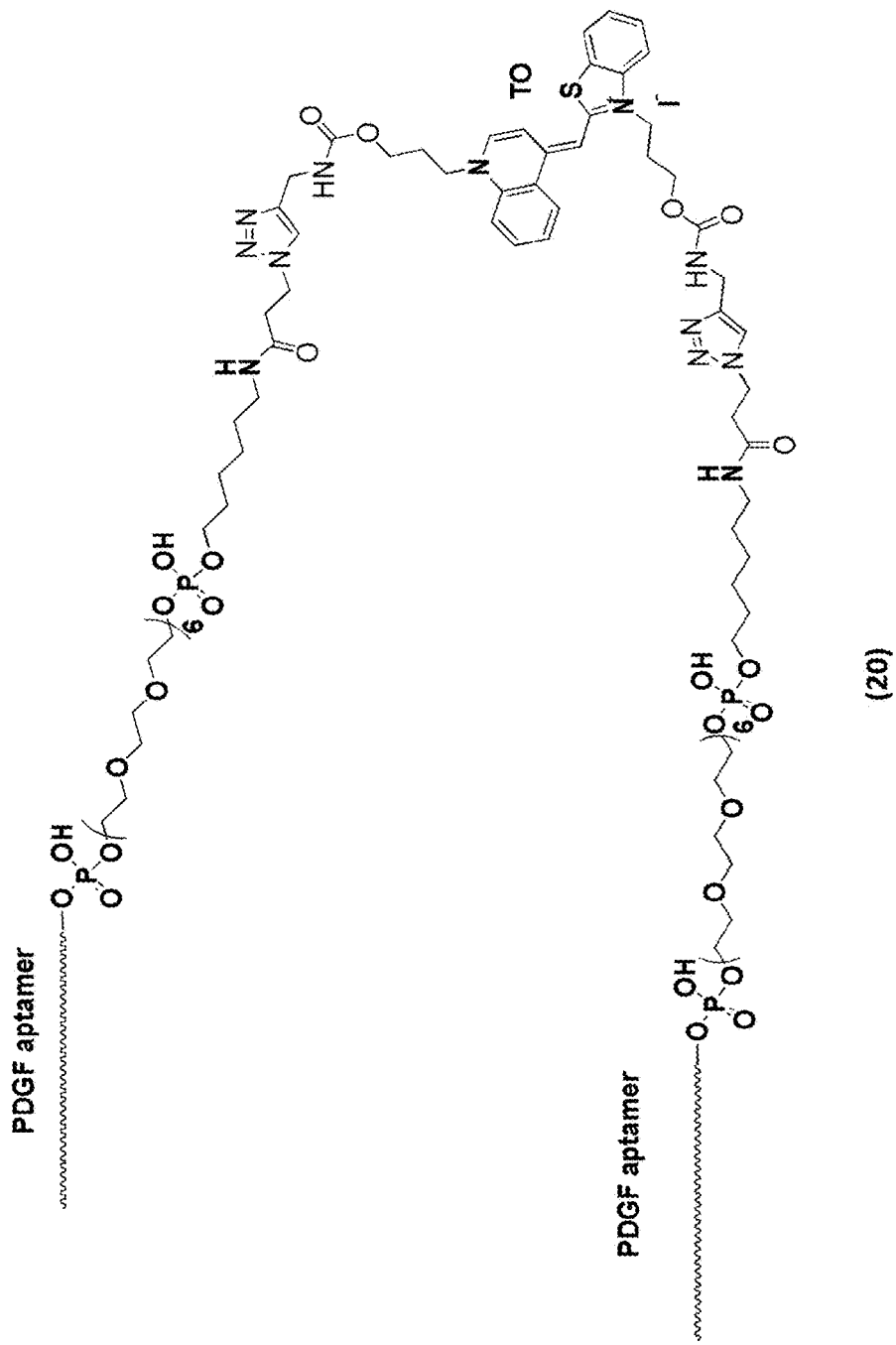
Figure 2C:
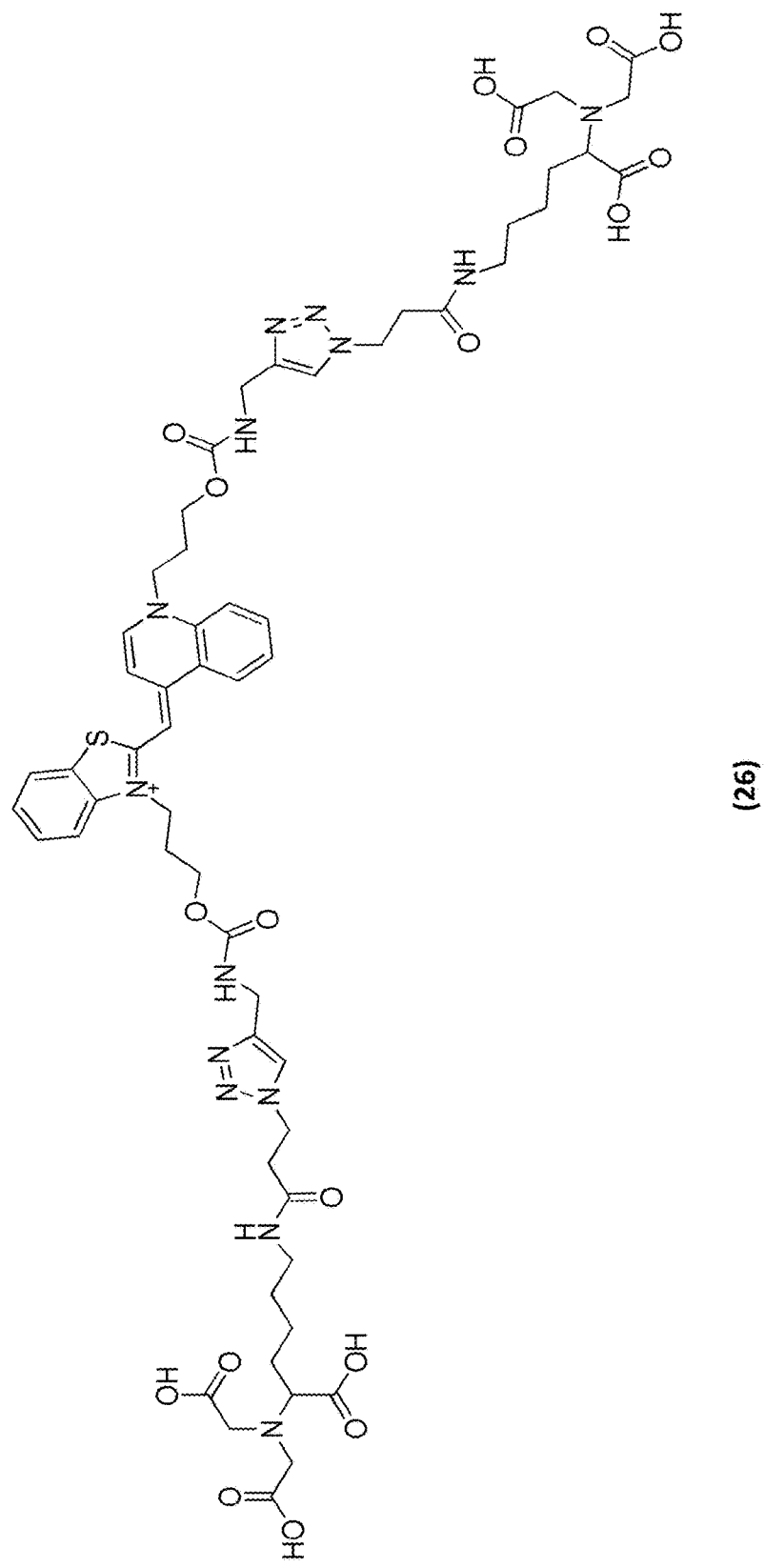
Figure 2D:
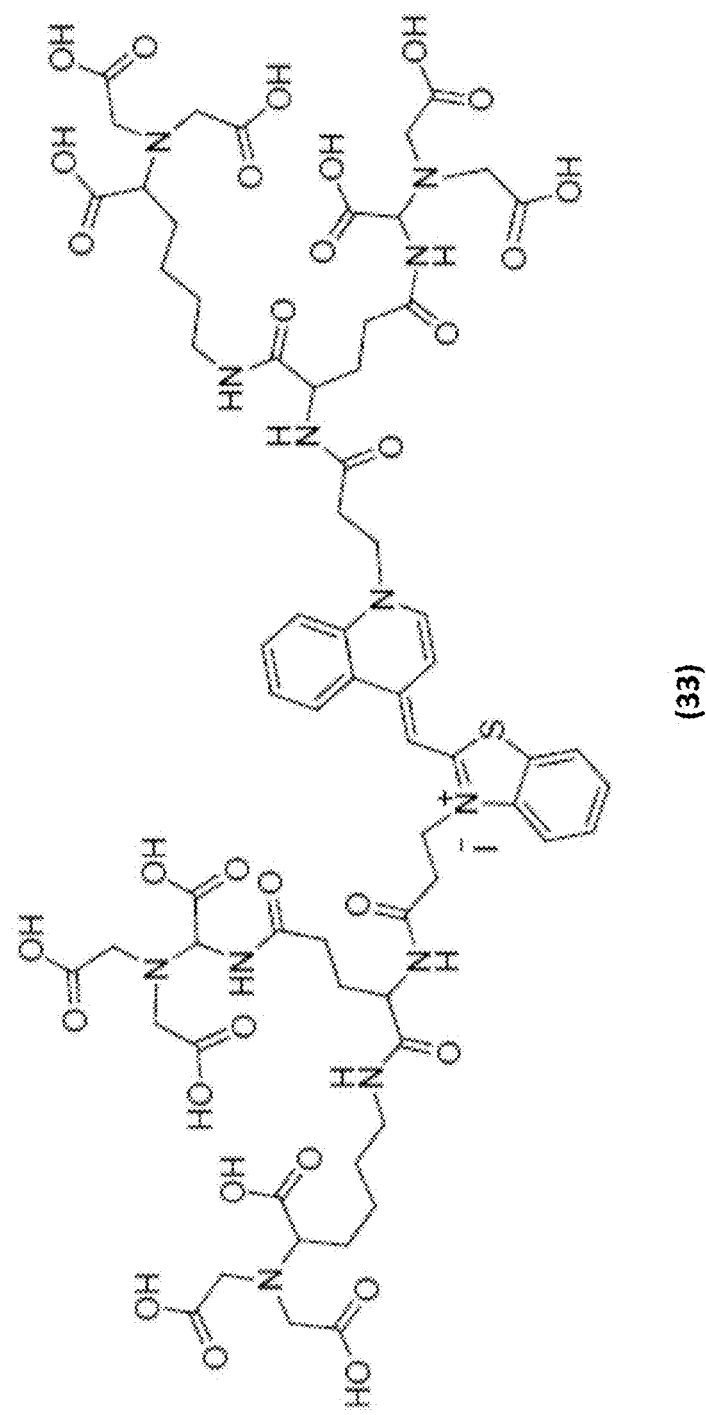
Figure 2E:
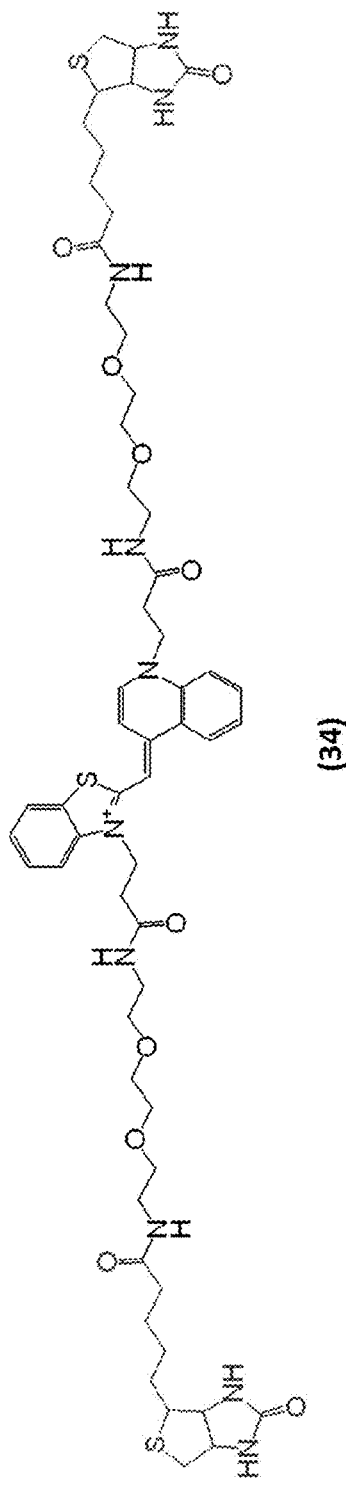
Figure 2F:
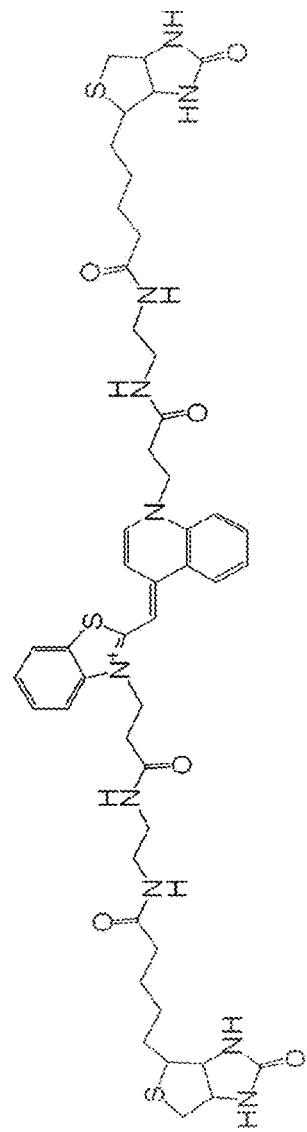

Thiazole Orange (TO) was selected as the signaling unit for the sensors of the invention because this asymmetrical cyanine dye exhibits remarkable 'turn-on' fluorescence response once the torsional motion between the benzothiazole and the quinoline rings in the excited-state is restricted, for example, upon binding to double-stranded DNA (FIG. 1C(a)).

It was anticipated that modifying TO with two protein binders would result in a TO-based protein identifier (TOPI) that is inherently non-fluorescent in the unbound state; however, it becomes highly emissive once its torsional motion is restricted upon binding to the protein of interest (POI, FIG. 1C(b)). The bivalent interaction mode of such sensor is another important property that should enable TOPI to bind its target with high affinity.

TOPI sensors can also be generated by modifying TO with one selective binder either at the benzothiazole or the quinoline ring (FIG. 1(b)). In this way, the selective binder will direct the sensor to the protein's binding site, while the interaction between the TO dye of the sensor and amino acids outside the binding site will restrict the torsional motion of the dye and will lead to an enhanced fluorescence.

The generality of this approach is demonstrated by the ability of TO based sensors as described herein below to detect members within various protein groups that were selected as case studies (i.e., glutathione-s-transferases (GSTs), avidin (Av), acetylcholinesterase (AChE), and His-tagged proteins).

Given that about 30% of human proteins are homodimers, and that a general and easily applicable procedure for preparing various bivalent 'turn-on' probes of this class is available, it is expected that TO based sensors in general, will contribute to the ability to detect and image proteins with fluorescent molecular sensors.

Accordingly, in one embodiment, this invention is directed to a fluorescent monomolecular sensor for detection and/or imaging of proteins, wherein said monomolecular sensor comprises a Thiazole Orange (TO) derivative and at least one selective protein binder. In another embodiment, the detected and/or imaged protein is a homodimer. In another embodiment, the detected and/or imaged protein has two identical binding sites (e.g., GST or Avidine). In another embodiment, the protein has a distinct binding site (e.g., AchE). In another embodiment, the protein has more than one distinct binding site, where each site may bind a different binder. In another embodiment, the detected and/or imaged protein is a disease biomarker. In another embodiment, the detected and/or imaged protein is a specific protein isoform. In another embodiment, the fluorescent monomolecular sensor is Thiazole Orange-based protein identifier (TOPI). In another embodiment, the TOPI comprises TO derivative and one selective protein binder. In another embodiment, the TOPI comprises TO derivative and two selective protein binders. In another embodiment, the TO derivative is covalently bonded to one selective protein binder. In another embodiment, the TO derivative is covalently bonded to two selective protein binders. In another embodiment, the TO derivative is covalently bonded to one selective protein binder through a linker. In another embodiment, the TO derivative is covalently bonded to two selective protein binders through linkers. In another embodiment, the selective binders are identical. In another embodiment, the selective binders are different.

A "selective protein binder" is defined herein as any compound or derivative thereof that can binds particular protein or protein groups with high affinity and selectivity, wherein the term "derivative" includes but not limited to alkyl derivatives, amide derivatives, carboxy derivatives, ether derivatives, ester derivatives, carbamate derivatives, phosphate derivative and the like. In one embodiment, the selective protein binder is an antagonist (protein inhibitor). In another embodiment, the selective protein binder is an agonist (protein activator). In another embodiment, the selective protein binder is a protein modulator (partial agonist/antagonist). In another embodiment, the selective binder is a synthetic inhibitor, a natural ligand or an aptamer that is selective toward a specific protein, protein group, or protein isoform. In another embodiment, the selective binder is a targeted protein receptor comprising a protein tag binder, wherein "protein tags" include, but not limited to: a His-tag, FLAG tag, HA tag, C-myc tag, AviTag, Calmodulin-tag, polyglutamate tag, E-tag, Myc-tag, S-tag, SBP-tag, Softag, Strep-tag, TC tag, V5 tag, VSV-tag, Xpress tag, etc. In another embodiment, the selective protein binder of this invention comprises any selective protein binder known in the art. In another embodiment, the selective protein binder comprises marimastat, ethacrynic acid, bisethacrynic acid, a metal complex of nitrilotriacetic acid (NTA) (His-tag binder), a metal complex of bis NTA (His-tag binder), a metal complex of tris-NTA (His-tag binder), Ni-nitrilotriacetic acid (Ni-NTA), bis-Ni-NTA, tris-Ni-NTA, PDGF-BB, heparin, FGF aptamer, biotin, tacrine, estrogen, DNA aptamer, RNA aptamer, peptide aldehyde, estrogen, suberoylanilidehydroxamic acid (SAHA), or a peptide binder. In another embodiment, the metal complex of NTA, metal complex of bis-NTA, and/or metal complex of tris NTA is a nickel or cobalt complex. In another embodiment, a selective binder is any molecule that can target different type of fusion proteins that contain certain protein tags such as: a polyhistidine tag, (e.g., 6×His-tag, 10×His-tag), tetra cysteine peptide (CCPGCC, TC tag), etc. In another embodiment, the selective protein binder comprises FlAsH or ReAsH (TC tag binder). In one embodiment, the selective binder comprises a His-tag binder. In another embodiment, the selective binder of this invention comprises Ni-nitrilotriacetic acid (Ni-NTA), bis-Ni-NTA, or tris-Ni-NTA.

A "linker" is defined herein as any compound derivative or moiety that covalently links between the Thiazole Orange core and the selective binder according to this invention. In another embodiment, the linker is hydrophilic linker. In another embodiment, the linker is flexible linker. In another embodiment, the linker is flexible hydrophilic linker. In another embodiment, the linker is a triazole derivative. In another embodiment, the linker is a carbamate derivative. In another embodiment, the linker is a $C_1$-$C_{12}$ alkyl derivative. In another embodiment, the linker is a $C_1$-$C_{12}$ alkyl ether derivative. In another embodiment, the linker is a phosphate derivative. In another embodiment, the linker is a polyethylene glycol (PEG) derivative. In another embodiment, the linker comprises one or more moieties selected from: substituted or unsubstituted linear or branched alkyl chain of 1-50 carbon atoms, substituted or unsubstituted linear or branched alkyl ether chain of 1-50 carbon atoms, polyethylene glycol (PEG) moiety, carbamate, triazole, amide, and phosphate. In another embodiment, the linker is a substituted or unsubstituted linear or branched alkyl chain of 1-12 carbon atoms, substituted or unsubstituted linear or branched alkyl ether chain of 1-50 carbon atoms, substituted or unsubstituted linear or branched alkyl phosphate chain of 1-50 carbon atoms, substituted or unsubstituted linear or branched alkyl amide chain of 1-50 carbon atoms, substituted or unsubstituted linear or branched alkyl diamide chain of 1-50 carbon atoms, substituted or unsubstituted linear or branched alkyl amine chain of 1-50 carbon atoms, substituted or unsubstituted linear or branched alkyl carbamate chain of 1-50 carbon atoms, substituted or unsubstituted linear or branched alkyl triazole chain of 1-50 carbon atoms or any combination thereof.

A unique property of sensors according to this invention is their ability to distinguish among proteins that have very similar binding sites (e.g. protein isoforms). It is further shown herein below that although one sensor can bind several proteins with similar affinities, these interactions lead to markedly distinct fluorescence responses. This property thus indicates that the emission of TO based sensors (TOPIs) is largely affected by the local molecular environment that is created for TO dye upon forming the sensor-protein complex.

Accordingly, in one embodiment, this invention is directed to a fluorescent monomolecular sensor for identifying disease biomarkers, wherein said monomolecular sensor comprises a Thiazole Orange (TO) derivative and at least one selective protein binder. In another embodiment, the monomolecular sensor comprises Thiazole Orange (TO) derivative and two selective protein binders. In another embodiment, the disease to biomarker is a specific protein. In another embodiment, the disease biomarker is a specific protein isoform. In another embodiment, the protein is a homodimer. In another embodiment, the protein has two identical binding sites. In another embodiment, the protein has a distinct binding site. In another embodiment, the protein has more than one distinct binding site, where each site may bind a different binder.

This invention is further directed to a fluorescent monomolecular sensor for tracking proteins in their native environments, wherein said monomolecular sensor comprises a Thiazole Orange (TO) derivative and at least one selective protein binder. In another embodiment, the monomolecular sensor comprises Thiazole Orange (TO) derivative and two selective protein binders. In another embodiment, the protein is a homodimer. In another embodiment, the protein has two identical binding sites. In another embodiment, the protein has a distinct binding site. In another embodiment, the protein has more than one distinct binding site, where each site may bind a different binder. In another embodiment, the native environment is blood, serum, plasma, urine, saliva, tissue, peritoneal, stool, mucus, tear, sweat, biopsy, sperm or a cerebrospinal fluid sample. In another embodiment, the native environment is within a cell. In another embodiment, the cell is a living cell, a fixed cell, a human cell, a recombinant primary culture cell, or a tissue culture cell. In another embodiment, the cell is comprised in a biological sample.

This invention is further directed to a fluorescent monomolecular sensor that can identify a specific protein at low concentrations and with a minimal background signal in biological medium, wherein said monomolecular sensor comprises a Thiazole Orange (TO) derivative and at least one selective protein binder. In another embodiment, the sensor comprises a Thiazole Orange (TO) derivative and two selective protein binders. In another embodiment, the protein is a homodimer. In another embodiment, the protein has two identical binding sites. In another embodiment, the protein has a distinct binding site. In another embodiment, the protein has more than one distinct binding site, where each site may bind a different binder. In another embodiment, the biological medium is blood, serum, plasma, urine, saliva, tissue, peritoneal, stool, mucus, tear, sweat, biopsy, sperm or a cerebrospinal fluid sample. In another embodiment, the biological medium is urine.

This invention is further directed to a TO-based protein identifier (TOPI) that is inherently non-fluorescent in the unbound state, however, it becomes highly emissive once its torsional motion is restricted upon binding to the protein of interest (POI), wherein said TOPI comprises a Thiazole Orange (TO) derivative and at least one selective protein binder. In another embodiment, the TOPI comprises a Thiazole Orange (TO) derivative and two selective protein binders. In another embodiment, the POI is a homodimer. In another embodiment, the POI has two identical binding sites. In another embodiment, the POI has a distinct binding site. In another embodiment, the POI has more than one distinct binding site, where each site may bind a different binder. In another embodiment, the POI is a specific protein isoform. In another embodiment, the POI is a specific protein group. In another embodiment, the TO derivative is covalently bonded to the selective protein binder. In another embodiment, the TO derivative is covalently bonded to two selective protein binders. In another embodiment, the TO derivative is covalently bonded to the selective protein binder through a linker. In another embodiment, the TO derivative is covalently bonded to two selective protein binders through linkers. In another embodiment, the selective binders are identical. In another embodiment, the selective binders are different.

In one embodiment, the monomolecular sensor does not generate any background signal in the absence of the desired bioanalyte. In another embodiment, said monomolecular sensor emit strongly in the presence of a desired protein target. In another embodiment, said monomolecular sensor is able to detect specific proteins at low concentration. In another embodiment, said monomolecular sensor is able to detect individual protein isoforms.

The ways by which these sensors can be applied in inhibitor screening, cellular imaging, and biomarker detection are also described herein below.

Accordingly, this invention is further directed to a TO-based protein identifier (TOPI) for use in inhibitor screening assays, wherein said TOPI comprises a Thiazole Orange (TO) derivative and at least one selective protein binder. In another embodiment, the TOPI comprises Thiazole Orange (TO) derivative and two selective protein binders. In another embodiment, a labelled substrate is not required for the screening assay. In another embodiment, the screening assay is a high-throughput assay.

In another embodiment, this invention is directed to a TO-based protein identifier (TOPI) for use in cellular imaging, wherein said TOPI comprises a Thiazole Orange (TO) derivative and at least one selective protein binders. In another embodiment, the TOPI comprises Thiazole Orange (TO) derivative and two selective protein binders. In another embodiment, a labelled substrate is not required for the cellular imaging.

In another embodiment, the Thiazole Orange (TO) derivative is covalently bonded to one selective protein binder. In another embodiment, the Thiazole Orange (TO) derivative is covalently bonded to two selective protein binders. In another embodiment, the Thiazole Orange (TO) derivative is covalently bonded to one selective protein binders through a linker. In another embodiment, the Thiazole Orange (TO) derivative is covalently bonded to two selective protein binders through linkers. In another embodiment, the selective binders are identical. In another embodiment, the selective binders are different. In another embodiment, said TOPI is sensor 14, 140, 20, 26, 33, 34, 35, 36, or 37. In another embodiment, said TOPI is sensor 14. In another embodiment, said TOPI is sensor 140. In another embodiment, said TOPI is sensor 34. In another embodiment, said TOPI is sensor 35. In another embodiment, said TOPI is sensor 36. In another embodiment, said TOPI is sensor 37. In another embodiment, said TOPI is sensor 20. In another embodiment, said TOPI is sensor 26. In another embodiment, said TOPI is sensor 33. In another embodiment, the identified protein is a homodimer. In another embodiment, the protein has two identical binding sites. In another embodiment, the protein has a distinct binding site. In another embodiment, the protein has more than one distinct binding site, where each site may bind a different binder.

In some embodiment, this invention is directed to a molecular sensor comprising a fluorophore and at least one selective binder wherein the fluorophore's emission is enhanced once the internal torsional motion of the fluorophore is restricted. In some embodiment, this invention is directed to a molecular sensor comprising a fluorophore and at least one selective protein binder wherein the fluorophore's emission is enhanced once the internal torsional motion of the fluorophore is restricted. The internal torsional motion of the fluorophore can be restricted either upon binding of the fluorophore derivative to two binding sites of a protein, or upon binding to one binding site and to the amino acids on the protein surface (e.g., by pi-pi interactions with the fluorophore's core). Non limiting examples of such fluorophores are Thiazole Orange or Malachite Green. In another embodiment, upon restriction of the fluorophore's torsional motion (i.e upon binding to an analyte), a fluorescent emission is generated. In another embodiment, upon restriction of the fluorophore's torsional motion (i.e upon binding to an analyte), the fluorescent emission is enhanced. In one embodiment, this invention is directed to a molecular sensor comprising Thiazole Orange derivative and at least one selective protein binder. In another embodiment, this invention is directed to a molecular sensor comprising Thiazole Orange derivative and two selective protein binders. In one to embodiment, this invention is directed to a molecular sensor comprising Thiazole Orange derivative covalently bonded to at least one selective protein binder. In one embodiment, this invention is directed to a molecular sensor comprising Thiazole Orange covalently bonded to two selective protein binders. In one embodiment, this invention is directed to a molecular sensor comprising Thiazole Orange derivative covalently bonded to four selective protein binders. In one embodiment, this invention is directed to a molecular sensor comprising Thiazole Orange derivative covalently bonded to one selective protein binder through a linker. In one embodiment, this invention is directed to a molecular sensor comprising Thiazole Orange derivative covalently bonded to two or four selective protein binders through linkers. In another embodiment, the protein binders are the same. In another embodiment, the protein binders are different. In another embodiment, the protein is a homodimer. In another embodiment, the protein has two identical binding sites. In another embodiment, the protein has a distinct binding site. In another embodiment, the protein has more than one distinct binding site, where each site may bind a different binder.

In one embodiment, the fluorescent enhancement is about 10 to 100 fold of the fluorescent of the sensor in the unbound state. In another embodiment, the fluorescent enhancement is about 20 to 70 fold of the fluorescent of the sensor in the unbound state. In another embodiment, the fluorescent enhancement is about 50 to 60 fold of the fluorescent of the sensor in the unbound state. In another embodiment, the fluorescent enhancement is about 55 fold of the fluorescent of the sensor in the unbound state. In another embodiment, the fluorescent enhancement is about 33 fold of the fluorescent of the sensor in the unbound state. In another embodiment, the fluorescent enhancement is about 22 fold of the fluorescent of the sensor in the unbound state. In another embodiment, the fluorescent enhancement is about 7 fold of the fluorescent of the sensor in the unbound state. In another embodiment, the fluorescent enhancement is about 16 fold of the fluorescent of the sensor in the unbound state.

Molecular Structures of Specific Thiazole Orange (TO)-Based Protein Identifiers (TOPIs) of the Invention In one embodiment, this invention provides a compound represented by the structure of formula IX:

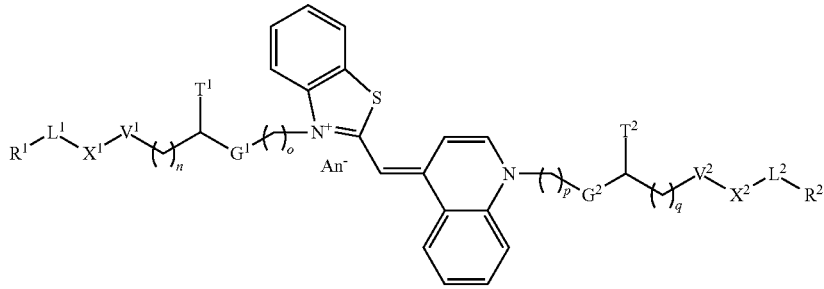

wherein
n, o, p and q are independently integers between 0 to 15;

An⁻ is tosylate (p-toluenesulfonate; $CH_3C_6H_4SO_3PF_6^-$, $CF_3COO^-$ I⁻, Cl⁻, Br⁻, or F⁻;

$G^1$ and $G^2$ are independently a bond, carbamate (—O—C(O)—NH or —NH—C(O)—O), amide [—C(O)—NH or —NH—C(O)], $C_1$-$C_{12}$ amine, alkyl amine, ester, ketone, O, N, S, carbonate, —O-alkyl-NH—, carbamoyl phosphate or phosphate;

$T^1$ is hydrogen or

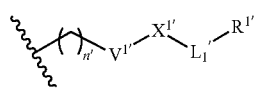

wherein, n' is between 0 to 15.

$T^2$ is hydrogen or

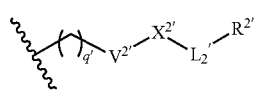

wherein q' is between 0 to 15.

$V^1$, $V^{1'}$, $V^2$ and $V^{2'}$ are independently a bond, a triazole, an amide [—C(O)NH or NHC(O)], —C(O)O—, —OC(O)—, O, NH, N-alkyl, S, —$PO_4H$—, alkyl ether, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$X^1$, $X^{1'}$, $X^2$ and $X^{2'}$ are independently a bond or $C_1$-$C_{12}$ alkyl, —C(O)NH—, —NHC(O), —C(O)O—, —OC(O)—, O, NH, N-alkyl, S, —$PO_4H$—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$L^1$, $L^{1'}$, $L^2$ and $L^{2'}$ are independently a bond or $C_1$-$C_{12}$ alkyl, C(O), —C(O)NH—, —NHC(O)—, —C(O)O—, —OC(O)—, O, NH, $C_1$-$C_{12}$—N-alkyl, S, —$PO_4H$, —$PO_4H$—$PO_4H$—{[($CH_2$)$_y$O]$_x$}$_z$—$PO_3H$—, wherein y is between 1-5, x is between 1-10 and z is between 1-10, —$PO_4H$-PEG, $C_1$-$C_{12}$ alkyl ether, $C_1$-$C_{12}$ alkylamine, $C_1$-$C_{12}$ alkyl-NH, —C(O)NH— to alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof; and $R^1$, $R^{1'}$, $R^2$ and $R^{2'}$ are independently hydrogen, halide, $SO_3^-$, CN, $NO_2$, phosphate or a selective protein binder; wherein at least one of $R^1$, $R^{1'}$, $R^2$ and $R^{2'}$ is a selective binder.

In another embodiment, the compound is a sensor. In another embodiment, the compound is a TO-based protein identifier (TOPI). In another embodiment, the protein is a homodimer. In another embodiment, $R^1$ and $R^2$ are both selective protein binders.

In one embodiment, this invention provides a compound represented by the structure of formula X:

X

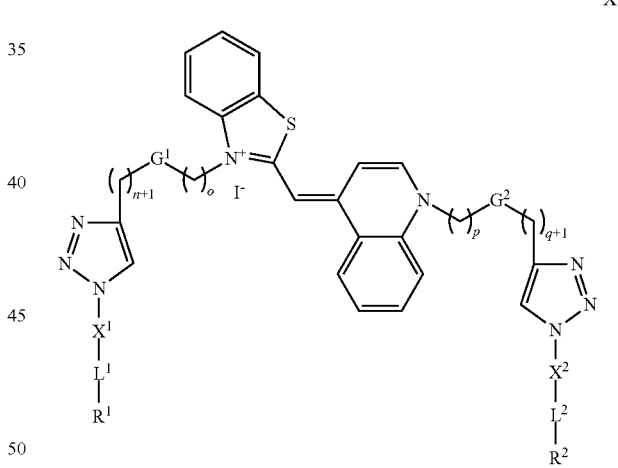

wherein
n, o, p and q are independently integers between 0 to 15;

$G^1$ and $G^2$ are independently a bond, carbamate (—O—C(O)—NH or —NH—C(O)—O), amide [—C(O)—NH or —NH—C(O)], amine, $C_1$-$C_{12}$ alkyl amine, ester, ketone, O, N, S, carbonate, —O-alkyl-NH—, carbamoyl phosphate or phosphate;

$X^1$, and $X^2$ are independently a bond or $C_1$-$C_{12}$ alkyl, —C(O)NH—, —NHC(O), —C(O)O—, —OC(O)—, O, NH, N-alkyl, S, —$PO_4H$—, $C_1$-$C_{12}$ alkyl ether, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$L^1$ and $L^2$ are independently a bond or $C_1$-$C_{12}$ alkyl, C(O), —C(O)NH—, —NHC(O)—, —C(O)O—, —OC(O)—, O, NH, N-alkyl, S, —PO$_4$H, —PO$_4$H—{[(CH$_2$)$_y$O]$_x$}$_z$—PO$_3$H—, wherein y is between 1-5, x is between 1-10 and z is between 1-10, —PO$_4$H-PEG, $C_1$-$C_{12}$ alkyl ether, $C_1$-$C_{12}$ alkylamine —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof; and $R^1$ and $R^2$ are independently hydrogen, halide, SO$_3^-$, CN, NO$_2$, phosphate or a selective protein binder; wherein at least one of $R^1$ and $R^2$ is a selective binder.

In another embodiment, the compound is a sensor. In another embodiment, the compound is a TO-based protein identifier. In another embodiment, $R^1$ and $R^2$ are both selective protein binders.

In one embodiment, this invention provides a compound represented by the structure of formula XI:

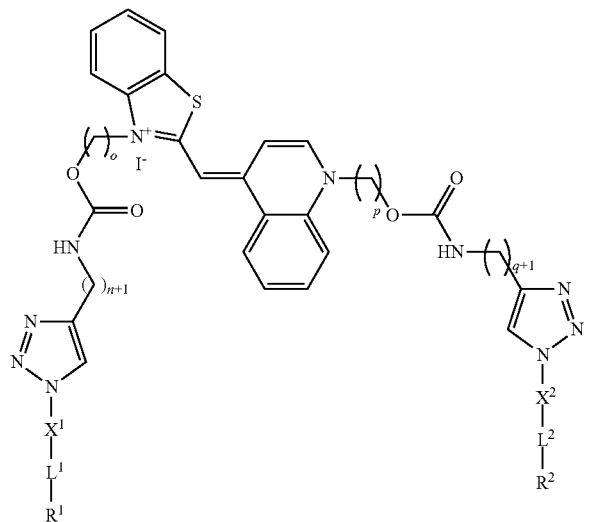

XI wherein n, o, p, q are independently integers between 1 to 15;

$X^1$, and $X^2$ are independently a bond or $C_1$-$C_5$ alkyl, —C(O)NH—, —NHC(O), —C(O)O—, —OC(O)—, O, NH, N-alkyl, S, —PO$_4$H—, alkyl ether, -alkyl-NHC(O)-alkyl, -alkyl-C(O)NH— alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$L^1$ and $L^2$ are independently a bond or $C_1$-$C_5$alkyl, C(O), —C(O)NH—, —NHC(O)—, —C(O)O—, —OC(O)—, O, NH, N-alkyl, S, —PO$_4$H, —PO$_4$H—{[(CH$_2$)$_y$O]$_x$}$_z$—PO$_3$H—, wherein y is between 1-5, x is between 1-10 and z is between 1-10, —PO$_4$H-PEG, alkyl ether, alkylamine —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof; and $R^1$ and $R^2$ are independently hydrogen, halide, SO$_3^-$, CN, NO$_2$, phosphate, or a selective protein binder; wherein at least one of $R^1$ and $R^2$ is a selective protein binder.

In another embodiment, the compound is a sensor. In another embodiment, the compound is a TO-based protein identifier. In another embodiment, $R^1$ and $R^2$ are both selective protein binders.

In one embodiment, this invention provides a compound represented by the structure of formula XII:

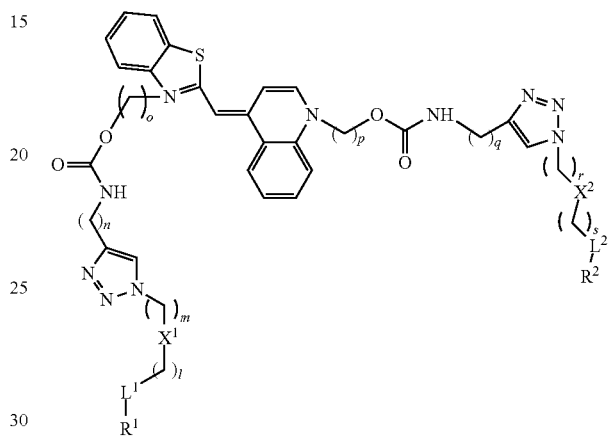

XII wherein l, m, r, s are independently integers between 0 to 15;

p, q, n, o are independently integers between 1 to 15;

$L^1$ and $L^2$ are independently a bond or $C_1$-$C_5$ alkyl, C(O), —C(O)NH—, —NHC(O)—, —C(O)O—, —OC(O)—, O, NH, N-alkyl, S, —PO$_4$H, —PO$_4$H—{[(CH$_2$)$_y$O]$_x$}$_z$—PO$_3$H—, wherein y is between 1-5, x is between 1-10 and z is between 1-10, —PO$_4$H-PEG, alkyl ether, alkylamine —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof; and $X^1$, and $X^2$ are independently a bond or $C_1$-$C_5$ alkyl, —C(O)NH—, —NHC(O), —C(O)O—, —OC(O)—, O, NH, N-alkyl, S, —PO$_4$H—, alkyl ether, -alkyl-NHC(O)-alkyl, -alkyl-C(O)NH— alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$R^1$ and $R^2$ are independently hydrogen, halide, SO$_3^-$, CN, NO$_2$, phosphate, or a selective protein binder; wherein at least one of $R^1$ and $R^2$ is a selective protein binder.

In another embodiment, the compound is a sensor. In another embodiment, the compound is a TO-based protein identifier. In another embodiment, $R^1$ and $R^2$ are both selective protein binders.

In one embodiment, this invention provides a compound represented by the to structure of formula XIII:

XIII

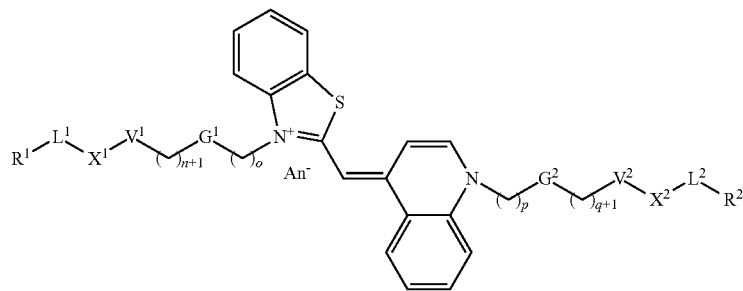

wherein
- n, o, p and q are independently integers between 0 to 15;
- An⁻ is a counter ion, selected from tosylate (p-toluenesulfonate; $CH_3C_6H_4SO_3^-$), $PF_6^-$, $CF_3COO^-$, $I^-$, $Cl^-$, $Br^-$, or $F^-$;
- $G^1$ and $G^2$ are independently a bond, carbamate (—O—C(O)—NH or —NH—C(O)—O), amide [—C(O)—NH or —NH—C(O)], amine, $C_1$-$C_{12}$ alkyl amine, ester, ketone, O, N, S, carbonate, —O-alkyl-NH—, carbamoyl phosphate or phosphate;
- $V^1$ and $V^2$ are independently a bond, a triazole, an amide [—C(O)NH or NHC(O)], —C(O)O—, —OC(O)—, O, NH, N-alkyl, S, —PO₄H—, $C_1$-$C_{12}$ alkyl ether, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;
- $X^1$ and $X^2$ are independently a bond or $C_1$-$C_{12}$ alkyl, —C(O)NH—, —NHC(O), —C(O)O—, —OC(O)—, O, NH, N-alkyl, S, —PO₄H—, $C_1$-$C_{12}$ alkyl ether, $C_1$-$C_{12}$ alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;
- $L^1$ and $L^2$ are independently a bond or $C_1$-$C_{12}$ alkyl, C(O), —C(O)NH—, —NHC(O)—, —C(O)O—, —OC(O)—, O, NH, N-alkyl, S, —PO₄H, —PO₄H—PO₄H—{[(CH₂)ᵧO]ₓ}ᵤ—PO₃H—, wherein y is between 1-5, x is between 1-10 and z is between 1-10, —PO₄H-PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof; and
- $R^1$ and $R^2$ are independently hydrogen, halide, $SO_3^-$, CN, $NO_2$, phosphate or a selective protein binder; wherein at least one of $R^1$ and $R^2$ is a selective protein binder.

In another embodiment, the compound is a sensor. In another embodiment, the compound is a TO-based protein identifier. In another embodiment, $R^1$ and $R^2$ are both selective protein binders.

In some embodiments, An⁻ of formula IX or XIII, is independently an iodide (c). In another embodiment, An⁻ of formula IX or XIII, is independently a chloride (Cl⁻). In another embodiment, An⁻ of formula IX or XIII, is independently a bromide (Br⁻). In another embodiment, An⁻ of formula IX or XIII, is independently a Fluoride (F). In another embodiment, An⁻ of formula IX or XIII, is independently a tosylate (p-toluenesulfonate; $CH_3C_6H_4SO_3^-$). In another embodiment, An⁻ of formula IX or XIII, is independently a $PF_6^-$. In another embodiment, An⁻ of formula IX or XIII, is independently $CF_3COO^-$.

In some embodiments, n, o, p, q, of any one of formula IX-XIII are independently an integer between 1-15. In another embodiment n, o, p, q of formula IX-XIII are independently an integer between 1-5. In another embodiment n, o, p, q, of formula IX-XIII are independently an integer between 1-10. In another n, o, p, q, of formula IX-XIII are independently an integer between 2-10. In another n, o, p, q, of formula IX-XIII are independently 1. In another n, o, p, q, of formula IX-XIII are independently 2. In another embodiment, n, o, p, q, of formula IX-XIII are independently 3. In another embodiment, n, o, p, q, of formula IX-XIII are independently 4. In another embodiment, n, o, p, q, of formula IX-XIII are independently 5. In another embodiment, n, o, p, q, of formula IX-XIII are independently 6. In another embodiment, o and p of formula IX-XIII are 2 or 3, and n and q are independently 1, 2 or 6.

In some embodiment, n' or q' of formula IX are independently an integer between 0-15. In another embodiment n' or q' of formula IX are independently 0. In another embodiment, n' or q' of formula IX are independently an integer between 1-5. In another embodiment, n' or q' of formula IX are independently an integer between 1-10. In another embodiment n' or q' of formula IX are independently an integer between 2-10. In another embodiment n' or q' of formula IX are independently 1. In another embodiment n' or q' of formula IX are independently 2.

In some embodiment, l, m, r, s of formula XII are independently an integer between 0-15. In another embodiment l, m, r, s of formula XII are independently an integer between 0-5. In another l, m, r, s of formula XII are independently an integer between 1-10. In another embodiment l, m, r, s of formula XII are independently an integer between 2-10.

In some embodiments of $G^1$ and $G^2$ of formula IX, X and XIII are independently a bond, carbamate [—OC(O)NH or NHC(O)], amide [—C(O)NH or NHC(O)], amine, alkyl amine, ester, ketone, O, N, S, carbonate, —O-alkyl-NH—, carbamoyl phosphate or phosphate. In another embodiment, $G^1$ and $G^2$ of formula IX, X and XIII are independently a bond. In another embodiment, $G^1$ and $G^2$ of formula IX, X and XIII are independently a carbamate. In another embodiment, $G^1$ and $G^2$ of formula IX, X and XIII are independently an amide. In another embodiment, $G^1$ and $G^2$ of formula IX, X and XIII are independently an amine (—NH—). In another embodiment, $G^1$ and $G^2$ of formula IX, X and XIII are independently an amine alkyl (—NH-alkyl-). In another embodiment, $G^1$ and $G^2$ of formula IX, X and XIII are independently an ester (—COO—). In another embodiment, $G^1$ and $G^2$ of formula IX, X and XIII are independently ketone. In another embodiment, $G^1$ and $G^2$ of formula IX, X and XIII are independently a carbonate. In another embodiment, $G^1$ and $G^2$ of formula IX, X and XIII are independently —O-alkyl-NH—. In another embodiment, $G^1$ and $G^2$ of formula IX, X and XIII are independently a carbamoyl phosphate. In another embodiment, $G^1$ and $G^2$ of formula IX, X and XIII are independently a phosphate. In another embodiment, $G^1$ and $G^2$ of formula IX, X and XIII are independently a $C_1$-$C_{12}$ alkyl amine.

In some embodiments, $X^1$ and $X^2$ of formula IX-XIII are each independently a bond. In some embodiments, $X^1$ and $X^2$ of formula IX-XIII are each independently a $C_1$-$C_{12}$ alkyl. In some embodiments, $X^1$ and $X^2$ of formula IX-XIII are each independently —C(O)NH—. In some embodiments, $X^1$ and $X^2$ of formula IX-XIII are each independently —NHC(O)—. In some embodiments, $X^1$ and $X^2$ of formula IX-XIII are each independently —C(O)O—. In some embodiments, $X^1$ and $X^2$ of formula IX-XIII are each independently —OC(O). In some embodiments, $X^1$ and $X^2$ of formula IX-XIII are each independently O. In some embodiments, $X^1$ and $X^2$ of formula IX-XIII are each independently NH. In some embodiments, $X^1$ and $X^2$ of formula IX-XIII are each independently $C_1$-$C_{12}$ alkyl-amine. In some embodiments, $X^1$ and $X^2$ of formula IX-XIII are each independently $C_1$-$C_{12}$ alkyl-NH. In some embodiments, $X^1$ and $X^2$ of formula IX-XIII are each independently N-alkyl. In some embodiments, $X^1$ and $X^2$ of formula IX-XIII are each independently S. In some embodiments, $X^1$ and $X^2$ of formula IX-XIII are each independently —PO$_4$H—. In some embodiments, $X^1$ and $X^2$ of formula IX-XIII are each independently $C_1$-$C_{12}$ alkyl ether. In some embodiments, $X^1$ and $X^2$ of formula IX-XIII are each independently alkyl amide. In some embodiments, $X^1$ and $X^2$ of formula IX-XIII are each independently -alkyl-NHC(O)-alkyl. In some embodiments, $X^1$ and $X^2$ of formula IX-XIII are each independently -alkyl-C(O)NH-alkyl. In some embodiments, $X^1$ and $X^2$ of formula IX-XIII are each independently alkyl diamide. In some embodiments, $X^1$ and $X^2$ of formula IX-XIII are each independently —NH-alkyl-NH—. In some embodiments, $X^1$ and $X^2$ of formula IX-XIII are each independently —O—alkyl-NH—. In some embodiments, $X^1$ and $X^2$ of formula IX-XIII are each independently —NH-alkyl-O—. In some embodiments, the alkyl of $X^1$ and $X^2$ of formula IX-XIII is optionally substituted and wherein said alkyl is optionally interrupted by a heteroatom consisting of O, N, P, S or combination thereof.

In some embodiments, $X^{1'}$ and $X^{2'}$ of formula IX are each independently a bond. In some embodiments, $X^{1'}$ and $X^{2'}$ of formula IX are each independently a $C_1$-$C_{12}$ alkyl. In some embodiments, $X^{1'}$ and $X^{2'}$ of formula IX are each independently —C(O)NH—. In some embodiments, $X^{1'}$ and $X^{2'}$ of formula IX are each independently —NHC(O)—. In some embodiments, $X^{1'}$ and $X^{2'}$ of formula IX are each independently —C(O)O—. In some embodiments, $X^{1'}$ and $X^{2'}$ of formula IX are each independently —OC(O). In some embodiments, $X^{1'}$ and $X^{2'}$ of formula IX are each independently O. In some embodiments, $X^{1'}$ and $X^{2'}$ of formula IX are each independently NH. In some embodiments, $X^{1'}$ and $X^{2'}$ of formula IX are each independently $C_1$-$C_{12}$ alkyl-amine. In some embodiments, $X^{1'}$ and $X^{2'}$ of formula IX are each independently $C_1$-$C_{12}$ alkyl-NH. In some embodiments, $X^{1'}$ and $X^{2'}$ of formula IX are each independently N-alkyl. In some embodiments, $X^{1'}$ and $X^{2'}$ of formula IX are each independently S. In some embodiments, $X^{1'}$ and $X^{2'}$ of formula IX are each independently —PO$_4$H—. In some embodiments, $X^{1'}$ and $X^{2'}$ of formula IX are each independently $C_1$-$C_{12}$ alkyl ether. In some embodiments, $X^{1'}$ and $X^{2'}$ of formula IX are each independently alkyl amide. In some embodiments, $X^{1'}$ and $X^{2'}$ of formula IX are each independently -alkyl-NHC(O)-alkyl. In some embodiments, $X^{1'}$ and $X^{2'}$ of formula IX are each independently -alkyl-C(O)NH-alkyl. In some embodiments, $X^{1'}$ and $X^{2'}$ of formula IX are each independently alkyl diamide. In some embodiments, $X^{1'}$ and $X^{2'}$ of formula IX are each independently —NH-alkyl-NH—. In some embodiments, $X^{1'}$ and $X^{2'}$ of formula IX are each independently —O-alkyl-NH—. In some embodiments, $X^{1'}$ and $X^{2'}$ of formula IX are each independently —NH-alkyl-O—. In some embodiments, the alkyl of $X^{1'}$ and $X^{2'}$ of formula IX is optionally substituted and wherein said alkyl is optionally interrupted by a heteroatom consisting of O, N, P, S or combination thereof.

In some embodiments, $L^1$ and $L^2$ of formula IX-XIII are each independently a bond. In some embodiments, $L^1$ and $L^2$ of formula IX-XIII are each independently $C_1$-$C_{12}$ alkyl. In some embodiments, $L^1$ and $L^2$ of formula IX-XIII are each independently —C(O). In some embodiments, $L^1$ and $L^2$ of formula IX-XIII are each independently —C(O)NH. In some embodiments, $L^1$ and $L^2$ of formula IX-XIII are each independently NHC(O). In some embodiments, $L^1$ and $L^2$ of formula IX-XIII are each independently —C(O)O—. In some embodiments, $L^1$ and $L^2$ of formula IX-XIII are each independently —OC(O)—. In some embodiments, $L^1$ and $L^2$ of formula IX-XIII are each independently O. In some embodiments, $L^1$ and $L^2$ of formula IX-XIII are each independently NH. In some embodiments, $L^1$ and $L^2$ of formula IX-XIII are each independently $C_1$-$C_{12}$ alkyl-NH. In some embodiments, $L^1$ and $L^2$ of formula IX-XIII are each independently $C_1$-$C_{12}$ alkylamine. In some embodiments, $L^1$ and $L^2$ of formula IX-XIII are each independently N-alkyl. In some embodiments, $L^1$ and $L^2$ of formula IX-XIII are each independently S. In some embodiments, $L^1$ and $L^2$ of formula IX-XIII are each independently —PO$_4$H—. In some embodiments, $L^1$ and $L^2$ of formula IX-XIII are each independently —PO$_4$H—PO$_4$H—{[(CH$_2$)$_y$O]$_x$}$_z$—PO$_3$H—, wherein y is between 1-5, x is between 1-10 and z is between 1-10. In some embodiments, y is 2, x is 3 and z is between 1 and 10. In some embodiments, y is 2, x is 3 and z is 6. In some embodiments, $L^1$ and $L^2$ of formula IX-XIII are each independently-PO$_4$H-PEG, wherein PEG refers to polyethylene glycol having molecular weight of between 300 g/mol to Ser. No. 10/000,000 g/mol. In some embodiments, $L^1$ and $L^2$ of formula IX-XIII are each independently $C_1$-$C_{12}$ alkyl ether. In some embodiments, $L^1$ and $L^2$ of formula IX-XIII are each independently alkylamide. In some embodiments, $L^1$ and $L^2$ of formula IX-XIII are each independently —C(O)NH-alkyl. In some embodiments, $L^1$ and $L^2$ of formula IX-XIII are each independently —NHC(O)-alkyl. In some embodiments, $L^1$ and $L^2$ of formula IX-XIII are each independently NH-alkyl-NH—. In some embodiments, $L^1$ and $L^2$ of formula IX-XIII are each independently —O-alkyl-NH—. In some embodiments $L^1$ and $L^2$ of formula IX-XIII are each independently —NH-alkyl-O—. In some embodiments, the alkyl of $L^1$ and $L^2$ of formula IX-XIII is optionally substituted and wherein said alkyl is optionally interrupted by an heteroatom consisting of O, N, P, S or combination thereof.

In some embodiments, $L^{1'}$ and $L^{2'}$ of formula IX are each independently a bond. In some embodiments, $L^{1'}$ and $L^{2'}$ of formula IX are each independently $C_1$-$C_{12}$ alkyl. In some embodiments, $L^{1'}$ and $L^{2'}$ of formula IX are each independently —C(O). In some embodiments, $L^{1'}$ and $L^{2'}$ of formula IX are each independently —C(O)NH. In some embodiments, $L^{1'}$ and $L^{2'}$ of formula IX are each independently NHC(O). In some embodiments, $L^{1'}$ and $L^{2'}$ of formula IX are each independently —C(O)O—. In some embodiments, $L^{1'}$ and $L^{2'}$ of formula IX are each independently —OC(O)—. In some embodiments, $L^{1'}$ and $L^{2'}$ of formula IX are each independently O. In some embodiments, $L^{1'}$ and $L^{2'}$ of formula IX are each independently NH. In some embodiments, $L^{1'}$ and $L^{2'}$ of formula IX are each independently $C_1$-$C_{12}$ alkyl-NH. In some embodiments, $L^{1'}$ and $L^{2'}$ of formula IX are each independently $C_1$-$C_{12}$ alkylamine In some embodiments, $L^{1'}$ and $L^{2'}$ of formula IX are each independently N-alkyl. In some embodiments, $L^{1'}$ and $L^{2'}$ of formula IX are each independently S. In some embodiments, $L^{1'}$ and $L^{2'}$ of formula IX are each independently —$PO_4H$—. In some embodiments, $L^{1'}$ and $L^{2'}$ of formula IX are each independently —$PO_4H$—$PO_4H$—$\{[(CH_2)_yO]_x\}_z$—$PO_3H$—, wherein y is between 1-5, x is between 1-10 and z is between 1-10. In some embodiments, y is 2, x is 3 and z is between 1 and 10. In some embodiments, y is 2, x is 3 and z is 6. In some embodiments, $L^{1'}$ and $L^{2'}$ of formula IX are each independently-$PO_4H$-PEG, wherein PEG refers to polyethylene glycol having molecular weight of between 300 g/mol to Ser. No. 10/000,000 g/mol. In some embodiments, $L^{1'}$ and $L^{2'}$ of formula IX are each independently $C_1$-$C_{12}$ alkyl ether. In some embodiments, $L^{1'}$ and $L^{2'}$ of formula IX are each independently alkylamide. In some embodiments, $L^{1'}$ and $L^{2'}$ of formula IX are each independently —C(O)NH-alkyl. In some embodiments, $L^{1'}$ and $L^{2'}$ of formula IX are each independently —NHC(O)-alkyl. In some embodiments, $L^{1'}$ and $L^{2'}$ of formula IX are each independently NH-alkyl-NH—. In some embodiments, $L^{1'}$ and $L^{2'}$ of formula IX are each independently —O-alkyl-NH—. In some embodiments $L^{1'}$ to and $L^{2'}$ of formula IX are each independently —NH-alkyl-O—. In some embodiments, the alkyl of $L^{1'}$ and $L^{2'}$ of formula IX is optionally substituted and wherein said alkyl is optionally interrupted by an heteroatom consisting of O, N, P, S or combination thereof.

In some embodiments, $V^1$ and $V^2$ of formula IX and/or XIII are each independently a triazole. In some embodiments, $V^1$ and $V^2$ of formula IX and/or XIII are each independently a bond. In some embodiments, $V^1$ and $V^2$ of formula IX and/or XIII are each independently an amide [—C(O)NH or NHC(O)]. In some embodiments, $V^1$ and $V^2$ of formula IX and/or XIII are each independently —C(O)O—. In some embodiments, $V^1$ and $V^2$ of formula IX and/or XIII are each independently —OC(O)—. In some embodiments, $V^1$ and $V^2$ of formula IX and/or XIII are each independently O. In some embodiments, $V^1$ and $V^2$ of formula IX and/or XIII are each independently NH. In some embodiments, $V^1$ and $V^2$ of formula IX and/or XIII are each independently N-alkyl. In some embodiments, $V^1$ and $V^2$ of formula IX and/or XIII are each independently S. In some embodiments, $V^1$ and $V^2$ of formula IX and/or XIII are each independently —$PO_4H$—. In some embodiments, $V^1$ and $V^2$ of formula IX and/or XIII are each independently alkyl ether. In some embodiments, $V^1$ and $V^2$ of formula IX and/or XIII are each independently —NH-alkyl-NH—. In some embodiments, $V^1$ and $V^2$ of formula IX and/or XIII are each independently —O-alkyl-NH—. In some embodiments, $V^1$ and $V^2$ of formula IX and/or XIII are each independently —NH-alkyl-O—. In some embodiments, the alkyl is optionally substituted. In some embodiments the alkyl is interrupted by an heteroatom consisting of O, N, P, S or combination thereof.

In some embodiments, $V^{1'}$ and $V^{2'}$ of formula IX are each independently a triazole. In some embodiments, $V^{1'}$ and $V^{2'}$ of formula IX are each independently a bond. In some embodiments, $V^{1'}$ and $V^{2'}$ of formula IX are each independently an amide [—C(O)NH or NHC(O)]. In some embodiments, $V^{1'}$ and $V^{2'}$ of formula IX are each independently —C(O)O—. In some embodiments, $V^{1'}$ and $V^{2'}$ of formula IX are each independently —OC(O)—. In some embodiments, $V^{1'}$ and $V^{2'}$ of formula IX are each independently O. In some embodiments, $V^{1'}$ and $V^{2'}$ of formula IX are each independently NH. In some embodiments, $V^{1'}$ and $V^{2'}$ of formula IX are each independently N-alkyl. In some embodiments, $V^{1'}$ and $V^{2'}$ of formula IX are each independently S. In some embodiments, $V^{1'}$ and $V^{2'}$ of formula IX are each independently —$PO_4H$—. In some embodiments, $V^{1'}$ and $V^{2'}$ of formula IX are each independently alkyl ether. In some embodiments, $V^{1'}$ and $V^{2'}$ of formula IX are each independently —NH-alkyl-NH—. In some embodiments, $V^{1'}$ and $V^{2'}$ of formula IX are each independently —O-alkyl-NH—. In some embodiments, $V^{1'}$ and $V^{2'}$ of formula IX are each independently —NH-alkyl-O—. In some embodiments, the alkyl is optionally substituted. In some embodiments the alkyl is interrupted by an heteroatom consisting of O, N, P, S or combination thereof.

In some embodiments, $R^1$, $R^{1'}$, $R^2$ and $R^{2'}$ of formula IX are each independently hydrogen, halide, $SO_3^-$, CN, $NO_2$, phosphate, or a selective protein binder; wherein at least one of $R^1$, $R^{1'}$, $R^2$ and $R^{2'}$ is a selective protein binder. In another embodiment, at least two of $R^1$, $R^{1'}$, $R^2$ and $R^{2'}$ of formula IX are selective protein binders. In another embodiment, $R^1$, $R^{1'}$, $R^2$ and $R^{2'}$ of formula IX are independently a selective protein binder. In another embodiment, $R^1$, $R^{1'}$, $R^2$ and $R^{2'}$ of formula IX are independently hydrogen. It is understood that if $L^1$, $L^{1'}$, $L^2$ or $L^{2'}$ is $C_1$-$C_{12}$ alkyl, C(O), C(O)O, C(O)NH, O, S, NH and $R^1$, $R^{1'}$, $R^2$ or $R^{2'}$ is independently hydrogen, then the end group of the sensors of IX is respectively, alkyl, C(O)H, C(O)OH, C(O)$NH_2$, OH, SH or $NH_2$ or if $L^1$, $L^{1'}$, $L^2$ or $L^{2'}$ is a bond and $X^1$, $X^{1'}$, $X^2$ and $X^{2'}$ is independently alkyl, C(O), C(O)O, C(O)NH, O, S, NH and $R^1$, $R^{1'}$, $R^2$ or $R^{2'}$ are hydrogen, then the end group of the sensors of IX is respectively $C_1$-$C_{12}$ alkyl, C(O)H, C(O)OH, C(O)$NH_2$, OH, SH or $NH_2$. In another embodiment, $R^1$, $R^{1'}$, $R^2$ and $R^{2'}$ of formula IX is each independently halide. In another embodiment, $R^1$, $R^{1'}$, $R^2$ and $R^{2'}$ of formula IX is each independently $SO_3^-$. In another embodiment, $R^1$, $R^{1'}$, $R^2$ and $R^{2'}$ of formula IX is each independently CN. In another embodiment, $R^1$, $R^{1'}$, $R^2$ and $R^{2'}$ of formula IX is each independently $NO_2$. In another embodiment, $R^1$, $R^{1'}$, $R^2$ and $R^{2'}$ of formula IX is each independently phosphate.

In some embodiments, $R^1$ and $R^2$ of formula X-XIII are each independently hydrogen, halide, $SO_3^-$, CN, $NO_2$, phosphate, or a selective protein binder; wherein at least one of $R^1$ and $R^2$ is a selective protein binder. In another embodiment, both $R^1$ and $R^2$ of formula X-XIII are selective protein binders. In another embodiment, $R^1$ and $R^2$ of formula X-XIII are each independently hydrogen. It is understood that if $L^1$ or $L^2$ is $C_1$-$C_{12}$ alkyl, C(O), C(O)O, C(O)NH, O, S, NH and $R^1$ or $R^2$ is independently hydrogen, then the end group of the sensors of X-XIII is respectively, alkyl, C(O)H, C(O)OH, C(O)$NH_2$, OH, SH or $NH_2$ or if $L^1$ or $L^2$ is a bond and $X^1$ and $X^2$ is independently alkyl, C(O), C(O)O, C(O)NH, O, S, NH and $R^1$ or $R^2$ are hydrogen, then the end group of the sensors of X-XIII is respectively $C_1$-$C_{12}$ alkyl, C(O)H, C(O)OH, C(O)$NH_2$, OH, SH or $NH_2$. In another embodiment, $R^1$ and $R^2$ of formula X-XIII are each independently halide. In another embodiment, $R^1$ and $R^2$ of formula X-XIII are each independently $SO_3^-$. In another embodiment, $R^1$ and $R^2$ of formula X-XIII are each independently CN. In another embodiment, $R^1$ and $R^2$ of formula X-XIII are each independently $NO_2$. In another embodiment, $R^1$ and $R^2$ of formula X-XIII are each independently a phosphate.

In some embodiment, the sensors of formula IX-XIII comprise a selective protein binder. In some embodiment, the sensors of formula IX-XIII comprise one selective protein binder. In some embodiment, the sensors of formula IX-XIII comprise two selective protein binders. In some embodiment, the sensors of formula IX comprise three selective protein binders. In some embodiment, the sensors of formula IX comprise four selective protein binders. Non limited examples of protein binders include: marimastat, ethacrynic acid, bisethacrynic acid, complexed nitrilotriacetic acid (NTA), complexed bis NTA and complexed tris-NTA, Ni-nitrilotriacetic acid (Ni-NTA), bis-Ni-NTA, tris-Ni-NTA, PDGF-BB, heparin, FGF aptamer, biotin, tacrine, or estrogen. In some embodiments, said NTA, bisNTA, or tris NTA is complexed with Ni(II), Co(II) or Co(III). In some embodiments, the sensors of this invention comprise two or more selective protein binders. In another embodiment, the protein binders are identical. In another embodiment, the protein binders are different. In another embodiment, the sensors of this invention comprise two selective protein binders, wherein the protein binders are identical. In another embodiment, the sensors of this invention comprise two selective protein binders, wherein the protein binders are different. In another embodiment, the sensors of this invention comprise three selective protein binders, wherein the protein binders are identical. In another embodiment, the sensors of this invention comprise three selective protein binders, wherein the protein binders are different. In another embodiment, the sensors of this invention comprise four selective protein binders, wherein the protein binders are identical. In another embodiment, the sensors of this invention comprise four selective protein binders, wherein the protein binders are different.

An "alkyl" or "alkylene" group refers, in one embodiment, to a saturated aliphatic hydrocarbon, including straight-chain and branched-chain. In one embodiment, the alkyl group has 1-50 carbons. In one embodiment, the alkyl group has 1-12 carbons. In another embodiment, the alkyl group has 1-7 carbons. In another embodiment, the alkyl group has 1-5 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy, carbonyl, amido, alkylamido, dialkylamido, nitro, amino, alkylamino, dialkylamino, carboxyl, thio and thioalkyl. In some embodiments the alkyl of this invention is optionally substituted and optionally interrupted by a heteroatom consisting of O, N, P, S or combination thereof. In another embodiment, the alkyl is —$CH_2)_6$—. In another embodiment, the alkyl is —$(CH_2)_2$—. In another embodiment, the alkyl is —$(CH_2)_3$—. In another embodiment, the alkyl is —$CH_2$—. In another embodiment, the alkyl is —$CH_2$—$CH(CH_2$—$OH)$—$(CH_2)_4$—. In another embodiment, the alkyl is —$CH_2$—$CH(CH_2$—$OH)$—. It is to be understood that unless defined differently, each moiety that includes the term "alkyl" generically, (e.g. NH-alkyl-NH—, —O-alkyl-NH—, N-alkyl, etc.), encompasses the various possibilities for the term "alkyl" as defined herein.

An "alkyl ether" of this invention refers to an alkyl as defined above interrupted by one or more oxygen atoms. In another embodiment, alkyl ether refers to a PEG (poly ethylene glycol). In another embodiment, alkyl ether refers to —$CH_2$—$CH_2$—O—. In one embodiment, the alkylether has 1-50 carbon atoms. In one embodiment, the alkylether has 1-6 carbon atoms. In another embodiment, the alkylether has 1-12 carbon atoms. In another embodiment, the alkylether has 1-20 carbon atoms. In another embodiment, the alkylether has 3 carbon atoms. In another embodiment, the alkylether has 4 carbon atoms. In another embodiment, the alkylether has 2-5 carbon atoms. In another embodiment, the alkylether has 2 carbon atoms. In another embodiment, the alkylether is —$CH_2$—$CH_2$—O—$CH_2$—.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when $R_1$, $R_2$ or $R_3$ in the compounds of the present invention is OR, then R is not OH.

In one embodiment, the term "halogen" or "halo" refers to a halogen, such as F, Cl, Br or I.

An "alkynyl" refers to unsaturated hydrocarbon which comprises at least one carbon-carbon triple bond. In one embodiment, the alkynyl group has 2-20 carbons. In another embodiment, the alkynyl has 2-12 carbons. In another embodiment, the alkynyl has 2-6 carbons. In another embodiment, the alkynyl has 2 carbons.

An "arylalkyl" group refers to an alkyl bound to an aryl, wherein alkyl and aryl are as defined above. An example of an aralkyl group is a benzyl group.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system.

An "alkyl amine" of this invention refers to an alkyl as defined above which has an amine moiety within the carbon atom chain. In another embodiment, alkyl amine refers to $(CH_2)_n$—NH—. In another embodiment, the amine moiety is at one end of the carbon chain. In another embodiment, the amine moiety is within the backbone of the carbon chain. In another embodiment, the alkyl amine is a substituted or unsubstituted linear or branched alkyl of 1-50 carbon atoms which has an amine moiety at one end. In another embodiment, the alkyl amine is a substituted or unsubstituted linear or branched alkyl of 1-6 carbon atoms which has an amine moiety at one end. In another embodiment, the alkyl amine is a substituted or unsubstituted linear or branched alkyl of 1-12 carbon atoms which has an amine moiety at one end. In another embodiment, the alkyl amine is a substituted or unsubstituted linear or branched alkyl of 1-3 carbon atoms which has an amine moiety at one end.

An "alkyl amide" of this invention refers to an alkyl as defined above which has an amide moiety at one end. In another embodiment, alkyl amide refers to $(CH_2)_n$—NHC(O). In another embodiment, alkyl amide refers to $(CH_2)_n$—C(O)NH wherein n is an integer between 1 and 10. In another embodiment, the alkyl amide is a substituted or unsubstituted linear or branched alkyl of 1-50 carbon atoms which has an amide moiety at one end. In another embodiment, the alkyl amide is a substituted or unsubstituted linear or branched alkyl of 1-6 carbon atoms which has an amide moiety at one end. In another embodiment, the alkyl amide is a substituted or unsubstituted linear or branched alkyl of 1-12 carbon atoms which has an amide moiety at one end. In another embodiment, the alkyl amide is a substituted or unsubstituted linear or branched alkyl of 1-3 carbon atoms which has an amide moiety at one end. In another embodiment, the alkyl amide is —$(CH_2)_6$—NHC(O). In another embodiment, the alkyl amide is —$(CH_2)_2$—NHC(O). In another embodiment, the alkyl amide is —$(CH_2)_3$—NHC(O). In another embodiment, the alkyl amide is —$CH_2$—NHC(O). In another embodiment, the alkyl amide is —$CH_2$—CH($CH_2$—OH)—$(CH_2)_4$—NHC(O). In another embodiment, the alkyl amide is $CH_2$—CH($CH_2$—OH)—NHC(O).

An "alkyl di-amide" of this invention refers to an alkyl as defined above which is interrupted by two amide moieties. In one embodiment, alkyl di-amide refers to $(CH_2)_n$—NHC(O)—$(CH_2)_m$—NHC(O) wherein n is an integer between 1 and 10. In another embodiment, the alkyl di-amide is a substituted or unsubstituted linear or branched alkyl of 1-6 carbon atoms which has an amide moiety at one end of the carbon chain and another amide moiety inside the backbone of the chain. In another embodiment, the alkyl di-amide is a substituted or unsubstituted linear or branched alkyl of 1-50 carbon atoms which has two amide moieties within the carbon chain. In another embodiment, the alkyl di-amide is a substituted or unsubstituted linear or branched alkyl of 2-12 carbon atoms which has two amide moieties within the carbon chain. In another embodiment, the alkyl di-amide is a substituted or unsubstituted linear or branched alkyl of 2-6 carbon atoms which has two amide moieties within the carbon chain. In another embodiment, the alkyl di-amide is a substituted or unsubstituted linear or branched alkyl of 1-20 carbon atoms which has two amide moieties within the carbon chain. In another embodiment, the alkyl di-amide is —$CH_2$—CH($CH_2$OH)—NHC(O)—$(CH_2)_2$—NHC(O)—. In another embodiment, the alkyl di-amide is —NHC(O)—$(CH_2)_2$—NHC(O)—.

An "alkyl triazole" of this invention refers to an alkyl as defined above which has a triazole moiety at one end. In one embodiment, alkyl triazole refers to $(CH_2)_n$-triazole wherein n is an integer between 1 and 10. In another embodiment n is 3. In another embodiment, the alkyl triazole is a substituted or unsubstituted linear or branched alkyl of 1-6 carbon atoms which has a triazole moiety at one end. In another embodiment, the alkyl triazole has 1-50 carbon atoms. In another embodiment, the alkyl triazole has 1-12 carbon atoms. In another embodiment, the alkyl triazole has 1-3 carbon atoms.

An "alkyl carbamate" of this invention refers to an alkyl as defined above which has a carbamate moiety at one end. In one embodiment, alkyl carbamate refers to $(CH_2)_n$—NH—(CO)—O— wherein n is an integer between 1 and 10. In another embodiment n is 3. In another embodiment, the alkyl carbamate is a substituted or unsubstituted linear or branched alkyl of 1-6 carbon atoms which has a carbamate moiety at one end. In another embodiment, the alkyl carbamate has 1-50 carbon atoms. In another embodiment, the alkyl carbamate has 1-12 carbon atoms. In another embodiment, the alkyl carbamate has 1-3 carbon atoms.

An "alkyl phosphate" of this invention refers to an alkyl as defined above which has a phosphate moiety at one end. In one embodiment, alkyl phosphate refers to $(CH_2)_n$—O—P(O)(OH)—O— wherein n is an integer between 1 and 10. In another embodiment n is 3. In another embodiment, the alkyl phosphate is a substituted or unsubstituted linear or branched alkyl of 1-6 carbon atoms which has a phosphate moiety at one end. In another embodiment, the alkyl phosphate has 1-50 carbon atoms. In another embodiment, the alkyl phosphate has 1-12 carbon atoms. In another embodiment, the alkyl phosphate has 1-3 carbon atoms.

The term "substituted" refer to substitutions that include one or more groups selected from: halogen, hydroxy, hydroxyalkyl, alkoxy, haloalkyl, carbonyl, amido, alkylamido, dialkylamido, nitro, cyano, amino, alkylamino, dialkylamino, carboxyl, thiol, thioalkyl and the like.

The following Table 1 presents some specific selective protein binders and their targeted proteins.

TABLE 1

Representative Target Proteins and Selective binders

| Target protein | Specific Binder | (R1, R2, R1', R2') |
|---|---|---|
| Lysozyme | DNA aptamer | lysozyme aptamer |
| Firbronectin | peptide binder to fibronectin (for example, VGVMYEYVPQVT) | peptide binding fibronectin |
| GSTs | Ethacrynic acid | |

TABLE 1-continued

Representative Target Proteins and Selective binders

| Target protein | Specific Binder | (R1, R2, R1', R2') |
|---|---|---|
| MMPs | Marimastat | |
| PSA | DNA or RNA aptamer | PSA aptamer |
| His-tagged Protein | complexed-NTA, complexed bis-NTA | coordinated/complexed with $Ni^{2+}$ $Co^{3+}$ or $Co^{2+}$. |
| Caspases | peptide aldehydes (for example, Ac-WEHD-CHO or Ac-DEVD-CHO or Z-VAD-FMK) | peptide binding caspase |
| β-amyloid | peptide binder to β-amyloid (for example, KLVFF) | peptide binding amyloid |
| Histone deacetylases (HDACs) | suberoylanilide hydroxamic acid (SAHA) derivative | |
| Estrogen Receptor (ER) | estrogen, estrone or estriol | |
| FGFs | modified heparin or FGF aptamer | FGF aptamer |

TABLE 1-continued

Representative Target Proteins and Selective binders

| Target protein | Specific Binder | (R1, R2, R1', R2') |
|---|---|---|
| Avidin, Streptavidin | biotin | 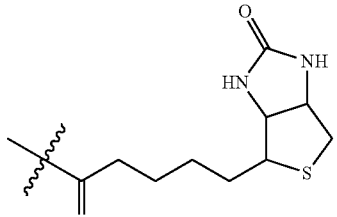 |
| Achetylcholine esterase | Tacrine | 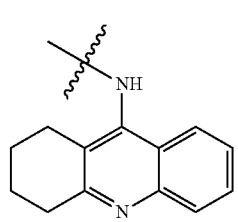 [SMILES: *Nc1c2c(nc3ccccc13)CCCC2] |

In some embodiments, the Thiazole Orange based sensor of this invention is represented by the structure of formula 14.

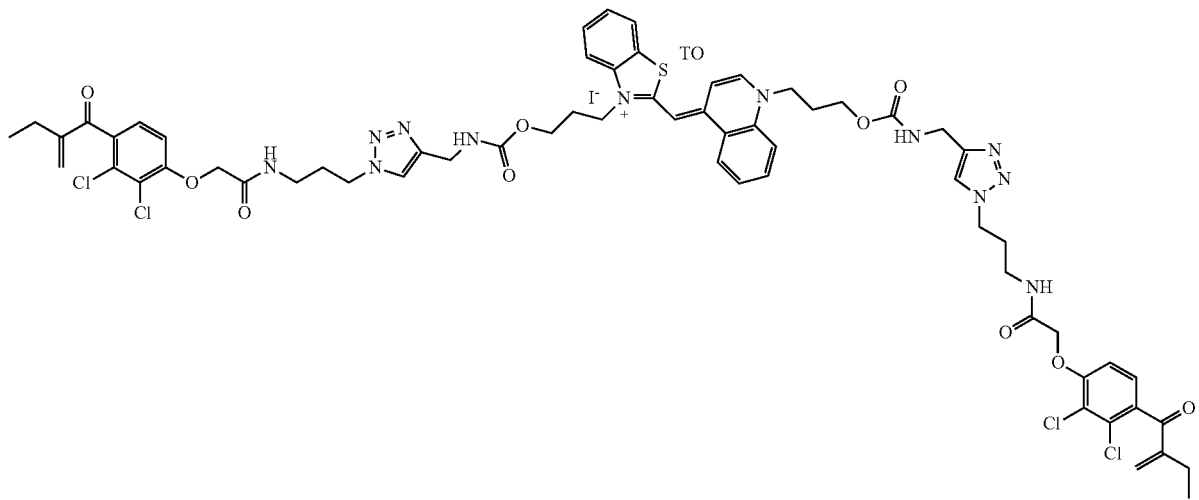

(14)

Sensor 14 comprises two ethacrynic acid (EA) moieties, and hence, its interaction with GSTs is expected to enhance its fluorescent signal.

In some embodiments, the Thiazole Orange based sensor of this invention is represented by the structure of formula 140.

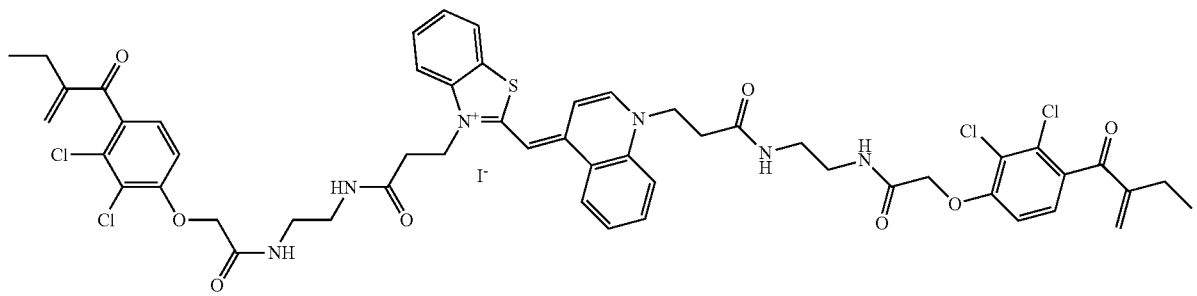

(140)

Sensor 140 comprises two ethacrynic acid (EA) moieties, and hence, its interaction with GSTs is expected to enhance its fluorescent signal.

In some embodiments, the Thiazole Orange based sensor of this invention is represented by the structure of formula 20:

(20)

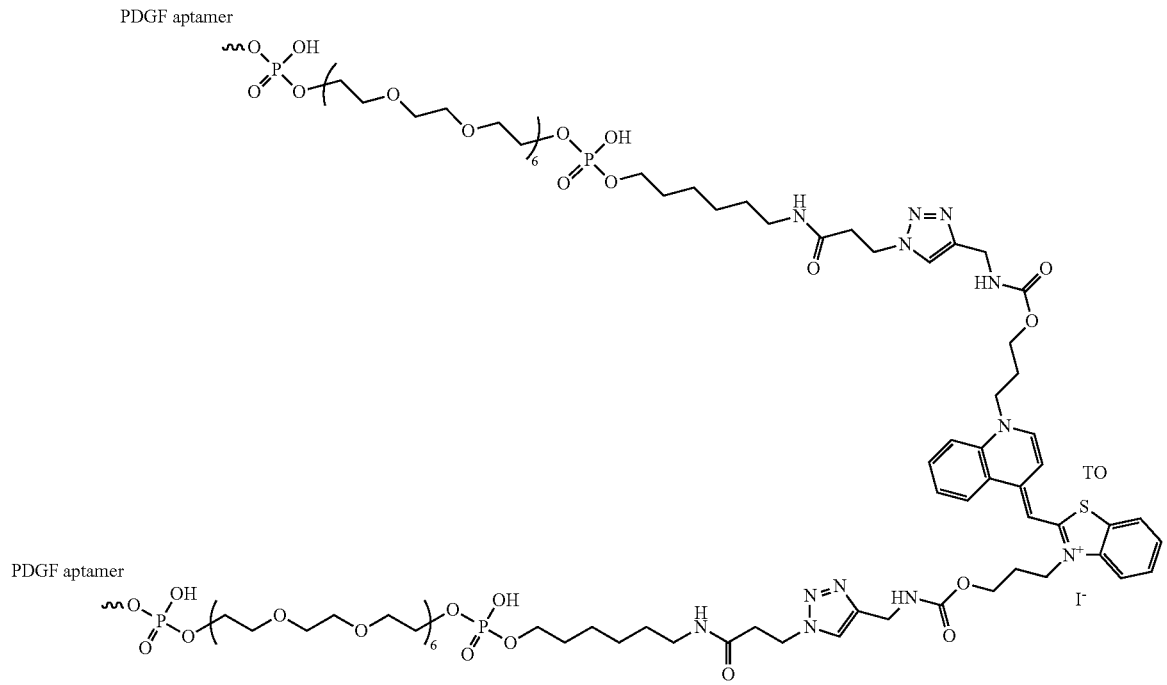

Sensor 20 consists of PDGF aptamers and hence, its interaction with platelet derived growth factor is expected to enhance its fluorescent signal upon interaction with the growth factor.

In some embodiments, the Thiazole Orange based sensor of this invention is represented by the structure of formula 26:

(26)

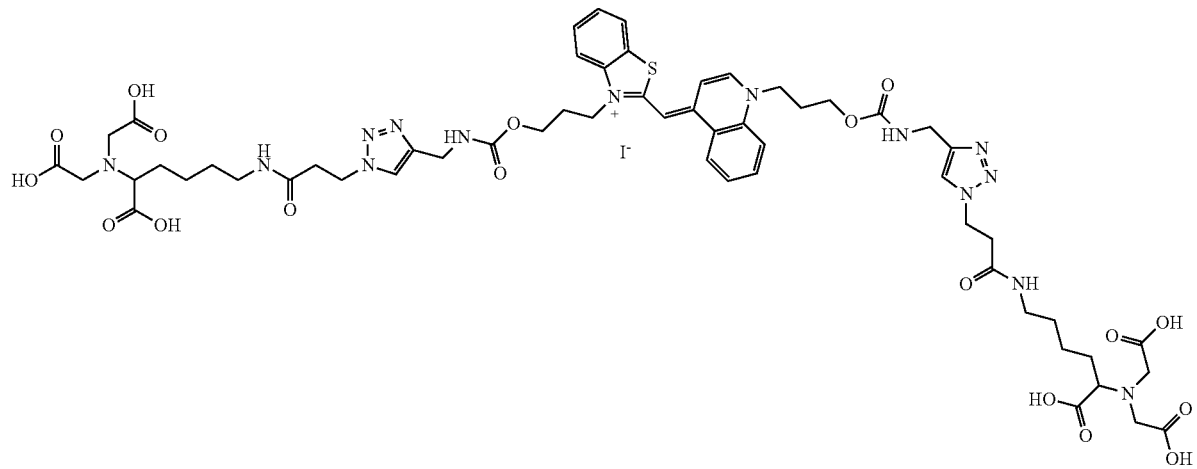

Sensor 26 consists of two NTA moieties and hence, the interaction of its Ni complex with His-tagged proteins is expected to enhance its fluorescent signal upon interaction with proteins such as His-tagged proteins.

In some embodiments, the Thiazole Orange based sensor of this invention is represented by the structure of formula 33:

Sensor 34 comprises two biotin moieties, and hence, its interaction with Avidin and/or Streptavidinis expected to enhance its fluorescent signal.

In some embodiments, the Thiazole Orange based sensor of this invention is represented by the structure of formula 35.

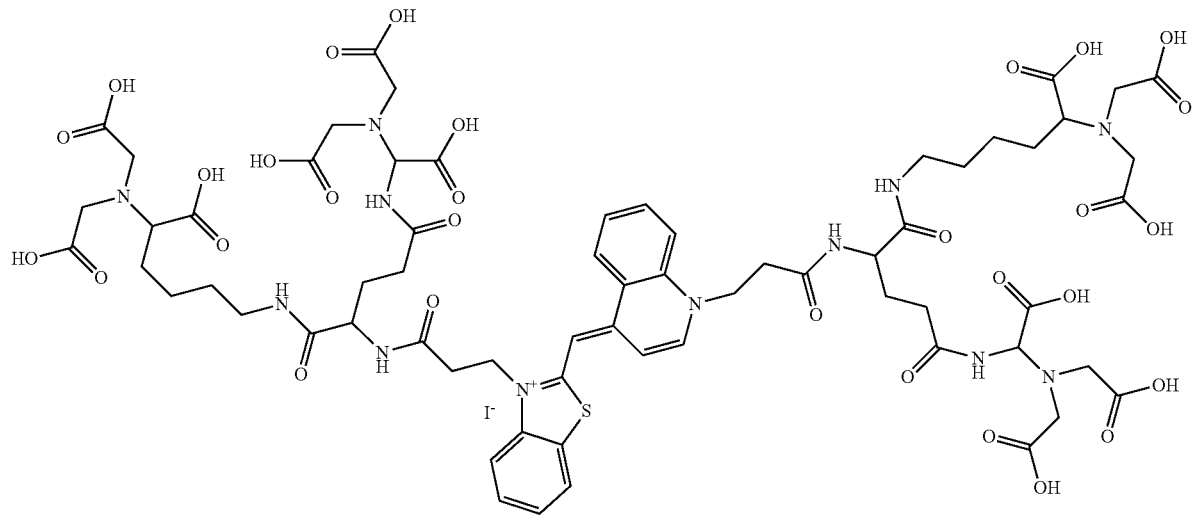

(33)

Sensor 33 consists of two bis-NTA moieties (or tetrakis-NTA) and hence, the interaction of its Ni complex with His-tagged proteins is expected to enhance its fluorescent signal upon interaction with proteins such as His-tagged proteins. In some embodiments, the NTA groups of sensor 26 and 33 are complexed with nickel and its interaction with His-tagged proteins is expected to enhance its fluorescent signal upon interaction with proteins such as His-tagged proteins.

In some embodiments, the Thiazole Orange based sensor of this invention is represented by the structure of formula 34.

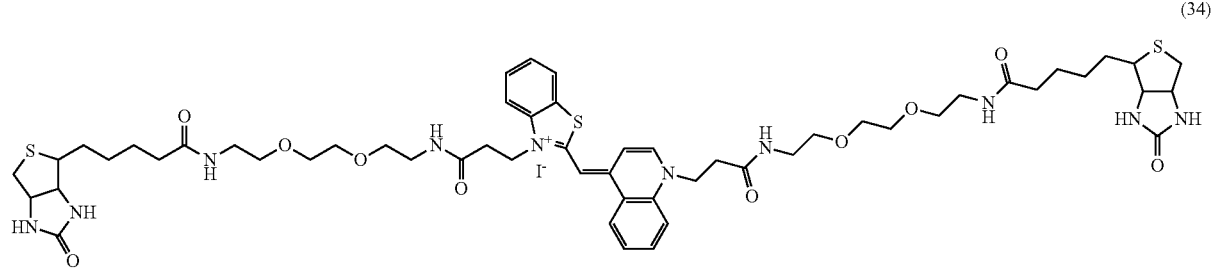 [SMILES: O=C(CCCCC1SCC2NC(=O)NC21)NCCOCCOCCNC(=O)CCN1C=C/C(=C\c2sc3ccccc3[n+]2CCC(=O)NCCOCCOCCNC(=O)CCCCC2SCC3NC(=O)NC32)c2ccccc21 ; [I-]]

(34)

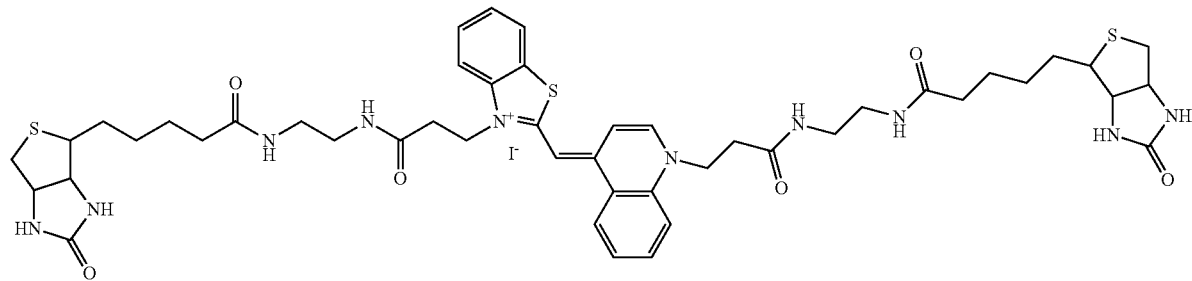

(35)

Sensor 35 comprises two biotin moieties, and hence, its interaction with Avidin and/or Streptavidin is expected to enhance its fluorescent signal.

In some embodiments, the Thiazole Orange based sensor of this invention is represented by the structure of formula 36.

Sensor 37 comprises two tacrine moieties, and hence, its interaction with Acetylcholinesterase (AChE) is expected to enhance its fluorescent signal.

Biological Applications of Sensors of the Invention

In some embodiments, this invention provides a method of diagnosing a disease by detecting/identifying a protein in

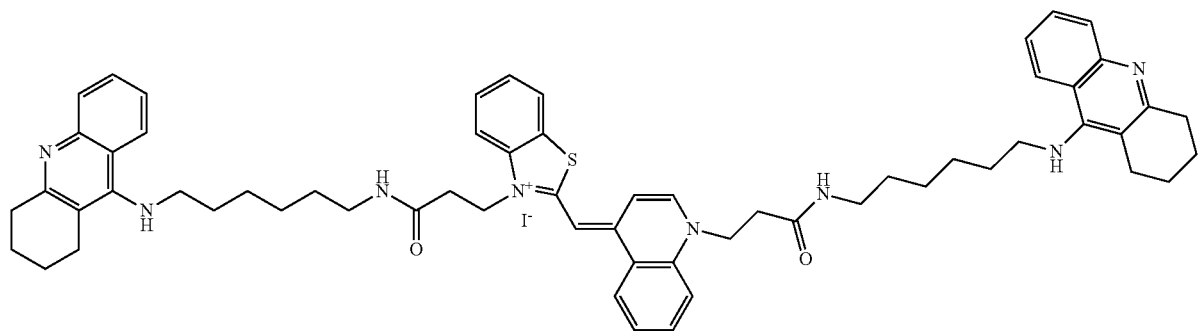

(36)

Sensor 36 comprises two tacrine moieties, and hence, its interaction with Acetylcholinesterase (AChE) is expected to enhance its fluorescent signal.

In some embodiments, the Thiazole Orange based sensor of this invention is represented by the structure of formula 37.

a biological medium comprising contacting a sensor of this invention and a protein, wherein contacting said protein and said sensor results in restricted rotation of said sensor and thereby to an enhancement in fluorescence signal, and thereby identifying/detecting said protein; wherein by detecting or identifying a protein biomarker in a biological

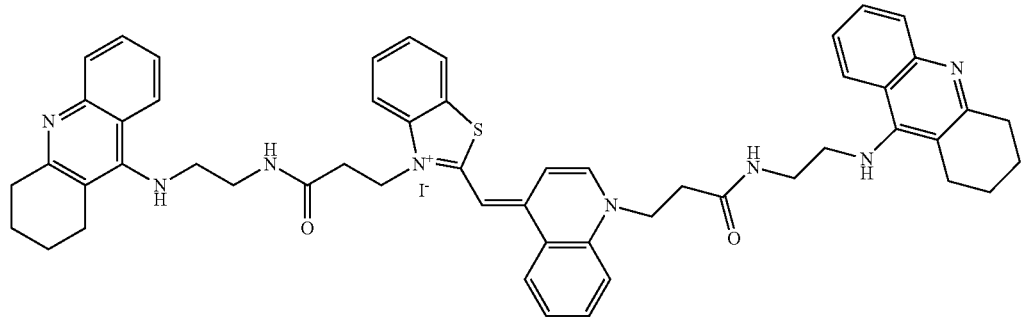

(37)

medium said protein biomarker being characteristic of a disease; or measuring a change in a concentration of a protein biomarker in said sample compared to normative values, wherein said change is characteristic of a disease; thereby, diagnosing a disease in a subject.

GSTs and AChE play a role in a myriad of cellular processes, and overexpression of these enzymes has been associated with various diseases. Hence, sensors for these proteins could potentially be applied in inhibitor screening, medical diagnosis, and cellular imaging. Conventional enzymatic assays, for example, which can straightforwardly detect high enzyme concentrations, are often unsuitable for distinguishing among isozymes, whereas isozyme detection by antibody-based techniques generally requires stepwise incubation and labelling steps.

In one embodiment, this invention is directed to a method for identifying disease biomarkers, said method comprises:
  a. collecting a biological sample from a subject;
  b. incubating a TOPI of this invention with said biological sample;
  c. measuring the fluorescence emission resulting from binding of said TOPI to a protein of interest (POI), which is a biomarker for a disease, in the sample;
wherein an enhancement in the emission intensity from said sample is an indicator of the presence of said POI, which is a biomarker for a disease, in said sample;
wherein said TOPI comprises a Thiazole Orange (TO) derivative and at least one selective protein binder.

In some embodiments, said disease is Alzheimer. In some embodiments, said disease is cancer. In certain embodiments, said cancer is breast cancer, lung cancer, colorectal cancer, pancreas cancer, bladder cancer, ovarian cancer, prostate cancer, or brain cancer. In other embodiments, said cancer is prostate cancer. In certain embodiments, said cancer is breast cancer. In some embodiments, the biomarker is GST protein. In some embodiments, the biomarker is GST protein isoform. In some embodiments, the biomarker is AChE.

In one embodiment, this invention is directed to a method for tracking a protein of interest (POI) in complex environment, said method comprises:
  a. collecting a biological sample from a complex environment;
  b. contacting a TOPI sensor of this invention with said biological sample;
  c. measuring the fluorescence resulting from binding of said TOPI with a protein of interest (POI), present in said complex environment;
wherein an enhancement in the emission intensity from said sample is an indicator of the presence of said POI in said sample; and
wherein said TOPI comprises a Thiazole Orange (TO) derivative, and at least one selective protein binder.

The term "complex environment" refers in one embodiment to a system that consists of many diverse and autonomous but interrelated and interdependent components. In another embodiment, the complex environment refers to the native environment of the protein of interest (POI). In another embodiment, the complex environment refers to a biological medium taken from a mammalian subject. In another embodiment, the subject is human. In another embodiment, the biological medium is: blood, serum, plasma, urine, saliva, tissue, peritoneal, stool, mucus, tear, sweat, biopsy, sperm or a cerebrospinal fluid sample.

In one embodiment, this invention is directed to a method of diagnosing a disease in a subject, said method comprises:
  a. collecting a biological sample from a subject;
  b. incubating a TOPI of this invention with said biological sample;
  c. measuring the fluorescence emission resulting from binding of said TOPI to a protein of interest (POI), which is a biomarker for said disease, in the sample;
wherein an enhancement in the emission intensity from said sample is an indicator of the presence of said POI, which is a biomarker for said disease, in said sample;
thereby diagnosing a disease in said subject.

In some embodiments, said disease is Alzheimer. In some embodiments, said disease is cancer. In certain embodiments, said cancer is breast cancer, lung cancer, colorectal cancer, pancreas cancer, bladder cancer, ovarian cancer, prostate cancer, or brain cancer. In other embodiments, said cancer is prostate cancer. In certain embodiments, said cancer is breast cancer.

In one embodiment, this invention is directed to a method of identifying a compound that binds to a protein of interest (POI), said method comprises:
  a. incubating a TOPI of this invention with a POI in solution;
  b. measuring the fluorescence intensity of said solution;
  c. adding a test compound to said solution;
  d. re-measuring the fluorescence intensity of said solution; and
  e. determining binding of said test compound to said POI based on a change in fluorescence intensity, wherein decreased fluorescent intensity indicates binding of said test compound to said POI;
thereby identifying a compound that binds said POI.

In another embodiment, the test compound is a protein, a peptide, a synthetic molecule, a small molecule, a drug or any combination thereof.

Figure 24:
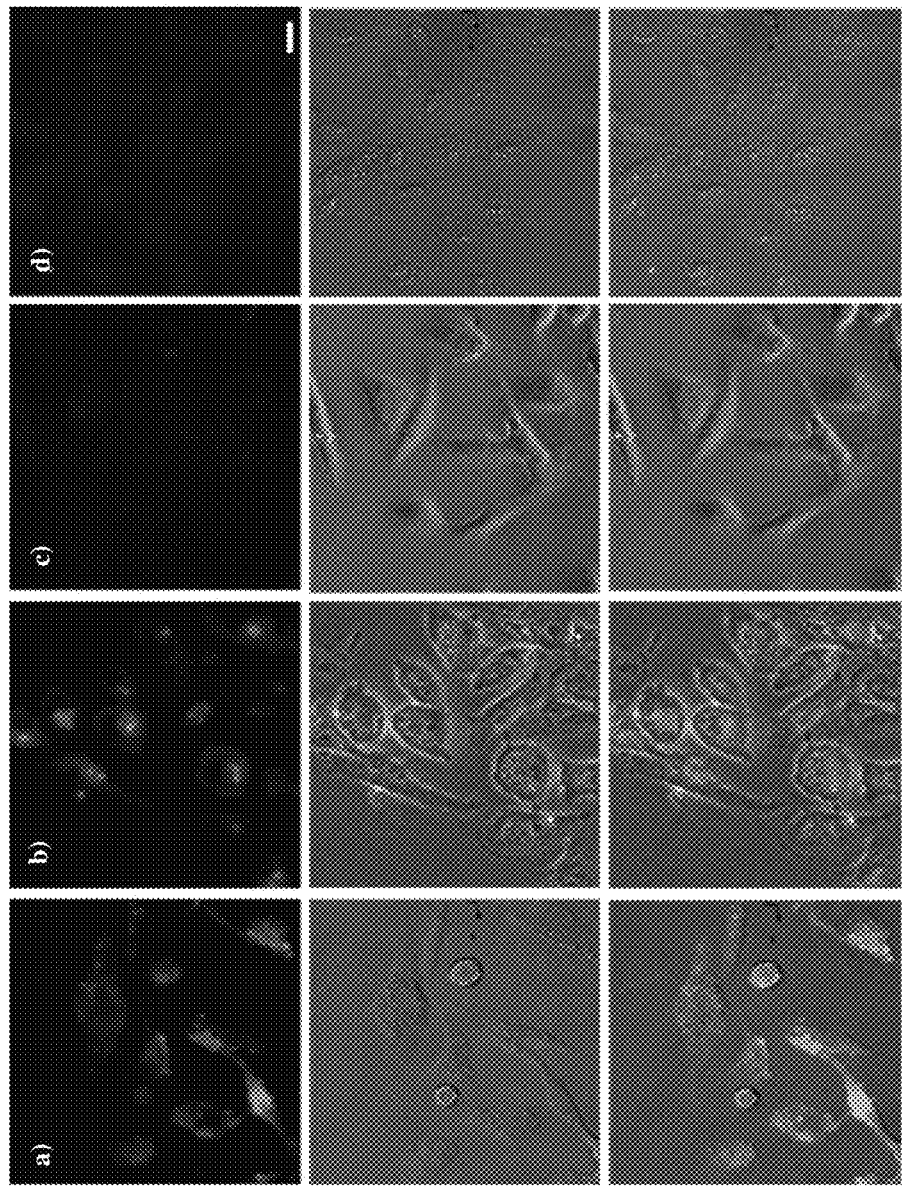
FIG. 24 depicts (Top) Fluorescent, (Middle) bright field and (Down) overlay images of MDA-MB-231 cancer cells, overexpressing GST-P1-1, after incubation with a) 140 (2 μM), b) TO (2 μM), and c) 140 (2 μM) and EA (50 μM). d) Images of healthy MCF-10A cells incubated with 140 (2 μM). The scale bar is 20 μm.

In some embodiments, it may be desirable to locate a POI within a cell. For example, GST-P1-1 is a cytosolic protein, whereas DNA is located in the nucleouse. Hence, the differences between a TOPI compound (e.g. compound 140) and the known DNA intercelator (i.e., TO) (FIG. 21e) could also be observed by monitoring their localization in live cells (FIG. 24).

In one embodiment, this invention is directed to a method for localizing a protein of interest (POI) within a cell, said method comprises:
  a. incubating cells comprising said POI with a TOPI of this invention;
  b. visualizing the fluorescence emission of said cells;
wherein an enhancement in the fluorescence emission is indicative of binding of said TOPI to a protein of interest (POI) in said cells.

In another embodiment, said method is used for cellular imaging. In another embodiment, said visualizing comprises observing under a microscope. In one embodiment, a fluorescent microscope is used to detect and localize the fluorescent signal. In another embodiment, a fluorescent microscope with a plate reader or the ability to record images at multiple locations over time is used to detect and localize the fluorescent signal. In another embodiment, said visualizing comprises fluorescence imaging. In another embodiment, said fluorescence is measured over time. In another embodiment, said cell is of a live cell. In another embodiment, said cell is a fixed cell. In one embodiment, said cell is a human cell. In another embodiment, said cell is a recombinant primary culture cell. In another embodiment, said cell is a tissue culture cell. In another embodiment, the cell is comprised in a biological sample. In another embodiment, the biological sample is blood, serum, plasma, urine, saliva, tissue, peritoneal, stool, mucus, tear, sweat, biopsy, sperm or a cerebrospinal fluid sample.

In one embodiment, this invention is directed to a method for cellular imaging, said method comprises:
  a. incubating a TOPI of this invention with a biological sample comprising a protein of interest (POI);

b. visualizing the fluorescence emission from said sample; wherein an enhancement in the fluorescence emission is indicative of binding of said TOPI to said protein of interest (POI) in said biological sample.

In another embodiment, said visualizing comprises observing under a microscope. In one embodiment, a fluorescent microscope is used to detect and localize the fluorescent signal. In another embodiment, a fluorescent microscope with a plate reader or the ability to record images at multiple locations over time is used to detect and localize the fluorescent signal. In another embodiment, said visualizing comprises fluorescence imaging. In another embodiment, said fluorescence is measured over time. In another embodiment, said cell is of a live cell. In another embodiment, said cell is a fixed cell. In one embodiment, said cell is a human cell. In another embodiment, said cell is a recombinant primary culture cell. In another embodiment, said cell is a tissue culture cell. In another embodiment, the cell is comprised in a biological sample. In another embodiment, the biological sample is blood, serum, plasma, urine, saliva, tissue, peritoneal, stool, mucus, tear, sweat, biopsy, sperm or a cerebrospinal fluid sample. In another embodiment, the cellular imaging is used for monitoring graft failure or regenerations following living donor liver transplantation (using GST proteins as biomarkers).

In one embodiment, this invention is directed to a method of diagnosing a disease in a subject by detecting a protein biomarker characteristic of a disease, said method comprising:
  a. collecting a biological sample from a subject;
  b. contacting said biological sample with a sensor of this invention, wherein said contacting results in restricted rotation of said sensor as a result of binding to a protein of interest (POI), thereby providing a unique optical signature; and
  c. measuring said optical signature;
thereby identifying said protein biomarker characteristic of a disease.

In some embodiments, said disease is Alzheimer. In some embodiments, said disease is cancer. In certain embodiments, said cancer is breast cancer, lung cancer, colorectal cancer, pancreas cancer, bladder cancer, ovarian cancer, prostate cancer, or brain cancer. In other embodiments, said cancer is prostate cancer. In certain embodiments, said cancer is breast cancer. In another embodiment, the disease is selected from: cancer (such as colorectal, prostate, breast, lung, gastric, pancreas, bladder, ovarian, or brain), hepatitis c, phenylketonuria, Alzheimer, type II diabetes, and familial hypercholesterolemia. In another embodiment, the disease is a renal tubular injury.

In another embodiment, and with respect to all methods described above, the POI is a homodimer. In another embodiment, the POI has two identical binding sites. In another embodiment, the protein is glutathione S-Transferase (GSTs) protein group. In another embodiment, the protein is glutathione S-Transferase (GSTs) protein isoform. In another embodiment, the POI is avidin (Av). In another embodiment, the POI is streptavidin (SAv). In another embodiment, the POI has a distinct binding site. In another embodiment, the POI is Acetylcholinesterase (AChE). In another embodiment, the POI has more than one distinct binding site, where each site may bind a different binder. In another embodiment, the POI is platelet derived growth factor. In another embodiment, the POI is a Histidine-tagged protein. In some embodiments, the POI is selected from: matrix metalloproteases (MMPs) protein and its isoforms, glutathione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, estrogen receptor (ER), Acetylcholinesterase, avidin, streptavidin or histone deacetylases (HDACs).

In some embodiments, and with respect to all methods described above, the sensor is a TOPI. In one embodiment, the TOPI comprises a TO derivative and one selective protein binder. In another embodiment, the TOPI comprises a TO derivative and two selective protein binders. In another embodiment, the TO derivative is covalently bonded to one selective protein binder. In another embodiment, the TO derivative is covalently bonded to two selective protein binders. In another embodiment, the TO derivative is covalently bonded to one selective protein binders through a linker. In another embodiment, the TO derivative is covalently bonded to two selective protein binders through linkers. In one embodiment, the TOPI is of formula IX. In one embodiment, the TOPI is of formula X. In one embodiment, the TOPI is of formula XI.

In one embodiment, the TOPI is of formula XII. In one embodiment, the TOPI is of formula XIII. In one embodiment, the TOPI is of formula 14. In one embodiment, the TOPI is of formula 140. In one embodiment, the TOPI is of formula 20. In one embodiment, the TOPI is of formula 26. In one embodiment, the TOPI is of formula 33. In one embodiment, the TOPI is of formula 34. In one embodiment, the TOPI is of formula 35. In one embodiment, the TOPI is of formula 36. In one embodiment, the TOPI is of formula 37.

In another embodiment, and with respect to all methods described above, a subject refers to a mammal, a human, a female or a male.

In one embodiment, the method of this invention is directed to a method of diagnosing a disease in a subject. In another embodiment, the disease is a protein based disease. Non limited examples of a disease are cancers (colorectal, prostate, breast, lung, gastric, pancreas, bladder, ovarian, or brain), hepatitis c, phenylketonuria, Alzheimer, type II diabetes, familial hypercholesterolemia. In another embodiment, the method of this invention is directed to identifying a renal tubular injury (using GST proteins as biomarkers). In another embodiment, the method of this invention is directed to monitoring graft failure or regenerations following living donor liver transplantation (using GST proteins as biomarkers).

In some embodiments, the methods are directed to a) differentiating between proteins and protein isoforms; b) identifying proteins and protein isoforms; c) detecting proteins and protein isoforms; d) cellular imaging of proteins and protein isoforms; e) identifying compounds that bind to specific proteins and protein isoforms; f) localizing proteins and protein isoforms within cells; or g) diagnosing a disease, in a biological medium or biofluids.

In one embodiment, the methods of this invention are directed to diagnosing a disease, detecting or identifying a protein and protein isoform in a biological medium. In another embodiment, the biological medium is a serum, a blood, a plasma, a urine, a saliva, a tissue, a peritoneal, a stool, a mucus, a tear, a sweat, a biopsy, a sperm or a cerebrospinal fluid sample. In another embodiment, the methods of this invention comprising contacting a sensor of formula IX-XIII and a protein, wherein contacting said protein and said sensor results in binding of said sensor to said protein which induces a restricted rotation for said sensor and thereby to a fluorescence enhancement and to a unique optical signature; thereby differentiating/identifying/ detecting/said protein and thereby diagnosing the disease associated with the protein. In another embodiment, the methods of this invention optionally comprise a step of isolating component from a biological sample. In another embodiment, "isolating components" refers to isolating cells having proteins; isolating sugars, isolating glycans, phosphates (non limiting examples include ATP, ADP, AMP, GMP), isolating phospholipids, isolating glycoprotein, a glycolipid or a proteoglycan from the biological sample.

A protein isoform refers to several different forms of the same protein, with slightly different amino acid sequences, but with similar activity. Different forms of a protein may be produced from related genes or may arise from the same gene by alternate splicing.

Binding of different proteins affects differently the optical properties of the photoluminescent, as well as induces a restricted rotation of the Thiazole Orange that would result in fluorescence enhancement. In some embodiments, the methods are directed to diagnosing a disease by identifying or detecting a protein biomarker. In one embodiment, a protein biomarker is a protein of interest (POI) as described hereinabove. In one embodiment, a protein biomarker is a glutathione S-Transferase (GSTs), wherein said GST is a biomarker for cancer. In another embodiment the GST comprises for example the following isoforms: GSTA1, GSTA2, GSTM1, GSTK1, GSTO1, GSTZ1, GSTT1 and GSTP1. In another embodiment, GST A1 is a biomarker for breast, lung, prostate and colorectal cancer. In another embodiment GST A2 is a biomarker for prostate and lung cancer. In another embodiment GST M1 is a biomarker for prostate and breast cancer. In another embodiment GST P1 is a biomarker for breast, lung and gastric cancer. In some embodiments, said glutathione S-Transferase (GSTs) is a biomarker for renal tubular injury. In some embodiments, said glutathione S-Transferase (GSTs) is a biomarker for kidney disease. In some embodiments, said glutathione S-Transferase (GSTs) is a biomarker for monitoring graft failure or regeneration following living donor liver transplantation. In another embodiment, the sensors of this invention differentiate between protein isoforms. In another embodiment, the sensors of this invention identify protein isoforms. In another embodiment, the sensors of this invention detect protein isoforms. In another embodiment, protein sensor 14 differentiates/identifies and detects GST-M1 isoform. In another embodiment, different length of the linkers between the Thiazole Orange and the protein selective binder will allow selectivity to different isoforms.

In some embodiments, the methods of this invention are directed to differentiating Fibroblast Growth Factors (FGFs) proteins. Characterization of FGFs that bind to an octasaccharide library of heparin/heparan sulfate revealed that positions 2-O-sulfate (A) and 6-0 sulfate (B), together or separated are essential for binding and that protein recognition involves sequences containing variable degrees of 6-O-sulfation of the A-B disaccharide unit. In another embodiment, an aptamer is a selective protein binder for FGF. In another embodiment, heparin is a selective protein binder for FGF.

In another embodiment, 12-sulfated-octasaccharide heparin is a selective protein binder for FGF.

In some embodiments, the methods of this invention are directed to differentiating and characterizing ER biomarkers. In another embodiment, the methods of this invention are directed to identifying ERα and ERβ biomarkers.

In some embodiments, the methods are directed to diagnosing a disease by identifying or detecting a protein biomarker. In one embodiment, a protein biomarker is achetylcholinesterase (AChE) protein, wherein said AChE is a biomarker for Alzheimer and tacrine is the protein selective binder.

In some embodiments, the methods are directed to diagnosing a disease by identifying or detecting a protein biomarker. In one embodiment, a protein biomarker is a matrix metalloproteases (MMPs) protein, wherein said MMP is a biomarker for cancer and marimastat is the protein binder. In another embodiment, the MMP comprises for example the following isoforms: MMP-1, MMP-2, MMP-7 or MMP-9. In another embodiment, the MMP-1 is a biomarker for breast, lung and colorectal cancer. In another embodiment, MMP-2 is a biomarker for pancreas, bladder, colorectal, ovarian, prostate, brain, pancreas, lung and colorectal cancer. In another embodiment, MMP-7 is a biomarker for pancreas, lung and colorectal cancer. In another embodiment, MMP-9 is a biomarker for breast, pancreas, bladder, lung, colorectal, ovarian, prostate and brain cancer. In another embodiment, the compounds of this invention differentiate between the MMP isoforms.

Various concentrations of biomarkers may be detected and measured by the methods described herein. Biomarkers at concentrations of between about 1-5 mM, 1-100 μM, 50-100 mg/mL, 50-500 nM or less than, e.g., 100 milligrams/milliliter (mg/ml), 10 mg/ml, 1 mg/ml, 100 micrograms/milliliter (μg/ml), 10 μg/ml, 1 μg/ml, 100 nanograms/milliliter (ng/ml), 10 ng/ml, 1 ng/ml, may be detected in the biological sample, and the concentration may be measured.

In one embodiment, the method of this invention is directed to a method of diagnosing a disease in a subject measuring a change in a concentration of a protein biomarker compared to normative values, wherein said change is characteristic of a disease. The term "normative value" refers to the concentration range of saccharide found in a normal healthy subject. The term "normative value" refers to the control.

In some embodiments, this invention provides a method of detecting a protein in a biological medium comprising contacting a sensor of formula IX-XIII and a protein, wherein contacting said protein and said sensor results in restricted rotation of said sensor and thereby to fluorescence enhancement, and thereby detecting said protein. In some embodiments, the sensor is of formula IX. In one embodiment, the sensor is of formula X. In one embodiment, the sensor is of formula XI. In one embodiment, the sensor is of formula XII. In one embodiment, the sensor is of formula XIII. In one embodiment, the sensor is of formula 14. In one embodiment, the sensor is of formula 140. In one embodiment, the sensor is of formula 20. In one embodiment, the sensor is of formula 26. In one embodiment, the sensor is of formula 33. In one embodiment, the sensor is 34. In one embodiment, the sensor is 35. In one embodiment, the sensor is 36. In one embodiment, the sensor is 37. In another embodiment, the protein is a homodimer. In another embodiment, the protein has two identical binding sites. In another embodiment, the protein has a distinct binding site. In another embodiment, the protein has more than one distinct binding site, where each site may bind a different binder. In another embodiment, the protein is a his-tag-labeled protein. In another embodiment, the protein is a GST in living cells. In another embodiment, the protein is avidin or streptavidin. In another embodiment, the protein is Acetylcholinesterase. In another embodiment, the sensor comprises a Thiazole Orange derivative and at least one specific protein binder. In another embodiment, the sensor comprises a Thiazole Orange derivative, covalently bonded to at least two specific protein binders. In another embodiment, the sensor comprises a Thiazole Orange derivative, covalently bonded to at least two specific protein binders through linkers.

In some embodiments, the methods of this invention comprise detecting, identifying specific protein isoforms or differentiating between proteins and protein isoforms. In another embodiment, the protein is matrix metalloproteases (MMPs) protein and its isoforms, glutathione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, estrogen receptor (ER), Acetylcholinesterase, avidin, streptavidin or histone deacetylases (HDACs). In other embodiments, said protein is a His-tagged protein. In certain embodiments, said protein is GST. In certain embodiments, said protein is Acetylcholinesterase. In certain embodiments, said protein is avidin or streptavidin.

In some embodiments, the sensors and methods of use thereof comprise a selective protein binder. In another embodiment, the selective protein binder is marimastat, ethacrynic acid, bisethacrynic acid, complexed nitrilotriacetic acid (NTA), complexed bis NTA, complexed tris-NTA, Ni-nitrilotriacetic acid (Ni-NTA), bis Ni-NTA, tris-Ni-NTA, PDGF-BB, heparin, FGF aptamer, estrogen, DNA aptamer, RNA aptamer, peptide aldehyde, estrogen, suberoylanilidehydroxamic acid (SAHA), biotin, tacrine, or a peptide binder. In other embodiments, said selective protein binder is marimastat, ethacrynic acid, bisethacrynic acid, complexed nitrilotriacetic acid (NTA), complexed bis NTA, complexed tris-NTA, Ni-nitrilotriacetic acid (Ni-NTA), bis (Ni-NTA), tris (NiNTA), PDGF-BB, biotin, tacrine, heparin or estrogen. In another embodiment, the complexed NTA, complexed bis-NTA, complexed tris NTA is a nickel or cobalt complex.

In some embodiments, the ethacrynic acid or bisethacrynic acid is selective to glutathione S-Transferase (GSTs) protein. In some embodiments, Ni-nitrilotriacetic acid (Ni-NTA), bis-NiNTA or tris-Ni-NTA is selective to a His-tag protein. In some embodiments, Co-nitrilotriacetic acid (Co-NTA), bis-Co-NTA or tris-Co-NTA is selective to a His-tag protein In some embodiments, the PDGF-BB, heparin and estrogen are selective to platelet derived growth factor, fibroblast growth factor and to estrogen receptor, respectively. In some embodiments, the tacrine is selective to Acetylcholinesterase (AChE) protein. In some embodiments, the biotin is selective to avidin and/or streptavidin.

In certain embodiments, the DNA aptamer is selective to lysozyme. In certain embodiments, said peptide binder is selective to firbronectin or β-amyloid. In some embodiments, the DNA or RNA aptamer is selective to PSA. In some embodiments, the peptide aldehyde is selective to caspases and the SAHA is selective to histone deacetylases (HDACs).

In some embodiments, the methods of this invention comprise diagnosing, detecting, identifying and/or differentiating between proteins and protein isoforms. In another embodiment, the detecting/identifying is performed by obtaining a fluorescence emission signal due to the interaction of the protein of interest (POI) and the sensor of this invention.

In some embodiments, said fluorescence signal indicates the presence of said protein of interest (POI) in said biological medium. In some embodiments, said fluorescence signal enhancement indicates the presence of said protein in said biological medium.

In some embodiments, the methods of this invention make use of a sensor of formula IX. In one embodiment, the methods of this invention make use of a sensor of formula X. In one embodiment, the methods of this invention make use of a sensor of formula XI. In one embodiment, the methods of this invention make use of a sensor of formula XII. In one embodiment, the methods of this invention make use of a sensor of formula XIII. In one embodiment, the methods of this invention make use of a sensor of formula 14. In one embodiment, the methods of this invention make use of a sensor of formula 140. In one embodiment, the methods of this invention make use of a sensor of formula 20. In one embodiment, the methods of this invention make use of a sensor of formula 26. In one embodiment, the methods of this invention make use of a sensor of formula 33. In one embodiment, the methods of this invention make use of a sensor of 34. In one embodiment, the methods of this invention make use of a sensor of 35. In one embodiment, the methods of this invention make use of a sensor of 36. In one embodiment, the methods of this invention make use of a sensor of 37.

The terms "comprises" and variations thereof do not have a limiting meaning where these terms appear in the description and claims.

Unless otherwise specified, "a," "an," "the," and "at least one" are used interchangeably and mean one or more than one.

The following examples are presented in order to more fully illustrate the preferred embodiments of the invention. They should in no way be construed, however, as limiting the broad scope of the invention.

EXAMPLES

Materials and Methods

All reagents and solvents were obtained from commercial suppliers and used without further purification. Human GST isoforms A1-1, A2-2, M1-1, and P1-1 were purchased from Oxford Biomedical Research. All protein concentrations were given by the manufacturers which is determined the Bradford protein assay. Recombinant human GST isoforms A1-1, A2-2, M1-1, and P1-1 were obtained from the Israel Structural Proteomics Center (Weizmann Institute of Science, Rehovot, Israel). GST T1-1, GST O1-1, GST Z1-1, GST K1-1, transferrin, Fibroblast growth factor 21 (FGF-21), and platelet-derived growth factor-BB (PDGF-BB) were purchased from ProSpec-Tany TechnoGene Ltd. (Ness Ziona, Israel). Torpedo californica acetylcholinesterase was a gift from Prof. Israel Silman Lab (Weizmann Institute of Science, Rehovot, Israel). Biotin (PEG)3 amine (41) and biotinyl ethylamine (42) were purchased from Chem-Impex International (Wood Dale, Ill.). Lysozyme (from chicken egg white), human serum albumin, and immunoglobulin G (IgG) were purchased from Sigma-Aldrich. Immunoglobulin A (IgA) and fibrinogen were obtained from Merck Millipore. Ethacrynic acid, aspirin, and 7-ethyl-10-hydroxy-camptothecin (SN-38) were purchased from Tokyo Chemical Industry Co., Ltd., Santa Cruz Biotechnology, Inc. and AK Scientific, Inc., respectively. Histamine dihydrochloride (ceplene), amikacin hydrate, quabain octahydrate, erythromycin, epinephrine, dopamine hydrochloride, azithromycin, digitoxin, roxithromycin, L-glutathione reduced, salicylic acid, 4-formyl benzoic acid, hexamethylenediamine, 1,2-diaminoethane and 9-chloro-1,2,3,4-tetrahydroacridine were obtained from Sigma-Aldrich. Aluminum-backed silica plates (Merck silica gel 60 F254) were used for thin layer chromatography (TLC) to monitor solution-phase reactions. TLC visualization was carried out using short wavelength ultraviolet (UV) light at 254 nm, with ninhydrine, bromocresole, or permanganate solutions. The $^1$H NMR spectra were recorded using 300 MHz, 400 MHz or 500 MHz Bruker Avance NMR spectrometer. The $^{13}$C NMR spectra were recorded using a 400 MHz Bruker Avance NMR spectrometer. Chemical shifts are reported in ppm on the 6 scale down field from TMS as the internal standard. The following abbreviations were used to describe the peaks: s-singlet, d-doublet, dd-double doublet, t-triplet, q-quartet, quin-quintet, m-multiplet, and br-broad.

Electronspray mass spectrometry was performed with a Micromass Platform LCZ-4000 instrument at the Weizmann Institute of Science mass spectrometry facility.

Matrix-assisted laser desorption ionization time-of-flight (MALDI-TOF) mass spectrometry was performed on an AB SCIEX 5800 System, equipped with an Nd:YAG (355 nm) laser with a 1 KHz pulse (Applied Biosystems), at the Weizmann Institute of Science mass spectrometry facility.

Analytical reversed-phase high-performance liquid chromatography (RP-HPLC) analysis was performed on a Waters liquid chromatography system equipped with a 2487 dual wavelength UV S4 detector, a 600 gradient pump, and a 717 plus Autosampler. Peptides were synthetized by an AAPPTec (Apex 3) automated peptide synthesizer. A Chromolith™ RP-18e column (4.6×100 mm; Merck) was used for analytical purposes. Preparative HPLC purifications were done on a Thermo Separation instrument (P200 pump, UV 100 detector) and a pre-packed Vydac C18 column Standard RP-HPLC conditions were as follows: mobile phase A=0.1% TFA in H$_2$O; mobile phase B: 0.1% TFA in 25:75, H$_2$O:CH$_3$CN. Synthetic molecules was screened by analytical HPLC using an eluent composition of 0-100% B for 10 minutes, 3 mL/min Gradients used for preparative HPLC differ in each separation. Details are given when necessary.

Enzymatic assays were carried out using a BioTek synergy H4 hybrid multiwell plate reader in clear flat-bottom polystyrene 384 well microplates (Corning). Fluorescence measurements were carried out using a BioTek synergy H4 hybrid multiwell plate reader in clear and black flat-bottom polystyrene NBS 384 well microplates (Corning). Concentration measurements were performed on a Varian Cary fluorimeter using quartz cuvettes.

The UV-Vis spectra were measured on a Varian Cary UV-Visible spectrophotometer, and emission spectra were recorded on a Varian Cary Eclipse fluorescence spectrophotometer with excitation and emission slit widths of 20 nm Example 1

Preparation of Thiazole Orange Based Sensors (TOPI)

Thiazole Orange (TO) was selected as the signaling unit for the sensors of the invention because this asymmetrical cyanine dye exhibits remarkable 'turn-on' fluorescence response once the torsional motion between the benzothiazole and the quinoline rings in the excited-state is restricted, for example, upon binding to double-stranded DNA (FIG. 1C(a)). This property has been elegantly used to construct low-noise forced intercalation probes (FIT-probes) for sensitive detection of RNA and DNA. Other hybridization probes as well as aptamer- or antibody-based sensors further demonstrate the versatile use of this dye for sensing applications, and also indicate that fixating of TO in its fluorescent form does not necessarily require intercalation between DNA base pairs.

It was anticipated that modifying TO with two protein binders would result in a TO-based protein identifier (TOPI) that is inherently non-fluorescent in the unbound state; however, it becomes highly emissive once its torsional motion is restricted upon binding to the protein of interest (POI, FIG. 1C(b)). The bivalent interaction mode of this sensor is another important property that should enable TOPI to bind its target with high affinity. This 'multivalency' principle has recently been used to increase the affinity of fluorescent molecular sensors (L. Motiei, Z. Pode, A. Koganitsky, D. Margulies, *Angew. Chem. Int. Ed.* 2014, 53, 9289).

It was hypothesized that because the interaction of the TO-core with the protein's surface (FIG. 1C(b)) can also affect the rotational motion of the dye, it should enable the sensor to respond differently to isoforms with distinct surface characteristics.

Based on these principles several TOPI sensors were prepared (FIG. 2), each one is appended either with two tacrine (sensors 36 and 37), ethacrynic amide (EA) (sensors 14 and 140), or biotin (sensors 34 and 35) moieties, which were intended to target adjacent binding sites within acetylcholinesterase (AChE), glutathione-s-transferases (GSTs), and avidin (Av) or streptavidin (SAv), respectively. Sensors from each group share the same protein binders, but differ in the lengths and/or structure of their linkers. AChE is an acetylcholine hydrolase that regulates the concentration of this transmitter at the synapse. The design of 36 and 37 is based on the ability of bis-tacrine inhibitors to interact both with the active site and the peripheral site of this enzyme. GSTs are a large family of dimeric enzymes that protect the organism from toxic species by conjugating glutathione (GSH) to a variety of electrophilic substrates. Compounds 14 and 140, which are appended with two GST inhibitors (EAs), were expected to detect members of this family by simultaneously binding to identical sites within these dimers. to GSTs and AChE play a role in a myriad of cellular processes, and overexpression of these enzymes has been associated with various diseases. Hence, sensors for these proteins could potentially be applied in inhibitor screening, medical diagnosis, and cellular imaging. Avidin (Av) and streptavidin (SAv) are protein tetramers produced from egg whites and bacterium *Streptomyces avidinii*, respectively. These tetramers share a similar biotin binding site but possess very distinct surfaces. Therefore, by measuring the fluorescent response of 34 and 35 to Av and SAv, as well as the response of 14 and 140 to different GST isoforms, it was aimed to understand whether the local molecular environment of TO plays a role in obtaining 'turn-on' fluorescent signals.

TABLE 2

Structures of TO-based sensors with selectivity toward acetylcholinesterase (AChE), glutathione-s-transferases (GSTs), and avidin (Av) or streptavidin (SAv). 40 and 8 are control compounds that lack specific protein binders.

| Compound | R | Target |
|---|---|---|
| 36 | amide-linked hexyl chain to NH-tacrine | AChE |
| 37 | amide-linked ethyl chain to NH-tacrine | AChE |
| 14 | ethyl carbamate-triazole-propyl-amide-CH₂-O-aryl(Cl₂)-ethacrynic acid (EA) | GST |
| 140 | amide-ethyl-amide-CH₂-O-aryl(Cl₂)-ethacrynic acid (EA) | GST |
| 34 | amide-ethyl-O-ethyl-O-ethyl-amide-biotin | Av, SAv |
| 35 | amide-ethyl-amide-biotin | Av, SAv |

TABLE 2-continued

Structures of TO-based sensors with selectivity toward acetylcholinesterase (AChE), glutathione-s-transferases (GSTs), and avidin (Av) or streptavidin (SAv). 40 and 8 are control compounds that lack specific protein binders.

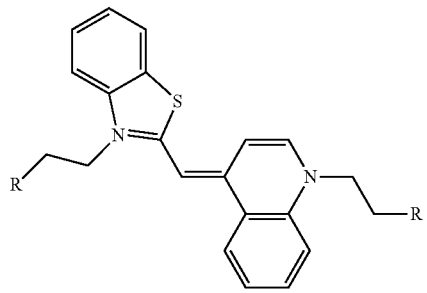

| Compound | R | Target |
|---|---|---|
| 20 | —O-C(=O)-NH-triazole-CH2CH2-C(=O)-NH-(CH2)6-O-P(O)(OH)-O-[CH2CH2O]6-P(O)(OH)-O-PDGF aptamer | PDGF |
| 26 | —O-C(=O)-NH-triazole-CH2CH2-C(=O)-NH-lysine-NTA | His-tagged protein or peptides |
| 33 | bis-NTA-lysine-glutamate-lysine-NTA conjugate | His-tagged protein or peptides |
| compounds 40 and 8 | —C(=O)OH or —O-C(=O)-NH-CH2-C≡CH | — |

Figure 3:
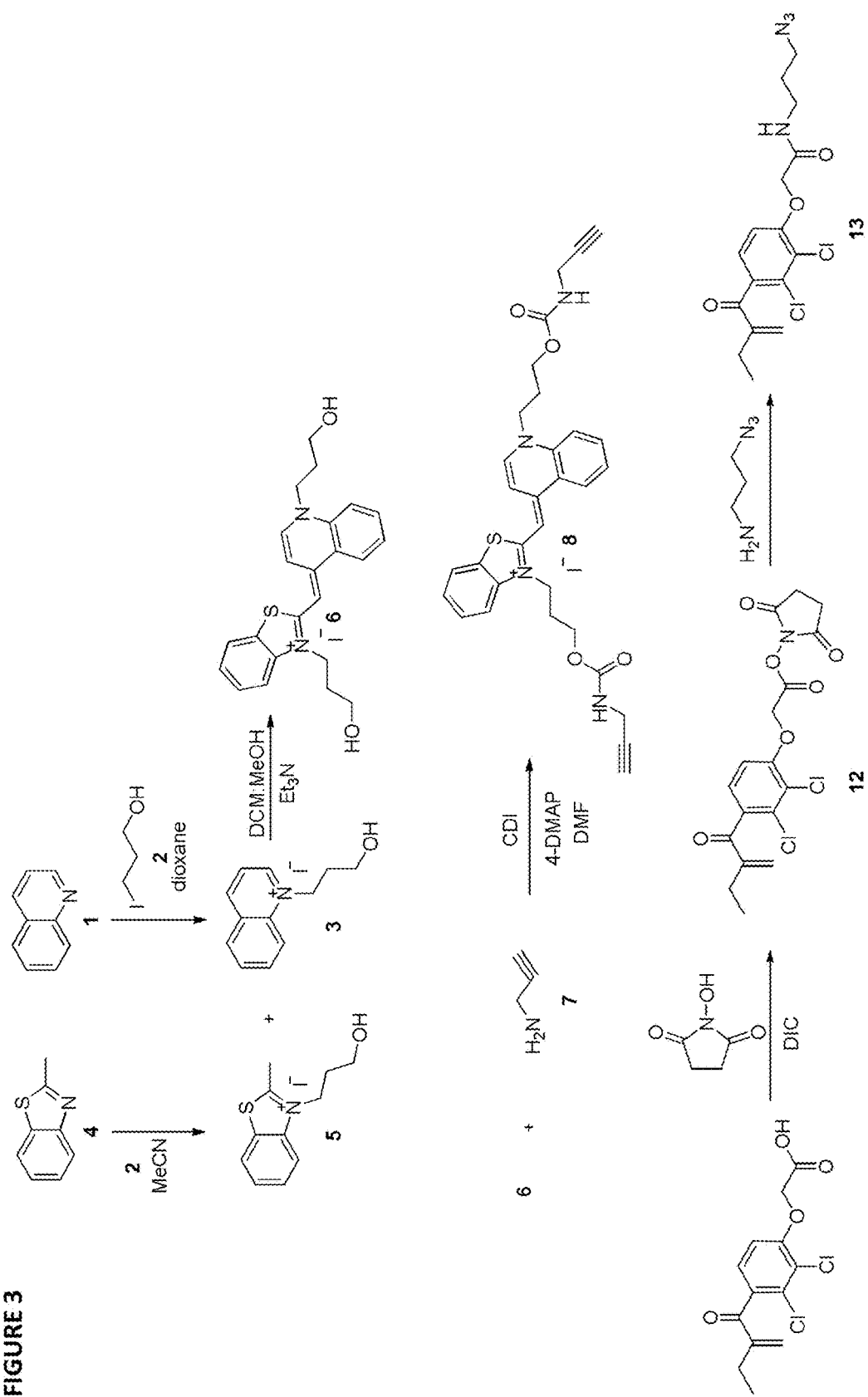
FIG. 3 depicts a synthetic scheme of sensors 14 and 140—GST sensors based on a TO-bisethacrynic acid conjugate.
Figure 3:
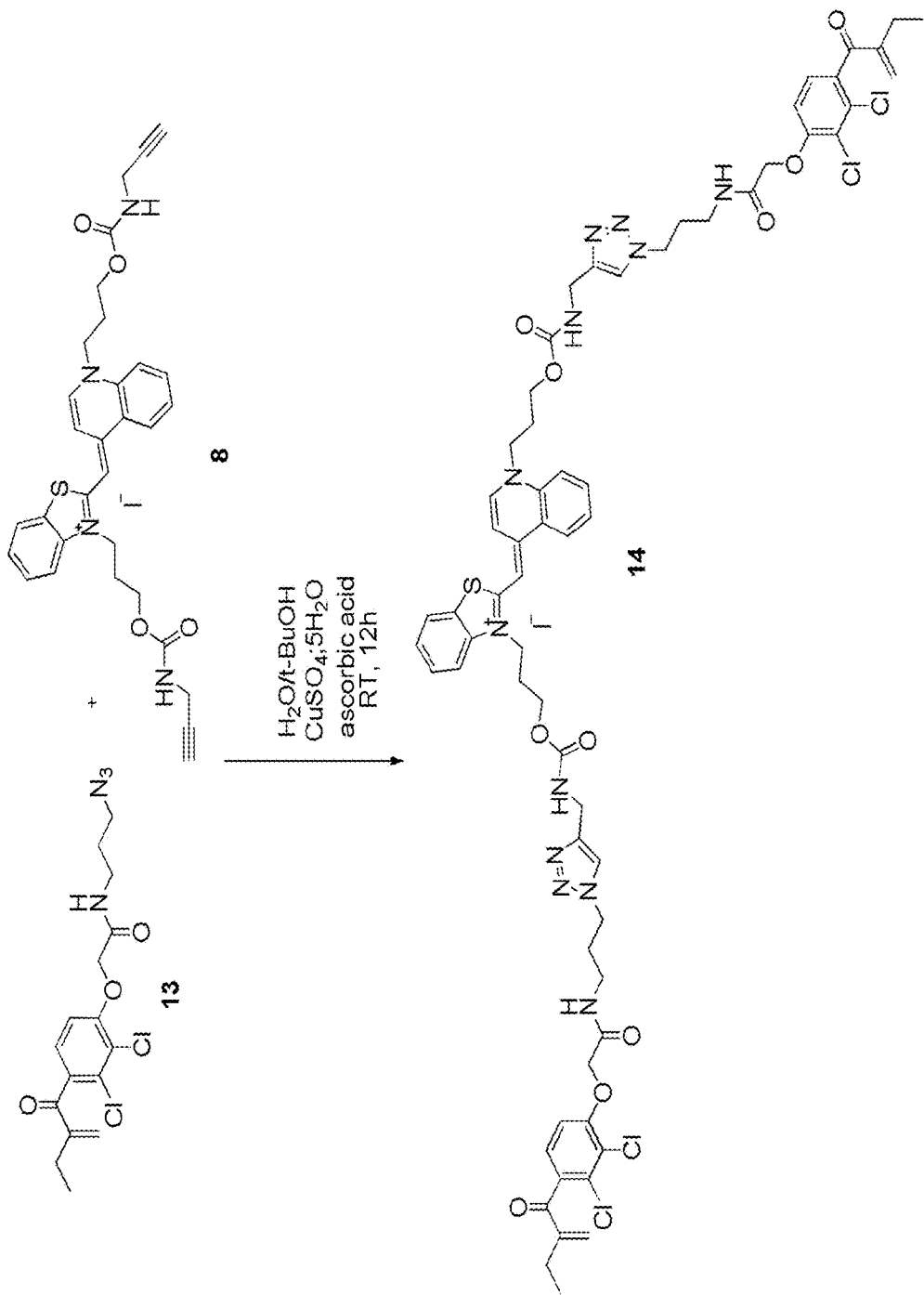
Figure 3:
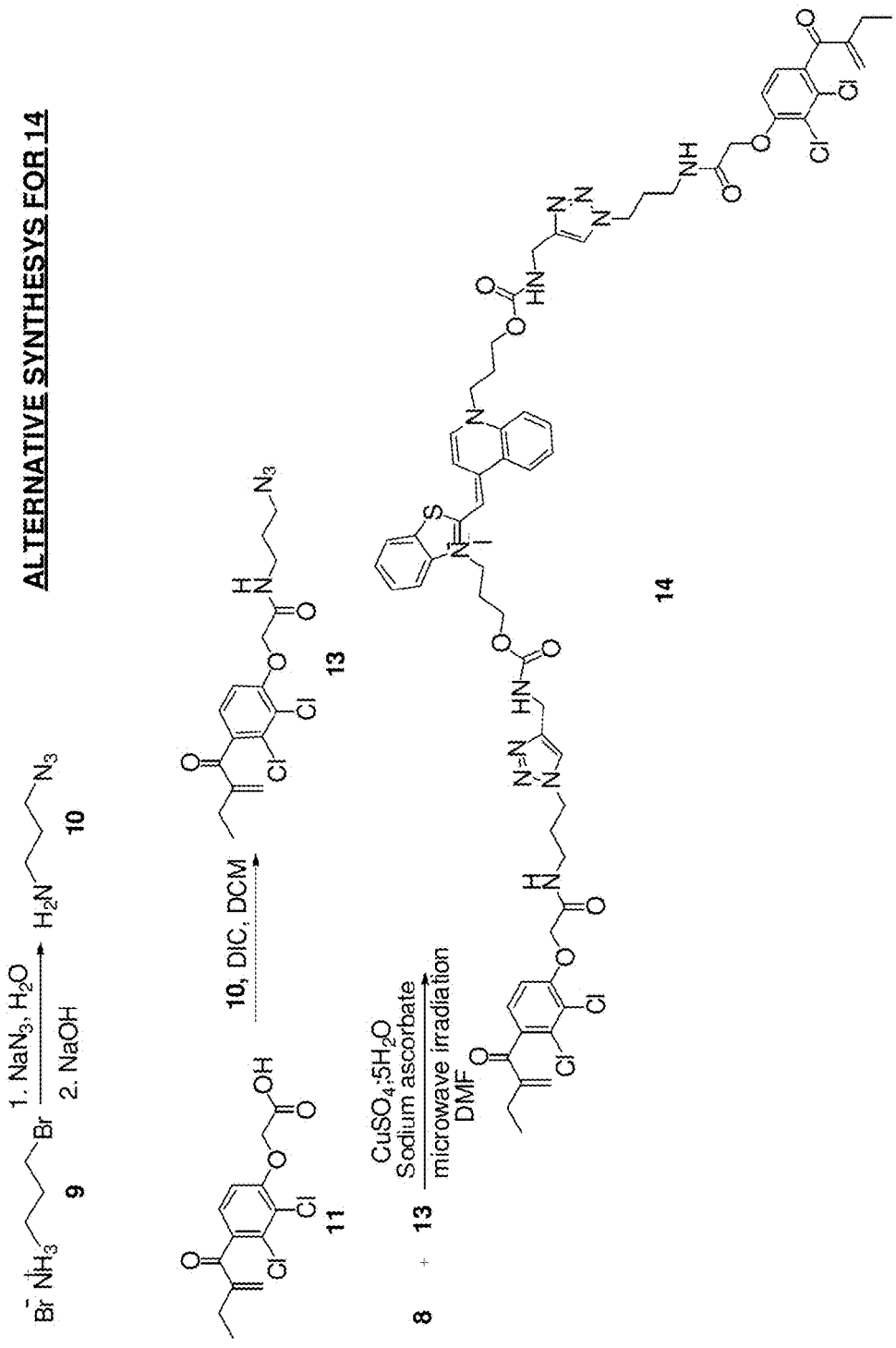
Figure 3:
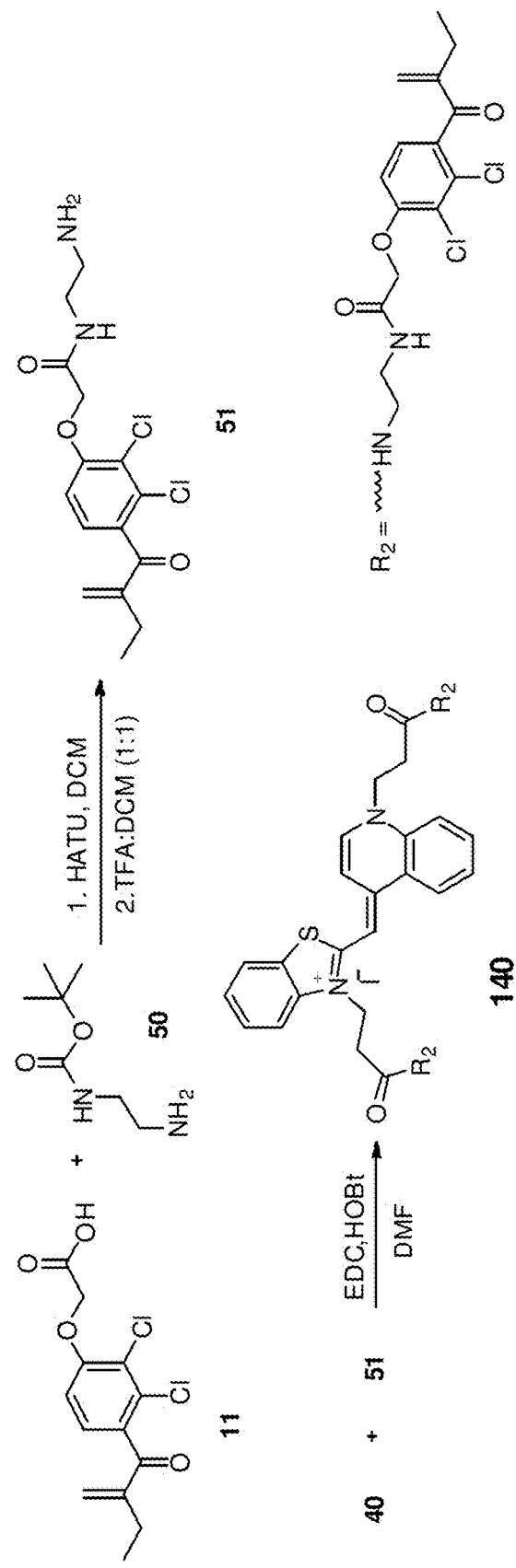

Synthesis of GST sensors based on Thiazole Orange (FIG. 3, sensors 14, 140)

1-(3-hydroxypropyl)quinolin-1-ium iodide (3)

3-iodo-1-propanol (2) was prepared according to a published procedure (D. Arian, L. Kovbasyuk and A. Mokhir, *J. Am. Chem. Soc.*, 2011, 133, 3972-3980).

3-iodo-1-propanol (2.45 mL, 25.5 mmol) was added to a solution of quinoline (1.01 mL, 8.5 mmol) in 9 mL of dioxane. The solution was stirred under reflux for 2.5 h. After cooling to room temperature, the product was precipitated by addition of acetone (6 mL). The residue was separated by filtration and washed with acetone to yield a yellow solid compound (2.1 g, 80%).

$^1$H NMR (300 MHz, DMSO-$d_6$): δ=2.14 (quin, J=6 Hz, 2H), 3.54 (t, J=6 Hz, 2H), 4.80 (bs, 1H, OH), 5.13 (t, J=6 Hz, 2H), 8.06 (t, J=7.5 Hz, 1H), 8.19 (dd, J=6 Hz, J=3 Hz, 1H), 8.29 (t, J=9 Hz, 1H), 8.50 (d, J=6 Hz, 1H), 8.60 (d, J=9 Hz, 1H), 9.30 (d, J=9 Hz, 1H), 9.54 (d, J=6 Hz, 1H). MS-ESI (m/z): calcd. for $C_{12}H_{14}NO$ [M−I] 188.15. found: 188.03.

3-(3-hydroxypropyl)-2-methylbenzothiazol-3-ium (5)

2-methylbenzothiazole (1.37 mL, 10.75 mmol) and 3-iodo-1-propanol (1 g, 5.38 mmol) were dissolved in 3 mL acetonitrile under $N_2$. The mixture was stirred under reflux for 91 h, then cooled to room temperature and stored in the fridge overnight. The precipitate was collected and washed three times with 1.5 mL cold Et2O, then dried under reduced pressure, yielding a white solid (90%). $^1$HNMR (300 MHz, DMSO-$d_6$): δ=2.04 (quin, J=6 Hz, 2H), 3.23 (s, 3H), 3.53 (t, J=6 Hz, 2H), 4.78 (t, J=6 Hz, 2H), 7.78 (t, J=9 Hz, 1H), 7.9 (t, J=9 Hz, 1H), 8.32 (d, J=9 Hz, 1H), 8.70 (d, J=9 Hz, 1H). MS-ESI (m/z): calcd. for $C_{11}H_{14}NOS$ [M−I] 208.3. found: 208.96.

3-(3-hydroxypropyl)-2-((1-(3-hydroxypropyl)quinolin-4(1H)ylidene)methyl)benzo thiazol-3-ium iodide (6)

Under nitrogen, 5 (1.5 g, 4.76 mmol) and 3 (1.91 g, 5.71 mmol) were dissolved in 28 mL $CH_2Cl_2$/MeOH (1:1, v:v) and then $Et_3N$ (1.63 ml, 11.7 mmol) was added. A deep red color immediately appeared. The reaction mixture was stirred under reflux overnight, and then cooled to room temperature. The reaction mixture was evaporated and washed with diethyl ether and ethyl acetate. The product was precipitated by addition of water. The residue was separated by filtration to yield a red solid material 0.91 g (39%).

$^1$H NMR (300 MHz, DMSO-$d_6$): δ=2.00 (quin, J=6 Hz, 2H), 3.50 (t, J=6 Hz, 2H), 3.57 (t, J=6 HZ, 2H), 4.62 (quin, J=6 Hz, 2H), 4.80 (t, J=6 Hz, 2H), 5.04 (t, J=6 Hz, 2H), 7.02 (s, 1H), 7.34-8.73 (m, 10H). MS-ESI (m/z): calcd. for $C_{23}H_{25}N_2O_2S$ [M−I] 393.6. found 393.18.

3-(3-((prop-2-yn-1-ylcarbamoyl)oxy)propyl)-2-((1-(3-((prop-2-yn-1-ylcarbamoyl)oxy) propyl)quinolin-4(1H)-ylidene)methyl)benzothiazol-3-ium iodide (8)

N,N'-carbonyldiimidazole (CDI) (0.343 g, 2.11 mmol) and 4-Dimethylaminopyridine (4-DMAP) (0.00035 g, 2.88× 10−3 mmol) were added to a solution of 6 (0.5 g, 0.96 mmol) in dry DMF (4.6 mL) and dry DCM (1 mL). The reaction mixture was stirred at room temperature for 4 h. Then, triethylamine (402 µL, 2.88 mmol) was added, the reaction mixture was cooled to 0° C., and propargylamine (135.4 µL, 2.11 mmol) was added dropwise. The mixture was stirred at room temperature for 48 h and monitored by TLC (10% DCM:MeOH) and HPLC. The reaction mixture was evaporated and purified by column chromatography (7-10% MeOH:DCM) to yield a dark red solid material (0.22 g, 33%).

$^1$H NMR (400 MHz, DMSO-$d_6$): δ=2.14-2.21 (m, 4H), 3.06-3.07 (m, 2H), 3.77-3.80 (m, 4H), 4.08-4.15 (m, 4H), 4.68 (m, 4H), 6.94 (s, 1H), 7.42-7.45 (m, 2H), 7.60-7.62 (t, J=8 Hz, 1H), 7.74-7.81 (m, 2H), 7.99-8.06 (m, 2H), 8.12 (d, J=8 Hz, 1H), 8.60 (d, J=8 Hz, 1H), 8.72 (d, J=12 Hz, 1H). $^{13}$C NMR (100 MHz, DMSO-$d_6$): δ=26.4, 28.2, 29.7, 42.7, 51.1, 61.0, 61.1, 72.8, 87.6, 108.1, 112.6, 117.7, 121.6, 122.8, 123.8, 124.2, 124.4, 125.6, 126.8, 128.1, 133.2, 136.9, 139.7, 144.2, 148.9, 155.6, 159.5. HRMS-ESI (m/z): calcd. for $C_{31}H_{13}N_4O_4S$ [M−I] 555.2061. found, 555.2072.

3-azidopropan-1-amine (10)

was prepared according to a published procedure [T. Mayer, M. E. Maier, *Eur. J. Org. Chem.* 2007, 2007, 4711-4720].

3-bromopropylamine hydrobromide (9) (1.5 g, 6.85 mmol) was added to a solution of sodium azide (1.336 g, 20.5 mmol) in 12 mL water. The reaction mixture was heated to 75° C. and stirred for 24 h and then cooled in an ice bath. To this cooled solution was added NaOH and the reaction mixture was stirred until the NaOH was fully dissolved. The reaction mixture was washed three times with diethylether, dried over $Na_2SO_4$, and evaporated in vacuum to afford clear oil (60%).

$^1$HNMR (300 MHz, $CDCl_3$): δ=1.58 (quin, J=6 Hz, 2H), 2.65 (t, J=6 Hz, 2H), 3.23 (t, J=6 Hz, 2H). ES-MS (m/z): calcd: 100.12. found: 101.07 (MH+), 123.02 (M$^+$ Na).

2,5-dioxopyrrolidin-1-yl 2-(2,3-dichloro-4-(2-methylenebutanoyl)phenoxy)acetate (12). (FIG. 3)

N-hydroxysuccinimide (0.455 g, 3.95 mmol) and N,N'-diisopropyldiimide (DIC) (510.8 µL, 3.29 mmol) were added to a solution of ethacrynic acid (1 g, 3.29 mmol) in 10 mL dry DCM. The reaction mixture was stirred at room temperature overnight and monitored by TLC (3% MeOH:DCM). The reaction mixture was washed twice with 0.1N HCl and brine (×2), dried over sodium sulfate, and further purified by combiflash (2% MeOH:DCM) to yield a clear oil (37%).

$^1$H NMR (300 MHz, CDCl3): δ=1.14 (t, J=9 Hz, 3H), 2.46 (guar, J=9 Hz, 6 Hz, 2H), 2.87 (s, 4H), 5.10 (s, 2H), 5.60 (s, 1H), 5.95 (s, 1H), 6.90 (d, J=3 Hz, 1H), 7.16 (d, J=3 Hz, 1H). ES-MS (m/z): calcd.: 399.21. found: 400.09 (MH+), 422.10 (M+Na), 823.14 (2M+Na).

N-(3-azidopropyl)-2-(2,3-dichloro-4-(2 methylenebutanoyl)phenoxy)acetamide (13)

3-azidopropan-1-amine (0.06 g, 0.501 mmol) was added to a solution of 12 (0.2 g, 0.501 mmol) in 2.5 mL dry DCM. The reaction mixture was stirred at room temperature overnight and monitored by TLC (5% MeOH:DCM). Then, the reaction mixture was washed three times with water, brine, and dried over sodium sulfate to yield clear oil (85%).

$^1$H NMR (300 MHz, CDCl3): δ=1.06 (t, J=6 Hz, 3H), 1.78 (quin, J=6 Hz, 9 Hz, 2H), 2.36 (guar, J=6 Hz, 2H), 3.32-3.43 (m, 4H), 4.50 (s, 2H), 5.51 (s, 1H), 5.88 (s, 1H), 6.80 (d, J=3 Hz, 1H), 7.02 (d, J=3 Hz, 1H). ES-MS (m/z): calcd.: 384.08. found: 407.13 (MH+), 791.19 (2M+Na), 1175.33 (3M+Na), 383.23 (M−H).

Alternative Synthesis to N-(3-azidopropyl)-2-(2,3-dichloro-4-(2-methylenebutanoyl)phenoxy)acetamide (13)

A solution of ethacrynic acid (0.744 g, 2.45 mmol) in dry DCM (10 mL) was cooled to 0° C. for 10 min. Then, DIC (380.1 µl, 2.45 mmol) and 3-azidopropylamine (0.27 g, 2.7 mmol) were added to the reaction mixture and the mixture was stirred at room temperature overnight and monitored by TLC (5% MeOH:DCM). The organic layer was washed three times with water, brine, and dried over sodium sulfate. The crude mixture was further purified by column chromatography (0-1% MeOH:DCM) to yield a clear oil (0.8 g, 85%).

$^1$H NMR (300 MHz, $CDCl_3$): δ=1.14 (t, J=6 Hz, 3H), 1.86 (quin, J=6 Hz, 2H), 2.46 (q, J=6 Hz, 2H), 3.42 (t, J=6 Hz, 2H), 3.49 (q, J=6 Hz, 2H), 4.57 (s, 2H), 5.58 (s, 1H), 5.95 (s, 1H), 6.85 (d, J=6 Hz, 1H), 6.97 (br-s, 1H), 7.18 (d, J=6 Hz, 1H). 13C NMR (100 MHz, $CDCl_3$): δ=12.5, 23.5, 28.8, 37.0, 49.6, 68.3, 111.0, 123.1, 127.4, 128.9, 131.7, 134.4, 150.3, 154.6, 167.0, 195.7. HRMS-ESI (m/z): calcd. for $C_{16}H_{18}Cl_2N_4NaO_3$ [M+Na] 407.0654. found: 407.0671.

3-(3-((((1-(3-(2-(2,3-dichloro-4-(2-methylenebutanoyl)phenoxy)acetamido)propyl)-1H-1,2,3-triazol-4-yl)methyl)carbamoyl)oxy)propyl)-2-((1-(3-((((1-(3-(2-(2,3-dichloro-4-(2-methylenebutanoyl)phenoxy)acetamido)propyl)-1H-1,2,3-triazol-4-yl)methyl)carbamoyl)oxy)propyl) quinolin-4 (1H)-ylidene)methyl)benzothiazol-3-ium iodide (14)

8 (3.3 mg, 4.83×10−3 mmol) and EA-azide 13, (3.71 mg, 9.67×10−3 mmol) were dissolved in 425 μL DMSO:H2O:tBuOH (1:1:1). After the required volume of ascorbic acid (0.1278 mg, 7.25×10−4 mmol, 15% mol) was added, the reaction mixture was degassed by bubbling argon gas for 30 seconds. Then, copper sulfate pentahydrate (0.06 mg, 2.42×10−4 mmol, 5% mol) was added to the solution and the solution was flushed with argon. The reaction mixture was stirred at room temperature overnight, evaporated, and purified by preparative HPLC (25%).

$^1$HNMR (300 MHz, DMSO-d6): δ=1.05 (t, J=6 Hz, 6H), 1.96 (m, 4H), 2.10 (m, 4H), 2.33 (q, 4H), 3.12 (d, 4H), 4.06-4.33 (m, 12H), 4.66 (t, 4H), 4.72 (s, 4H), 5.53 (s, 2H), 6.04 (s, 2H), 6.93 (s, 1H), 7.06-8.75 (m, 16H). ES-MS (m/z): calcd.: 1323. found: 1325 (M+), 674.3 (M+Na)/2.

Alternative Route for Synthesis of Compound 14 (FIG. 3):

A solution of 8 (5 mg, 7.33×10$^{-3}$ mmol) in DMF (300 μL) was degassed by bubbling argon gas. After addition of sodium ascorbate (2.9 mg, 0.0146 mmol in 100 μL water), the reaction mixture was degassed again for 30 seconds. Then, copper sulfate pentahydrate (3.66 mg, 0.0146 mmol in 100 μL water) was added and the mixture was flushed with argon. After adding 13 (8.44 mg, 0.0219 mmol), the reaction mixture was exposed to microwave irradiation for 3 min at 100° C. The solvent was evaporated under reduced pressure and the residue was purified by reversed-phase HPLC (5.46 mg, 51%). The desired product was stores at −20° C.

$^1$HNMR (500 MHz, DMSO-d$_6$): δ=1.05 (t, J=5 Hz, 6H), 1.96 (q, J=5 Hz, 4H), 2.16 (m, 4H), 2.34 (m, 4H), 3.13 (m, 4H), 4.06 (m, 2H), 4.20 (dd, J=5 Hz, J=15 Hz, 4H), 4.32 (q, J=5 Hz, 4H), 4.66 (m, 4H), 4.72 (s, 4H), 5.53 (s, 2H), 6.04 (s, 2H), 6.93 (s, 1H), 7.07 (d, J=10 Hz, 2H), 7.32 (d, J=10 Hz, 2H), 7.40-7.44 (m, 2H), 7.58 (t, J=10 Hz, 1H), 7.70-7.78 (m, 4H), 7.93-7.96 (m, 3H), 8.05 (d, J=10 Hz, 1H), 8.11-8.15 (m, 3H), 8.60 (d, J=5 Hz, 1H), 8.73 (d, J=5 Hz, 1H). $^{13}$C NMR (100 MHz, DMSO-d$_6$): δ=12.2, 22.7, 26.5, 28.2, 28.8, 29.6, 35.6, 42.7, 46.9, 51.1, 60.7, 60.9, 67.9, 87.6, 108.1, 111.9, 112.6, 117.2, 117.7, 121.2, 122.5, 122.7, 123.8, 124.2, 124.4, 125.6, 126.7, 127.3, 128.1, 128.9, 129.3, 132.4, 133.1, 136.9, 139.7, 144.2, 148.8, 149.3, 155.4, 158.1, 159.5, 166.6, 194.8. HRMS-ESI (m/z): calcd. for $C_{63}H_{67}O_4N_{12}O_{10}S$ [M−I] 1323.3578. found: 1323.3574.

The Synthesis of (E)-3-(34(2-(2-(2,3-dichloro-4-(2-methylenebutanoyl)phenoxy)acetamido)ethyl)amino)-3-oxopropyl)-2-((1-(3-((2-(2-(2,3-dichloro-4-(2-methylenebutanoyl)phenoxy)acetamido)ethyl)amino)-3-oxopropyl)quinolin-4(1H)-ylidene)methyl)benzo[d]thiazol-3-ium iodide (Compound 140)

N-(2-aminoethyl)-2-(2,3-dichloro-4-(2-methylenebutanoyl)phenoxy)acetamide (51)

Ethacrynic acid (500 mg, 1.65 mmol) was dissolved in 5 mL dry DCM, the reaction mixture was cooled to 0° C. for 15 min, and HATU (0.75 g, 19.8 mmol), tert-butyl(2-aminoethyl)carbamate (313.3 μL, 1.98 mmol) and DIPEA (344.8 μL, 1.98 mmol) were added. The reaction mixture was stirred at room temperature overnight and monitored by HPLC and TLC (10% DCM:MeOH). The organic layer was washed four times with water and brine, and then dried over sodium sulfate. The crude mixture was further purified by column chromatography (2% MeOH:DCM) to yield a clear oil (0.35 g, 48%).

$^1$H NMR (400 MHz, CDCl$_3$): δ=1.14 (t, J=8 Hz, 3H), 1.41 (s, 9H), 2.46 (q, J=8 Hz, 2H), 3.31 (q, J=8 Hz, 2H), 3.50 (q, J=8 Hz, 2H), 4.58 (s, 2H), 5.58 (s, 1H), 5.95 (s, 1H), 6.86 (d, J=8 Hz, 1H), 7.18 (d, J=8 Hz, 1H). MS-ESI (m/z): calcd. for $C_{20}H_{26}Cl_2N_2O_5$ [M+Na] 467.12. found 467.18.

Trifluoroacetic acid (1 mL) was added to a solution of the crude (90 mg, 0.2 mmol) in DCM (1 mL) and the reaction was stirred at room temperature for 2 h. After completion of the reaction, the solvent was evaporated and the mixture was washed 6 times with DCM and evaporated for 2 h under high vacuum. This compound was used for the next step without further purification.

Compound 140.

EDCI (41.95 mg, 0.22 mmol) and HOBT (29.57 mg, 0.22 mmol) were added to a solution of 40 (50 mg, 0.09 mmol) in dry DMF (1 mL) at 0° C. This mixture was kept at 0° C. for 15 min. Then, 51, (69 mg, 0.200 mmol) was added and the solution was basified to pH-7 with DIPEA (95 μL, 0.547 mmol), the reaction mixture was stirred at room temperature overnight and monitored by HPLC. The crude was purified by reversed-phase HPLC (20.64 mg, 18%).

$^1$H NMR (400 MHz, CDCl$_3$): δ=1.06 (t, J=8 Hz, 6H), 2.35 (q, J=8 Hz, 4H), 2.70 (m, 4H), 3.11 (s, 8H), 4.65 (d, J=12 Hz, 4H), 4.80 (m, 4H), 5.53 (s, 2H), 6.03 (s, 2H), 7.03 (s, 1H), 7.06-7.09 (m, 2H), 7.28-7.35 (m, 3H), 7.41 (t, J=8 Hz, 1H), 7.60 (t, J=8 Hz, 1H), 7.75 (m, 2H), 7.96-8.06 (m, 4H), 8.13-8.20 (m, 3H), 8.57 (d, J=8 Hz, 1H), 8.75 (d, J=8 Hz, 1H). $^{13}$C NMR (100 MHz, DMSO-d$_6$): δ=12.3, 22.9, 33.2, 34.3, 38.1, 42.5, 50.7, 67.8, 88.1, 107.8, 111.9, 112.9, 117.9, 121.1, 122.8, 123.9, 124.3, 124.5, 125.8, 126.8, 127.4, 128.1, 129.3, 132.48, 132.49, 133.2, 136.9, 139.8, 145.0, 148.9, 149.3, 155.3, 159.5, 166.8, 169.2, 169.7, 195.1. HRMS-ESI (m/z): calcd. for $C_{53}H_{53}Cl_4N_6O_8S$ [M−I] 1073.2400. found 1073.2407.

Example 2

Synthesis of other TO based sensors [(34), (35), (36), (37), (20), (26), (33)]

Figure 4:
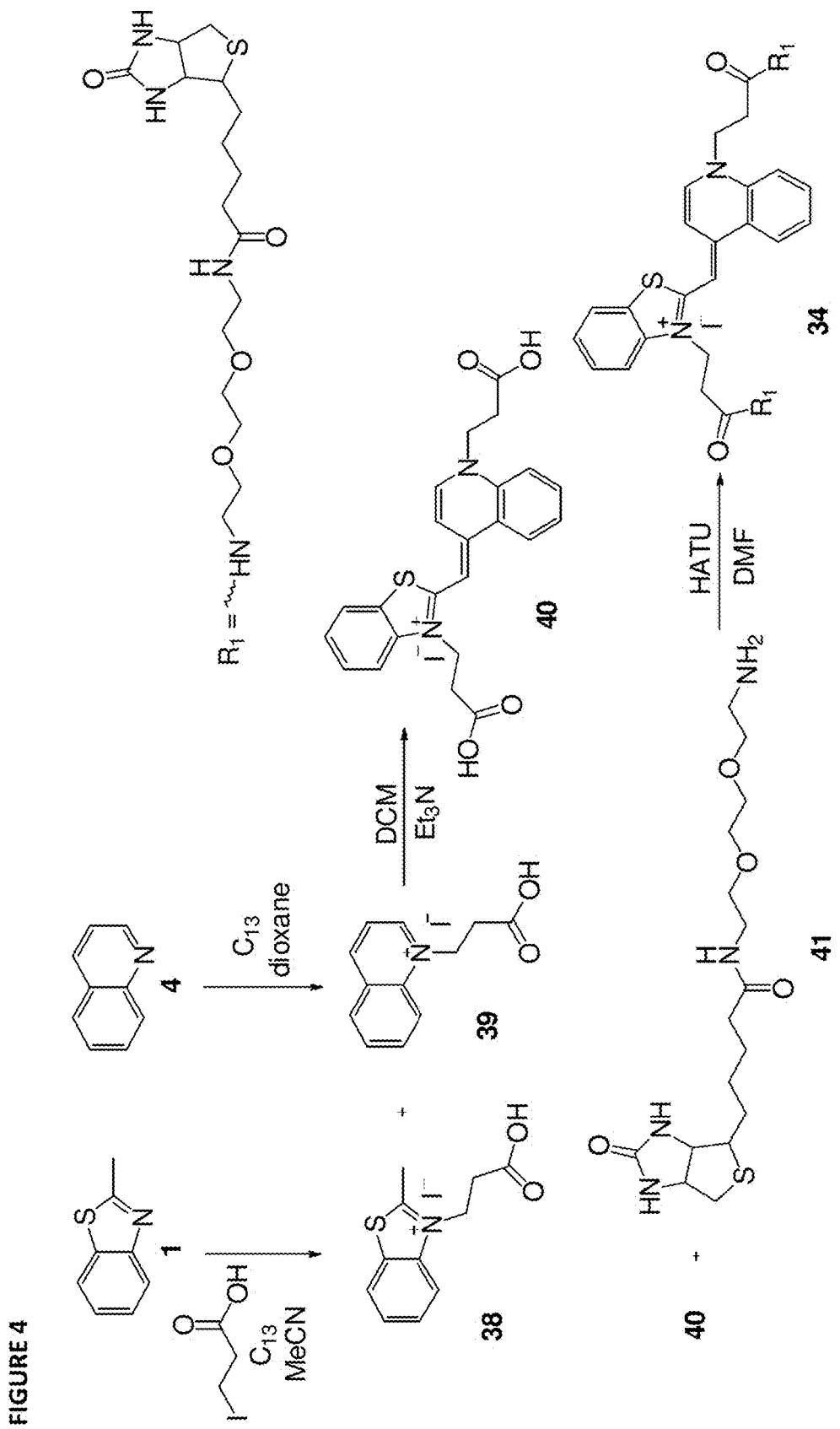
FIG. 4 depicts synthetic scheme for sensors 34 and 35 an avidin/streptavidin sensors based on a TO-bis-biotin conjugate.

A. Synthesis of Sensor (34) and (35) (FIG. 4)

3-(2-carboxyethyl)-2-methylbenzo[d]thiazol-3-ium iodide (38)

2-methylbenzothiazole 1 (636 μL, 5 mmol) and 3-iodopropionic acid (2.29 g, 15 mmol) were mixed together under nitrogen. The mixture was stirred and heated at 110° C. overnight. The solid was suspended in methanol:Et$_2$O solution (1:2, total 60 mL solution). The precipitate was filtered and washed with Et$_2$O, then dried under reduced pressure to yield a white solid (1.2 g, 68%).

$^1$H NMR (300 MHz, DMSO-d$_6$): δ=2.98 (t, J=6 Hz, 2H), 3.26 (s, 3H), 4.89 (t, J=6 Hz, 2H), 7.77-7.91 (m, 2H), 8.35-8.46 (m, 2H), 12.73 (br-s, 1H). MS-ESI (m/z): calcd. for $C_{11}H_{12}NO_2S$ [M−I] 222.05. found 221.96.

1-(2-carboxyethyl)quinolin-1-ium iodide (39)

3-iodopropionic acid (5.56 g, 27.9 mmol) was added to a solution of quinoline 4 (2.74 mL, 23.23 mmol) in 30 mL of dioxane. The solution was stirred under reflux for 23 h. After cooling to room temperature, the solvent was removed and the precipitate was washed twice with hexane and six times with acetone yielding a bright yellow solid (5.6 g, 73% yield).

$^1$H NMR (300 MHz, DMSO-d$_6$): δ=3.08 (t, J=6 Hz, 2H), 5.26 (t, J=6 Hz, 2H), 8.06 (t, J=6 Hz, 1H), 8.17-8.31 (m, 2H), 8.50 (d, J=6 Hz, 1H), 8.63 (d, J=9 Hz, 1H), 9.29 (d, J=9 Hz, 1H), 9.58 (d, J=6 Hz, 1H), 12.75 (br-s, 1H). MS-ESI (m/z): calcd. for $C_{12}H_{12}NO_2$ [M−I] 202.08. found 201.92.

(E)-3-(2-carboxyethyl)-2-((1-(2-carboxyethyl)quinolin-4-(1H)ylidene)methyl)benzothiazol-3-ium iodide (40)

Triethylamine (2.12 mL, 15.2 mmol) was added to a suspension of 39 (0.5 g, 1.52 mmol) and 38 (0.53 g, 1.52 mmol) in 6 mL dry CH2Cl2. A deep red color was immediately formed. The reaction mixture was stirred at room temperature overnight. Then the solvent was evaporated and re-dissolved in 1:1 mixture of MeOH:ethyl acetate (total 100 mL). After reducing the volume to half by evaporation under vacuum, the residue was kept overnight at room temperature until a solid is formed. The precipitate was collected and washed with methanol, then dried under reduced pressure to yield a red solid material (190 mg, 23% yield.

$^1$H NMR (400 MHz, DMSO-d$_6$): δ=2.41 (t, J=8 Hz, 2H), 2.46 (t, J=8 Hz, 2H), 3.97 (m, 4H), 5.96 (s, 1H), 6.24 (d, J=4 Hz, 1H), 6.37 (t, J=8 Hz, 1H), 6.68-6.78 (m, 2H), 6.84 (d, J=8 Hz, 1H), 7.22 (d, J=8 Hz, 1H), 7.35 (t, J=8 Hz, 1H), 7.50 (t, J=8 Hz, 1H), 7.63 (d, J=8 Hz, 1H), 7.81 (d, J=8 Hz, 1H). $^{13}$C NMR (100 MHz, DMSO-d$_6$): 35.1, 36.5, 43.6, 51.5, 87.2, 107.6, 111.5, 116.9, 121.8, 123.4, 123.5, 124.2, 124.7, 126.9, 127.6, 133.0, 136.0, 138.2, 142.6, 146.9, 158.3, 177.8, 178.0. HRMS-ESI (m/z): calcd. for $C_{23}H_{21}N_2O_4S$ [M−I] 421.1217. found, 421.1220.

Sensor 34.

40 (20 mg, 0.036 mmol) was dissolved in 500 μL dry DMF. Then, HATU (31 mg, 0.8 mmol), 41 (30.05 mg, 0.8 mmol) and DIPEA (14 μl, 0.08 mmol) were added. The reaction mixture was stirred at room temperature overnight and monitored by HPLC. The solvent was evaporated under reduced pressure and the residue was purified by reversed-phase HPLC (5.13 mg, 11%).

$^1$HNMR (400 MHz, DMSO-d$_6$): δ=1.24-1.64 (m, 12H), 2.04 (t, J=8 Hz, 4H), 2.60 (d, J=12 Hz, 2H), 2.74-2.84 (m, 6H), 3.06-3.11 (m, 2H), 3.12-3.20 (m, 8H), 3.24-3.4 (m, 12H), 3.45 (s, 4H), 4.11-4.14 (m, 2H), 4.29-4.32 (m, 2H), 4.82 (q, J=8 Hz, 4H), 6.30 (m, 4H), 7.06 (s, 1H), 7.37-7.45 (m, 2H), 7.60-7.80 (m, 5H), 7.99-8.05 (m, 3H), 8.13-8.15 (m, 2H), 8.55 (d, J=8 Hz, 1H), 8.76 (d, J=8 Hz, 1H). $^{13}$C NMR (100 MHz, DMSO-d$_6$): δ=25.0, 27.8, 27.9, 33.2, 34.2, 34.9, 38.2, 38.6, 42.6, 50.6, 55.1, 59.1, 60.9, 68.7, 69.2, 88.1, 107.7, 112.88, 117.8, 122.6, 123.8, 124.2, 124.4, 125.6, 126.6, 127.9, 133.1, 136.8, 139.7, 144.8, 148.7, 159.5, 162.5, 168.8, 169.5, 171.9. HRMS-ESI (m/z): calcd. for $C_{55}H_{77}N_{10}O_{10}S_3$ [M−I] 1133.4981. found, 1133.4970.

Sensor 35.

40 (20 mg, 0.036 mmol) was dissolved in 500 μl dry DMF. Then HATU (31 mg, 0.8 mmol), 42 (23 mg, 0.8 mmol) and DIPEA (14 μL, 0.08 mmol) were added. The reaction mixture was stirred at room temperature overnight and monitored by HPLC. The solvent was then evaporated under reduced pressure and the residue was purified by reversed-phase HPLC (6 mg, 15%).

$^1$HNMR (400 MHz, DMSO-d$_6$): δ=1.25-1.61 (m, 12H), 1.98-2.04 (m, 4H), 2.26-2.34 (m, 4H), 2.56-2.59 (m, 2H), 2.66-2.82 (m, 6H), 2.99-3.07 (m, 10H), 4.10-4.13 (m, 2H), 4.28-4.31 (m, 2H), 4.83 (q, J=8 Hz, 4H), 6.27, 6.29 (s, 2H), 6.38 (br-s, 2H), 7.06 (s, 1H), 7.39-7.45 (m, 2H), 7.60-7.67 (m, 2H), 7.74-7.80 (m, 2H), 7.97-8.05 (m, 3H), 8.15 (d, J=8 Hz, 1H), 8.57 (d, J=8 Hz, 1H), 8.77 (d, J=8 Hz, 1H). HRMS-ESI (m/z): calcd. for $C_{23}H_{61}N_2O_4S$ [M−I] 957.3932. found, 957.3923.

Figure 5:
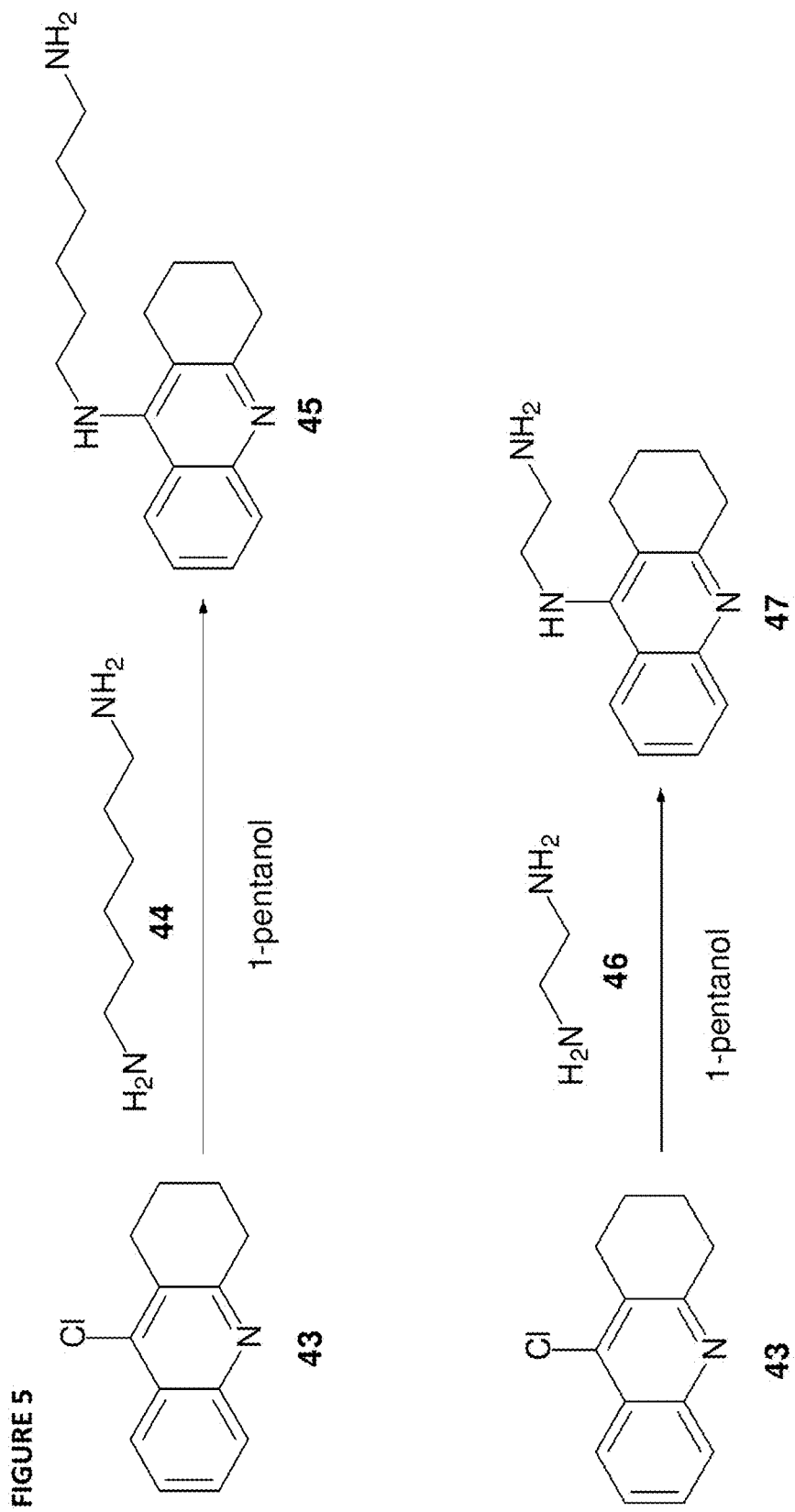
FIG. 5 depicts a synthetic scheme for sensors 36 and 37 an acetylcholinesterase sensors based on a TO-bis-tacrine conjugate.

B. Synthesis of Sensors 36 and 37 (FIG. 5)

N-(1,2,3,4-tetrahydroacridin-9-yl)hexane-1,6-diamine (45)

43 (200 mg, 0.918 mmol) and hexamethylenediamine, 44, (359.84 μL, 2.75 mmol) were refluxed in 1 mL pentanol for 16 h. Then, the reaction mixture was cooled to room temperature and evaporated under reduced pressure. The crude was purified by column chromatography (9:1:1, DCM:MeOH:NH3) to yield a brown oil (115.26 mg, 42%).

$^1$HNMR (400 MHz, CDCl$_3$): δ=1.34-1.45 (m, 6H), 1.64 (quin, J=8 Hz, 2H), 1.91 (m, 4H), 2.64-2.70 (m, 4H), 3.05 (m, 2H), 3.47 (t, J=8 Hz, 2H), 3.94 (br-s, 1H), 7.33 (t, J=8 Hz, 1H), 7.53 (t, J=8 Hz, 1H), 7.88-7.95 (m, 2H). $^{13}$C NMR (100 MHz, CDCl3): δ=22.9, 23.1, 24.9, 26.7, 26.9, 31.8, 33.6, 34.1, 42.1, 49.5, 116.0, 120.3, 122.9, 123.7, 128.4, 128.8, 147.5, 150.9, 158.5. HRMS-ESI (m/z): calcd. for $C_{19}H_{27}N_3$ [M+H] 298.2283. found, 298.2267.

Sensor 36.

EDCI (8.39 mg, 0.044 mmol) and HOBT (5.93 mg, 0.0438 mmol) were added to a solution of 40 (10 mg, 0.018 mmol) in dry DMF (1 mL) at 0° C. This mixture was kept at 0° C. for 15 min. Then, 45 (11.93 mg, 0.04 mmol) was added and the reaction mixture was stirred at room temperature overnight and monitored by HPLC. The solvent was evaporated under reduced pressure and the residue was purified by reversed-phase HPLC (3.21 mg, 15%)

$^1$HNMR (400 MHz, DMSO-d$_6$): δ=1.12-1.32 (m, 12H), 1.60-1.69 (m, 4H), 1.83 (m, 8H), 2.62 (m, 4H), 2.68-2.77 (m, 4H), 2.93-3.0 (m, 8H), 3.77 (q, J=8 Hz, 4H), 4.74-4.83 (m, 4H), 7.03 (s, 1H), 7.33-7.40 (m, 2H), 7.51-7.59 (m, 2H), 7.63-7.70 (m, 2H), 7.75 (t, J=8 Hz, 1H), 7.80-7.85 (m, 4H), 7.94-8.05 (m, 3H), 8.13 (d, J=8 Hz, 1H), 8.33 (t, J=8 Hz, 1H), 8.54 (d, J=8 Hz, 1H), 8.75 (d, J=8 Hz, 1H). $^{13}$C NMR (100 MHz, DMSO-d$_6$): δ=20.1, 21.2, 23.6, 25.5, 25.7, 27.7, 28.6, 29.6, 33.3, 34.3, 38.4, 42.7, 47.1, 50.7, 88.1, 107.6, 111.0, 112.8, 115.3, 117.8, 118.9, 122.5, 123.7, 124.2, 124.3, 124.7, 124.8, 125.6, 126.6, 127.9, 132.5, 133.1, 136.8, 137.6, 139.6, 144.8, 148.7, 150.4, 155.5, 159.4, 168.5, 169.1. HRMS-ESI (m/z): calcd. for $C_{61}H_{71}N_8O_2S$ [M−I] 979.5415. found, 979.5419.

N-(1,2,3,4-tetrahydroacridin-9-yl)ethane-1,2-diamine (47)

43 (200 mg, 0.918 mmol) and 1,2-diaminoethane, 46, (184.1 μL, 2.75 mmol) were refluxed in 1 mL pentanol for 16 h. Then, the reaction mixture was cooled to room temperature and evaporated under reduced pressure. The crude was purified by column chromatography (9:1:1 DCM:MeOH:NH3) to yield a brown oil (70.45 mg, 32%).

$^1$HNMR (300 MHz, CDCl$_3$): δ=1.92 (m, 4H), 2.75 (m, 2H), 2.99 (t, J=6 Hz, 2H), 3.12 (m, 2H), 3.60 (t, J=6 Hz, 2H), 7.36 (t, J=9 Hz, 1H), 7.58 (t, J=9 Hz, 1H), 8.06 (d, J=9 Hz, 2H). $^{13}$C NMR (100 MHz, CDCl$_3$): δ=22.9, 23.1, 24.9, 34.0, 42.5, 51.1, 116.6, 120.5, 122.9, 123.8, 128.4, 128.7, 147.4, 151.1, 158.5. HRMS-ESI (m/z): calcd. for $C_{15}H_{19}N_3$ [M+H] 242.1657. found, 242.1660.

Sensor (37).

EDCI (8.39 mg, 0.0438 mmol) and HOBT (5.93 mg, 0.044 mmol) were added to a solution of 40 (10 mg, 0.0182 mmol) in dry DMF (1 mL) at 0° C. The reaction mixture was kept at 0° C. for 15 min. Then, 47 (9.67 mg, 0.04 mmol) was added and the reaction mixture was stirred at room temperature overnight and monitored by HPLC. The solvent was evaporated under reduced pressure and the residue was purified by reversed-phase HPLC (2.85 mg, 16%).

$^1$HNMR (400 MHz, DMSO-$d_6$): δ=1.75-1.82 (m, 8H), 2.44 (m, 4H), 2.74-2.80 (m, 4H), 2.90-2.93 (m, 4H), 3.38-3.43 (m, 4H), 3.75-3.85 (m, 4H), 4.71-4.76 (m, 4H), 5.06 (t, J=8 Hz, 1H), 5.31 (t, J=8 Hz, 1H), 6.86 (s, 1H), 7.04 (d, J=8 Hz, 1H), 7.32-7.47 (m, 3H), 7.57-7.78 (m, 7H), 7.82-7.93 (m, 2H), 7.97 (d, J=12 Hz, 1H), 8.08-8.10 (m, 1H), 8.27-8.31 (m, 1H), 8.9 (d, J=8 Hz, 1H), 8.55 (t, J=8 Hz, 1H), 8.61-8.63 (m, 1H). HRMS-ESI (m/z): calcd. for $C_{53}H_{55}N_8O_2S$ [M−I] 867.4163. found, 867.4166.

Figure 6:
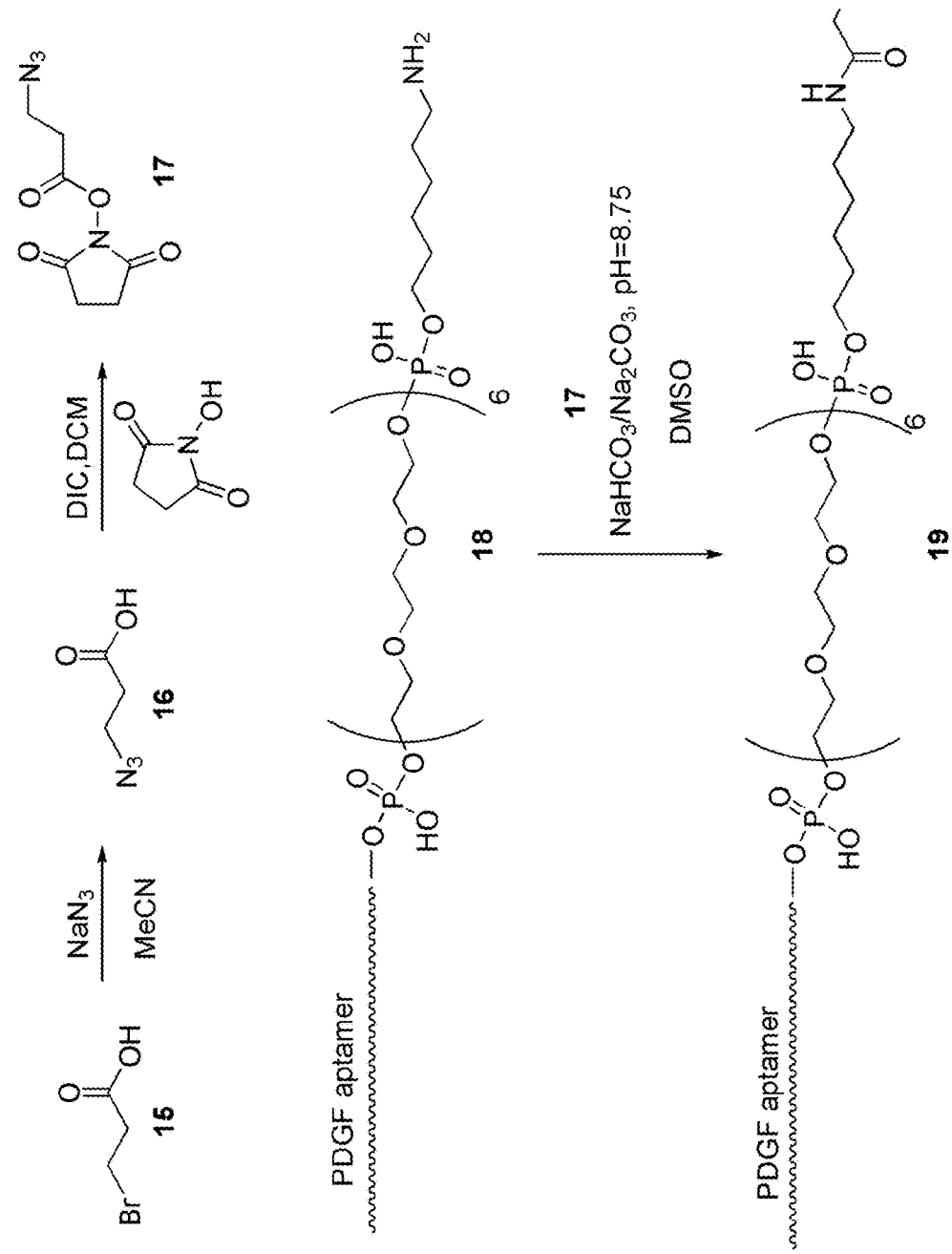
FIG. 6 depicts a synthetic scheme of sensor 20—a PDGF-BB sensor based on a TO-bis PDGF aptamer.
Figure 6:
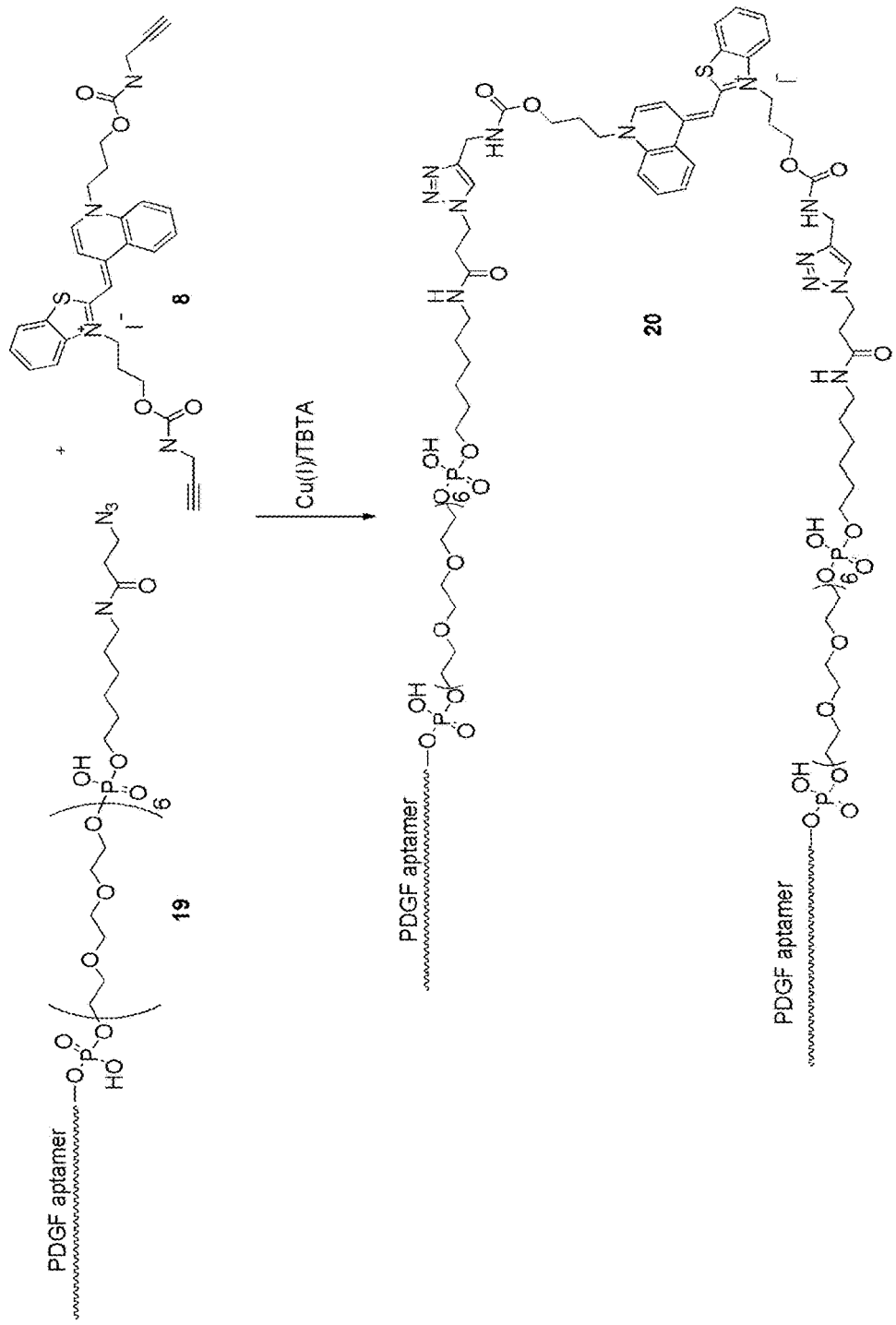

C. Synthesis of PDGF-BB Sensor Based on Thiazole Orange (FIG. 6, Sensor 20)

3-azidopropanoic acid (16)

Sodium azide (3 g, 46 mmol) was added to a solution of 3-bromopropionic acid (6 g, 39.2 mmol) in 60 mL acetonitrile. The reaction mixture was refluxed for 8 h at 75° C. After filtration and evaporation, 50 mL ethyl acetate was added and the mixture was washed with 0.1M HCl (×3), H2O 2O (×3), brine, dried over MgSO4 and concentrated at reduce pressure, yielding 1.85 g (40%).

$^1$HNMR (300 MHz, CDCl3): δ=2.65 (t, J=6 Hz, 2H); 3.59 (t, J=6 Hz, 2H); 10.85 (bs, 1H). ES-MS (m/z): calcd.: 115.04. found: 137.93 (M+Na), 113.95 (M−H).

3-azidopropanoic acid succinimidyl ester (17)

N-hydroxysuccinimide (0.96 g, 8.347 mmol) and N,N'-diisopropyldiimide (DIC) (1.077 mL, 6.956 mmol) were added to a solution of 3-azidopropionic acid (0.8 g, 6.956 mmol) in 8 mL dry DCM. The reaction mixture was stirred at room temperature overnight and monitored by TLC (3% MeOH:DCM). The reaction mixture was washed twice with 0.1N HCl and brine (×2), dried over sodium sulfate and further purified by combiflash (2% MeOH:DCM) to yield a clear oil (47%).

$^1$HNMR (300 MHz, CDCl3): δ=2.84 (s, 4H); 2.88 (t, J=6 Hz, 2H); 3.68 (t, J=6 Hz, 2H). ES-MS (m/z): calcd: 212.05. found: 235.03 (M+Na).

Azide-Modified PDGF-Aptamer (19).

PDGF aptamer (100 nmol) was dissolved in water (34 µL). $Na_2CO_3$/$NaHCO_3$ buffer (86 µL, 0.5M, pH 8.75) was added and incubated for 12 h at room temperature with 15 µmol of compound 17 in 1.2 mL of DMSO. The crude oligonucleotide was desalted by Micro Spin™ G-25 columns (GE Healthcare) according to the manufacturer's instructions and purified by reversed-phase HPLC. Yield: 22 nmol (22%).

MALDI-TOF MS (m/z):calcd.: 15087. found: 15295.3.

Thiazole Orange-DNA Conjugate (20).

Triethylammonium acetate buffer (10 µL, 0.1M, pH 7.0) was added to a solution of TO-dialkyne 8 (2 nmol) in DMSO. The azide-modified oligonucleotide (19) (20 nmol, 10 equiv.) was dissolved in water and added to the mixture. Then ascorbic acid (40 µL, 5 mM) was added and the reaction mixture was degassed by bubbling argon gas for 30 seconds. After Copper(I)-TBTA (20 µL, 10 mM) was added, the solution was flushed with argon and mixed thoroughly. The reaction solution was stirred at room temperature overnight. The desired product, 20, was purified by reversed-phase HPLC. Yield: 2 nmol (10%).

MALDI-TOF MS (m/z):calcd.: 30856. found: 31202.59.

Figure 7:
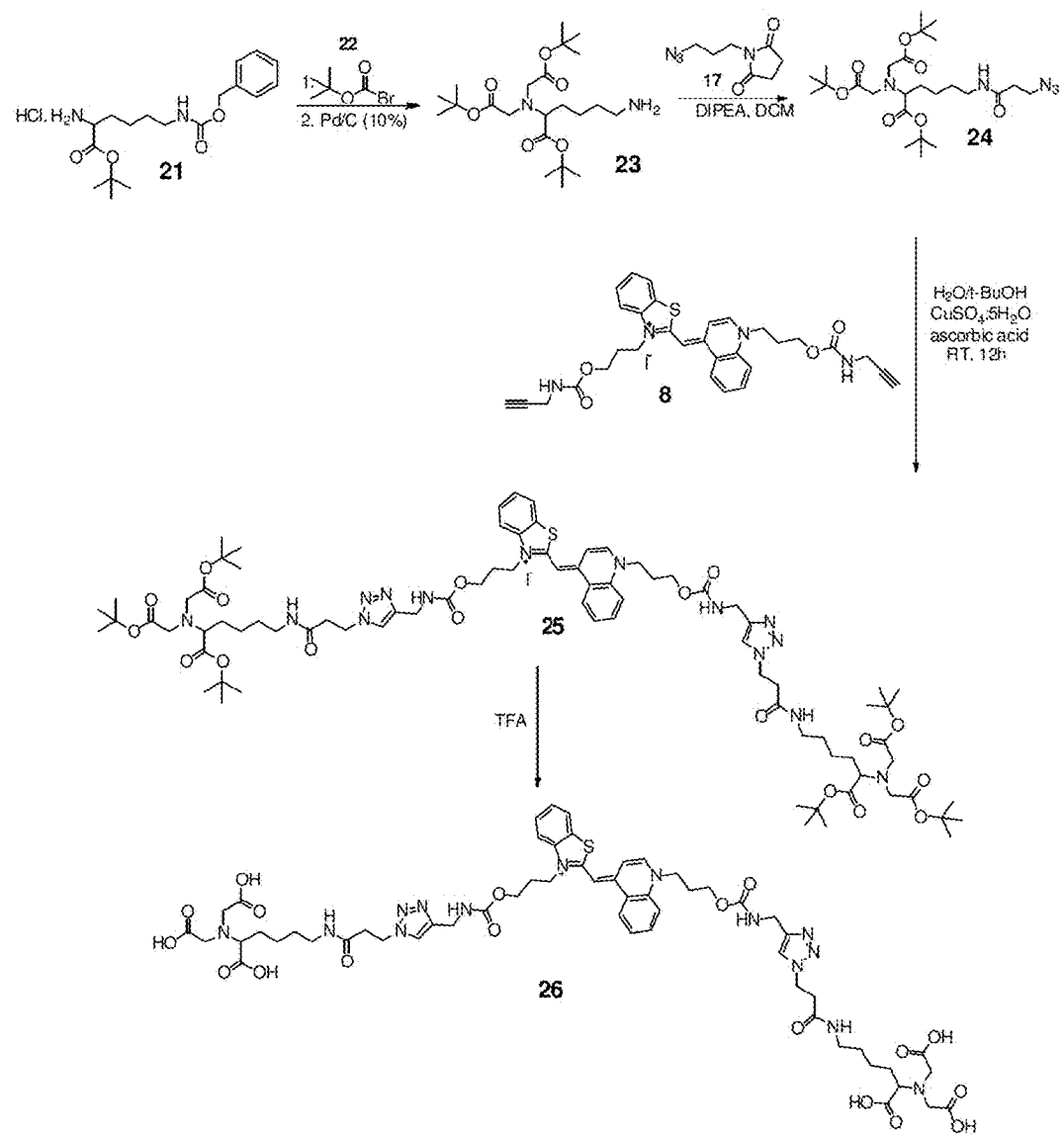
FIG. 7 depicts a synthetic scheme of sensor 26—a Histidine tagged proteins based on a TO-bis-Ni-NTA.

D. Synthesis of Histidine Tagged Protein Sensor Based on Thiazole Orange (FIG. 7, Sensor 26)

2-(Bis-tert-butoxycarbonylmethyl-amino)-6-carboxyamino-hexanoic acid tert-butyl ester (23)

Tert-Butyl bromoacetate (1.59 mL, 10.8 mmol) and DIPEA (2.30 mL, 13.5 mmol) were added sequentially to a solution of N-benzyloxycarbonyl-L-lysine tert-butyl ester (21) (1.00 g, 2.7 mmol) in DMF (25 mL). The reaction mixture was purged with argon and then continuously stirred overnight at 55° C. The reaction mixture was evaporated in vacuum at 60° C. Hexane:ethylacetate (3:1, 15 mL) mixture was added to the partially solidified reaction mixture. The reaction mixture was filtered over a sintered glass funnel and the precipitate was washed three times with the same solvent (3×10 mL). The filtrate was concentrated under reduced pressure and purified by combiflash (9% hexane/ethylacetate). Yield: 0.572 g (65%).

$^1$HNMR (300 MHz, CDCl3); δ=1.42 (s, 18H), 1.44 (s, 9H), 1.52 (m, 4H), 1.61 (m, 2H), 3.17 (m, 2H), 3.28 (t, J=6 Hz, 1H), 3.44 (q, J=18 Hz, 4H), 5.07 (s, 2H), 5.13 (t, 1H), 7.33 (m, 5H). ES-MS (m/z): calcd.: 564.71. found: 587.36 (M+Na), 1151.69 (2M+Na).

Benzyl deprotection was obtained by dissolving the intermediate (0.572 g, 1.01 mmol) in methanol (28.6 ml); the resulting solution was purged with argon followed by addition of 10% Pd/C (11 mg). The reaction mixture was stirred overnight under a H2 atmosphere at room temperature. Pd/C was removed by filtration over celite and the reaction mixture was evaporated under reduced pressure, yielding compound 23. Yield: 0.420 g (96%).

$^1$NMR (300 MHz, CDCl3); δ=1.42 (s, 18H), 1.44 (s, 9H), 1.52 (m, 4H), 1.64 (m, 2H), 2.55 (bs, 2H), 2.73 (t, J=6 Hz, 2H), 3.31 (t, J=6 Hz, 1H), 3.47 (q, J=14 Hz, 4H). ES-MS (m/z): calcd: 430.58. found: 431.35 (MH+), 453.36 (M+Na), 861.61 (2M+1), 883.61 (2M+Na).

di-tert-butyl 2,2'4(6-(3-azidopropanamido)-1-(tert-butoxy)-1-oxohexan-2-yl)azanediyl)diacetate (24)

DIPEA (93 µL, 0.534 mmol) was added to a solution of amino-modified nitrilo-triacetic-acid (NTA) 23 (0.23 g, 0.534 mmol) and 3-azidopropanoic acid succinimidyl ester 17 (0.136 g, 0.640 mmol) in dry DCM (2.5 mL). The reaction mixture was stirred at room temperature overnight and monitored by TLC (5% MeOH:DCM). The reaction mixture was washed three times with water (10 mL) and brine (10 mL), dried over sodium sulfate and evaporated under vacuum. Yield: 0.085 g (30%).

$^1$HNMR (300 MHz, $CDCl_3$); δ=1.44 (s, 18H), 1.47 (s, 9H), 1.50 (m, 6H), 1.60 (m, 2H), 2.48 (t, J=6 Hz, 2H), 3.30 (m, 4H), 3.43 (t, 1H) 3.60 (t, J=6 Hz, 2H), 6.53 (bs, 1H). ES-MS (m/z): calcd: 527.33. found: 550.36 (M+Na), 1077.74 (2M+Na).

Thiazole Orange with Nitrilotriacetic Acid (NTA) (25 and 26)

8 (3.3 mg, 4.83×10$^{-3}$ mmol) and NTA-$N_3$, 24, (6.378 mg, 0.012 mmol) were dissolved in 375 µL DMSO:$H_2$O:tBuOH (1:1:1). Then ascorbic acid (0.1278 mg, 7.25×10$^{-4}$ mmol, 15% mol) was added and the reaction mixture was degassed by bubbling argon gas for 30 seconds. Then, copper sulfate pentahydrate (0.06 mg, 2.42×10$^{-4}$ mmol, 5% mol) was added to the solution and the solution was flushed with argon. The reaction mixture was stirred at room temperature overnight, evaporated, and purified by preparative HPLC (25%).

ES-MS (m/z): calcd.: 1610. found: 1610.08 (M$^+$), 816.80 (M+Na)/2, 552.26 (M+2Na)/3.

TFA deprotection was performed in TFA:DCM (50%:50%) at room temperature for 5 h to obtain the desired product, compound 26.

Figure 8:
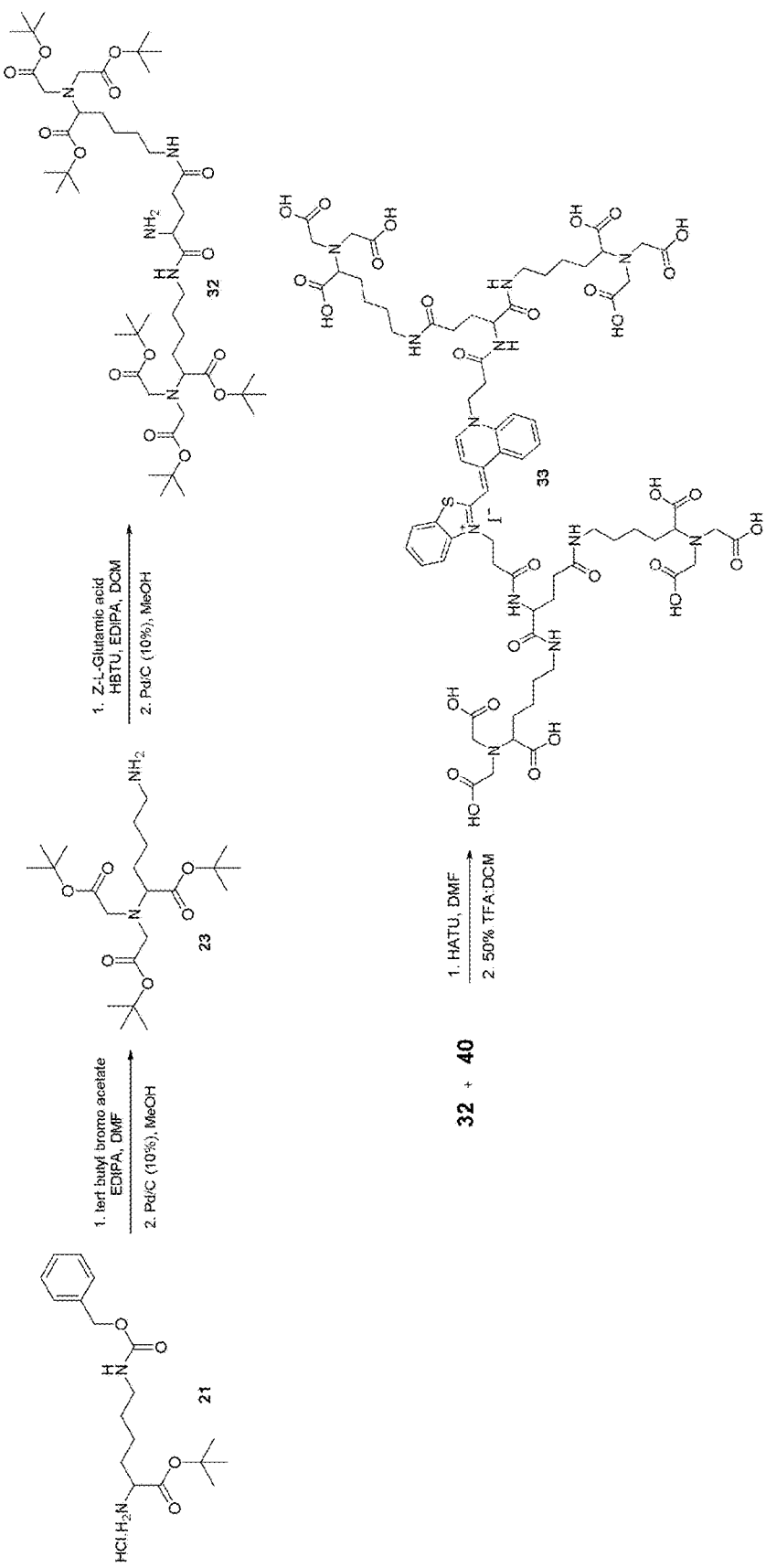
FIG. 8 depicts the synthetic scheme of sensor 33—a Histidine tagged proteins based on a TO-tetrakis-Ni-NTA 33.

E. Synthesis of 3-(3-oxo-3-((1,3,19,21-tetracarboxy-2,20-bis(carboxymethyl)-9,13-dioxo-2,8,14,20-tetraazahenicosan-10-yl)amino)propyl)-2-((1-(3-oxo-3-((1,3,19,21-tetracarboxy-2,20-bis(carboxymethyl)-9,13-dioxo-2,8,14,20-tetraazahenicosan-10-yl)amino) propyl)quinolin-4(1H)-ylidene)methyl)benzo thiazol-3-ium iodide (FIG. 8, sensor 33)

Tetra-tert-butyl-10-amino-2,20-bis(2-(tert-butoxy)-2-oxoethyl)-9,13-dioxo-2,8,14,20-tetraazahenicosane-1,3,19,21-tetracarboxylate (32)

23 (0.25 g, 0.58 mmol) was dissolved in dry dichloromethane (40 ml) then cooled in an ice bath to 0° C. Then Z-L-Glutamic acid (0.0576 g, 0.205 mmol), HBTU (0.225 g, 0.594 mmol) and DIPEA (124.8 µl, 0.716 mmol) were added. The resulted slurry solution was purged with $N_2$ and stirred overnight at room temperature. The volatiles were then removed under reduced pressure and the crude was partitioned between dichloromethane (25 ml) and water (3×7.5 ml). The organic phase was dried over anhydrous sodium sulphate and the volatiles were removed under reduced pressure to obtain an oily mass which was further purified by combiflash with DCM:MeOH. Yield: 0.99 g (0.9 mmol), 90%.

$^1$HNMR (300 MHz, CDCl$_3$); δ=1.43 (s, 36H), 1.45 (s, 18H), 1.45-1.67 (m, 12H), 2.30-2.36 (m, 2H), 3.2-3.3 (m, 2H), 3.36-3.5 (m, 6H), 3.46 (m, 8H), 3.56 (m, 1H), 6.34 (d, 1H), 6.55 (s, 1H), 7.07 (s, 1H), 7.34 (s, 5H). ES-MS (m/z): calcd: 1105.68. found: 1106.76 (MH+), 1129.76 (M+Na), 564.94 ((M+Na)/2).

Benzyl group was deprotected by dissolving the intermediate (0.572 g, 1.01 mmol) in methanol (28.6 ml); the resulting solution was purged with argon followed by addition of 10% Pd/C (11 mg). The reaction mixture was stirred overnight under a H$_2$ atmosphere at room temperature. Pd/C was removed by filtration over celite and the reaction mixture was evaporated under reduced pressure, yielding compound 3. Yield: 0.420 g (96%).

$^1$HNMR (300 MHz, CDCl$_3$); δ=1.43 (s, 36H), 1.45 (s, 18H), 1.47-1.65 (m, 12H), 2.37-2.44 (m, 2H), 3.2-3.3 (m, 2H), 3.36-3.5 (m, 6H), 3.46 (m, 8H), 3.56 (m, 1H). ES-MS (m/z): calcd: 971.64. found: 972.66 (MH+), 994.59 (M+Na), 497.87 ((M+Na+H)/2), 508.83 ((M+2Na)/2).

3-(3-oxo-34(1,3,19,21-tetracarboxy-2,20-bis(carboxymethyl)-9,13-dioxo-2,8,14,20-tetraazahenicosan-10-yl)amino)propyl)-2-((1-(3-oxo-3-((1,3,19, 21-tetracarboxy-2,20-bis(carboxymethyl)-9,13-dioxo-2,8,14,20-tetraazahenicosan-10-yl)amino) propyl)quinolin-4(1H)-ylidene)methyl)benzo thiazol-3-ium iodide (33)

31 (50 mg, 0.091 mmol) was dissolved in 1.2 ml dry DMF, HATU (76.26 mg, 0.2 mmol), Bis NTA (32, 194.9 mg, 0.2 mmol) and DIPEA (63.53 µL, 0.364 mmol) were added. The reaction mixture was stirred under RT overnight and evaporated under reduced pressure. Then the reaction mixture was re-dissolved in 50 ml DCM and extracted with water (3×10 ml) and dried over Na$_2$SO$_4$. The crude was further purified by combiflash with DCM:MeOH.

ES-MS (m/z): calcd: 2455.29. found: 2328 (M–I$^-$), 1187 ((M+2Na–I$^-$)/2), 1176.5 ((M+Na+H–I$^-$)/2), 799.62 ((M+3Na)/3), 792.02 ((M+2Na+H–I$^-$)/3), 784.4 ((M+Na+2H–I$^-$)/3).

Deprotection of Tert-Butyl:

TO-bis NTA (5.5 mg, 2.2 mmol) was dissolved in 500 µL DCM and 500 µL TFA. The reaction mixture was stirred at RT for 5 h, then the mixture was evaporated to yield the desired product.

ES-MS (m/z): calcd: 1782.54. found: 1655 (M–I$^-$), 840.3 ((M+Na+H–I$^-$)/2) 559.87 to ((M+Na+2H–I$^-$)/3).

Example 3

Spectral Characterization of Thiazole Orange (TO) Derivatives (Sensor 14)

Figure 9:
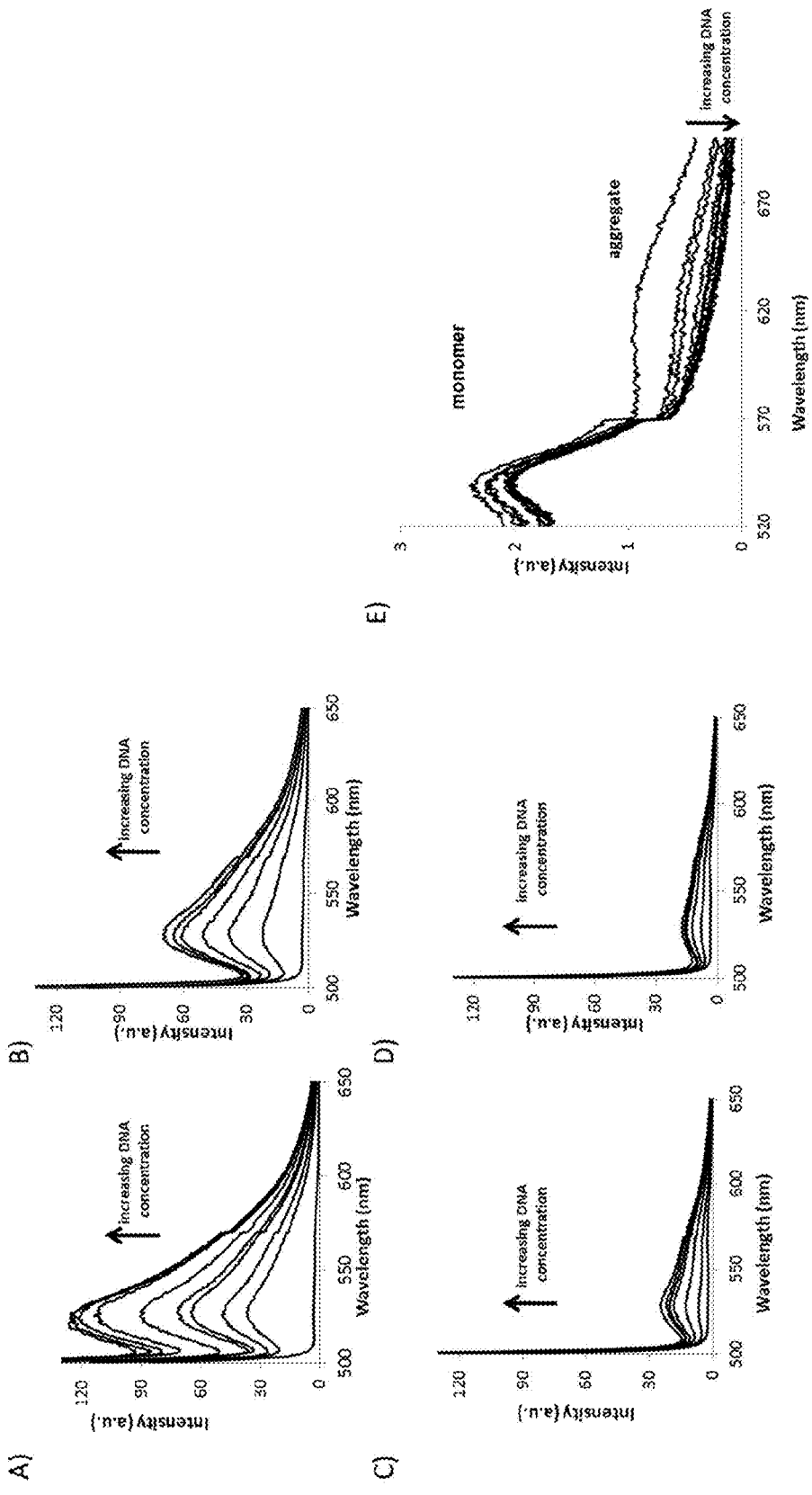
FIG. 9 depicts enhancement of the fluorescence of the different TO derivatives (500 nM) upon addition of 100-900 nM dsDNA in PBS buffer pH=6.5. Figure A)—Unmodified TO; B)—Diol-modified TO (compound 6); C)—Mono-alkyne modified TO; D)—dialkyne modified TO (compound 8); E)—Ethacrynic acid modified, TO (compound 14). $\lambda_{ex}$=480 nm in A-D and $\lambda_{ex}$=4460 nm in E. (See structures in Table 3, Example 3).

Different TO derivatives (Table 3) were incubated with increasing concentrations of double-stranded DNA and compared their fluorescence emission prior to and after their incubation in PBS buffer, pH=6.5 (FIG. 9).

TABLE 3

Structure of different TO derivatives

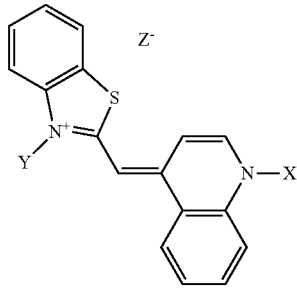

| TO derivative | X | Y | Z |
|---|---|---|---|
| Unmodified TO | X = ⌇CH$_3$ | Y = ⌇CH$_3$ | OTs$^-$ |
| diol-modified TO, compound 6 | X = ⌇∕∖OH | Y = ⌇∕∖OH | I$^-$ |

TABLE 3-continued

Structure of different TO derivatives

[Structure shown: benzothiazolium-methylidene-quinoline cyanine core with substituents Y on benzothiazole N⁺, X on quinoline N, and counterion Z⁻]

| TO derivative | X | Y | Z |
|---|---|---|---|
| monoalkyne-modified TO (compound 27) | X = ~~~CH₂CH₂CH₂—OH   or   ~~~CH₂CH₂—O—C(=O)—NH—CH₂—C≡CH | Y = ~~~CH₂CH₂—O—C(=O)—NH—CH₂—C≡CH   or   ~~~CH₂CH₂—OH | I⁻ |
| dialkyne-modified TO, Compound 8 | X = ~~~CH₂CH₂—O—C(=O)—NH—CH₂—C≡CH | Y = ~~~CH₂CH₂—O—C(=O)—NH—CH₂—C≡CH | I⁻ |
| ethacrynic acid-modified, Compound 14 | | | I⁻ |

In all cases enhanced fluorescence at 530 nm was observed. The addition of dsDNA induces a smaller increase in the emission of all derivatives. The molecular sensor 14, in particular, did not exhibit any change in its fluorescence at 530 nm upon addition of dsDNA. These findings can be attributed to steric effects, in which bulkier substituents hinder the free rotation of TO and, at the same time, disrupt the intercalation of the two heterocycles with dsDNA. In addition, only in the case of sensor 14, which consists of two large ethactynic acid moieties, an emission at 625 nm also observed (FIG. 9E), indicating that the EA moieties not only prevent their binding to DNA, they also promote the formation of H-aggregates, presumably due to additional van der Waals interactions and p-stacking.

Figure 10:
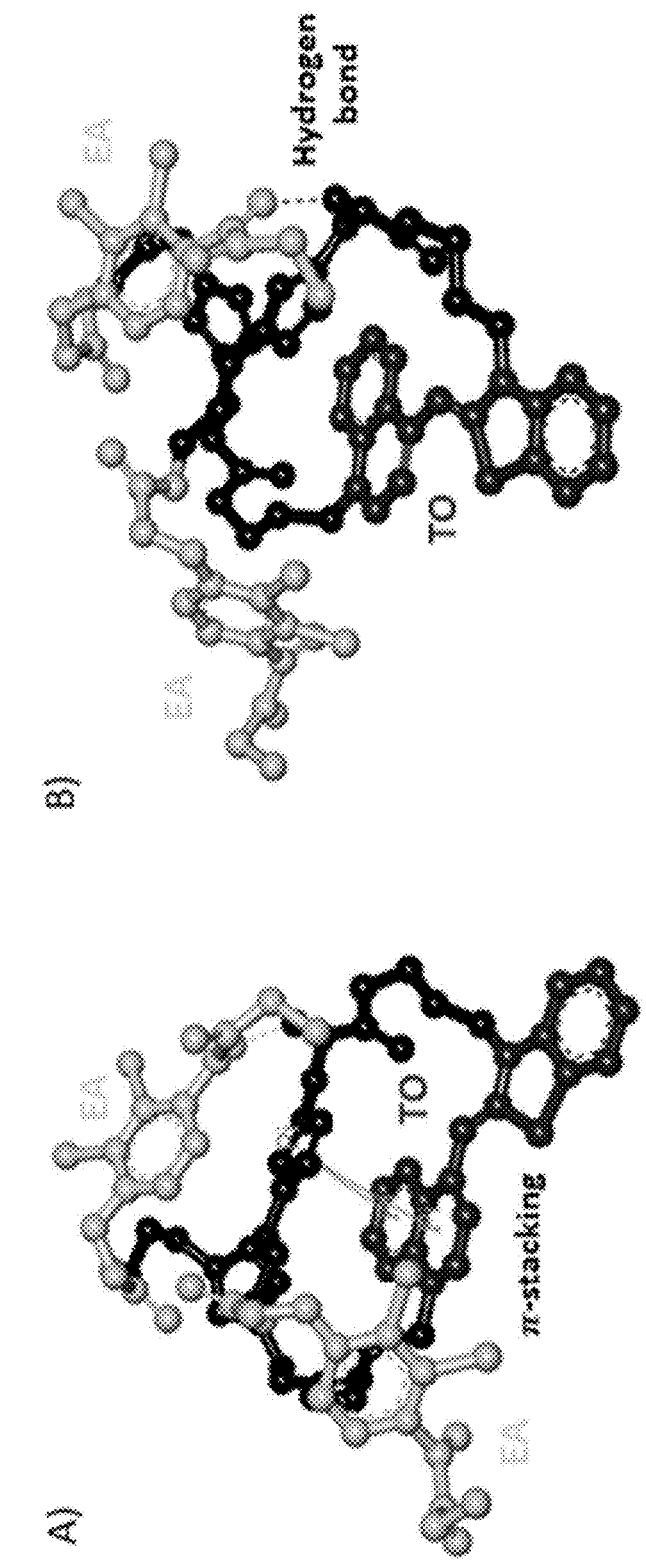
FIG. 10 depicts a DFT optimized structure of sensor 14. A) intramolecular π-stacking between triazole and quinolone rings. B) hydrogen bond between the carbonyl of ethacrynic acid and the carbamate nitrogen. These interactions are expected to restrict the torsional motion of the TO core and the closed conformation of this foldamer should prevent its interaction with dsDNA.

The structure of 14 was optimized by using density functional theory (DFT). The DFT calculations show that the sensor 14 adopts a folded structure in which triazole group forms π-ineraction with the quinoline ring (FIG. 10A) and carbonyl group of ethacrynic acid is hydrogen bonded to the nitrogen of the carbamate (FIG. 10B). These interactions are expected to restrict the torsional motion of the TO core and the closed conformation of this foldamer should prevent its interaction with dsDNA.

Figure 11:
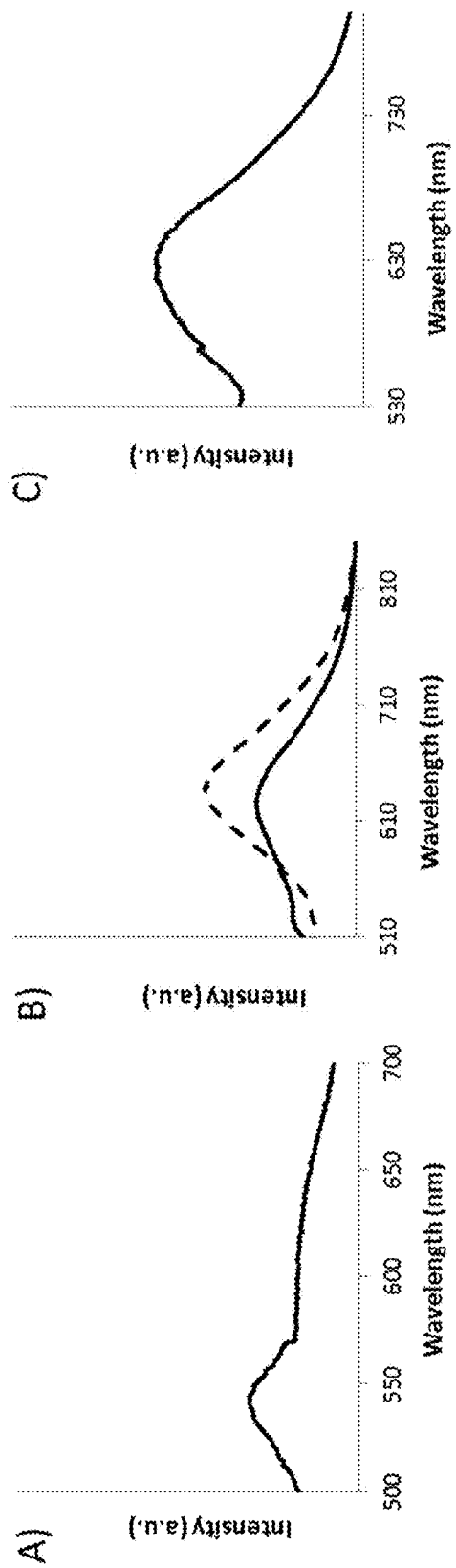

To confirm that the unique emission of sensor 14 at 625 nm was due to self-aggregation, the emission of an unmodified TO obtained under different conditions such as different temperatures and concentrations were compared. As shown in FIG. 11A, the emission spectrum of an unmodified TO (3 μM) consists of two main peaks: a typical monomer fluorescence at 540 nm and a dimer emission at 625 nm Increasing the concentration of TO to 30 μM resulted, in a reduction in the monomer's emission and an enhancement in the dimmer's fluorescence (FIG. 11B solid line 25°). Cooling the mixture to 5° C. completely eliminated TO monomer emission (FIG. 11B, dashed line) and led to an emission spectrum that is comparable to that of sensor 14 at 3 μM and at RT (FIG. 11C).

Example 4

Fluorescence Detection of Different Proteins by TOPI Sensors of the Invention

Figure 12:
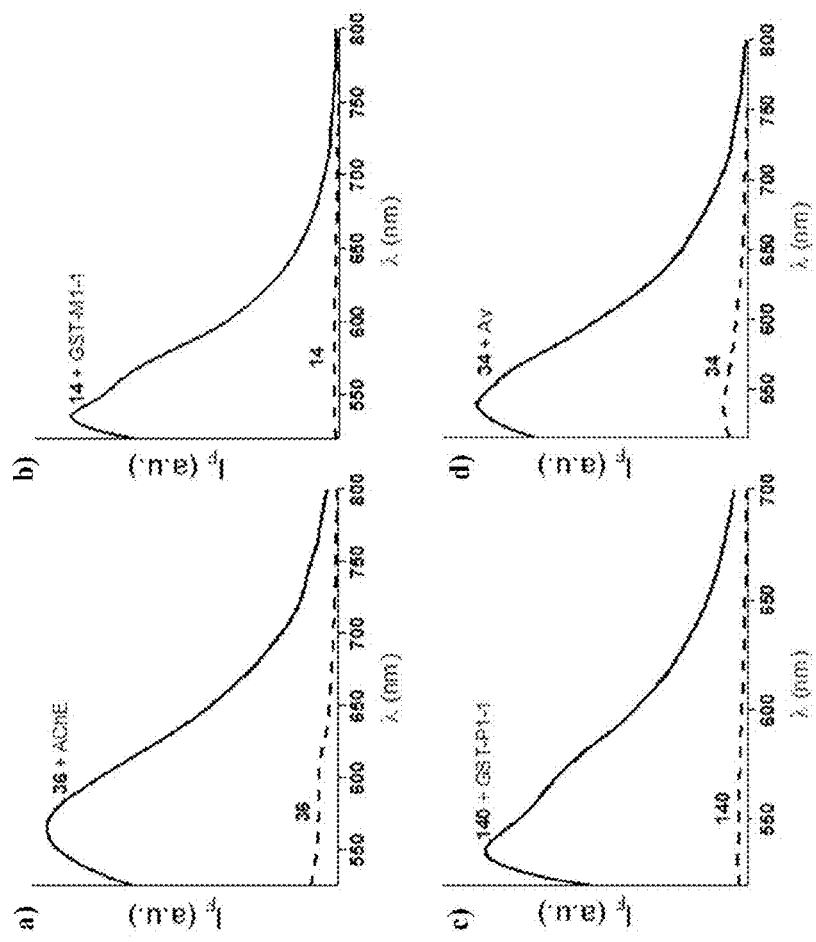
FIG. 12 depicts changes in the fluorescence signal of the most efficient TOPI sensors: a) 36, b) 14, c) 140, and d) 34 (100 nM each) upon the addition of 90 nM of AChE, GST-M1-1, GST-P1-1, and Av, respectively. Excitation wavelengths: a) $\lambda_{ex}$=505 nm, b and c) $\lambda_{ex}$=500 nm, d) $\lambda_{ex}$=495 nm
Figure 13:
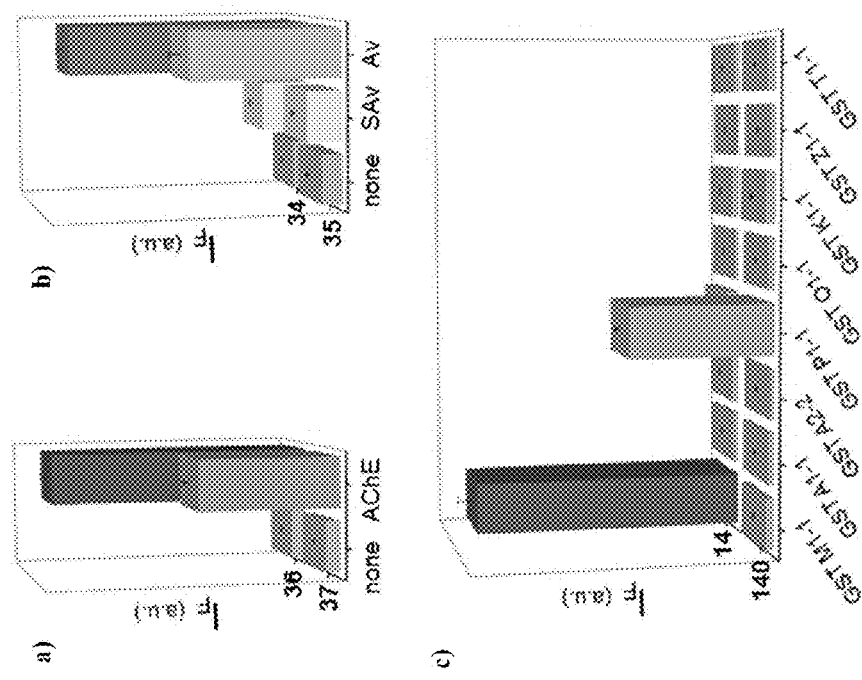
FIG. 13 depicts fluorescence response of 100 nM of a) 36 and 37, b) 34 and 35, and c) 14 and 140, to the addition of 90 nM of AChE, Av and SAv, and various GST isozymes, respectively.

The most efficient TOPI sensors were identified (FIG. 12) by measuring the fluorescence of the six sensors (100 nM) in the absence and presence of their targets (90 nM) (FIG. 13). These measurements revealed that the TOPI sensors not only can identify their targets at low nanomolar concentrations and with high S/N rations—their properties can also be adjusted through the systematic modification of the length and type of linkers.

The ability of compounds 14 and 140 to bind and detect GSTs, a multi-isozyme family that protects the organism from toxic species by conjugating glutathione (GSH) to a variety of electrophilic substrates, was tested. Owing to their role in a myriad of cellular processes and their association with various diseases, as well as their prevalent use as fusion proteins, detecting these enzymes is important for various applications, including inhibitor screening, medical diagnosis, and cellular imaging. For example, to achieve pattern-based GST sensors, recently, a bis-EA inhibitor that can simultaneously bind the two active sites of these dimeric enzymes, was used. In compound 14 and 140, the two EAs were conjugated to the benzothiazole and quinoline rings of TO, not only to achieve tight binding, but also to facilitate the restriction of its intramolecular twisting upon binding to GSTs (FIG. 1C(b)).

Figure 21:
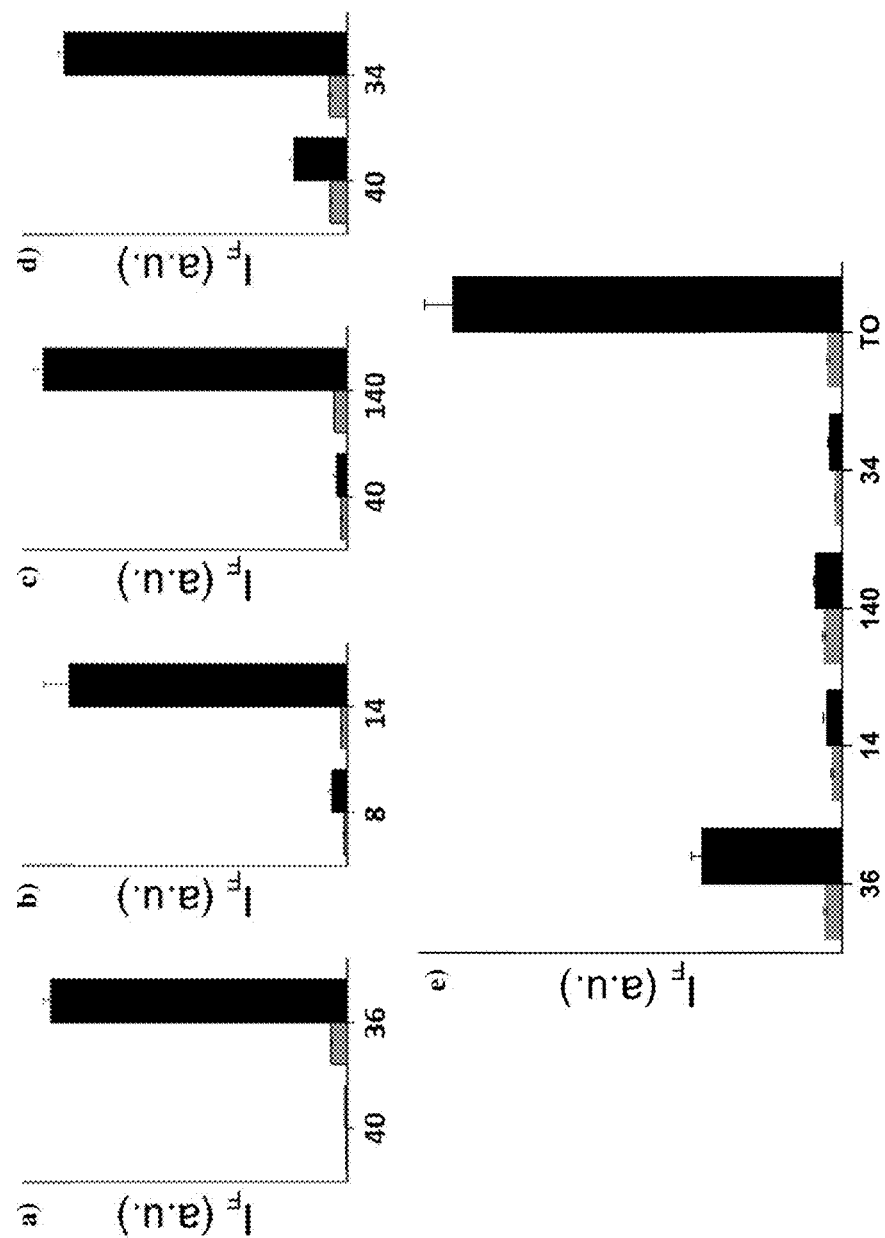
FIG. 21 depicts fluorescence emission of a) 36, b) 14, c) 140, and d) 34 or control compounds 40 or 8 before (grey) and after (black) the addition of AChE, GST-M1-1, GST-P1-1, and Av, respectively (90 nM). (e) Fluorescence of TOPIs and TO (100 nM each) before (grey) and after (black) the addition of dsDNA (400 nM).

Sensor 34 and sensor 35 were designed to detect the avidin (Av) and streptavidin (SAv) tetramers by binding to adjacent biotin binding sites, while sensor 36 and sensor 37 were designed to identify AChE, an important biomarker for the Alzheimer disease, by simultaneously targeting its active site and peripheral site (FIG. 21).

As shown in FIGS. 12 and 13, Av and AChE could be detected by sensor 34 and sensor 36, respectively, at low nanomolar concentration and with high S/N ratios. Sensor 36, for example, which exhibited 22 fold enhancement in its emission, was found to be more efficient than 37, although both sensors could detect AChE (FIG. 13a). to Both of these sensors, however, exhibited high specificity toward their targets (FIGS. 13 and 20) and sensor 36 was found to be a strong bivalent inhibitor of the AChE enzyme (FIG. 16a).

Sensor 34 could detect Av and to a lesser extent SAv (FIGS. 12d and 13b), which can be attributed to binding of TO to surface regions with negative potential connecting the proximate biotin binding sites of Av and SAv. The emission of 34 was more significantly enhanced (16 fold) when compared with 35 (7 fold) (FIG. 13b); however, both sensors responded strongly to Av and weakly to SAv.

The fact that sensor 35 and sensor 37 were found to be less efficient (FIG. 13(a,b)) indicates that the performance of such sensors, could be further improved through a systematic modification of their linkers.

Whereas 36 and 37, or 34 and 35 exhibited similar response trends, the emission of 14 and 140 was distinctly affected by different GST isozymes.

Figure 14:
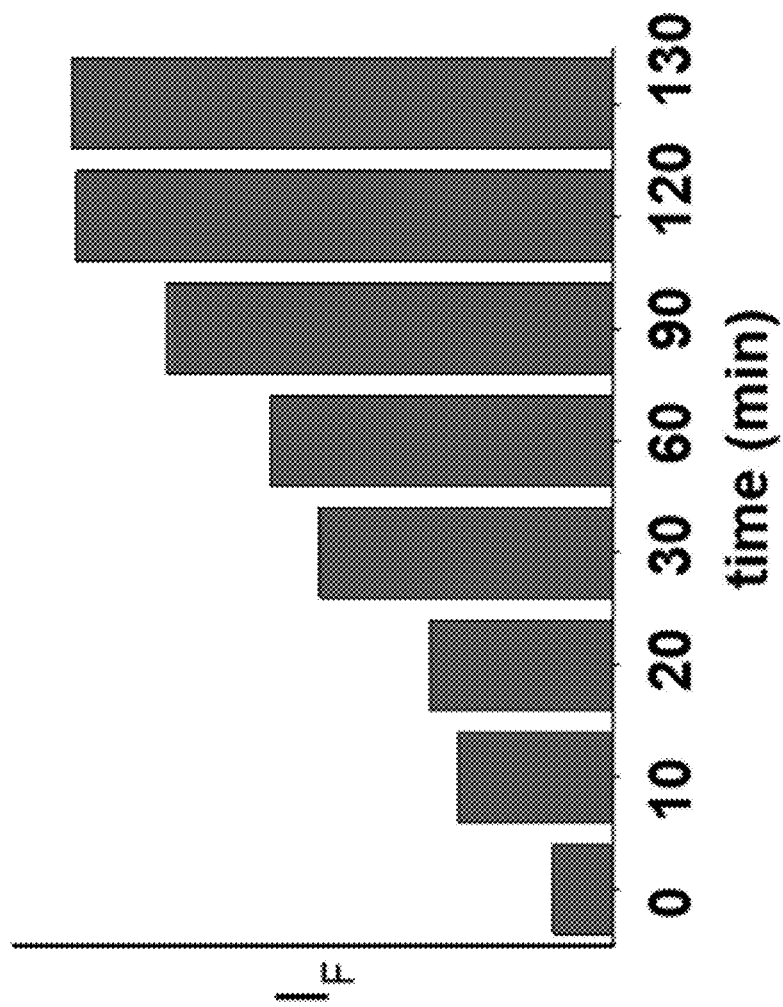
FIG. 14 depicts fluorescence response of compound 14 (100 nM) in the presence of 90 nM of GST P1-1 over a period of 2 h in phosphate buffer (5 mM, pH=6.5), $\lambda_{ex}$=500 nm

Incubation of 14 with eight GST isozymes (e.g., GST-M1-1, GST-A1-1, GST-A2-2, GST-P1-1, GST-Z1-1, GST-01-1, GST-K1-1, and GST-T1-1) resulted in an immediate fluorescence enhancement (55 fold) only in the presence of GST-M1-1 (FIG. 13c), whereas for 140, a strong (33 fold) turn-on fluorescence signal was observed only when it was incubated with GST-P1-1 (FIG. 13c). Interestingly, in the presence of GST-P1-1 the emission of 14 was slowly increased over a period of 2 hours (FIG. 14), which may result from distinct binding kinetics or from structural or chemical transformations that occur upon binding.

Figure 15:
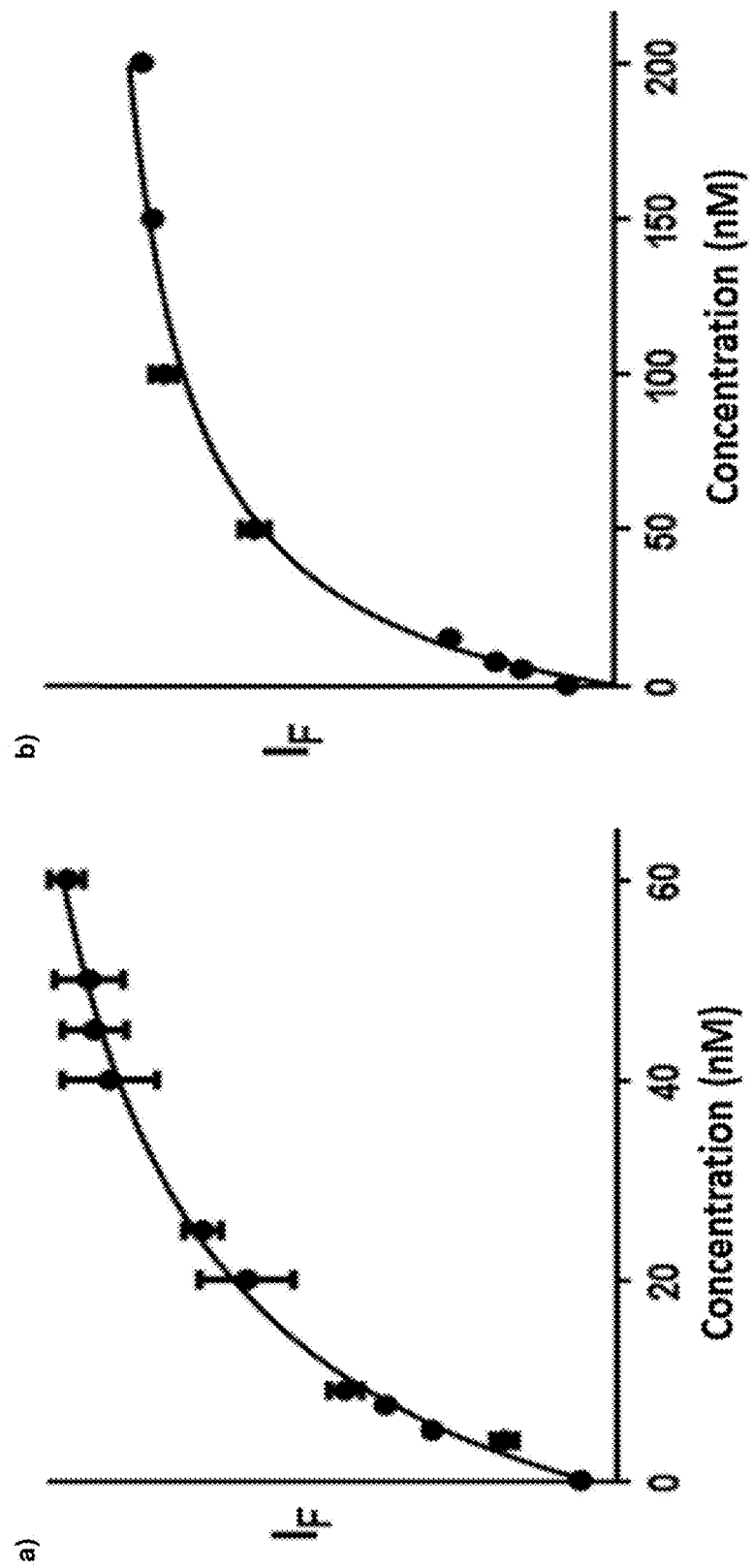
FIG. 15 depicts binding curves obtained for a) GST-M1-1 and compound 14 and b) GST-P1-1 and compound 140 determined by monitoring the emission signal (normalized) of compound 14 or compound 140 upon a gradual addition of GST M1-1 or GST P1-1. The approximate dissociation constants between GST-M1-1 and compound 14, and GST-P1-1 and compound 140 were found to be $K_d$=16.4±2.14 nM, $K_d$=28.97±5.21 nM, respectively.

The approximate dissociation constants for the 14-GST-M1-1 ($K_d$=16 nM±2) and 140-GST-P1-1 ($K_d$=29 nM±5) interactions were also obtained by performing fluorescence binding studies, in which the changes in the emission upon incremental addition of each protein were followed (FIG. 15).

Experimental Details

Fluorescence Measurements (GST Sensing)

Based on the obtained binding constants (FIG. 15), a concentration of 100 nM sensor was chosen for GST sensing. This concentration should ensure strong binding and a high S/N ratio. The fluorescence intensity of sensor 14 or 140 (100 nM) in phosphate buffer (5 mM, pH=6.5) was recorded before and after the addition of 90 nM of different GST isoforms (GST A1-1, GST A2-2, GST P1-1, GST M1-1, GST 01-1, GST K1-1, GST Z1-1, and GST T1-1) using a microplate reader and an excitation wavelength of 500 nm. For sensor 14, fluorescence values were recorded immediately after addition of the GSTs (FIGS. 12b and 13c). The emission of sensor 140 was recorded after 30 mM incubation.

Av and SAv Sensing

Experimental Details

The fluorescence intensity of sensor 34 (100 nM) or sensor 35 (100 nM) in phosphate buffer (15 mM, pH=7.3) was recorded before and after the addition of 90 nM Av or SAv using a microplate reader. Excitation wavelengths for sensor 34 and sensor 35 were 495 nm and 505 nm, respectively. Fluorescence values were recorded immediately after addition of the proteins (FIGS. 12d and 13b).

AChE Sensing

Experimental Details

The fluorescence intensity of sensor 36 (100 nM) or sensor 37 (100 nM) in a phosphate buffer (20 mM, pH=8) was recorded before and after the addition of 90 nM AChE using a microplate reader. Excitation wavelengths for sensor 36 and sensor 37 were 505 nm and 510 nm, respectively. Fluorescence values were recorded immediately after addition of the proteins (FIGS. 12a and 13a).

Example 5

Enzymatic Assays

Figure 16:
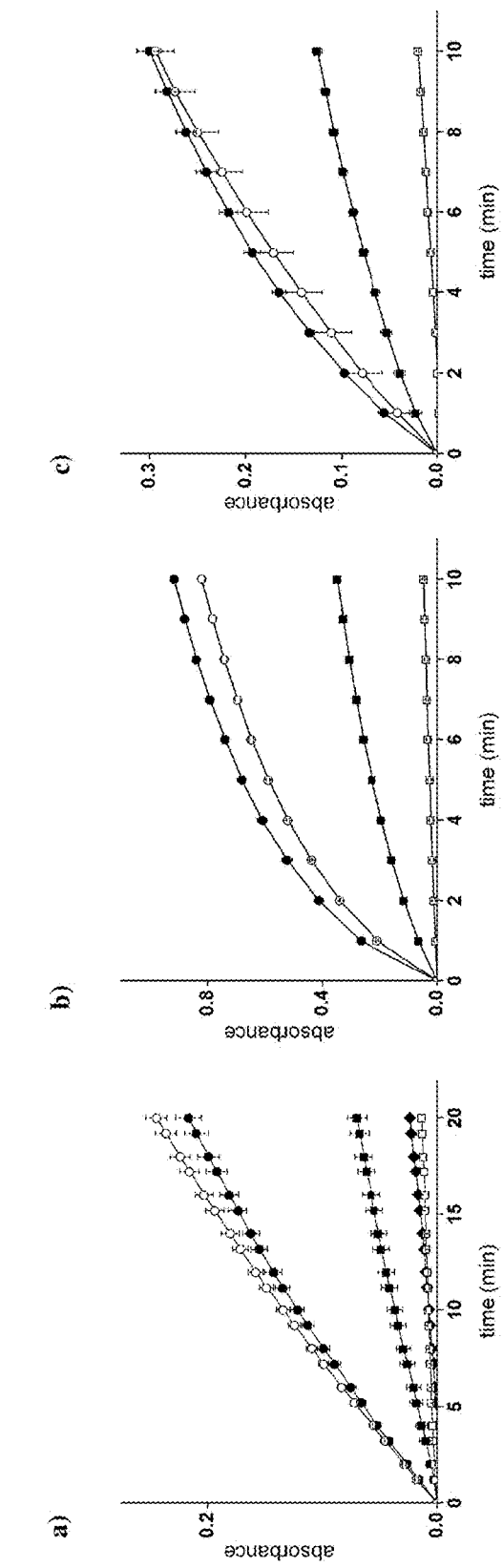
FIG. 16 depicts a) Enzymatic activity of AChE (8 μM) (●) in the presence of 50 nM tacrine (■), 5 μM 8 (○), 2 μM 37 (♦), and 50 nM 36 (□). b, c) Enzymatic activity of 20 nM of GST-M1-1 (b) or GST-P1-1 (c) in the absence (●) and the presence of 500 nM of 14 or 140 (□), respectively, as well as with 5 μM EA (■) or control compounds (40 or 8) (○).
Figure 17:
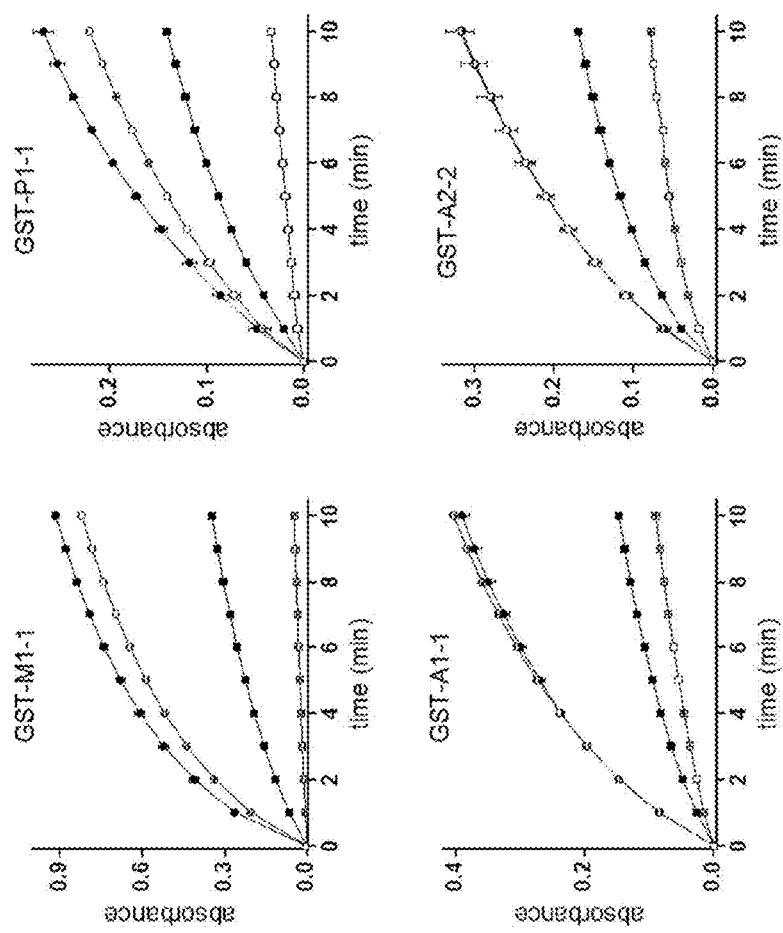
FIG. 17 depicts enzymatic activity of different GST isozymes (20 nM) in the absence (●) and the presence of 5 μM EA (■) 5 μM compound 8(○), or 500 nM compound 14 (□). Enzymatic activity was monitored at 340 nm.

Enzymatic inhibition assays were performed to elucidate the sensing mechanism underlying TOPI sensors (FIGS. 16 and 17). Specifically, these assays were used to determine whether TOPIs bind their targets (a) at the active site, and (b) through a bivalent interaction mode (FIGS. 16 and 17). In addition, these assays were used to investigate (c) whether the local molecular environment of the TO dye plays a role in obtaining enhanced fluorescence signals (FIG. 17). As shown in FIG. 16, the catalytic activity of AChE, GST-M1-1, and GST-P1-1 was followed in the absence and presence of the corresponding sensor (500 nM), as well as with the monovalent inhibitor (tacrine or EA) or a control TO derivative (40 or 8) that lacks the inhibitors. The fact that the three enzymes were hardly inhibited by the control compounds and that the TOPI sensors were found to be considerably more potent than the monovalent inhibitors confirms the manifestation of the "multivalency effect", which results from the simultaneous binding of each sensor at two binding sites within the enzyme.

The same enzymatic assays were used to determine the approximate inhibition constant for the 36—AChE ($K_i$=0.32 nM±0.04), 14—GST-M1-1 (Ki=4 nM±0.6), 14—to GST-A2-2 ($K_i$=20 nM±3), 14—GST-P1-1 ($K_i$=49 nM±5), 14—GST-A1-1 ($K_i$=454 nM±52) and 140—GST-P1-1 (Ki=28.09 nM±3.81) interactions (FIG. 1B, 19 and Table 4) indicating the possibility of detecting these proteins in the low nanomolar range. The $K_i$ values for 14 and 140 are in the same range of the $K_d$ values derived from the fluorescence assay (FIG. 15), which further validates that these sensors bind at the active site, and that non-specific binding of the TO moiety is not the cause of the enhanced emission.

Next, enzymatic assays were used to investigate the reason for the selective response of some of the TOPI sensors toward specific protein isoforms (FIG. 13c). This selectivity may result from enhanced affinity toward these isoforms. Alternatively, these sensors might also bind to the other (non-detected) isoforms, which would indicate that this unique isoform discrimination results from differences in the molecular environment of the protein-bound TO. FIG. 17 shows the catalytic activity of GST-A1-1 and GST-A2-2 in the presence and absence of 14. Although these isozymes could not be detected by 14, both of them were strongly inhibited by this sensor with a $K_i$ value of 20 nM and 450 nM, respectively (FIG. 18), indicating a bivalent sensor-protein interaction. Considering that SAv was also hardly detected by 34 and 35, despite its remarkable affinity to biotin ($K_d=10^{-14}$ M), it can be concluded that the selective detection of isoforms does not result from isozyme-specific binding. Instead, the interaction of TO with amino acid side chains in its surroundings must play an important role in achieving a turn-on emission signal. Inspection of the crystal structures and electrostatic maps of the different GSTs reveals that they possess very similar structures. In GST-M1-1 and GST-P1-1, in particular, even the crevices between the EA binding sites have very similar dimensions and are negatively charged. This structural similarity indicates that the TOPI sensors are sensitive to subtle changes in the protein structure, a property that could be either advantageous or limiting.

TABLE 4

Approximate inhibition constants of different GST isoforms by sensor 14.

| GST isoform | $K_i$ [nM] |
|---|---|
| GST P1-1 | 48.45 ± 5.05 |
| GST A1-1 | 453.8 ± 51.84 |
| GST A2-2 | 19.56 ± 2.76 |
| GST M1-1 | 4.27 ± 0.57 |

Experimental Details

GST Kinetic Measurements and Inhibitory Constants

Inhibition of GST-A1-1, GST-M1-1, GST P1-1, and GST-A2-2 activity by sensor 14 was tested using a method developed by Habig et al. [W. H. Habig, M. J. Pabst, W. B. Jakoby, *J. Biol. Chem.* 1974, 249, 7130] (FIGS. 16- and 19). The concentrations of different GSTs, GSH, and CDNB were 20 nM, 350 µM, and 700 µM, respectively. The GST activity was measured spectrophotometrically using chloro-2,4-dinitrobenzene (CDNB) and GSH as substrates, in phosphate buffer (10 mM, pH 6.5). In a typical experiment, GST and sensors 14 or 140 were incubated for 10 mM at 25° C. and then GSH and CDNB were subsequently added. The formation of S-(2,4-dinitrophenyl)-glutathione was monitored using the microplate reader at 2, =340 nm. In order to obtain the inhibition constant, the enzymatic assays were performed using three different concentrations of GSTs (20, 60, and 100 nM) and sensor 14 or 140 (10 nM-15 µM). The concentrations of GSH and CDNB were 3 mM and 1.5 mM, respectively. The $K_m$ values were determined using 20 nM of each GST isoform, 3 mM GSH, and variable CDNB concentrations (50 µM-2 mM). Data were fit to the Michaelis-Menten equation using Sigmaplot version 12.0 statistical software (Systat) to obtain the $K_m$ values. The obtained $K_m$ values were 350 µM, 600 µM, 375 µM, and 450 µM for GST-M1-1, GST-P1-1, GST-A1-1, and GST-A2-2, respectively.

Figure 18:
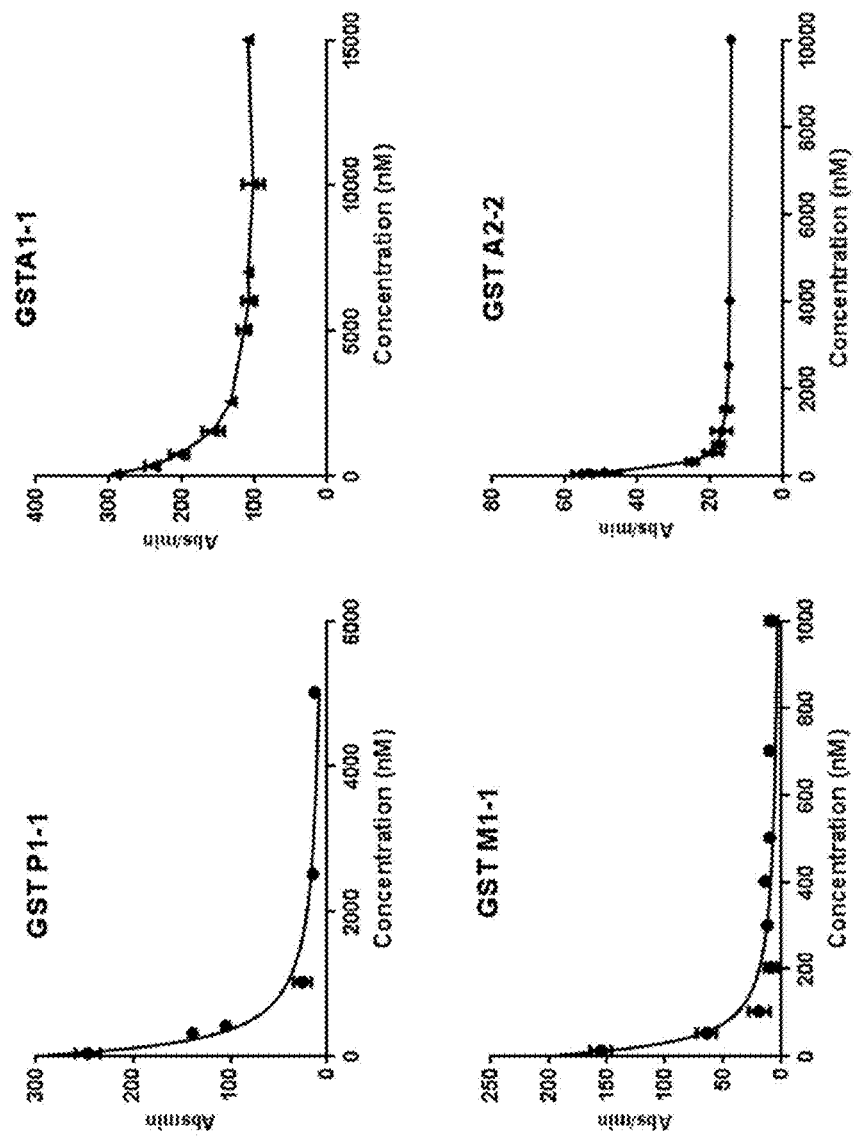
FIG. 18 depicts representative global nonlinear fit of GST P1-1 (100 nM), GST A1-1 (100 nM), GST M1-1 (20 nM), and GST A2-2 (20 nM) by compound 14. The GSH and CDNB concentrations were 3 mM and 1.5 mM, respectively.
Figure 19:
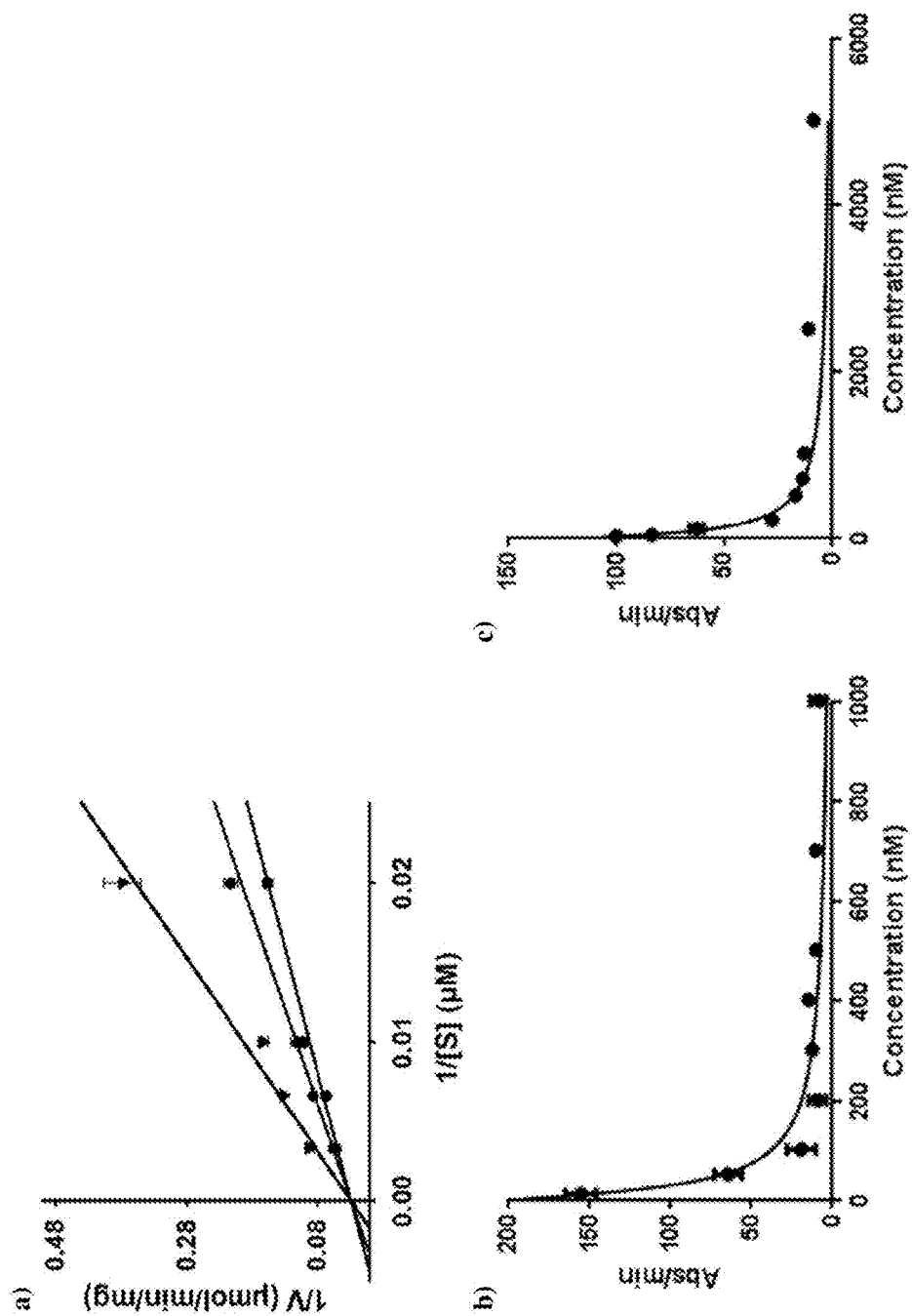
FIG. 19 depicts a) Lineweaver-Burk plot of inhibition of AChE activity by sensor 36. Acetylthiocoline iodide was used as substrate of AChE. Data points show inhibitor (sensor 36) concentrations of 0 (■), 0.1 (●), and 0.5 (▼) nM. Inhibition of GST-M1-1 (panel b) and GST-P1-1 (panel c) by sensor 14 and 140, respectively. The GSH and CDNB concentrations were 3 mM and 1.5 mM, respectively. Additional details are given in Example 5.

The data were analyzed using Graphpad Prism 6.0 and fitted to the Morrison equation for tight binding substrates (FIG. 18 and FIG. 19(b,c)).

$$Y = \frac{V_0 \left(1 - (E+X+Q) - \{(E+X+Q)^2 - 4 \cdot E \cdot X\}^{\frac{1}{2}}\right)}{2 \cdot E},$$

$$Q = K_i \cdot \left(1 + \frac{S}{K_m}\right)$$

where Y is the enzyme activity, X is different concentrations of inhibitor (compound 14 or 140), E is the enzyme concentration, S is the concentration of substrate, $K_m$ is the Michaelis-Menten constant determined in an experiment without inhibitor, and $V_0$ is the initial velocity.

The inhibition constant obtained for GST isoforms (GST M1-1, GST P1-1, GST A1-1, and GST A2-2) are listed in Table 4 for compound 14.

Experimental Details

Dissociation Constants

Figure 31:
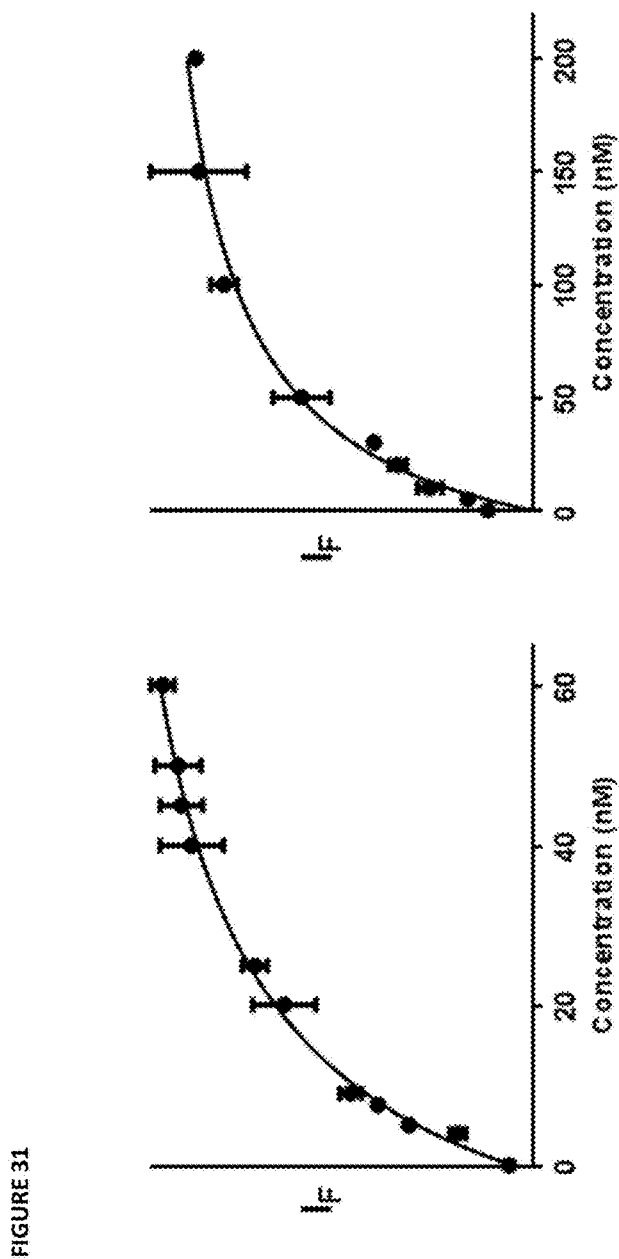
FIG. 31 depicts Binding curves obtained for sensor 14 with a) GST-M1-1 and b) GST-P1-1 by following the sensor's emission signal (normalized) upon a gradual addition of GST M1-1 or GST P1-1.

The approximate dissociation constants were determined for GST-M1-1 and GST-P1-1. For these experiments, the concentration of the sensor was chosen according to the enzymatic assays (Ki values, FIGS. 18, 19). It was chosen to be lower than the $K_i$ (expected $K_d$), but such that would also generate a detectable and reproducible emission signal in the plate reader. For GST-M1-1, sensor 14 (5 nM), and various concentrations of GST M1-1 (0, 2, 3, 4, 5, 6, 7.5, 20, 25, 40, 45, 50, and 60 nM) were incubated in phosphate buffer (5 mM, pH=6.5) and the fluorescent intensities were recorded at $\lambda_{ex}$=500 nm. Similarly, for GST-P1-1, sensor 140 (20 nM) and various concentrations of GST P1-1 (0, 5, 10, 20, 30, 50, 100, 150, and 200 nM) were incubated in phosphate buffer (5 mM, pH=6.5) for 30 mM and the fluorescent intensities were recorded at $\lambda_{ex}$=500 nm (FIGS. 15, 31). The data were analyzed using Graphpad Prism 6.0 and fitted to the equation: $Y=B_{max} \cdot X/(k_d+X)$ where $B_{max}$ is the maximum binding and X is the concentration of protein. The approximate dissociation constants between GST-M1-1 and compound 14, and and GST-P1-1 and compound 140 were found to be $K_d$=16.4±2.14 nM and $K_d$=28.97±5.21 nM, respectively (FIG. 15).

AChE Kinetic Measurements

Experimental Details

Inhibition of AChE activity by sensor 36 and sensor 37 was tested according to a published method by Ellman et al [G. L. Ellman, K. D. Courtney, R. M. Featherstone, Biochem. Pharmacol. 1961, 7, 88-95]. The AChE activity was measured spectrophotometrically using 5,5'-dithiobis(2-nitrobenzoic acid) (DTNB) and acetylthiocholine iodide as substrates, in phosphate buffer (50 mM, pH 8.0). In a typical experiment, AChE and sensor 36 (50 nM) or sensor 37 (2 µM) were incubated for 10 mM at 25° C. and then DTNB and acetylthiocholine iodide were subsequently added. The final concentrations of AChE, DTNB, and acetylthiocholine iodide were 8 µM, 0.4 mM, and 0.4 mM, respectively. The AChE activity was monitored using a microplate reader at λ=410 nm (FIG. 16a). Sensor 36 demonstrated full inhibition at low nanomolar concentration, while sensor 37 inhibited the AChE activity only at 2 µM. For the control assays, the activity of AChE was evaluated using 50 nM of 9-chloro-1,2,3,4-tetrahydroacridine (THA, tacrine), a known AChE inhibitor, and using a 10-fold excess (5 µM) of a control TO derivative 40, which lacks the AChE inhibitors.

To obtain $K_i$ value, the initial velocities were measured for six different concentrations of Sensor 36, ranging from 0 to 2 nM and for six different concentrations of acetylthiocholine iodide (25-300 µM). The initial velocities were fitted into an equation that corresponds to complete competitive inhibition:

$$v = \frac{V_{max}}{\left[1+\left(\frac{K_m}{S}\right)\left(1+\frac{I}{K_i}\right)\right]}$$

using Sigmaplot 12.0 statistical software (Systat). An inhibition constant of $K_i$=0.31 nM±0.04 was obtained for Sensor 36.

Example 6

Selectivity Studies

Figure 20:
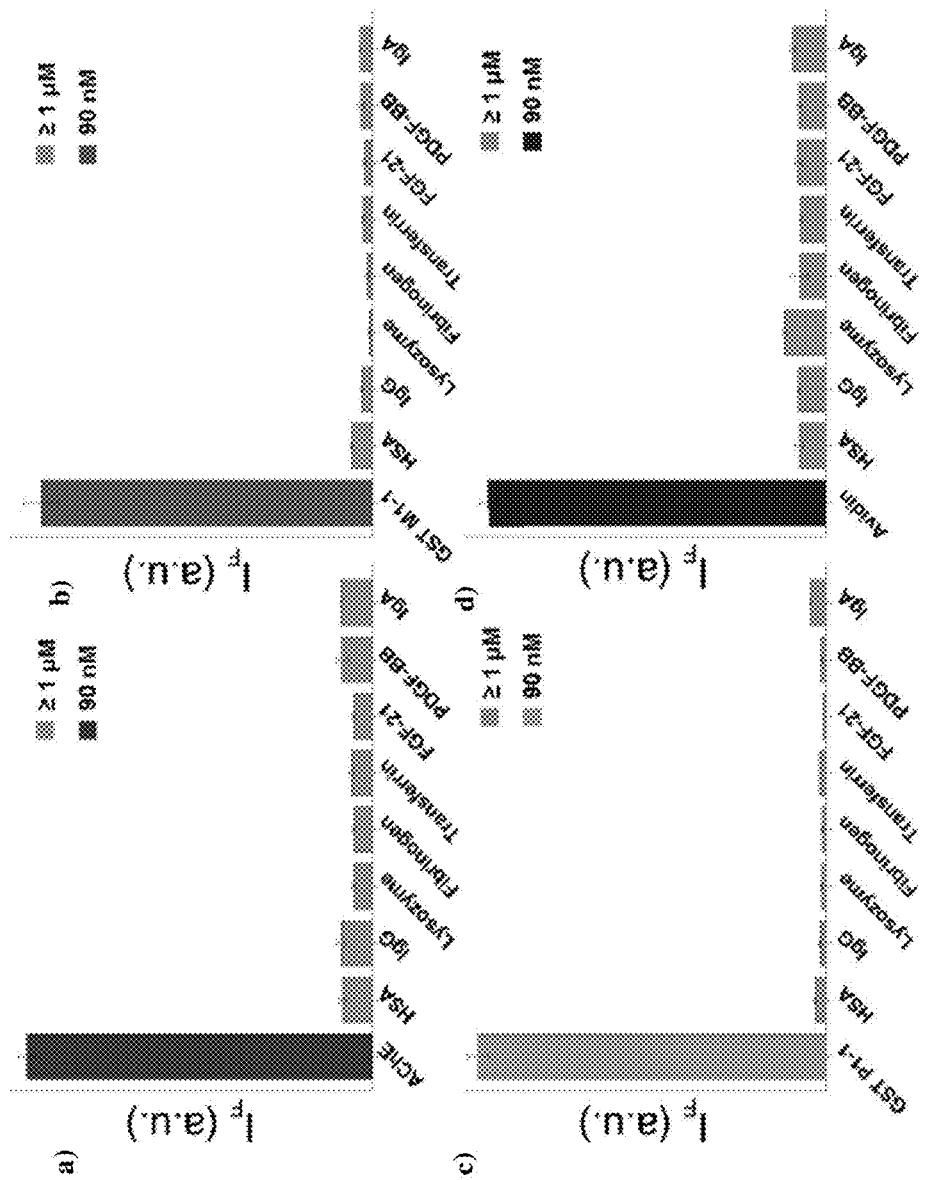
FIG. 20 depicts fluorescence responses of a) 36, b) 14, c) 140, and d) 34 to the addition of the corresponding protein target (90 nM) or an excess (>1 μM) of serum proteins.

To test the selectivity of the best TOPI sensors (FIG. 12, sensors 36, 14, 140, and 34) toward their targets, three additional fluorescence experiments were performed (FIGS. 20 and 21). In the first, it was confirmed that these sensors do not respond to the addition of a large excess of other proteins (1-2 µM) (FIG. 20). These include common serum proteins such as human serum albumin (HSA), which are notorious for forming non-specific interactions. In a second experiment it was shown that the control TO derivatives, which lack the specific protein binders (Table 2), do not fluoresce in the presence of the detected proteins (FIG. 21a-d). Hence, this experiment further shows that it is the strong interaction of the specific protein binders (Table 2) that enhances a weak and non-specific interaction between the TO-core of these sensors and the surface of the POIs. Finally, it was tested whether the emission of these sensors is triggered by the addition of double-stranded DNA (dsDNA) (FIG. 21e).

The sensors of this invention rely on an intercalating dye as the main sensing element and therefore, the goal of this experiment was to test the sensitivity of TOPIs to the presence of nucleic acids, which are prevalent in various biological samples. The strong fluorescence signal generated by the known intercalator (i.e., TO) and the weaker emission generated by TOPIs under the same conditions indicate that the bulky substituents disrupt the intercalation of the sensor with DNA. TOPI sensors 14, 140 and 34, in particular, exhibited negligible fluorescence responses to the addition of dsDNA, which demonstrates the feasibility of converting the known DNA intercalator (i.e., TO) into a highly specific protein sensor.

Experimental Details

GST M1-1 Sensing in the Presence of Other GST Isoforms

Figure 22:
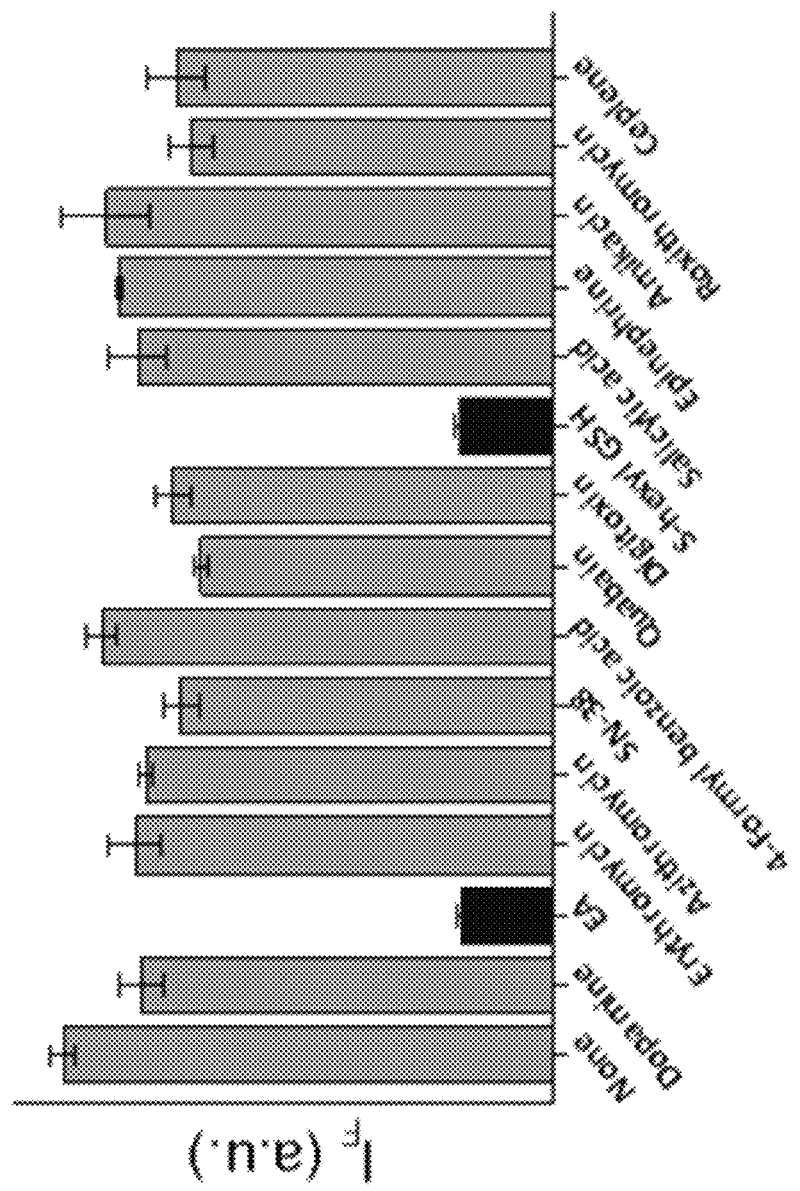
FIG. 22 Displacement assay in which the sensor 14-GST-M1-1 complex (90 nM) is treated with 50 μM of randomly selected drugs (grey) as well as with the known GST inhibitor, (EA) and s-hexyl GSH (GSH) (black).
Figure 23:
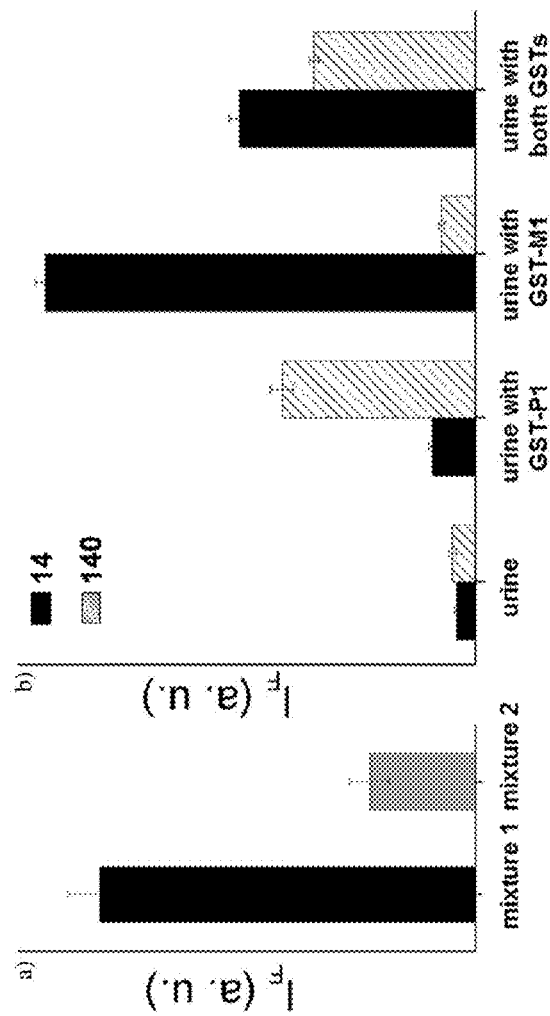
FIG. 23 depicts a) detection of GST-M1-1 by compound 14 in a mixture (mixture 1) of multiple GST isozymes (GST A1-1, GST A2-2, GST P1-1, GST T1-1, GST K1-1, GST 01-1, and GST Z1-1, 20 nM each). Mixture 2 contains the same isozymes without GST-M1-1. b) Analyzing the content of GST-M1-1 and GST-P1-1 (800 ng/mL each) in human urine by measuring the response of compound 14 (■) and compound 140 (▨) to each sample.

The ability of sensor 14 to selectively bind to GST M1-1 was tested in the presence of all other GST isoforms. Two different mixtures of GST isoforms were prepared: one that contained all the GST isoforms (20 nM of each GST, in total 160 nM) (A1-1, A2-2, P1-1, M1-1, T1-1, O1-1, Z1-1, and K1-1) and the second mixture to contained all the GST isoforms except GST-M1-1. The fluorescence of sensor 14 (100 nM) in phosphate buffer (5 mM, pH=6.5) was recorded before and after the addition of each GST mixture (FIGS. 22a and 23a).

Experimental Details

Control Experiments

For the control experiments with serum proteins (FIG. 20), 2 µM of lysozyme, PDGF-BB, IgA, IgG, FGF-21, fibrinogen, and transferrin and 1 µM of HSA were used. In the control experiments with dsDNA (FIG. 21e), two complementary ODNs (oligo A and oligo T, 20 bp) were incubated at 95° C. for five minutes and then annealed at room temperature for 30 minutes. Fluorescence intensities of TO (100 nM) or sensor 36, 14, 140 and 34 (100 nM) were recorded before and after the addition of a dsDNA (400 nM) in phosphate buffer (5 mM, pH=6.5) at $\lambda_{ex}$=500 nm.

Example 7

Protein Detection in Biofluids and in Live Cells

Cellular Imaging

GST-P1-1 is a cytosolic protein, whereas DNA is located in the nucleouse. Hence, the differences between compound 140 and the known DNA intercelator (i.e., TO) (FIG. 21e) could also be observed by monitoring their localization in live cells (FIG. 24). Breast cancer cells (MDA-MB-231), known to overexpress GST-P1-1, were incubated with TO or compound 140, as well as with compound 140 and an excess of EA. Fluorescent imaging shows a difference in the localization of these sensors according to their biomolecule targets. Whereas treatment with the TO intercalator led to a strong green emission mainly from the nucleus (FIG. 24b), the fluorescence generated by compound 140 was distributed within the cell (FIG. 24a). This emission was eliminated in the presence of EA (FIG. 24c), which is expected from the displacement of the sensor by the GST inhibitor (FIG. 22b). A much weaker emission signal was observed when compound 140 was incubated with healthy MCF-10A cells (FIG. 24d), which further demonstrates the compatibility of the TOPI sensors with live cell imaging applications.

Biomarker Detection

The suitability of the sensors according to this invention to be applied in biomarker detection was tested. In these experiments, it was demonstrated how the selective response of some of the TOPI sensors to particular protein isoforms could be used to circumvent the challenge of identifying specific isoforms within mixtures. In the case of GSTs, for example, conventional enzymatic activity assays are generally unsuitable for distinguishing between isozymes, whereas detecting specific isozymes using antibody-based techniques is not high-throughput.

In these experiments, first, the ability of compound 14 (100 nM) to detect GST-M1-1 (20 nM) in an isozyme mixture (mixture 1; FIG. 23a) containing seven additional GSTs (20 nM each) was tested and compared the resulting emission to that generated in a solution containing only seven other isozymes (mixture 2; FIG. 3a). The selective detection of GST-M1-1 in a mixture of isoforms could be achieved not only due to the strong compound 14-GST-M1-1 interaction and excellent fluorescence response of the sensor (55 fold), but also owing to the low background emission (FIG. 12), which enabled the use of an excess compound 14 (100 nM) and thus, to ensure that the other isozymes will not compete with the sensor-GST-M1-1 interaction.

Biomarker Detection in Biological Sample

In the next step compound 14 and compound 140 were used to sense specific GST isozymes in human urine (FIG. 23b). Elevated levels of specific GST isozymes, such as GST-P1-1, have been detected in several kidney-related diseases. Hence, by discriminating among isozymes in urine (FIG. 23b) the aim was demonstrating the applicability of this approach to biomarker detection, Human urine samples were spiked with medicinally relevant concentrations of GST-P1-1 (800 ng/mL), as well as GST-M1-1, and their combination. Isozyme analysis was achieved by enriching the GST content of each sample using a GSH column subjecting it to compound 14 and compound 140. As shown in FIG. 23b, the resulting fluorescence intensities provided a clear-cut analysis of the isozyme composition within each sample. This experiment also highlights the differences between the system according to this invention and common techniques used in biomarker detection. Conventional enzymatic assays, for example, which can straightforwardly detect high enzyme concentrations, are often unsuitable for distinguishing among isozymes, whereas isozyme detection by antibody-based techniques generally requires stepwise incubation and labelling steps.

Experimental Details GST Sensing in Urine Samples

Fresh urine samples were desalted by ultrafiltration using 3-kDa cutoff Centricon Plus-70 filters (Millipore, MA) according to manufacturer's procedure. Then GST-P1-1 (60 μg), GST M1-1 (54 μg) or combination of both were added to 150 μL of desalted urine samples and each urine sample was incubated with 50 μL of pre-washed Glutathione Sepharose™ affinity beads (GE Healthcare, UK) and gently agitated by end-over-end rotation at room temperature for 1 h. After separation of supernatant from the beads, the beads were washed with phosphate binding buffer (10 mM, pH 7.3 containing 140 mM NaCl, 2.7 mM KCl, and 1 mM dithiothreitol) to remove the non-specifically bound proteins. GSTs were then eluted from the beads using 100 μL of 10 mM reduced L-glutathione in Tris-HCl buffer (50 mM, pH=8) and collected by centrifuging (500×g, 1 min) Finally, the excess of GSH was removed by ultrafiltration using 3 kDa cutoff centrifugal filters (Amicon Ultra, Millipore).

For the sensing experiments, sensors 14 and 140 (100 nM) were dispensed into 384-well microplates and then fluorescence intensities were recorded following excitation at 500 nm. Then, urine samples containing GST M1-1, GST P1-1 or both (final concentration of 100 nM of GST) were added to each well and the fluorescence intensity values were recorded again. While fluorescence values for urine samples containing GST-M1-1 were recorded immediately, fluorescence values for urine samples containing GST-P1-1 were recorded after 30 mM incubation. These experiments were performed in triplicate.

Experimental Details—Cell Imaging

MDA-MB-231 cells were maintained in RPMI supplemented with 10% FBS, L-glutamine, and antibiotics. MCF-10A cells were cultured as previously described.[6] $5\times10^4$ cells, of each type, were plated in 24-well culture dish and allowed to adhere for 24 hours before the experiment. Cells were then rinsed twice with PBS (10 mM, pH=7.4) and were incubated with 2 μM of sensor 140 in PBS for 15 minutes at 37° C. Similarly, control experiments were performed following incubation of MDA-MB-231 cells with TO (2 μM) as well as with sensor 140 (2 μM) and an excess of EA (50 μM in PBS). Cells were then washed twice with PBS, and imaged using an Olympus IX51 fluorescent microscope equipped with U-MNIBA3 Fluorescence filter to cube (excitation 470-495, emission 510-550). Cell images were analyzed using imageJ.

Example 8

Modeling the Interactions of Compound 14 in the GST Binding Site

A probable reason for the specificity of sensor 14 can be deduced by inspecting the crystal structures and electrostatic potential maps of GST A1-1, GST A2-2, GST P1-1 and GST M1-1, which reveal that the crevice between the two EA binding sites is negatively charged only for GST M1-1 and GST P1-1. In addition, alignment of the sequence segments that form these crevices shows that only in GST-M1 three methionine residues (i.e., M104, M108, and M112) generate a well-defined hydrophobic patch right above a negative side chain of E100, which is not conserved among other GST variants. An illustration model for compound 14-GST-M1-1 interaction (not shown) shows that the TO unit of the sensor can be easily accommodated within this region. Hence, it is likely that upon binding to GST-M1-1, hydrophobic and electrostatic interactions between hydrophobic and negatively charged regions in the crevice and the aromatic and positively-charged dye strengthen the binding of the dye inside the crevice, which leads to a selective optical response.

Example 9

Dissociation Constants for Specific Sensor 14 GST Isoforms Complexes

The approximate dissociation constants of sensor 14 from the two detectable enzymes, GST-M1-1 and GST-P1-1, were obtained by performing fluorescence binding studies, in which the changes in the emission of sensor 14 upon incremental addition of each protein were followed (FIG. 31). The $K_d$ values obtained for the interaction between sensor 14 and GST-M1-1 ($K_d$=16 nM±2) or GST-P1-1 ($K_d$=38 nM±8) are in the same range of the $K_i$ values derived from the enzymatic assay (Table 4), which further validates that the binding of sensor 14 at the enzyme's active site is responsible for the enhancement in the emission signal (FIG. 1C(b)). These experiments also demonstrate another important feature of the sensor: the ability to operate with hardly any background signal, which enables one to detect GST-M1-1 at low nanomolar concentrations.

Example 10

Sensor 14 as a High-Throughput Inhibitor for Screening Assays

Because sensor 14 is able to detect relatively low GST concentrations, another potential application for such sensors is in high-throughput inhibitor screening assays that, similar to the enzymatic assays, do not require using large amounts of enzymes. A possible advantage of such systems, however, is that they abrogate the need for using labelled substrates and following the reaction kinetics. Such sensors could, therefore, complement other label-free enzyme assays that rely on indicator displacement mechanisms. The high affinity and specificity of the TOPI sensors toward their targets were also demonstrated by using them to identify inhibitors. In the following assay (FIG. 16b) the sensor 14-GST-M1-1 complex was subjected to various compounds and the displacement of sensor 14 by "hit" compounds was identified by observing a reduction in the emission intensity.

Figure 25:
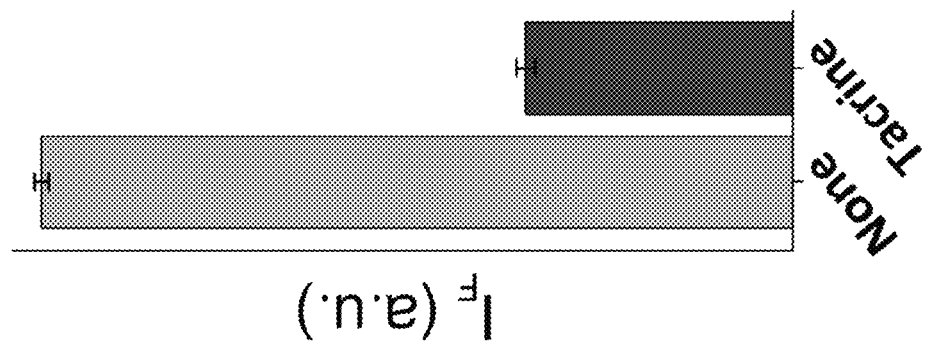
FIG. 25 depicts a displacement assay in which the sensor 36—AChE complex (90 nM, grey) is treated with 50 μM tacrine (dark grey).

To demonstrate the relevance of such sensors to drug discovery applications, the sensor 14-GST-M1-1 complex was treated with a random library of known drugs, as well as with the known GST inhibitors: (EA) and the GSH substrate. Fluorescence intensities were recorded before and after the addition of different drugs (50 µM) to a mixture of sensor 14 (90 nM) and GST M1-1 (90 nM). The selective identification of EA and s-hexyl GSH (FIG. 22b) as well as the displacement of AChE-bound 36 by tacrine as described below (FIG. 25), not only confirms the relevance of such sensors to drug discovery applications it also provides evidence for the selectivity of sensor 14 and for the proposed sensing mechanism, in which the sensor's response originates from the binding to the enzyme's active sites.

Screening Assay with Different Known Drugs

Experimental Details

In these assays, the sensor 14-GST-M1-1 complex was subjected to various compounds and the displacement of sensor 14 by "hit" compounds is identified by observing a reduction in the emission intensity. The sensor 14-GST-M1-1 complex was treated with a random library of known drugs. Fluorescence intensities were recorded before and after the addition of different drugs (50 µM) to a mixture of sensor 14 (90 nM) and GST M1-1 (90 nM) (FIG. 22b).

Example 11

Fluorescence Measurements of TO Based Sensor 14 Control Experiments Earlier Experiments The bivalent fluorescent molecular sensor of the present invention such as compound 14 consists of two components. The first is a fluorescent reporter based on Thiazole Orange (TO), which is known to fluoresce only upon restriction of its torsional motion. The second component is a specific protein binder, Glutathione S-Transferase (GST) binder, ethacrynic acid. In the absence of the protein, TO rotates freely in solution and therefore, the emission of the sensor is quenched. Upon protein binding, this rotation is restricted and a fluorescent emission at 540 nm is generated. FIG. 21e show that the molecular sensor 14 loses its ability to intercalate with dsDNA since it did not exhibit any change in its fluorescence at 540 nm upon addition of dsDNA-).

Example 12

TO Based Sensor—PDGF-BB (Sensor 20)

Figure 26:
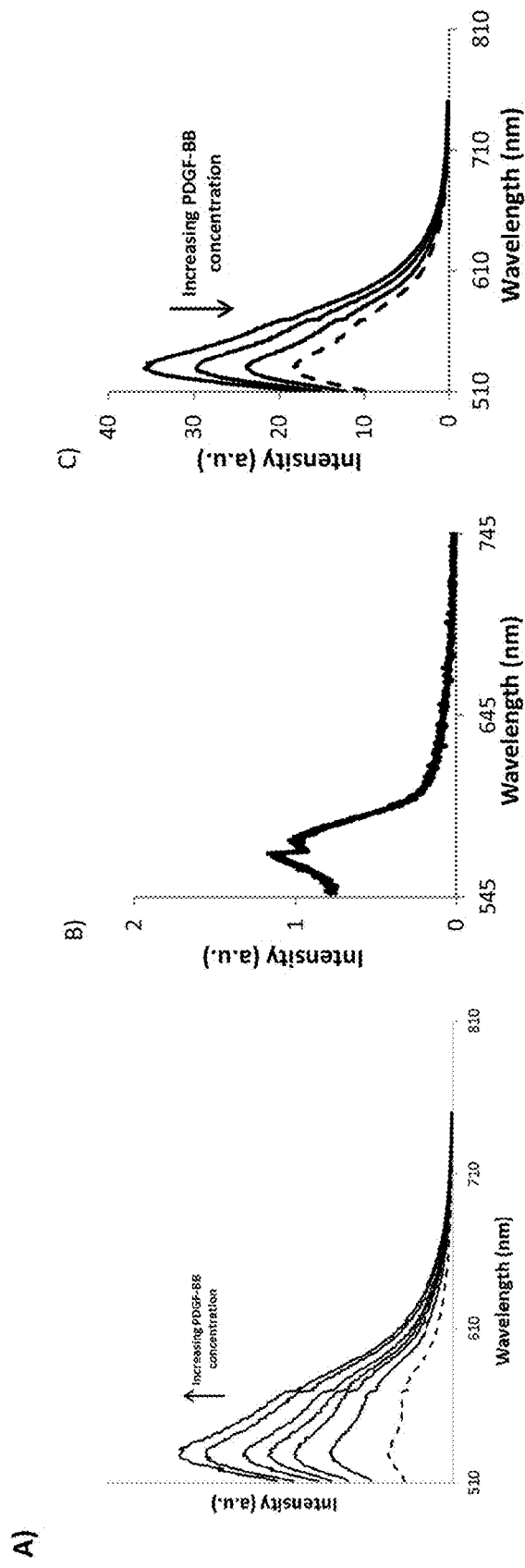
FIG. 26 presents a fluorescence spectra of TO-bisaptamer (100 nM) (sensor 20) upon addition of increasing concentrations (33.3, 66.6, 99.9, 133.2, 166.5 and 199.8 nM) of PDGF-BB in water $\lambda_{ex}$=480 nm (A). In control experiments, PDGF-BB was incrementally added to an unmodified TO (B) or to an unmodified TO and a free aptamer—(C). $\lambda_{ex}$=480 nm

Changes in the emission of TO based sensor 20 (100 nM) in water upon incremental addition of PDGF-BB (0-200 nM) were measured (FIG. 26A). As controls, PDGF-BB was also added to a solution of an unmodified TO (FIG. 26B), as well as to a mixture of an unmodified TO and a free aptamer (FIG. 26C). Only in the presence of compound 20 there was a significant increase in emission signal observed and at low nanomolar PDGF-BB concentrations.

Figure 27:
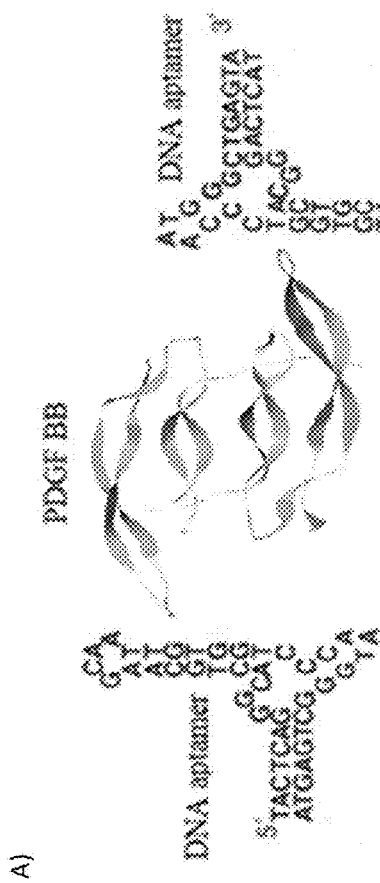
FIG. 27 depicts A) a schematic representation of the homo/dimeric PDGF-BB bound by two DNA-aptamers. B) a fluorescence emission spectra of sensor 20 (100 nM) at different temperatures (5° C., 10° C., and 25° C.). C) Fluorescence emission spectra of sensor 20 (100 nM) upon incremental addition of 30 mM NaCl, and D) 1 mM $MgCl_2$ in an aqueous solution, $\lambda_{ex}$=480 nm.
Figure 27:
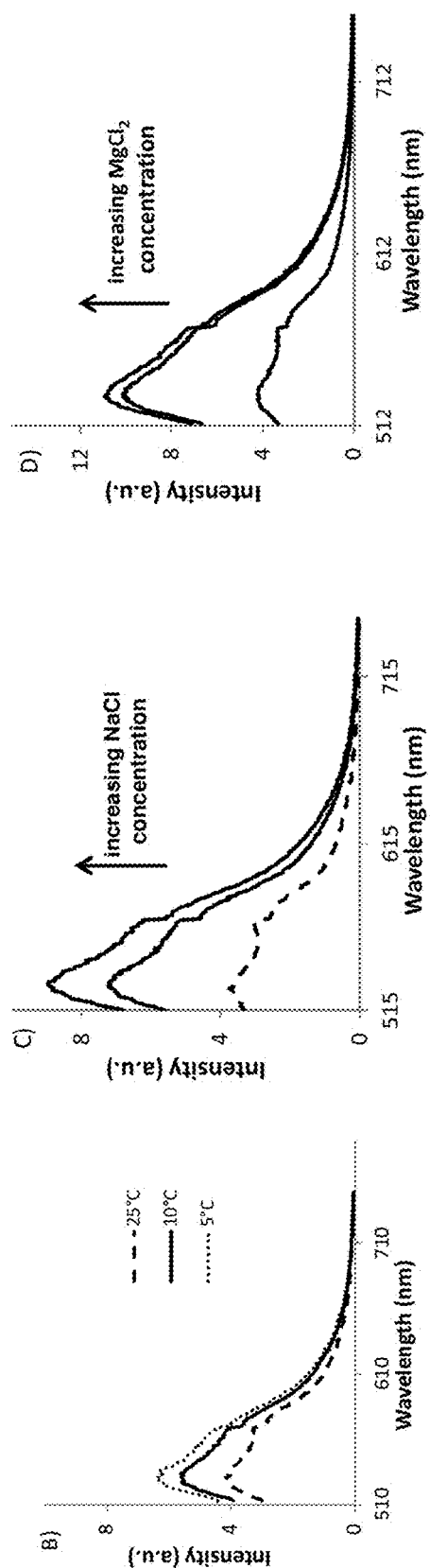

In addition, mixing 100 nM aptamer and unmodified TO led to a significant increase in the fluorescence signal even in the absence of PDGF-BB (FIG. 26C). Furthermore, the addition of the growth factor to this mixture induced a quenching of the emission. A logical explanation for this phenomenon is that TO intercalates with the hairpin aptamer (FIG. 27A) and that PDGF-BB interferes with this intercalation.

While in water, compound 20 detected PDGF-BB with high sensitivity; in PBS buffer the sensor generated a high emission signal even in the absence of the protein, presumably due to a high metal ion concentration that stabilizes duplex formation (FIG. 27A) and leads to intercalation of the sensor. This hypothesis was confirmed by measuring the fluorescence of compound 20 under low temperatures (FIG. 27B) and increasing metal ion ($Mg^{+2}$, $Na^{+1}$) concentrations (FIG. 27C, D), both of which are known to stabilize duplex formation. The increase in fluorescence intensity at lower temperatures and at higher salt concentrations indicates that stabilization of the hairpin aptamers is responsible for this undesired background signal.

Example 13

Activity of TO-Bis Ni-NTA (Sensor 33)

Figure 28:
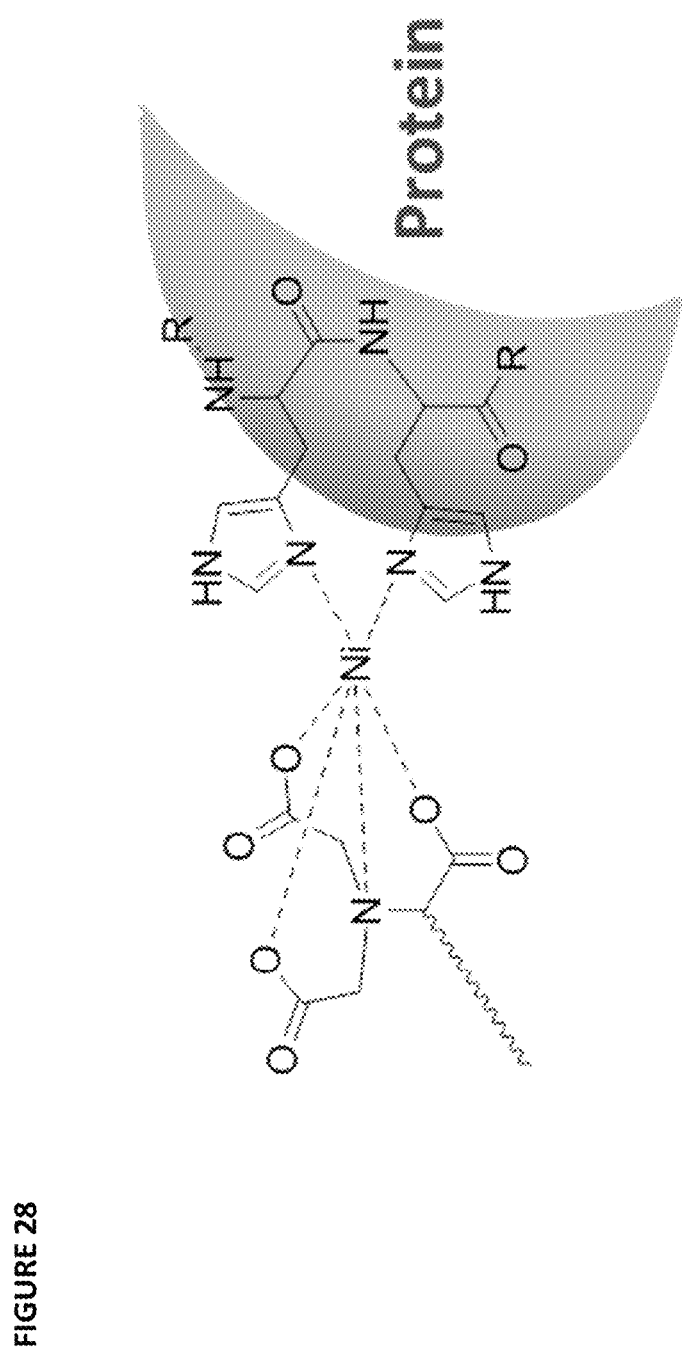
FIG. 28 depicts the interaction between a His-tagged protein and Ni-NTA.

A library of peptides with different numbers of polyhistidine has been designed to evaluate their interaction with TO-bis Ni-NTA (33). Each Ni-NTA coordinates with two histidines from the His-tagged protein or polyhistidine peptide to form a stable complex (FIG. 28).

The library is synthesized on solid support using split and mix protocol. The resulting "one-bead-one-compound" library will be tested for binding using "on-bead" screening assays. The positive hits will be then resynthesized and purified by HPLC to confirm the binding to TO-bis Ni-NTA derivative and to evaluate the fluorescent enhancement in solution. Table 5 represents a small library of this kind.

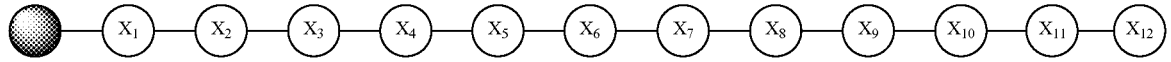

Solid Support

TABLE 5

A representative library of polyhistidine peptides.

| | Entry | $X_1$ | $X_2$ | $X_3$ | $X_4$ | $X_5$ | $X_6$ | $X_7$ | $X_8$ | $X_9$ | $X_{10}$ |
|---|---|---|---|---|---|---|---|---|---|---|---|
| SEQ ID NO. 1 | 1 | His | His | His | His | His | His | His | His | His | His |
| SEQ ID NO. 2 | 2 | His | His | His | His | Trp | Trp | His | His | His | His |
| SEQ ID NO. 3 | 3 | His | His | His | His | Trp | Trp | His | His | His | His |
| SEQ ID NO. 4 | 4 | His | His | His | His | Phe | Phe | His | His | His | His |
| SEQ ID NO. 5 | 5 | His | His | Phe | Phe | His | His | Trp | Trp | His | His |
| SEQ ID NO. 6 | 6 | His | His | Trp | Trp | His | His | Trp | Trp | His | His |

TABLE 5-continued

A representative library of polyhistidine peptides.

| | Entry | $X_1$ | $X_2$ | $X_3$ | $X_4$ | $X_5$ | $X_6$ | $X_7$ | $X_8$ | $X_9$ | $X_{10}$ |
|---|---|---|---|---|---|---|---|---|---|---|---|
| SEQ ID NO. 7 | 7 | His | His | Trp | Trp | His | His | Leu | Leu | His | His |
| SEQ ID NO. 8 | 8 | His | His | His | His | Phe | Phe | His | His | Leu | Leu |

Figure 29:
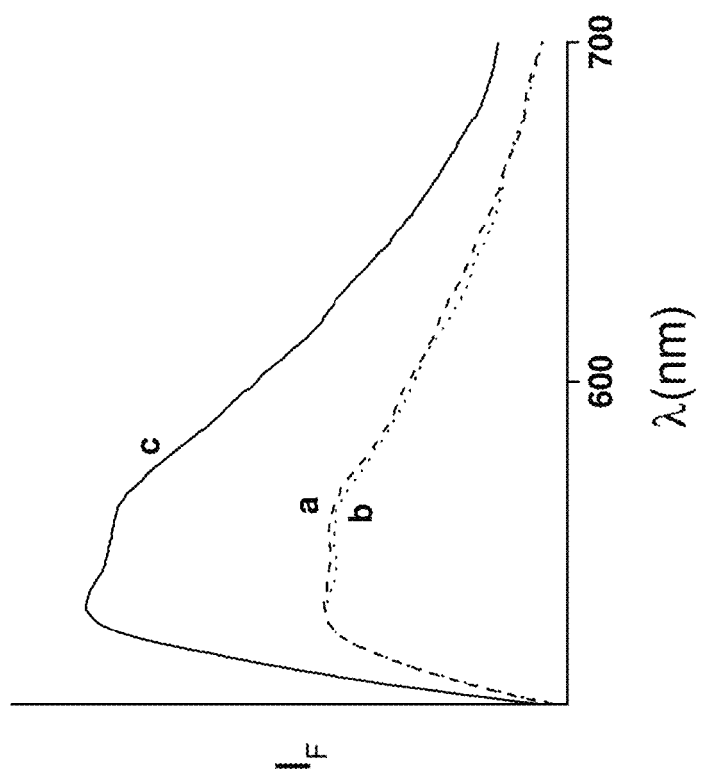
FIG. 29 depicts fluorescence spectra of (a) 500 nM TO-tetrakis-Ni-NTA (33), following addition of $NiCl_2$ (3 μM) (b) and then (c) polyhistidine peptide (1 μM).

Bivalent interaction of complex of 33 with $NiCl_2$ with a peptide 1 (entry 1, Table 5) was tested by adding the peptide (1 μM) to a solution of compound 33 (500 nM) in a phosphate buffer (10 mM, pH=7.4). Upon addition of peptide to the TO-bis-Ni-NTA, a significant enhancement in the fluorescence signal was observed (FIG. 29).

Example 14

Modeling of the Interaction Between 14 with Different GSTs

Structures of GST-A1-1, GST-A2-2, GST-M1-1, and GST-P1-1, were taken from the Protein Databank codes 1gsf, 2wju, 1xwk and 2gss, respectively. All these GST variants are dimers characterized by a deep and narrow crevice between the monomers. Two molecules of ethacrynic acid (EA) bind to the GST dimer in pockets at the edges of the crevice.

The sequences of the four GST variants were aligned based on manual structure alignments of the proteins. FIG. 30 presents a sequence alignment of segments that line the inter-monomer crevice. The residues that point into the crevice are identical in GST-A1-1 and GST-A2-2 but differ in the two other structures. GST-M1-1 has more hydrophobic residues than the other variants. In particular, the three methionine residues, M104, M108 and M112 located in a helix form a hydrophobic patch. In GST-M1-1 the bottom of the crevice in negative because of the side chain of E100 that is not conserved in other GST variants.

Overlay of the four structures shows that the inter monomer crevice in GST-A1-1 and GST-A2-2 is significantly wider than in GST-P1-1 and GST-M1-1. A quantitative estimate of the width of the crevice was obtained by calculating the average distance between the Ca atoms of residues 97, 100, 101, 104, 105 and 108 in one monomer to the corresponding Ca atoms in the other monomer; these residues line the central part of the crevice. The average distances for GST-A1-1, GST-A2-2, GST-P1-1 and GST-M1-1 are 17.3 Å, 15.8 Å, 11.7 Å and 11.4 Å, respectively. Clearly the crevice in GST-A1-1 and GST-A2-2 is wider than in the two other variants.

In summary, the crevice between the GST monomers displays different characteristics in the three structures: (1) It is narrower in GST-M1-1 and GST-P1-1 than in GST-A1-1 and GST-A2-2; (2) The bottom of the crevice is negative in GST-M1-1 and GST-P1-1 and neutral in GST-A1-1 and GST-A2-2; (3) The "walls" of the crevice have a hydrophobic patch at the center in GST-M1-1 but not in the three other variants. Based on these features the proposed TO binding site is within the crevice, approximately at its center.

In order to illustrate the proposed binding mode 14 was manually docked into the inter-monomer crevice of GST-M1-1. The two inhibitory moieties of 14 were positioned in the EA binding sites and the TO moiety was positioned at the center of the crevice. The torsion angles of the linker were adjusted to commonly observed values for each type of atom. The ligand was then energy minimized within the crevice, using Discovery Studio (Accelrys Inc., CA).

The docking model shows that the narrow crevice in GST-M1-1 can accommodate the ligand without requiring conformation changes in the protein. The size of the crevice dictates a planar conformation of the TO moiety. It is possible to place the whole ligand within the crevice with the EA moieties in the same general location as EA in the structure of GST-P1-1. The negative potential at the bottom of GST-M1-1 and GST-P1-1 attracts the TO moiety into the crevice whereas in GST-A1-1 and GST-A2-2 the electrostatic potential at the bottom is neutral. In the latter variants the potential is negative near the top of the crevice and TO moiety might bind there. In this location the crevice is particularly wide and the TO moiety is not likely to be planar. The hydrophobic "methionine patch" in GST-M1-1 can favorably interact with the aromatic rings of TO, strengthening the binding of the ligand inside the crevice.

Example 15

Biotin Binding Sites within Avidin and Streptavidin

The overall structures of avidin (PDB code 1wtp) and streptavidin (PDB code 4bx7) are very similar, with RMSD of 2.2 Å calculated for the Ca atoms of the tetramer. The tetramer binds four biotin molecules, however only one choice of two biotin sites seems appropriate for sensor 34 and sensor 35 binding, with the two sites on the same face of the tetramer, the biotin $CO_2$ groups pointing generally at each other and located at an appropriate distance.

Docking sensor 34 and sensor 35 to avidin and streptavidin, with the biotin moieties positioned in the binding sites suggested that both proteins can bind the ligands as both have surface regions with negative potential that can bind the TO moiety.

Example 16

Tacrine Binding Sites within Acetylcholinesterase

The structure of AChE bound to a bivalent inhibitor (PDB code 2 ckm) shows that the two tacrine groups bind simultaneously at the enzyme's active and the peripheral sites. The electrostatic potential in the active site gorge of AChE and around the entrance to the gorge is negative and the bis-tacrine inhibitor binds with one tacrine moiety deep in the active site and the other in a peripheral site near the entrance to the gorge.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed:

1. A fluorescent monomolecular sensor, wherein said sensor is a Thiazole Orange-based protein identifier (TOPI) comprising a Thiazole Orange (TO) derivative and at least-one selective protein binders; wherein said sensor is represented by the structure of formula IX:

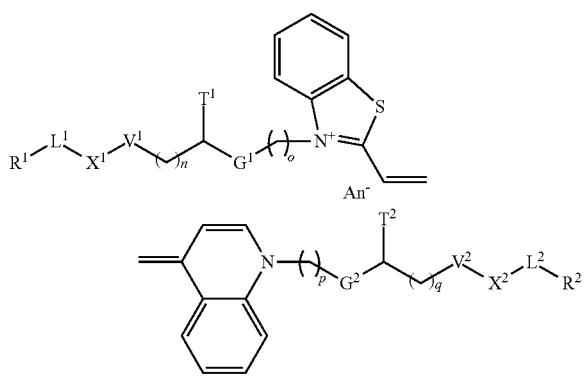

wherein n, o, p and q are independently integers between 0 to 15;

$An^-$ is a counter ion, selected from tosylate (p-toluene-sulfonate; $CH_3C_6H_4SO_3^-$), $PF_6^-$, $CF_3COO^-$, $I^-$, $Cl^-$, $Br^-$, or $F^-$;

$G^1$ and $G^2$ are independently a bond, carbamate, amide, amine, $C_1$-$C_{12}$ alkyl amine, ester, ketone, O, N, S, carbonate, —O-alkyl-NH—, carbamoyl phosphate or phosphate;

$T^1$ is hydrogen or

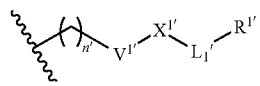

wherein, n' is between 0 and 15;

$T^2$ is hydrogen or

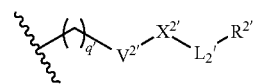

wherein q' is between 0 and 15;

V¹, V¹', V² and V²' are independently a bond, a triazole, an amide [—C(O)NH or —NHC(O)], —C(O)O—, —OC(O)—, O, NH, N-alkyl, S, —PO₄H—, $C_1$-$C_{12}$ alkyl ether, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof X¹, X¹', X² and X²' are independently a bond or $C_1$-$C_{12}$alkyl, —C(O)NH—, —NHC(O), —C(O)O—, —OC(O)—, O, NH, N-alkyl, S, —PO₄H—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

L¹, L¹', L² and L²' are independently a bond or $C_1$-$C_{12}$ alkyl, C(O), —C(O)NH—, —NHC(O)—, —C(O)O—, —OC(O)—, O, NH, $C_1$-$C_{12}$ N-alkyl, S, —PO₄H, —PO₄H—{[(CH₂)$_y$O]$_x$}$_z$—PO₃H—, wherein y is between 1-5, x is between 1-10 and z is between 1-10, —PO₄H—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O— alkyl-NH—, —NH-alkyl-O—, wherein said alkyl is optionally substituted and wherein said alkyl is optionally interrupted by an heteroatom consisting of O, N, P, S or combination thereof; and R¹, R¹', R² and R²' are independently hydrogen, halide, SO₃⁻, CN, NO₂, phosphate, SO₃⁻ or a selective protein binder;

wherein at least one of R¹, R¹', R² and R²' is a protein selective binder.

2. The sensor of claim 1, wherein said TOPI comprises two selective protein binders.

3. The sensor of claim 2, wherein said protein is a homodimer.

4. The sensor of claim 1, wherein said selective binder comprises: marimastat, ethacrynic acid, bisethacrynic acid, metal complex of nitrilotriacetic acid (NTA), metal complex of his NTA, metal complex of tris-NTA, PDGF-BB, heparin, FGF aptamer, biotin, tacrine, estrogen, DNA aptamer, RNA aptamer, peptide aldehyde, estrogen, suberoylanilidehydroxamic acid (SAHA), a peptide binder or any combination thereof.

5. The sensor according to claim 1, represented by the structure of formula XIII:

6. The sensor of claim 5, represented by the structure of formula X:

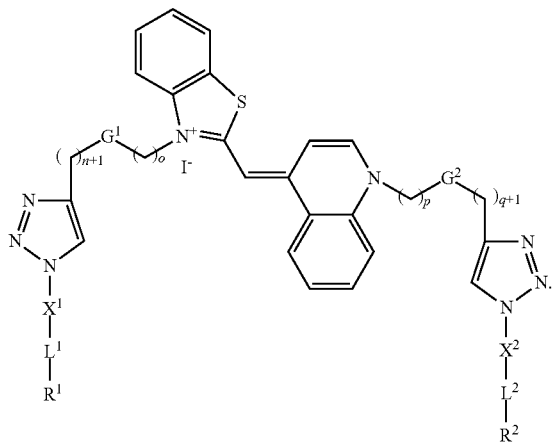

XIII

7. The sensor of claim 6, wherein said sensor is represented by the structure of formula XI:

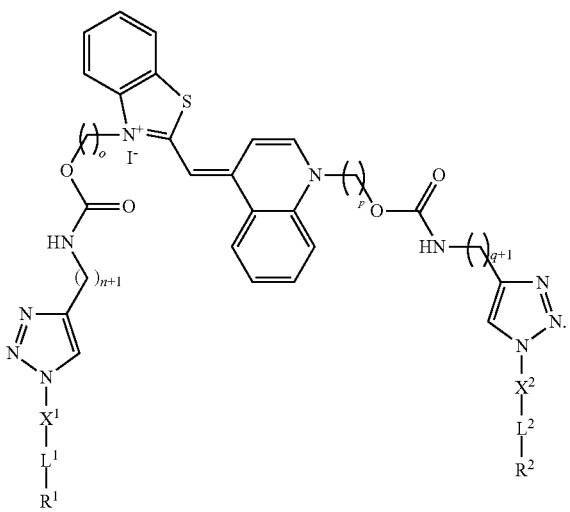

XI

8. The sensor of claim 1, wherein T¹ and T² are hydrogens.

XIII

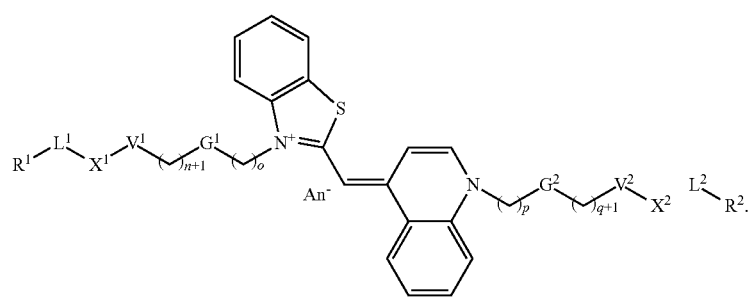

9. The sensor of claim 1, wherein said $G^1$ and $G^2$ are each independently a carbamate or an amide.

10. The sensor of claim 1, wherein said $V^1$ and $V^2$ are each independently a triazole, an O, an NH or a bond.

11. The sensor of claim 1, wherein said $X^1$ and $X^2$ are each independently a $C_1$-$C_{12}$ alkyl, a $C_1$-$C_{12}$ alkyl-NH, a $C_1$-$C_{12}$ alkylether, -alkyl-C(O)NH-alkyl or a bond.

12. The sensor of claim 1, wherein said $L^1$ and $L^2$ are each independently a bond, —$PO_4H$—$\{[(CH_2)_yO]_x\}_z$—$PO_3H$—, wherein y is 2, x is 3 and z is 6; —$PO_4H$-PEG; $C_1$-$C_{12}$ alkyl-NH or a $C_1$-$C_{12}$ alkyl.

13. The sensor of claim 1, wherein said o and p are each independently 2 or 3.

14. The sensor of claim 1, wherein said n and q are each independently 0, 1, 2 or 5.

15. The sensor of claim 1, wherein $R^1$ and $R^2$ are both a selective binder.

16. The sensor of claim 1, wherein said $V^1$ and $V^2$ are identical; $X^1$ and $X^2$ are identical; $L^1$ and $L^2$ are identical; $R^1$ and $R^2$ are identical; o and p are identical; and n and q are identical.

17. The sensor of claim 1, wherein said sensor is compound 14, 140, 20, 26, 33, 34, 35, 36, or 37:

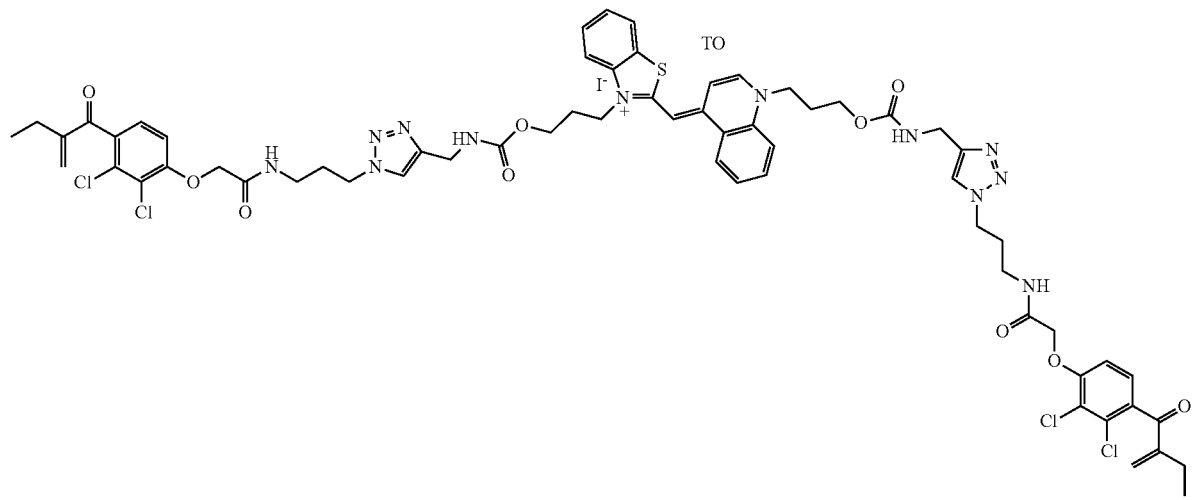

140

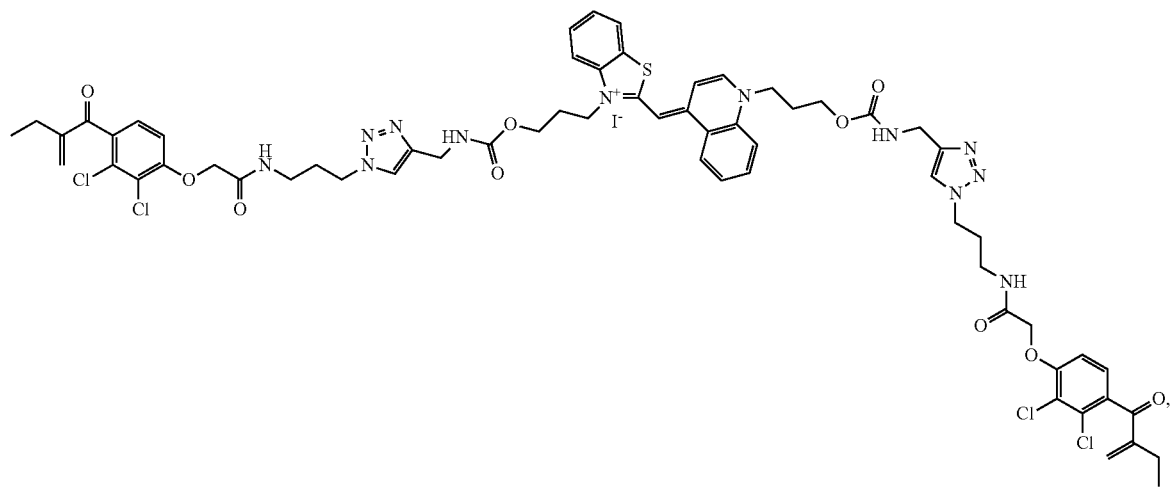

140

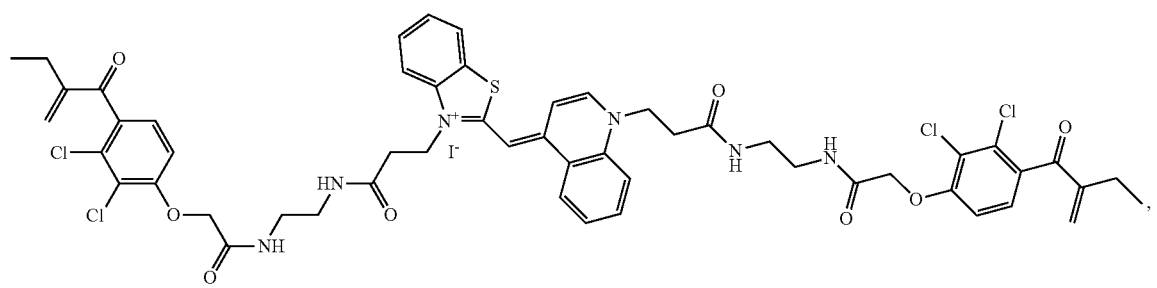

-continued
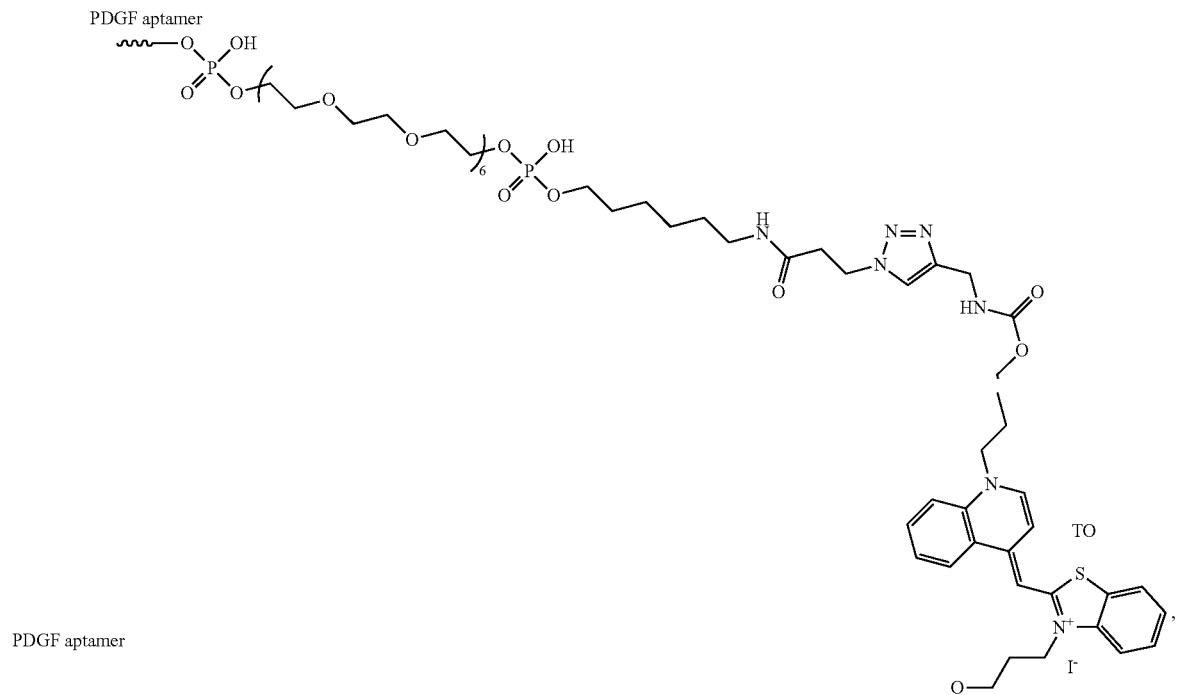
20
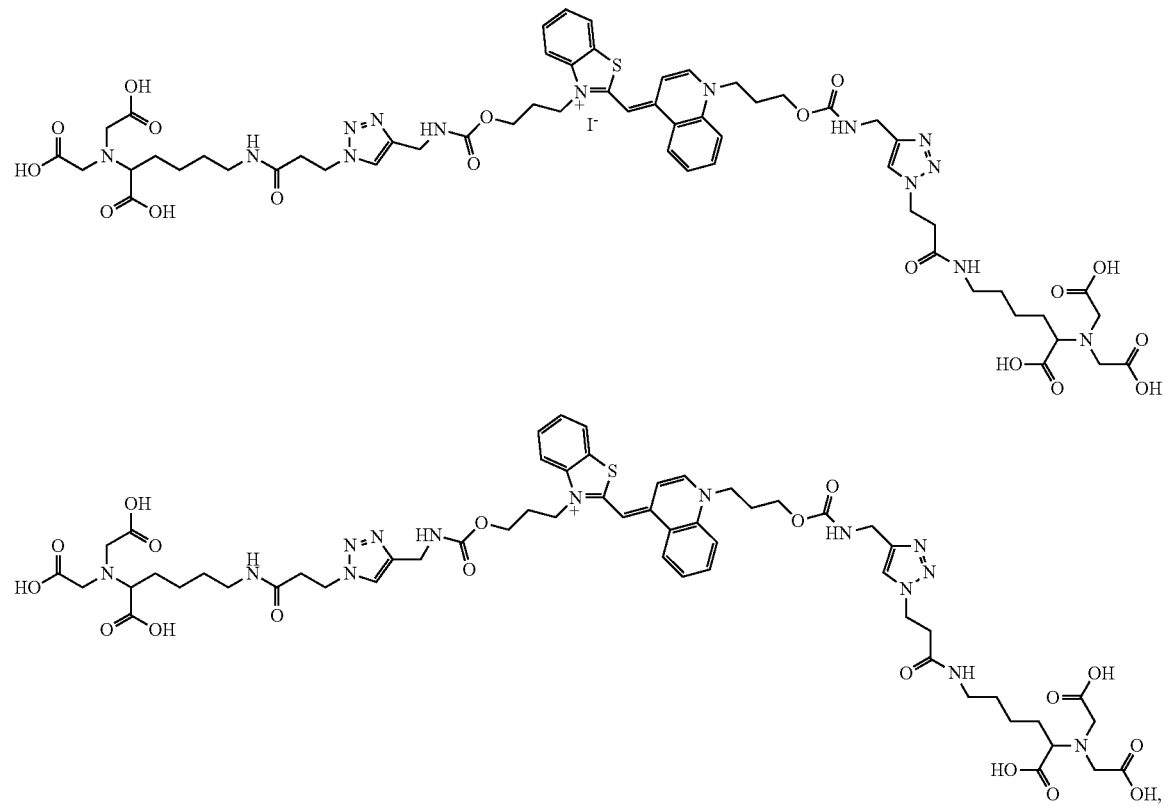
26

-continued
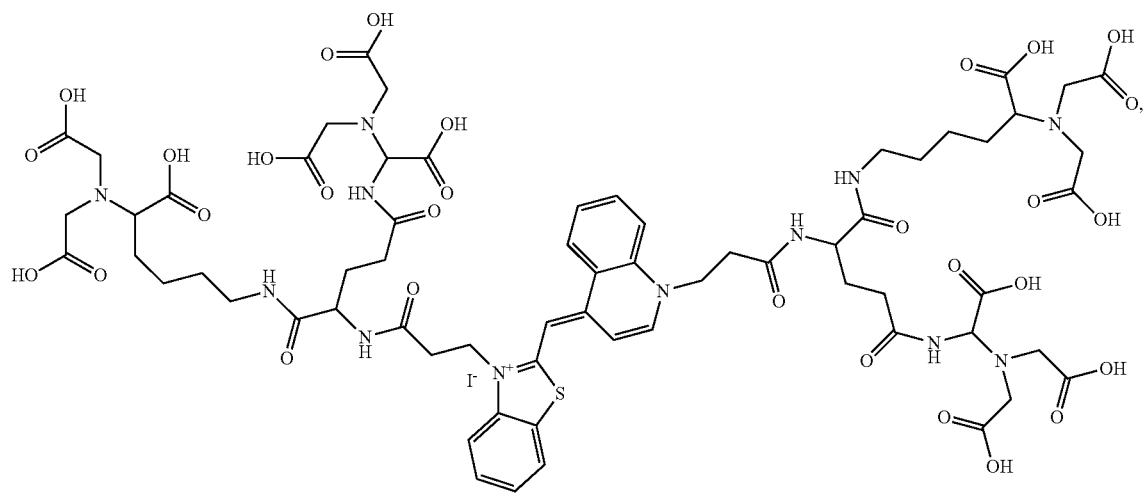
33
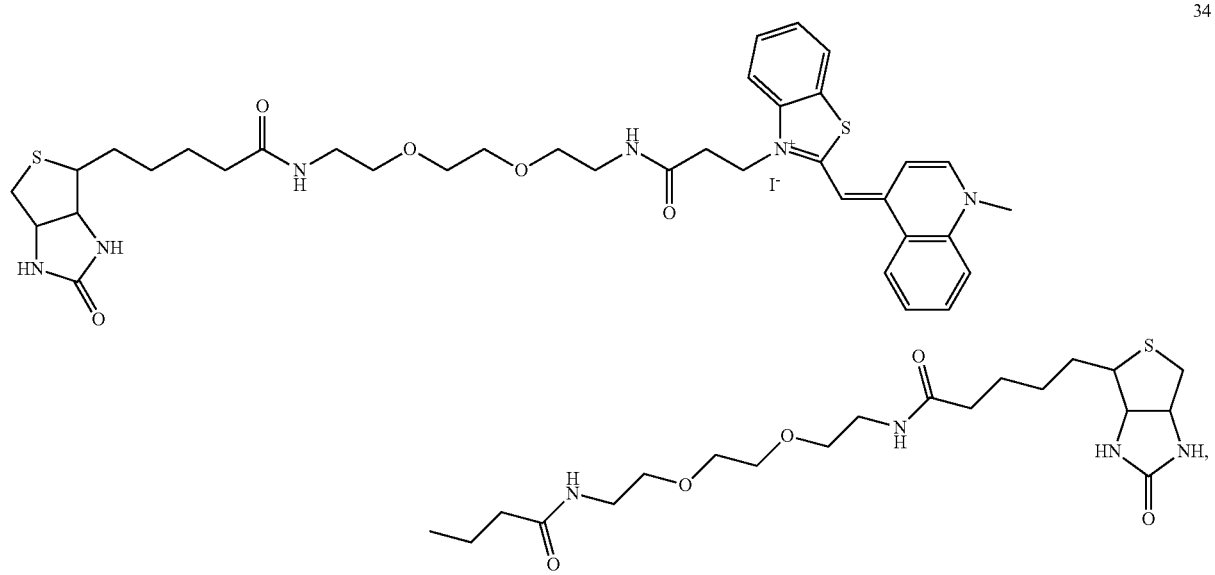
34
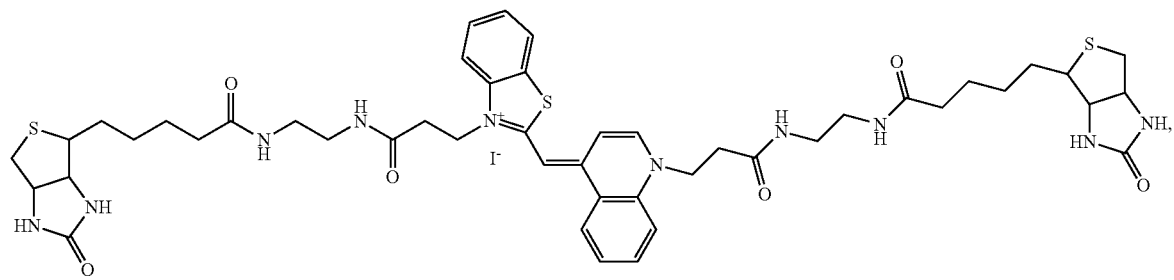
35
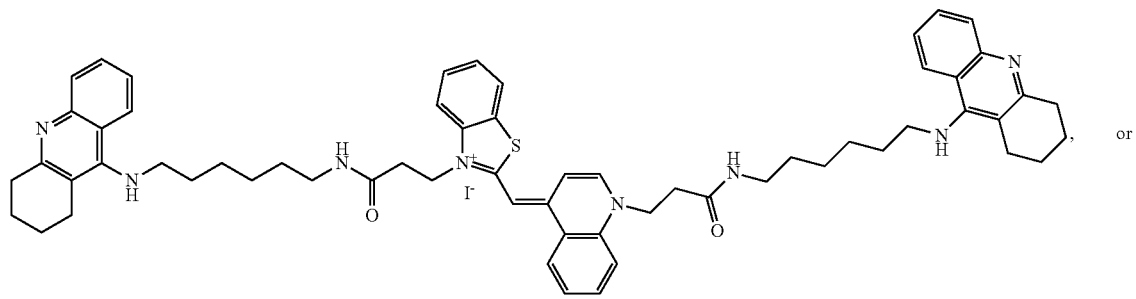
36

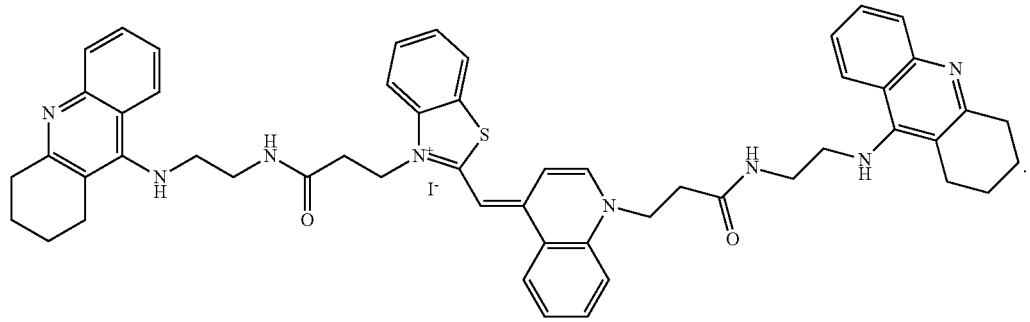

37

18. A method of detecting a protein of interest (POI) in a biological medium, said method comprise:
   a. measuring an optical signal of the sensor of claim 1;
   b. placing said sensor in said biological medium;
   c. re-measuring the optical signal of said sensor in said biological medium,
   wherein an enhancement in the optical signal of said sensor indicates on the presence of said POI in said biological medium.

19. The method of claim 18, wherein said optical signal is fluorescence emission.

20. The method of claim 18, wherein said POI is matrix metalloproteases (MMPs) protein and its isoforms, glutathione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, avidin, streptavidin, Acetylcholinesterase or histone deacetylases (HDACs).

21. The method of claim 18, wherein said biological medium is blood, tissue, serum, or urine.

22. The method of claim 20, wherein said GST is a biomarker for cancer, renal tubular injury and for monitoring graft failure or regeneration following living donor liver transplantation.

23. The method of claim 22, wherein said GST comprises isoforms GSTA1, GSTA2, GSTM1, GSTK1, GSTO1, GSTZ1, GSTT1 and GSTP1 and said method further differentiates between said isoforms.

24. The method of claim 18, wherein said POI is achetylcholine esterase (AChE), wherein said AChE is a biomarker for Alzheimer disease.

25. The method of claim 18, wherein said sensor is compound 14, 140, 20, 26, 33, 34, 35, 36, or 37:

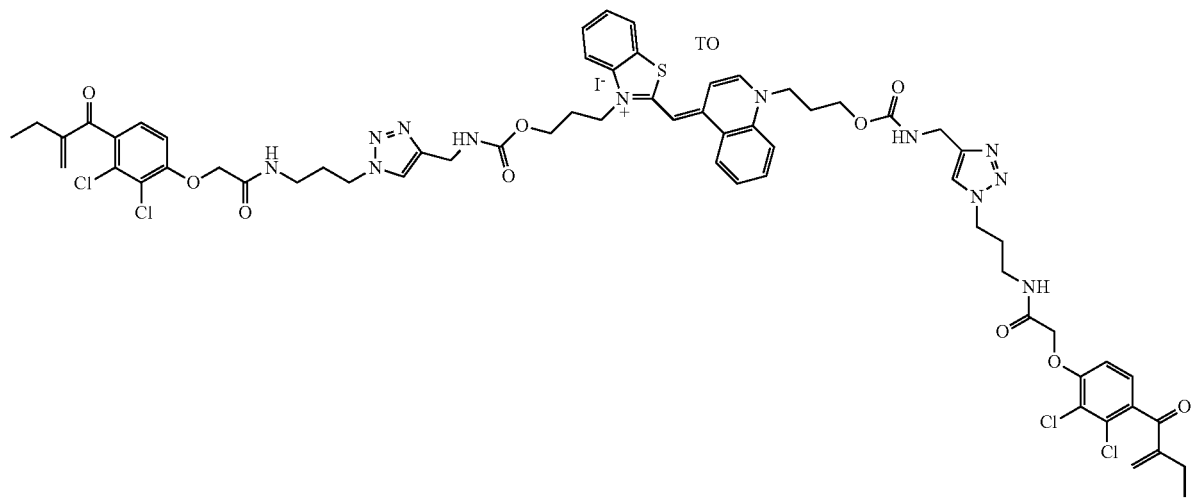

14

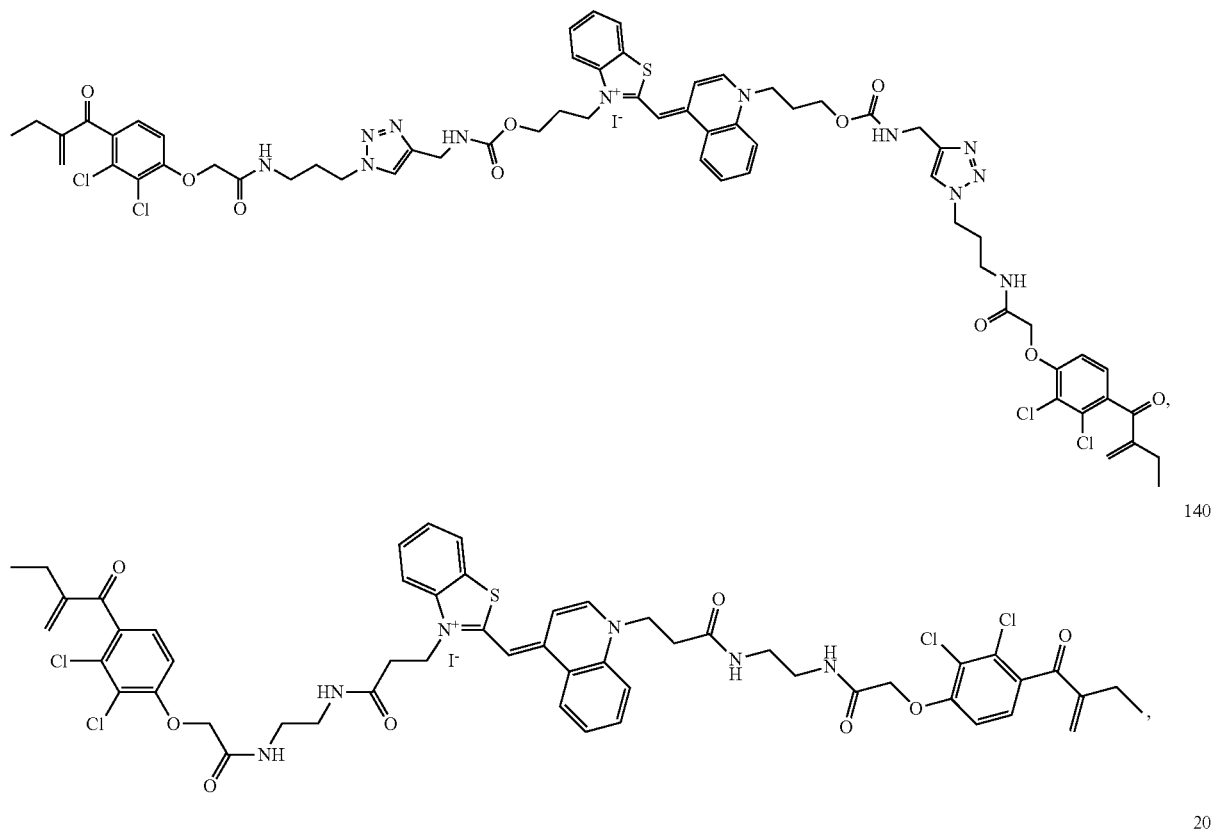

-continued
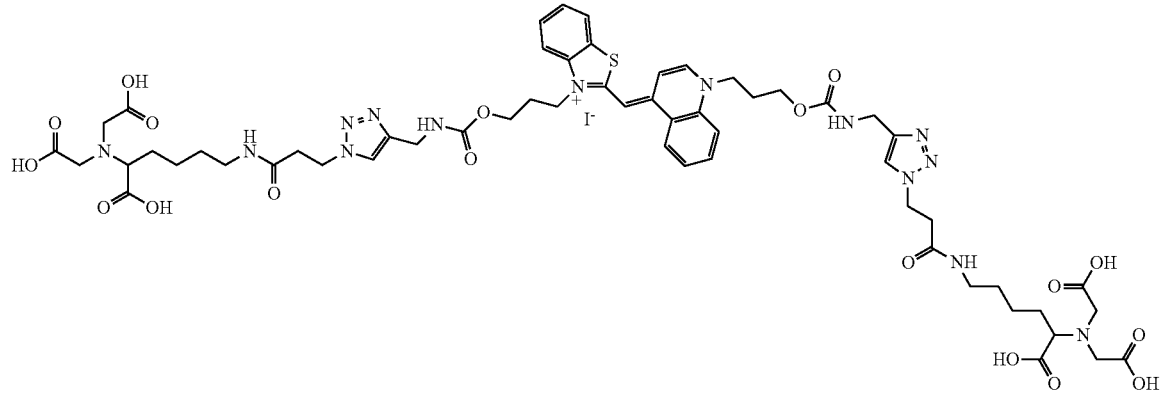
26
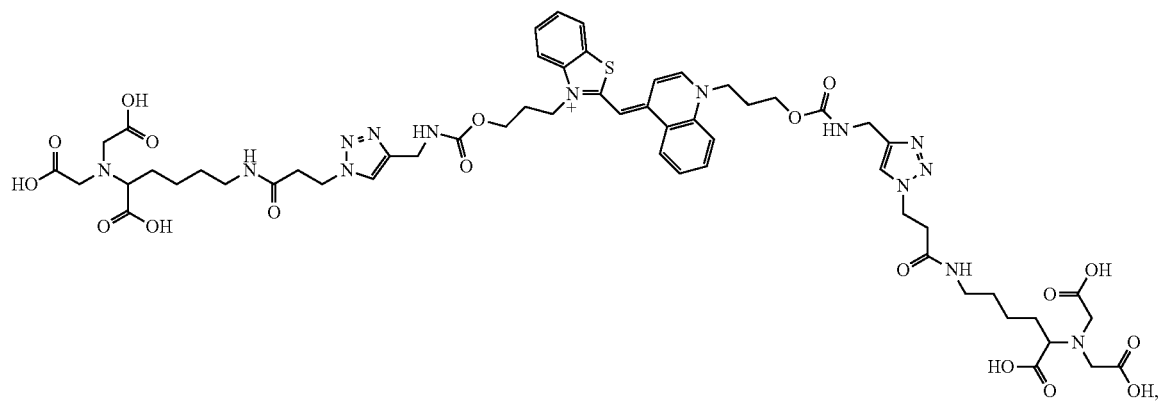
33
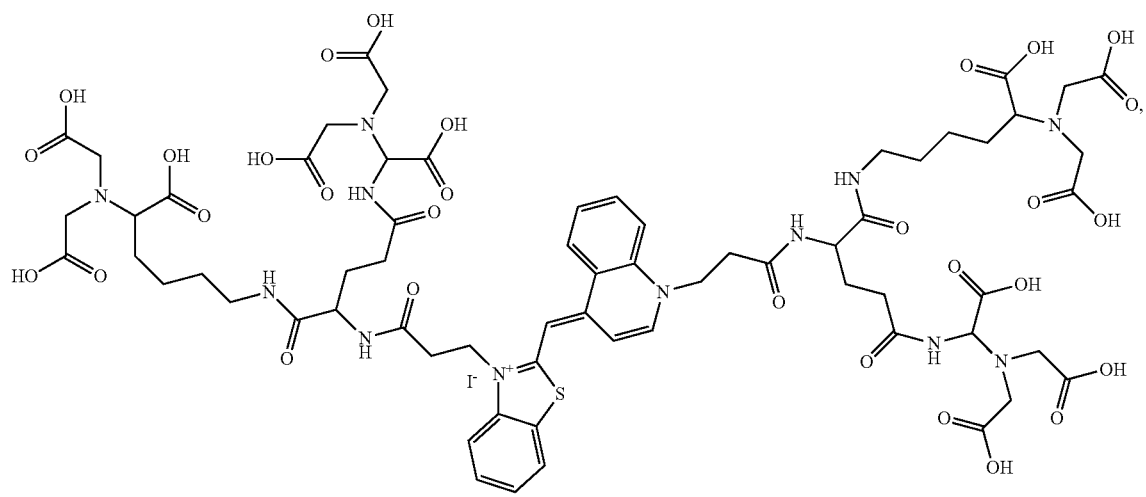
34
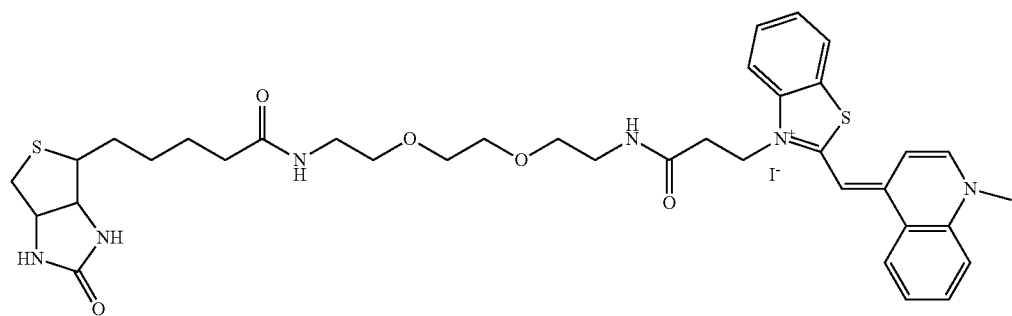

-continued

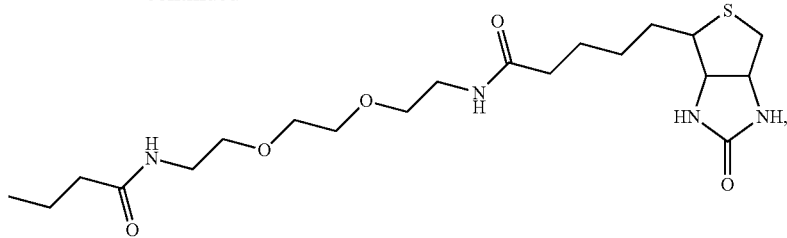

35

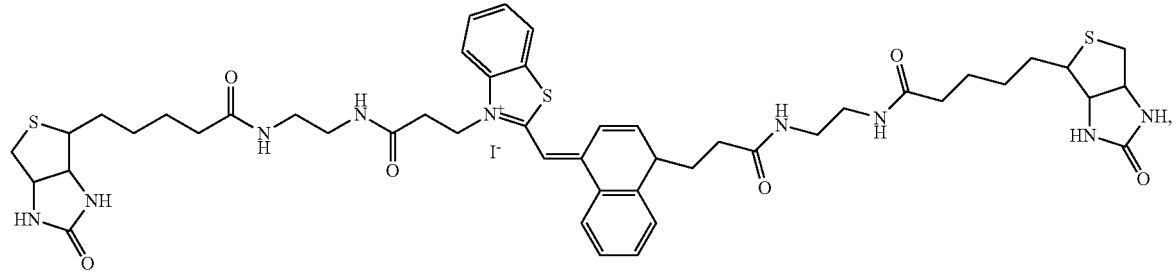

36

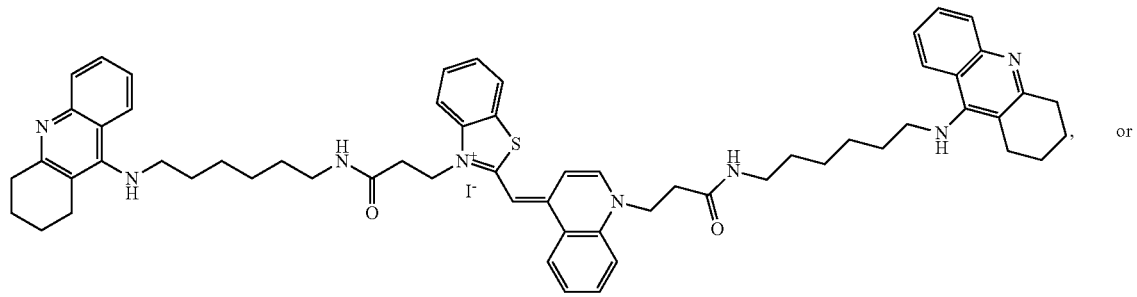

or

37

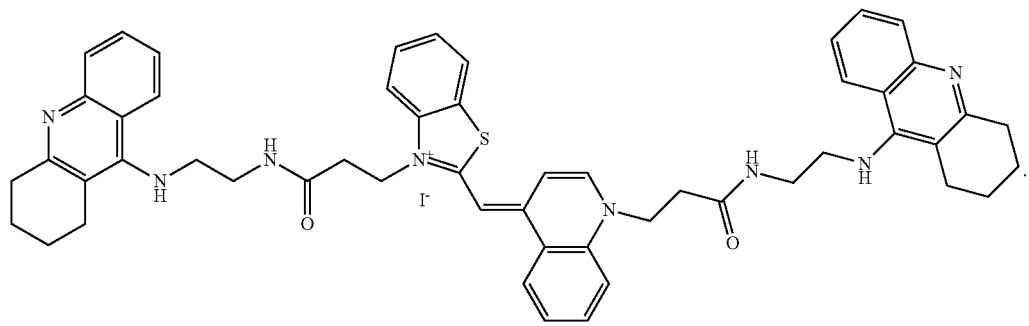

26. A method for identifying a disease biomarker in a subject, said method comprises:
   (a) collecting a biological sample from a subject;
   (b) incubating said biological sample with a sensor according to claim 1;
   (c) measuring the fluorescence resulting from binding of said sensor to a protein of interest (POI), which is a biomarker for a disease, in said sample;
wherein an enhancement in the emission intensity from said sample is an indicator of the presence of said POI in said sample.

27. The method of claim 26, wherein said disease is cancer or Alzheimer.

28. The method of claim 27, wherein said cancer is breast cancer, lung cancer, colorectal cancer, pancreas cancer, bladder cancer, ovarian cancer, prostate cancer, or brain cancer.

29. The method of claim 26, wherein said POI is matrix metalloproteases (MMPs) protein and its isoforms, gluta- thione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, avidin, streptavidin, Acetylcholinesterase or histone deacetylases (HDACs).

30. A method of identifying a compound that binds a protein of interest (POI), said method comprises:
   a. incubating a sensor according to claim 1 with said POI in solution;
   b. measuring the fluorescence intensity of said solution;
   c. adding a test compound to said solution;
   d. re-measuring the fluorescence intensity of said solution; and
   e. determining binding of said test compound to said POI based on a change in fluorescence intensity, wherein decreased fluorescent intensity indicates binding of said test compound to said POI;
thereby identifying a compound that binds said POI.

31. The method of claim 30, wherein said POI is matrix metalloproteases (MMPs) protein and its isoforms, glutathione S-Transferase (GSTs) protein and its isoforms, platelet derived growth factor, Histidine-tagged proteins, estrogen receptor, fibroblast growth factor (FGF), caspases, PSA, fibronecin, lysozyme, β-amyloid, avidin, streptavidin, Acetylcholinesterase or histone deacetylases (HDACs).

32. The method of claim 30, wherein said sensor is compound 14, 140, 20, 26, 33, 34, 35, 36, or 37.

33. A method for localizing a protein of interest (POI) within a cell, said method comprises:
  a. incubating cells comprising said POI with a sensor according to claim 1;
  b. visualizing the fluorescence emission of said cells; wherein an enhancement in the fluorescence emission is indicative of binding of said sensor to a protein of interest (POI) in said cells.

34. The method of claim 33, wherein said cells are living cells.

35. A compound, represented by the structure of formula IX:

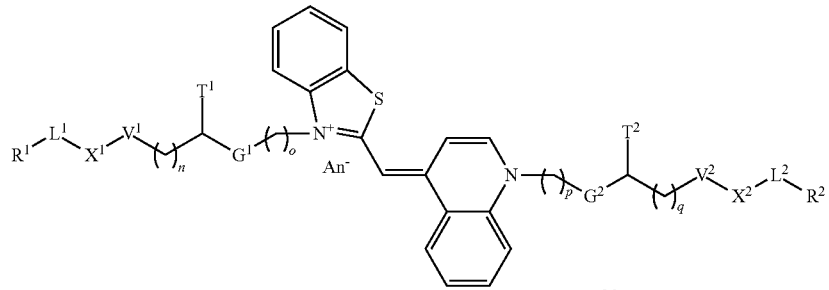

wherein
  n, o, p and q are independently integers between 0 to 15;
  An⁻ is a counter ion, selected from tosylate (p-toluenesulfonate; $CH_3C_6H_4SO_3^-$), $PF_6^-$, $CF_3COO^-$, $I^-$, $Cl^-$, $Br^-$, or $F^-$;
  $G^1$ and $G^2$ are independently a bond, carbamate, amide, amine, $C_1$-$C_{12}$ alkyl amine, ester, ketone, O, N, S, carbonate, —O-alkyl-NH—, carbamoyl phosphate or phosphate;
  $T^1$ is hydrogen or

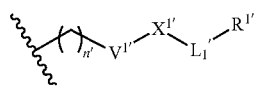

wherein, n' is between 0 and 15;
  $T^2$ is hydrogen or

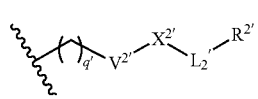

wherein q' is between 0 and 15;

$V^1$, $V^{1'}$, $V^2$ and $V^{2'}$ are independently a bond, a triazole, an amide [—C(O)NH or —NHC(O)], —C(O)O—, —OC(O)—, O, NH, N-alkyl, S, —PO$_4$H—, $C_1$-$C_{12}$ alkyl ether, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof $X^1$, $X^{1'}$, $X^2$ and $X^{2'}$ are independently a bond or $C_1$-$C_{12}$alkyl, —C(O)NH—, —NHC(O), —C(O)O—, —OC(O)—, O, NH, N-alkyl, S, —PO$_4$H—, $C_1$-$C_{12}$ alkyl ether, $C_1$-$C_{12}$-alkyl-NH, -alkyl-NHC(O)-alkyl, -alkyl-C(O)NH-alkyl, —NH-alkyl-NH—, —O-alkyl-NH—, —NH-alkyl-O— wherein said alkyl is optionally substituted and wherein said alkyl is optionally interrupted by an heteroatom consisting of O, N, P, S or combination thereof;

$L^1$, $L^{1'}$, $L^2$ and $L^{2'}$ are independently a bond or $C_1$-$C_{12}$ alkyl, C(O), —C(O)NH—, —NHC(O)—, —C(O)O—, —OC(O)—, O, NH, $C_1$-$C_{12}$ N-alkyl, S, —PO$_4$H, —PO$_4$H—{[(CH$_2$)$_y$O]$_x$}$_z$—PO$_3$H—, wherein y is between 1-5, x is between 1-10 and z is between 1-10, —PO$_4$H—PEG, $C_1$-$C_{12}$ alkyl ether, $C_1$-$C_{12}$ alkylamine, $C_1$-$C_{12}$ alkyl-NH, —C(O)NH-alkyl, —NHC(O)-alkyl, NH-alkyl-NH—, —O-alkyl-NH—, —NH-alkyl-O—, wherein said alkyl is optionally substituted and wherein said alkyl is optionally interrupted by an heteroatom consisting of O, N, P, S or combination thereof; and $R^1$, $R^{1'}$, $R^2$ and $R^{2'}$ are independently hydrogen, halide, $SO_3^-$, CN, $NO_2$, phosphate, $SO_3^-$ or a selective protein binder;

wherein at least one of $R^1$, $R^{1'}$, $R^2$ and $R^{2'}$ is a protein selective binder.

36. The compound according to claim 35, represented by the structure of formula XIII:

XIII

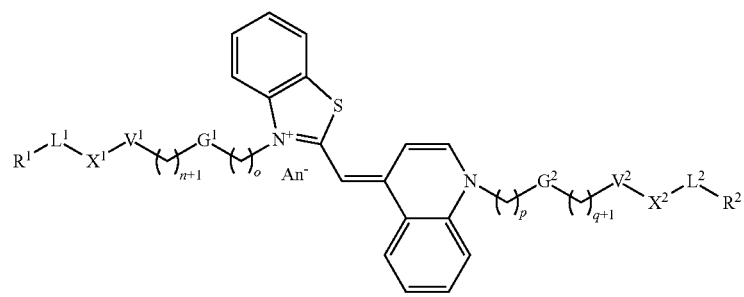

wherein n, o, p, q, An⁻, $V^1$, $V^2$, $G^1$, $G^2$, $X^1$, $X^2$, $L^1$, $L^2$, $R^1$ and $R^2$ are as defined in claim 35.

37. The compound of claim 36, represented by the structure of formula X:

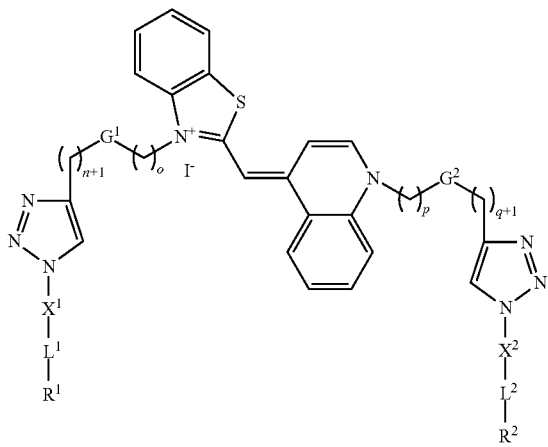

wherein n, o, p, q, $G^1$, $G^2$, $X^1$, $X^2$, $L^1$, $L^2$, $R^1$ and $R^2$ are as defined in claim 35.

38. The compound of claim 37, wherein said sensor is represented by the structure of formula XI:

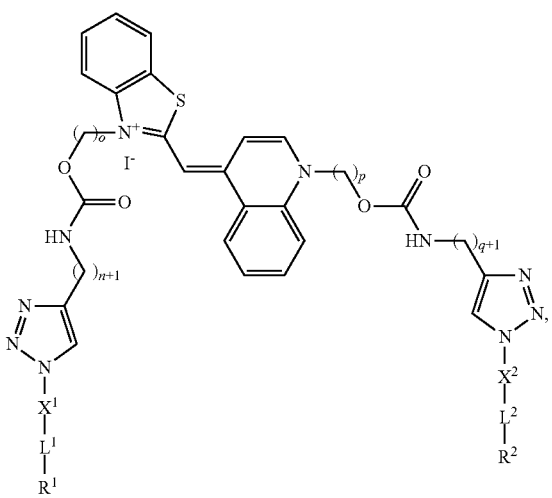

wherein n, o, p, q, $X^1$, $X^2$, $L^1$, $L^2$, $R^1$ and $R^2$ are as defined in claim 35.

39. The compound according to claim 35, wherein said selective protein binder is ethacrynic acid, bisethacrynic acid, marimastat, biotin, tacrine, a metal complex of nitrilotriacetic acid (NTA), a metal complex of bis-NTA, a metal complex of tris-NTA, Ni-nitrilotriacetic acid (Ni-NTA), bis-Ni-NTA, tris-Ni-NTA, PDGF-BB, heparin, FGF aptamer, estrogen, DNA aptamer, RNA aptamer, peptide aldehyde, suberoylanilidehydroxamic acid (SAHA), estrogen, or a peptide binder.

40. The compound of claim 39, wherein said ethacrynic acid or bisethacrynic acid is selective to glutathione S-Transferase (GSTs) protein; said Ni-nitrilotriacetic acid (Ni-NTA), bis-Ni-NTA or tris-Ni-NTA is selective to a His-tag protein; said PDGF-BB, heparin and estrogen are selective to platelet derived growth factor, fibroblast growth factor and to estrogen receptor, respectively; said DNA aptamer is selective to lysozyme; said peptide binder is selective to firbronectin or β-amyloid; said DNA or RNA aptamer is selective to PSA; and said peptide aldehyde is selective to caspases and said SAHA is selective to histone deacetylases (HDACs).

41. The compound of claim 35, wherein $T^1$ and $T^2$ are hydrogens.

42. The compound of claim 35, wherein said $G^1$ and $G^2$ are each independently a carbamate or an amide.

43. The compound of claim 35, wherein said $V^1$ and $V^2$ are each independently a triazole, an O, an NH or a bond.

44. The compound of claim 35, wherein said $X^1$ and $X^2$ are each independently a $C_1$-$C_{12}$ alkyl, a $C_1$-$C_{12}$ alkyl-NH, a $C_1$-$C_{12}$ alkylether, -alkyl-C(O)NH-alkyl or a bond.

45. The compound of claim 35, wherein said $L^1$ and $L^2$ are each independently a bond, —$PO_4H$—$\{[(CH_2)_yO]_x\}_z$—$PO_3H$—, wherein y is 2, x is 3 and z is 6; —$PO_4H$—PEG; $C_1$-$C_{12}$ alkyl-NH or a $C_1$-$C_{12}$ alkyl.

46. The compound of claim 35, wherein said o and p are each independently 2 or 3.

47. The compound of claim 35, wherein said n and q are each independently 0, 1, 2 or 5.

48. The compound of claim 35, wherein $R^1$ and $R^2$ are both a selective binder.

49. The compound of claim 35, wherein said $V^1$ and $V^2$ are identical; $X^1$ and $X^2$ are identical; $L^1$ and $L^2$ are identical; $R^1$ and $R^2$ are identical; o and p are identical; and n and q are identical.

50. The compound of claim 35, wherein said sensor is compound 14, 140, 20, 26, 33, 34, 35, 36, or 37:

109
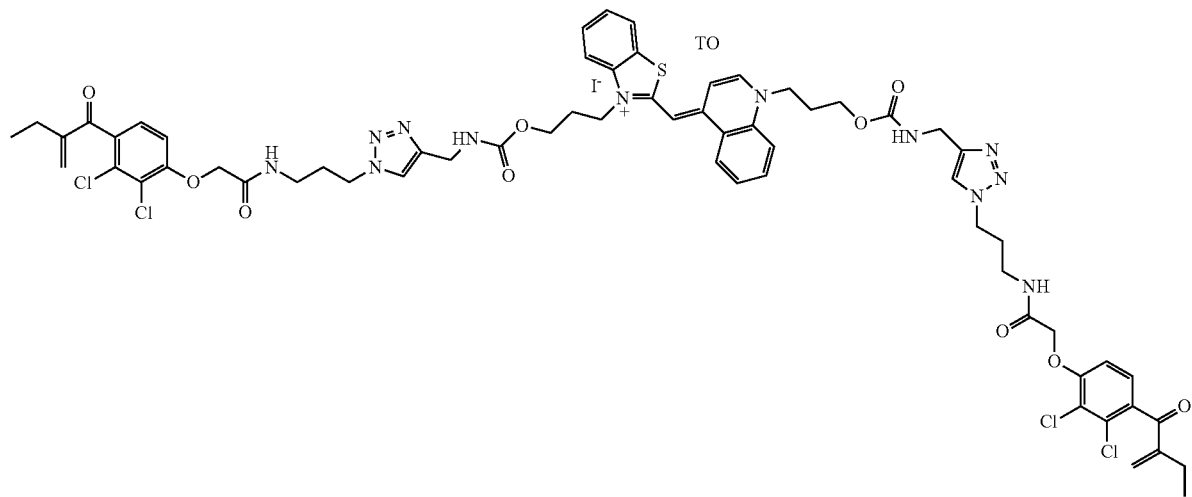
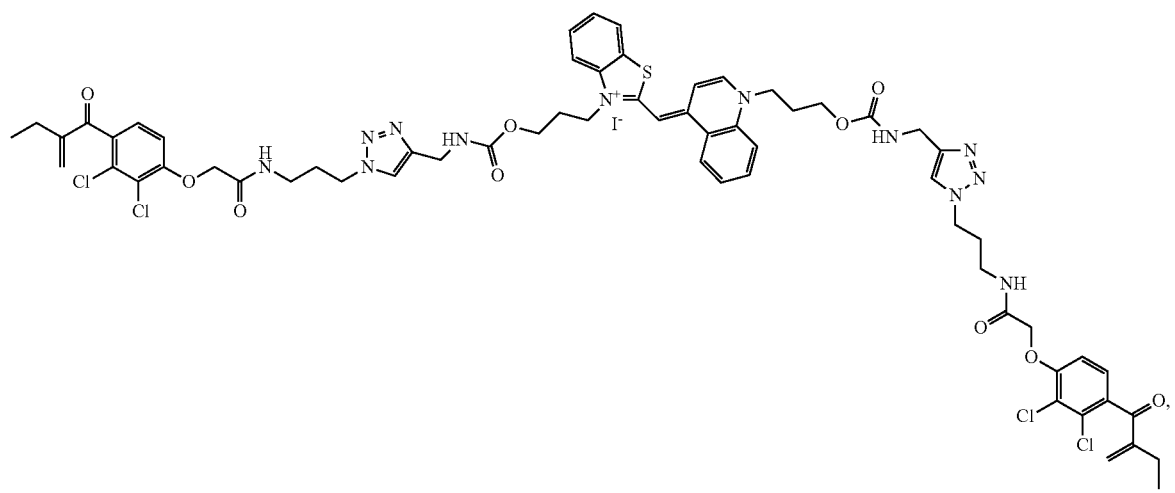
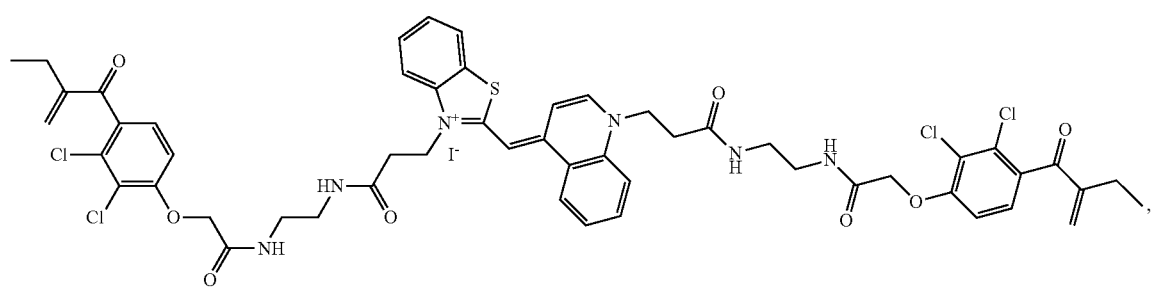

-continued
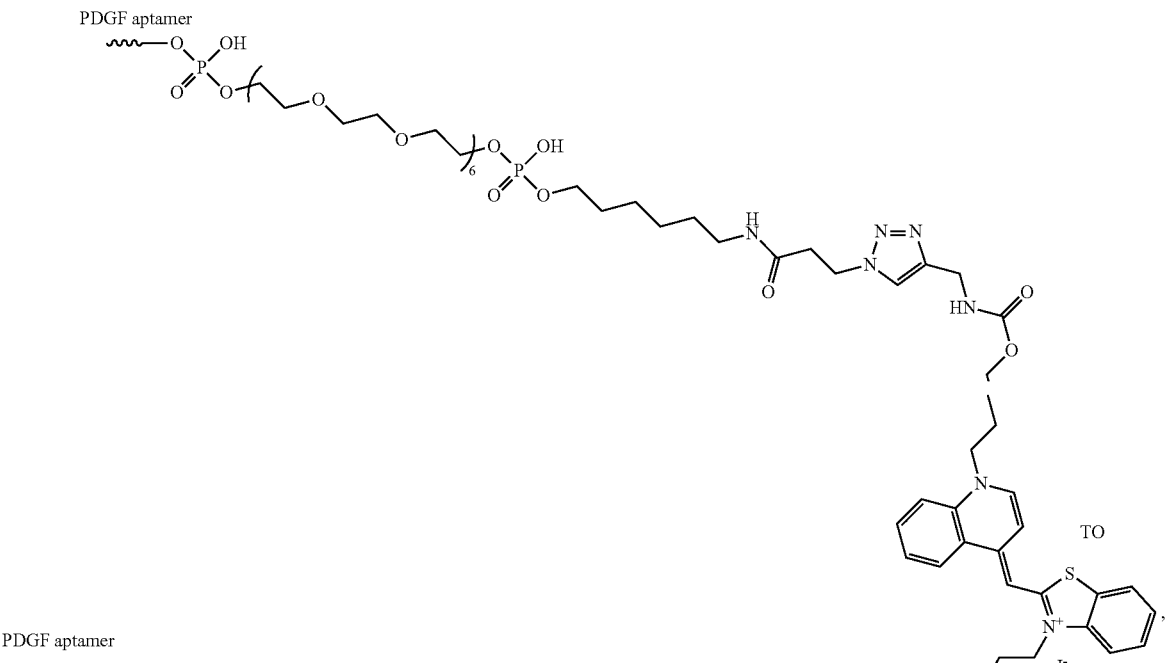
20
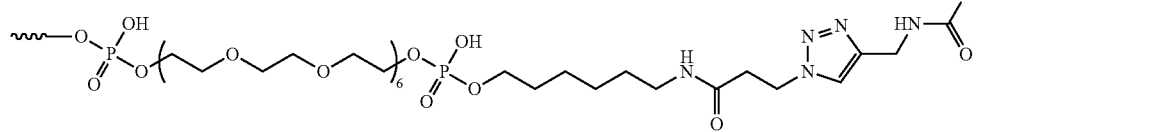
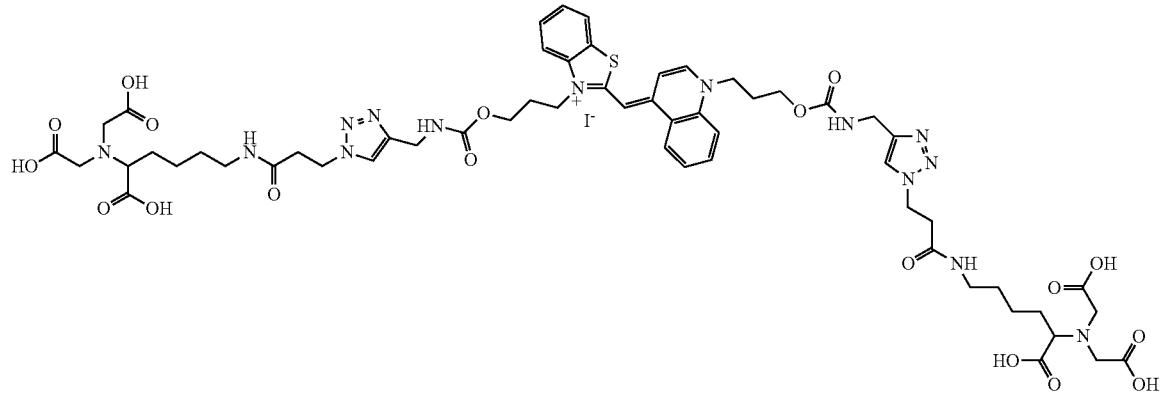
26
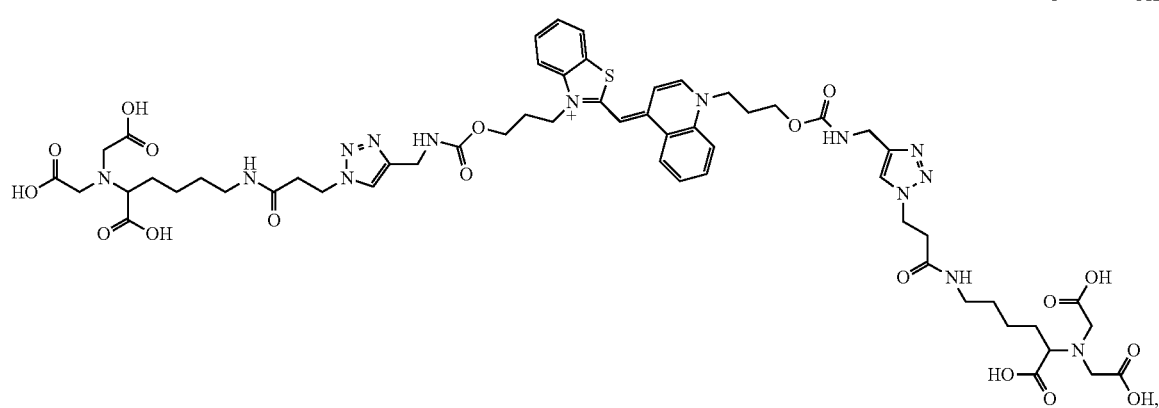

-continued
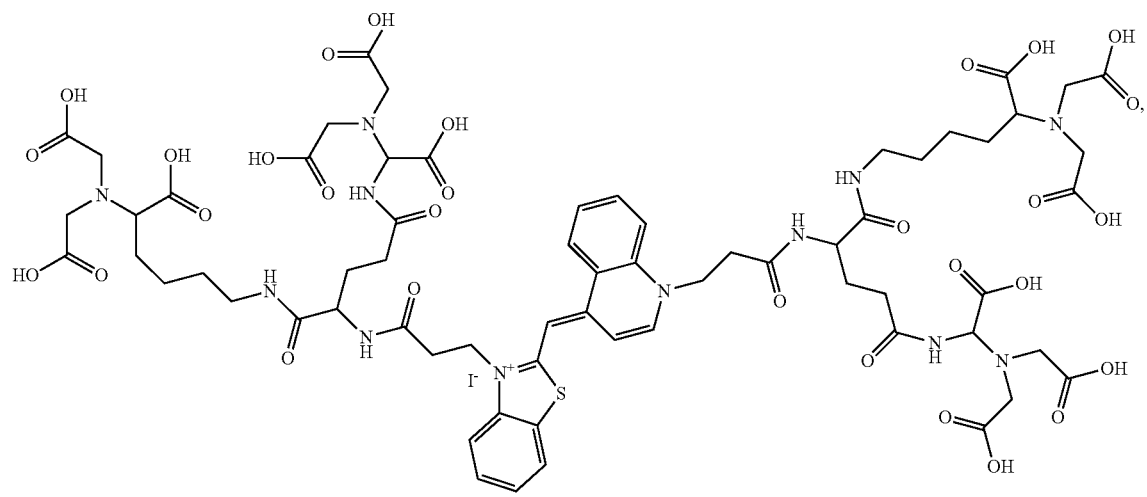
33
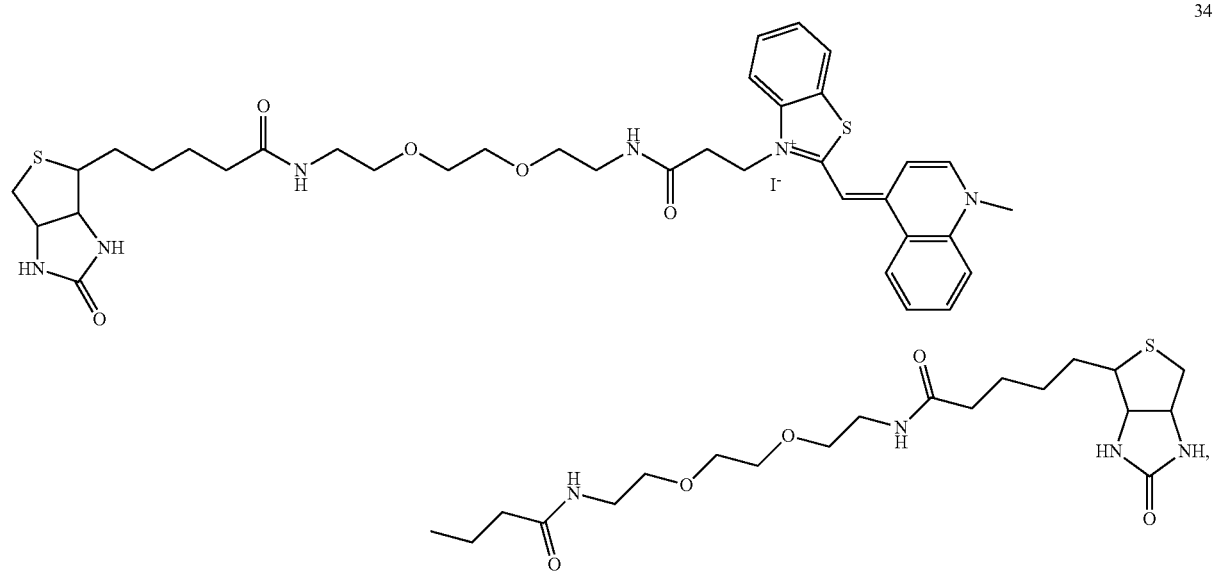
34
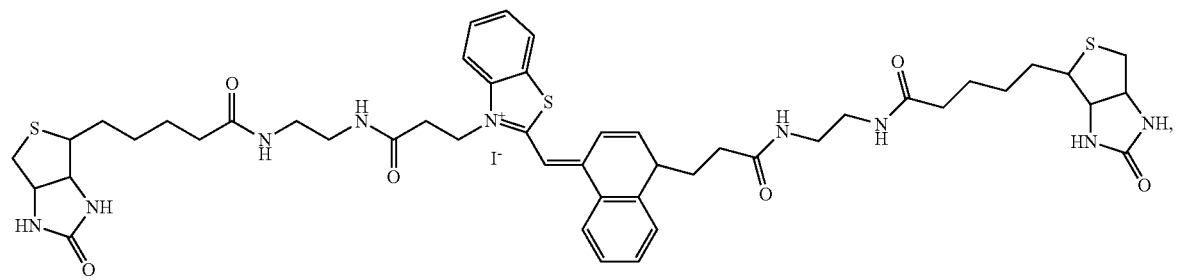
35
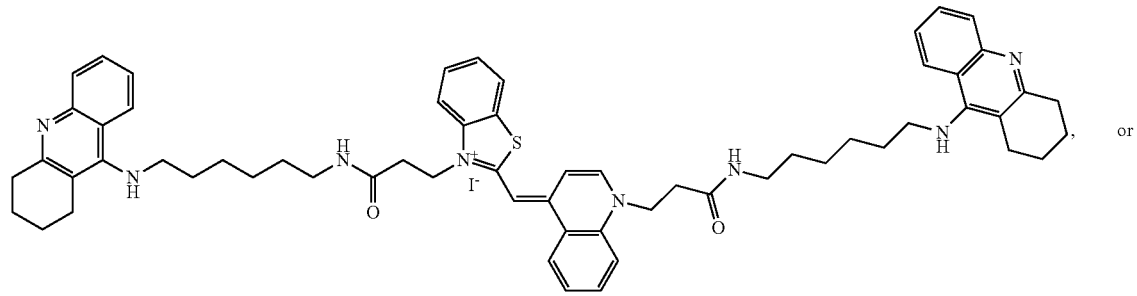
36

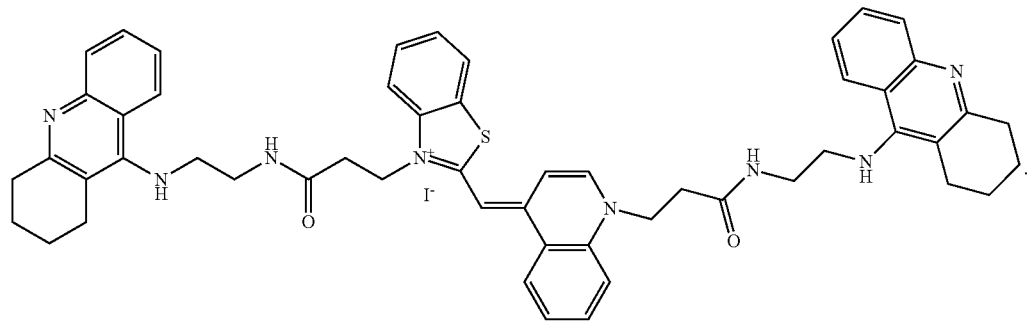
* * * * *